US007734424B1

(12) United States Patent
Rogan

(10) Patent No.: US 7,734,424 B1
(45) Date of Patent: Jun. 8, 2010

(54) AB INITIO GENERATION OF SINGLE COPY GENOMIC PROBES

(76) Inventor: Peter K. Rogan, 12226 Gillette Rd., Overland Park, KS (US) 66213

( * ) Notice: Subject to any disclaimer, the term of this patent is extended or adjusted under 35 U.S.C. 154(b) by 0 days.

(21) Appl. No.: 11/324,102

(22) Filed: Dec. 30, 2005

Related U.S. Application Data

(60) Provisional application No. 60/687,945, filed on Jun. 7, 2005.

(51) Int. Cl.
*G01N 33/00* (2006.01)

(52) U.S. Cl. .......................................... 702/19; 702/20

(58) Field of Classification Search .................... 702/19
See application file for complete search history.

(56) References Cited

U.S. PATENT DOCUMENTS

| | | | |
|---|---|---|---|
| 6,150,160 | A | 11/2000 | Kazazian, Jr. |
| 6,828,097 | B1 | 12/2004 | Knoll et al. |
| 7,014,997 | B2 | 3/2006 | Knoll et al. |
| 2003/0022204 | A1 | 1/2003 | Lansdorp |
| 2003/0044822 | A1 | 3/2003 | Fletcher et al. |
| 2003/0108943 | A1 | 6/2003 | Gray et al. |
| 2003/0194718 | A1 | 10/2003 | Tomita et al. |
| 2004/0161773 | A1 | 8/2004 | Rogan et al. |
| 2004/0241734 | A1 | 12/2004 | Davis |
| 2005/0064450 | A1 | 3/2005 | Lucas et al. |

FOREIGN PATENT DOCUMENTS

WO WO 01/88089 A2 * 11/2001

OTHER PUBLICATIONS

Claverie, Human molecular genomics, vol. 6,No. 10, p. 1735-1744, 1997.*

Li et al, Molecular ecology, vol. 11, p. 2453-2465, 2002.*

Jurka et al., Computers Chem., vol. 20, No. 1, p. 119-121, 1996.*

Eisenbarth et al. (Human Molecular Genetics, vol. 10, No. 24, 2833-2839, 2001).*

Altschul, S.F., et al., "Basic Local Alignment Search Tool," J Mol Biol, 1990, pp. 403-410, vol. 215/3.

Bardoni, et al., "Isolation and Characterization of a Family of Sequences Dispersed on the Human X Chromosome," Cytogenet and Cell Genet, Human Gene Mapping 9, Abstracts of Workshop Presentations, Paris Conference, 1987, p. 575.

Batzoglou, S., et al., "Human and Mouse Gene Structure: Comparative Analysis and Application to Exon Prediction," Genome Res, 2000, pp. 950-958, vol. 10.

Buhler, J., "Efficient Large-Scale Sequence Comparison by Locality-Sensitive Hashing," Bioinformatics, 2001, pp. 419-428, vol. 17/5.

Carrillo, H., et al., "The Multiple Sequence Alignment Problem in Biology," SIAM J Applied Math, 1988, pp. 1073-1082, vol. 48/5.

Chang, P-C, et al., "Design and Assessment of Fast Algorithm for Identifying Specific Probes for Human and Mouse Genes," Bioinformatics, 2003, pp. 1311-1317, vol. 19/11.

Craig, J.M., et al., "Removal of Repetitive Sequences from FISH Probes Using PCR-Assisted Affinity Chromatography," Hum Genet, 1997, pp. 472-476, vol. 100/3-4.

Delcher, A.L., et al., "Alignment of Whole Genomes," Nucl Acids Res, 1999, pp. 2369-2376, vol. 27/11.

Devereux, J., et al., "A Comprehensive Set of Sequence Analysis Programs for the VAX," Nucl Acids Res, 1984, pp. 387-395, vol. 12/1.

Dover, G., "Molecular Drive," Trends in Genetics, 2002, pp. 587-589, vol. 18/11.

Edgar, R.C., et al., "PILER: Identification and Classification of Genomic Repeats," Bioinformatics, 2005, pp. i152-i158, vol. 21(Supp 1).

Healy, J., et al., "Annotating Large Genomes with Exact Word Matches," Genome Res, 2003, pp. 2306-2315, vol. 13.

Howell, M.D., et al., "Rapid Identification of Hybridization Probes for Chromosomal Walking," Gene, 1987, pp. 41-45, vol. 55.

Jareborg, N., et al., "Comparative Analysis of Noncoding Regions of 77 Orthologous Mouse and Human Gene Pairs," Genome Res, 1999, pp. 815-824, vol. 9.

Jurka, J., "Repeats in Genomic DNA: Mining and Meaning," Curr Opin In Struct Biol, 1998, pp. 333-337, vol. 8/3.

Kent, W.J., et al., "Conservation, Regulation, Synteny, and Introns in a Large-Scale C. Briggsae-C. Elegans Genomic Alignment," Genome Res, 2000, pp. 1115-1125, vol. 10.

Kent, W.J., "BLAT—The Blast-Like Alignment Tool," Genome Res, 2002, pp. 656-664, vol. 12.

Lighter, P., et al., "Delineation of Individual Human Chromosomes in Metaphase and Interphase Cells by in Situ Suppression Hybridization Using Recombinant DNA Libraries," Hum Genet, 1988, pp. 224-234, vol. 80/3.

Morgenstern, B., et al., "DIALIGN: Finding Local Similarities by Multiple Sequence Alignment," Bioinformatics, 1998, pp. 290-294, vol. 14/3.

Mottez, E., et al., "Conservation in the 5' Region of the Long Interspersed Mouse L1 Repeat: Implication of Comparative Sequence Analysis," Nucl Acids Res, 1986, pp. 3119-3136, vol. 14/7.

Nakamura, Y., et al., "Variable Number of Tandem Repeat (VNTR) Markers for Human Gene Mapping," Science, 1987, pp. 1616-1622, vol. 235.

Newkirk, H.L., et al., "Distortion of Quantitative Genomic and Expression Hybridization by Cot-1 DNA: Mitigation of this Effect," Nucl Acids Res, 2005, pp. e191 (8 pages), vol. 33/22.

Newkirk, H.L., et al., "Determination of Genomic Copy Number with Quantitative Microsphere Hybridization," Human Mutation, 2006, pp. 376-386, vol. 27/4.

(Continued)

*Primary Examiner*—Karlheinz R Skowronek
(74) *Attorney, Agent, or Firm*—Senniger Powers LLP

(57) ABSTRACT

Single copy sequences suitable for use as DNA probes can be defined by computational analysis of genomic sequences. The present invention provides an ab initio method for identification of single copy sequences for use as probes which obviates the need to compare genomic sequences with existing catalogs of repetitive sequences. By dividing a target reference sequence into a series of shorter contiguous sequence windows and comparing these sequences with the reference genome sequence, one can identify single copy sequences in a genome. Probes can then be designed and produced from these single copy intervals.

16 Claims, 2 Drawing Sheets

OTHER PUBLICATIONS

Price, A.L., et al., "De Novo Identification of Repeat Families in Large Genomes," Bioinformatics, 2005, pp. i351-i358, vol. 21(Supp 1).

Rogan, P.K., et al., "L1 Repeat Elements in the Human ϵ-Gγ-Globin Gene Intergenic Region: Sequence Analysis and Concerted Evolution with this Family," Mol Biol, 1987, pp. 327-342, vol. 4/4.

Schwartz, S., et al., "PipMaker—A Web Server for Aligning Two Genomic DNA Sequences," Genome Res, 2000, pp. 577-586, vol. 10.

Smit, A.F.A., "The Origin of Interspersed Repeats in the Human Genome," Current Opin in Gen & Dev, 1996, pp. 743-748, vol. 6/6.

Vincens, P., et al., "A Strategy for Finding Regions of Similarity in Complete Genome Sequences," Bioinformatics, 1998, pp. 715-725, vol. 14/8.

Zhang, Z., et al., "A Greedy Algorithm for Aligning DNA Sequences," J of Comp Biol, 2000, pp. 203-214, vol. 7/1-2.

Gene Expression: vol. 2, Eukaryotic Chromosomes, 1983, Lewin, B., Ed., Wiley, p. 503, Wiley & Sons, Inc., New York.

Faranda, S., et al., "Human Genes Encoding Renin-Binding Protein and Host Cell Factor are Closely Linked in Xq28 and Transcribed in the Same Direction," 1995, Gene, 155:237-239.

Vermeesch, J.R., et al., "Interstitial Telomeric Sequences at the Junction Site of a Jumping Translocation," 1997, Hum Genet, 99:735-737.

* cited by examiner

102
USER
104
COMPUTING DEVICE
106
COMPUTER-READABLE MEDIUM
108
FIRST GENOME COMPARISON COMPONENT
110
SECOND GENOME COMPARISON COMPONENT
112
SUBSEQUENCE COMPONENT

AB INITIO GENERATION OF SINGLE COPY GENOMIC PROBES

CROSS REFERENCE TO RELATED APPLICATIONS

This application claims the benefit of U.S. Ser. No. 60/687,945, filed Jun. 7, 2005. The contents of U.S. Ser. No. 60/687,945 and of Disclosure Document No. 576,582, filed May 3, 2005, are each hereby incorporated herein by reference.

This invention was made with Government support under Grant No. 1R41CA112692-01 awarded by the National Institutes of Health. The Government has certain rights in the invention.

COMPUTER PROGRAM CONTAINING SEQUENCE LISTING ON CD-ROM

The file of this patent includes duplicate copies of a read-only compact disc (CD-ROM) with a memory file entitled PHY9990.ST25.TXT which is in ASCII file format. The file was created on Dec. 29, 2005, using PatentIn Version 3.1 and is a size of 395 KB. This text document contains the Sequence Listing for this application. This Patent Application includes references to the Sequence Listing contained on the CD-ROM. The CD-ROM and the PHY9990.ST25.TXT file contained thereon are hereby incorporated herein by reference into this Patent Application.

FIELD OF THE INVENTION

The present invention generally relates to ab initio methods of computationally determining the locations of single copy intervals in genomes for use as probes.

BACKGROUND

Conventional hybridization studies with genome-derived nucleic acid probes require unlabeled Cot-1 DNA fractions to block cross-hybridization of repetitive sequences contained within these probes in eukaryotic genomes. This is necessary, because to achieve the specificity needed to identify, detect or quantify unique sequences contained in nucleic acid probes, confounding hybridization from repetitive sequences must be eliminated. Repetitive sequences comprise at least 50% of the human genome and contain a diverse set of distinct families (Smit, Curr Opin Genet Dev. 1996, 6(6):743-8). Despite the lack of selection for their function and broad, often variable degrees of orthology, such sequences often display sequence conservation throughout mammalian evolution (Rogan et al. Mol Biol Evol. 1987, 4(4):327-42; Mottez et al. Nucleic Acids Res. 1986, 14(7):3119-36), principally because they have properties of semiautonomous transposable elements that promote frequent amplification during host organism evolution, originally termed molecular drive by Dover (Dover, Trends Genet. 2002, 18(11):587-9). It is desirable to remove such sequences in most clinical diagnostic applications; because of their ubiquity throughout the genome, their presence can interfere with the development of probes for unique regions of the genome that correspond to functional genes whose structures must be preserved because they are essential for normal development and health.

Repetitive sequences are often interspersed with unique or single copy genes, especially in eukaryotic genomes, and their removal from genomic probes is essential to ensure that diagnostic probes specifically recognize only a single location in the genome. These sequences can be eliminated by laboratory techniques designed to sequester them away from labeled probes containing both single copy and interspersed repetitive sequences (Lichter et al. Hum Genet. 1988, 80(3):224-34; Craig et al. Hum Genet 1997, 100:472-476), by blocking their hybridization, or by deducing the single copy sequences by comparisons of known genomic reference sequences with comprehensive databases of consensus sequences that are representative of established repetitive sequence families and subfamilies (Jurka, Curr Opin Struct Biol. 1998, 8(3):333-7).

Cot-1 DNA is often used to attempt to suppress cross-hybridization of repetitive sequences to probes. The problem with attempting to suppress repeat hybridization with Cot-1 DNA is that it can result in enhanced non-specific hybridization between probes and genomic targets. Specifically, it has been demonstrated that Cot-1 added to target DNA actually enhanced hybridization to genomic probes containing conserved repetitive elements (Newkirk, H. L. et al., Nuc. Acids Res. 2005, 33(22):e191). In addition to repetitive sequences, Cot-1 was also found to be enriched for linked single copy sequences (Newkirk, H. L. et al., Nuc. Acids Res. 2005, 33(22):e191). Adventitious association between these sequences and probes distorts quantitative measurements of the probes hybridized to desired genomic targets. This also affects the reproducibility of hybridization assays with sources of genomic DNA, in particular, and can also impact hybridization to mRNAs that contain repetitive sequences (typically found in the untranslated regions of transcripts). The increased non-specific hybridization that occurs when using Cot-1 to block repeat sequence hybridization has particularly adverse effects on microarray studies which depend on quantification of signals obtained by hybridization to the unblocked presumably single copy sequences.

The elimination of Cot-1 DNA, either by sequestering repeats or by blocking their hybridization, was accomplished by direct synthesis of probes lacking repeat sequences. Knoll et al., U.S. Pat. No. 6,828,097 (termed '097 patent), discloses a procedure for determining the locations of single copy intervals and design of probes for hybridization to their complementary locations in the human genome. It is disclosed that the procedure can be implemented for any genome in which a comprehensive catalog of repetitive sequences is available. Presumed single copy sequences containing repetitive elements will cross-hybridize to multiple locations in the genome. Where hybridization occurs in too many genomic locations, the lack of specificity adversely impacts the utility of the probes in diagnosing disease. Therefore, methods from which single copy sequences can be deduced without requiring a comparison of the genomic sequence with a comprehensive database of consensus repetitive sequence family members would represent an improvement over current in silico methods of identifying single copy intervals and the ensuing probes.

Methods have been developed which can align the sequences of different, related, or the same complete genomes from which the locations of individual repetitive sequences in the genome can be inferred. One such example is the maximal unique matching algorithm which builds suffix trees from all maximal length unique matches (MUM) between sequence strings (Delcher et al. Nuc. Acids Res. 1999, 27:2369-2376). Repeats can be detected in a genome because they are found in overlapping MUMs that are not necessarily contiguous in that genome. Once repeat sequence elements are identified through such comparisons, families of related repeat sequences can be identified through comparisons of individual family members with the genome sequence itself. Another popular method, the BLAT algorithm (Kent et al. Genome Res. 2002, 12:656-64), is a rapid alignment method that uses a hash-index algorithm to quickly find sequences similar to a particular test sequence in a genome; it is not, however, an ab initio approach for single copy sequence identification. Other comparative alignment tools useful for detecting repeat sequences include ASSIRC (Vincens et al. Bioinformatics 1998, 14:715-725), DIALIGN (Morgenstern et al Bioinformatics. 1998, 14(3):290-4.), DBA (Jareborg et al. Genome Res. 1999, 9(9):815-24), GLASS (Batzoglou et al. Genome Res. 2000, 10(7):950-8), LSH-ALL-PAIRS (Buhler, Bioinformatics. 2001, 17(5):419-28), MEGABLAST (Zhang J Comput Biol. 2000, 7(1-2):203-14), PIPMaker (Schwartz et al. Genome Res. 2000, 10(4):577-86), SSAHA (www.sangerac.uk/Software/analysis/SSAHA), and WABA (Kent and Zahler Genome Res. 2000, 10(8):1115-25).

U.S. application Ser. No. 10/229,058 discloses that sequences can be screened for the presence of known repetitive sequence families (e.g., Alu elements); however the details of these screening procedures are not disclosed. U.S. application Ser. No. 10/132,002 discloses a procedure for detecting repetitive sequences experimentally, but does not disclose the identification of single copy sequences. U.S. application Ser. No. 10/833,954 discloses that in situ hybridization of a mixture of single copy and repetitive sequences can be performed in the absence of blocking nucleic acids that prevent cross hybridization of repetitive sequences. A formulation of a hybridization reagent and washing conditions that could mitigate such cross-hybridization are disclosed, but no information is provided regarding the location of single copy and repetitive sequences within the probe segment. U.S. Ser. No. 10/132,993 discloses laboratory chromatographic methods to remove repetitive sequences from genomic DNA to make probes that are substantially complementary to single copy intervals. In this application, the locations or the specific single copy sequences are not determined prior to experimentally removing the repeat sequences. A very similar approach is described in U.S. application Ser. No. 10/798,949, in which repetitive sequences are subtracted by hybridization, and single copy sequences are subsequently amplified using so called unique sequence primers. Subtraction hybridization is not a robust technique, because low- to middle-reiteration frequency repeats are not completely eliminated under the hybridization conditions typically used in these studies. Therefore, the selection of these primers could result in the production of probes that are contaminated with repetitive sequence elements. Similarly, in U.S. application Ser. No. 10/229,058, the repetitive sequences are fractionated by hybridization methods prior to library production and sequencing. Presumably, the single copy sequences would be revealed after library enrichment; however U.S. Ser. No. 10/229,058 does not teach how to identify the precise boundaries of these sequences in the genome, and it does not teach the method of determining how to identify single copy sequences for use as probes. U.S. Ser. No. 10/330,089 is the most recent of several continuation applications which infer the single copy nature of cloned sequences by their lack of hybridization to total genomic DNA, which is highly enriched in repetitive elements. The specific single copy sequences are not revealed by this approach. Furthermore, the present applicants have demonstrated that the single copy sequences produced according to this method are contaminated with repetitive sequences, since they are particularly insensitive to the detection of low- to moderate-abundance repetitive sequence family members. See U.S. Pat. No. 6,828,097, Prosecution History.

While several of these approaches can find locally similar repetitive sequences without comparison to a library of sequences (as in Knoll et al., U.S. Pat. No. 6,828,097), their objective is to identify repetitive sequences and multiple copies of related sequences found in the genomes of different individuals or species. These approaches do not involve the use of repetitive sequences to infer the presence of single copy sequence intervals (between adjacent repetitive sequences in the genome) for the development of useful single copy probes from the intervening regions between the deduced repetitive sequences. These algorithms therefore produce libraries similar to that used in the '097 patent, and the sequences contained in these libraries will be similar to those already known. These algorithms do not describe inferred single copy intervals, or in particular, the use of probes obtained from those deduced intervals.

SUMMARY OF THE INVENTION

The present invention relates to the computational design of nucleic acid probes that exclusively contain sequences found at a single location in a reference genome sequence.

A method is described to identify single copy regions in a target genome interval of known sequence and then preparing probes from these regions, principally for the detection of chromosomal and genomic abnormalities by nucleic acid hybridization. The method divides the target genome interval into consecutive sequence subintervals and compares each of the subintervals with the reference genome sequence. Those subintervals which are found once within the reference genome sequence, typically referred to as single copy intervals, serve as sequences that serve as a starting point for subsequent analysis. To more precisely localize the single copy sequences, i.e., the single copies of sequences that appear within a single copy interval, these subsequences may either be further resected into non-overlapping sub-subintervals or they may be modified by selecting windows that overlap the original single copy subintervals, but which are displaced by one or more nucleotides from the original genomic coordinates in either the telomeric or centromeric direction. Typically, as series of overlapping sub-subintervals are derived from the original sequence by extending the subinterval at one end of the sub-subsequence and shortening the sub-subsequence by the same length at the other end. The directionality of the overlapping sub-subsequence set is dictated by the orientation of the single copy subsequence adjacent to the subsequence that contains one or more repeat elements. The overlapping sub-subsequences are selected so that their displacement moves toward the location of the single copy subsequence. The overlapping sub-subsequences are compared with the genome reference sequence and the procedure is iterated by progressively decreasing the degree of overlap until either the overlapped interval demonstrates multiple regions of similarity in the reference genome or the end of the chromosome is reached. The single copy sequences thus obtained are then used to prepare probes either by direct nucleic acid synthesis, amplification or by retrieval and purification of these sequences from recombinant clones or genomic DNA.

In the present application, the probes are labeled and then hybridized to chromosomes from patients or cell lines. However, those of skill in the art will appreciate that the probes can be fixed on a surface or matrix and hybridized with genomic DNA or cDNA from patients or control specimens that have been labeled by chemical, fluorescent, or radioactive modification. With the present invention, it is not necessary to suppress hybridization of repetitive sequences with unlabeled Cot-1 nucleic acids when annealing these probes to their unique chromosomal locations in the genomes of patient samples or cell line chromosomal DNA.

The ab initio methods described in the instant invention are capable of identifying both the same repeat families that have been previously catalogued in the art and new repeat sequence families that have not been previously recognized in the art.

Another advantage of the present invention is that such ab initio methods can be used to deduce single copy sequences in instances of biological species for which catalogs of repetitive sequences have not been previously derived.

DETAILED DESCRIPTION OF THE INVENTION

Figure 1:
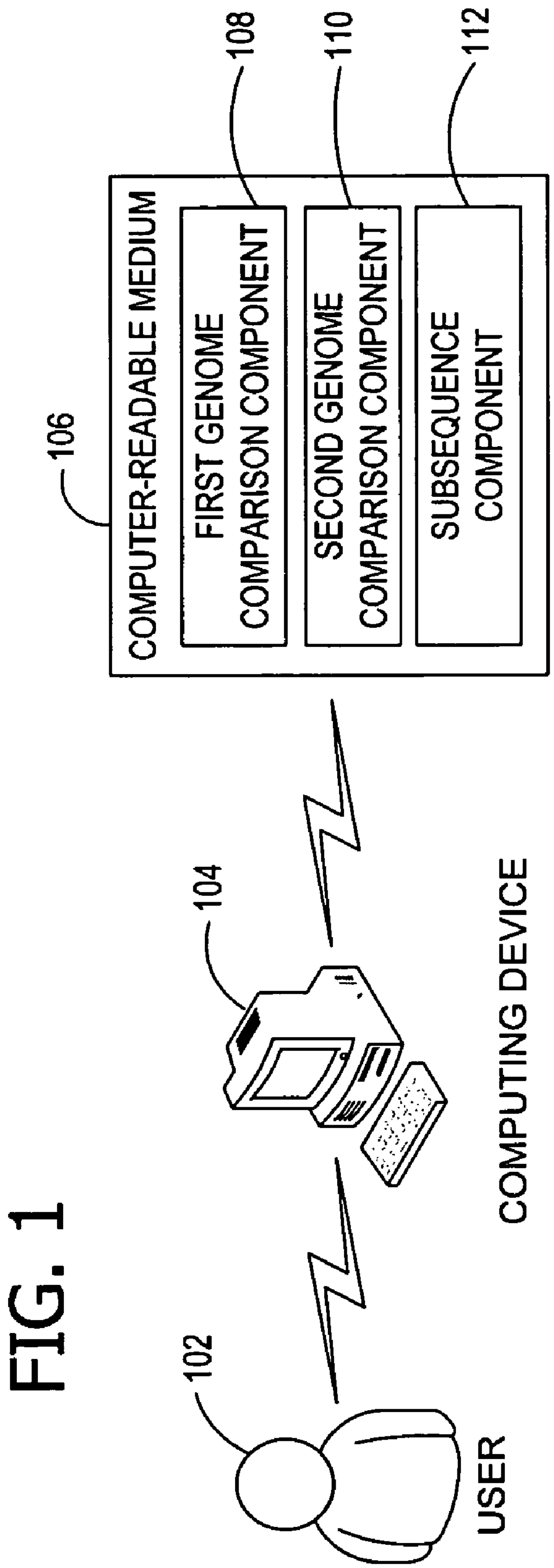
FIG. 1 is a block diagram illustrating a user interacting with a computing environment in one embodiment of the invention.

The present invention is concerned with nucleic acid (e.g., DNA or RNA) hybridization probes for detection of genetic or neoplastic disorders, such as for example Monosomy 1p36 syndrome, Wolf-Hirschorn Syndrome, Cri-du-Chat Syndrome, Williams Syndrome, Langer-Giedeon Syndrome, Chronic myelogenous leukemia, Acute lymphocytic leukemia, Aneuploidy for chromosome 13 (eg. Patau Syndrome), Prader-Willi Syndrome, Angelman Syndrome & Chromosome 15 duplication Syndrome, Acute Myelogenous leukemia Type M4, Rubenstein-Taybi Syndrome, Smith-Magenis Syndrome, Charcot-Marie-Tooth Disease Type 1A, Miller-Dieker Syndrome, Alagille Syndrome, Down Syndrome, DiGeorgeNelocardiofacial Syndrome, Schizophrenia, Kallman Syndrome, Turner and Leri-Weill Syndromes, and subtelomeric chromosome rearrangements associated with idiopathic mental retardation, sex chromosome aneuploidy, and monosomy chromosome 22. See, for example, U.S. Ser. No. 09/854,867.

The probes are in the form of nucleic acid fragments or a collection of labeled nucleic acid fragments whose hybridization to a target sequence can be detected. The invention also pertains to methods of developing, generating and labeling or chemical modification of such probes, and to uses thereof. Chemical modifications of such probes can be used to permanently attach them to solid surfaces such as polystyrene microspheres or glass slides for subsequent hybridization to nucleic acids obtained, for example, from a patient for diagnosis of a genetic disorder, such as, for example, the syndromes described in U.S. Ser. No. 09/854,867, or of various cancers, such as, for example, breast cancer associated with amplification of the HER2/NEU gene, neuroblastoma associated with amplification of the N-myc gene, melanoma associated with chromosome deletions of p16/CDKN2A gene, chromosome translocations activating oncogenes associated with Chronic myelogenous leukemia (BCR/ABL1), Acute lymphocytic leukemia, B-cell lymphoma, prostate carcinoma, chromosome inversions such as that found in Acute Myelogenous leukemia-Type M4, and losses of heterozygosity for example, monosomies for chromosome 7q, 1p, 17p, and 8p. This list of chromosome abnormalities is provided for purposes of illustrating the types of abnormalities suitable for detection with probes of the art. There are many other art-recognized abnormalities which are diagnostic for neoplasia that involve gain or loss of copies of other genes and chromosomes, but result from the same or similar common mechanisms of chromosome rearrangement presented in these examples.

Various aspects of the present invention obviate the need to compare the sequence of the genomic interval from which single copy intervals and probes are derived with a database of existing repetitive sequences. Generally, a genomic subsequence is compared with the sequence of the complete haploid genome that contains that genomic subsequence. Assuming the subsequence is sufficiently long, there is a high probability that it will contain at least one repetitive element, sometimes also referred to as a repetitive or repeat sequence. Repetitive elements are detected by counting the number of times that the subsequence occurs in the genome. Typically, the presence of more than one copy of a sequence would exclude that sequence from being defined for use as an ab initio single copy probe; however, the presence of the same sequence tandemly repeated fewer than 10 times at a single location, preferably fewer than 8 times, more preferably fewer than 5 times, and still more preferably fewer than 3 times, in the genome may still be useful for detection of chromosome abnormalities if such internal tandem repetition does not display copy number polymorphism in populations. The locations of the repetitive elements are determined by aligning the subsequence with each of the genomic copies and determining the boundaries of the common multicopy sequence intervals. Single copy intervals will only align to a single genomic location. Accordingly, repetitive sequences, and therefore, single copy sequences as well, are deduced by ab initio methods rather than being derived from a preexisting repetitive sequence database.

One aspect of the invention, therefore, is probes that hybridize with the deduced single copy sequences. The probes hereof may be used with any nucleic acid target that contains the complementary single copy sequence as well as potentially repetitive sequences. These target sequences may include, but are not limited to chromosomal or purified nuclear DNA, heteronuclear RNA, cDNA or mRNA species that contain repetitive sequences as integral components of the transcript. In the ensuing detailed explanation, the usual case of a DNA target sequence and DNA probes is discussed; however, those skilled in the art will understand that the discussion is equally applicable (with art-recognized differences owing to the nature of the target sequences and probes) to other nucleic acid species.

One characteristic of the probes of the present invention is that they are made up of "single copy" or "unique" DNA sequences which are both complementary to at least a portion of the target DNA region of interest and essentially free of sequences complementary to repeat sequences within the genome of which the target region is a part. Accordingly, a probe made up of a single copy or unique sequence is complementary to essentially only one sequence in the corresponding genome. As used herein, a "repeat sequence" or "repetitive sequence" is a sequence which appears at least about twice in the genome of which the target DNA is a part. Typically, a repeat sequence will appear in a genome at least about 5 times, preferably about 50 times, more preferably about 200 times, and even more preferably about 1000 times. Factors affecting the number of times a repeat sequence appears in a genome include, for example, the size of the genome, evolutionary age of the repeat (degree of divergence from other related sequences), the mechanism(s) of copy number increase, and the relevance of pathogens which integrate into the host genome, horizontal genetic transfer (if any), and associative mating between individuals who are heterozygous for repetitive sequence copy number. A repeat sequence will generally have a sequence identity between repeats of at least about 60%, preferably at least about 70%, more preferably at least about 80%, still more preferably at least about 90%, even more preferably at least about 95%, and most preferably about 99%, and will be of sufficient length or have other qualities which would cause it to interfere with the desired specific hybridization of the probe to the target DNA, i.e., the probe would hybridize with one or more copies of the repeat sequence. Generally, a repetitive sequence appears at least about 5 times in the genome, preferably at least about 50 times, and most preferably at least about 200 times and has a length of at least about 20 nucleotides, preferably at least about 40 nucleotides, more preferably at least about 50 nucleotides, still more preferably at least about 75 nucleotides, and even more preferably at least about 100 nucleotides. Repeat sequences can be of any variety, including, for example, tandem, interspersed, palindromic or shared repetitive sequences (with some copies in the target region and some elsewhere in the genome), and can appear near the centromeres of chromosomes, distributed over a single chromosome, or throughout some or all chromosomes. This definition of a repeat includes closely related members of the same multigene family, since the utility of the probes is related to the unique locations on chromosomes. However, typically, repeat sequences are sufficiently degenerate such that most elements do not express physiologically useful proteins. Nevertheless, repeat sequences may exhibit length polymorphism such that they may be present in some individuals and absent in others. However when this is the case, complex repeats must be distinguished by copy number polymorphisms (which may contain multiple repeat elements and single copy sequences, and indeed, complete genes, in some cases). The instant invention utilizes the current assembly of a singe or composite genome. One of skill in the art would recognize that polymorphisms that duplicate or delete repetitive sequence in different individuals will require that probes derived therefrom may not be present at a single location in the diploid genome. Therefore, as additional reference genome sequences from different individuals are publicly available, genomic probes of the art are compared with each reference genome to verify their single copy nature in each of the populations for which the probe is to be employed.

Repeat sequences occur in multiple copies in the haploid genome. The number of copies of any family of related repetitive sequences can range from ten to hundreds of thousands, depending on a number of factors, including, for example, mechanisms of slipped mispairing during DNA replication, amplification by unscheduled DNA replication, expansion or contraction through unequal or illegitimate crossover or gene conversion, transposition, transduction, or viral integration, or retrotransposition. The Alu family of repetitive DNA are exemplary of the latter numerous variety. The copies of a repeat may be clustered or interspersed throughout the genome. Repeats may be clustered in one or more locations in the genome, such as, for example, repetitive sequences occurring near the centromeres of each chromosome, and variable number tandem repeats (VNTRs; Nakamura et al, Science, 1987; 235: 1616); or the repeat sequences may be distributed over a single chromosome, such as, for example, repeats found only on the X chromosome as described by Bardoni et al., Cytogenet. Cell Genet., 46: 575 (1987); or the repeats may be distributed over all the chromosomes, such as, for example, the Alu (SINE), and L1 (LINE) families of repetitive sequences.

Simple repeats of low complexity can be found within genes but are more commonly found in non-coding genomic sequences. Such repeated elements consist of mono-, di-, tri-, tetra-, or penta-nucleotide core sequence elements arrayed in tandem units. Often the number of tandem units comprising these repeated sequences varies at the identical locations among genomes from different individuals. These repetitive elements can be found by searching for consecutive runs of the core sequence elements in genomic sequences.

As used herein, "sequence identity" refers to a relationship between two or more polynucleotide sequences, namely a reference genome sequence and a test sequence from a genomic region of interest, i.e. containing one or more potential probe sequence(s) to be compared with the reference sequence. Sequence identity is determined by comparing the test sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if, at that position, the nucleotides are identical. The total number of such position identities is then divided by the total number of nucleotides or residues in the reference sequence to give a percent sequence identity. Sequence identity can be readily calculated by known methods including, but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988). Preferred methods to determine sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCBI, NLM, NIH, Bethesda, Md. 20894, Altschul, S. F. et al., J. Molec. Biol., 215:403410 (1990)). These programs optimally align sequences using default gap weights in order to produce the highest level of sequence identity between the test and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 differences per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted, inserted, or substituted with another nucleotide, or a number of nucleotides up to 5% of the total nucleotides in the reference sequence may be inserted into the reference sequence. Inversions in either sequence are detected by these computer programs based on the similarity of the reference sequence to the antisense strand of the homologous test sequence. These variants of the reference sequence may occur at the 5' or 3' terminal positions of the reference nucleotide sequence or anywhere between those terminal positions, interspersed either individually among nucleotides in the reference sequence or in one or more contiguous groups within the reference sequence.

It should be understood that BLAST, BLAT, and similar heuristic algorithms do not provide the sequences of all of the matches (in the genome) above the specified expected value threshold; however, they tend to indicate the degree to which a sequence may be repetitive. Sequences which match numerous genomic locations (generally on the order of hundreds) tend to be quite abundant and well conserved. Sequences which match several genomic locations tend to be either less common or less well conserved between paralogs. Sequences which match a single location in the genome are expected to be single copy, since the stringency of recognizing pairwise matches with the WU-BLAST algorithm has been deliberately relaxed to detect weakly similar genomic copies of any input sequence.

The single copy probes of the invention preferably have a length of at least about 25 nucleotides, preferably at least about 40 nucleotides, more preferably at least about 50 nucleotides, still more preferably at least about 75 nucleotides, and even more preferably at least about 100 nucleotides. Probes of this length are sufficient for Southern blot analyses, bead suspension hybridization, and microarray hybridization. However, if other analyses such as fluorescence in situ hybridization (FISH) are employed, the probes should be somewhat longer, i.e., at least about 500 nucleotides, preferably at least about 1000 nucleotides, and even more preferably at least about 2000 nucleotides in length. Factors used in determining the length of the probes include, for example, the type of analysis or hybridization method to be used, sequence specificity (i.e. complexity of the probe), nucleotide content (which dictates the optimal annealing temperature of the probe), the amount of secondary structure that the probe may adopt (which can be predicted with available software programs), and replication timing (synchronous vs asynchronous) of the genomic target sequence. The probes can be used to detect virtually any type of chromosomal rearrangement, such as, for example, deletions, duplications, insertions, additions, markers, inversions or translocations.

In addition to FISH, computationally determined single copy genomic hybridization probes may be used in a quantitative microsphere suspension hybridization assay to determine copy number of a specific sequence relative to a reference sequence or standard curve (Newkirk et al, Human Mutation, in press (2006)). Those of skill in the art would also recognize that single copy probes used as probes for microarrays would have properties similar to microsphere hybridization, since in both platforms the probes are attached to a solid phase substrate and hybridized to either labeled genomic DNA or to cDNA. Single copy probes have been shown to be more accurate for copy number determination than probes containing repetitive sequences that utilize Cot-1 DNA for suppression of cross hybridization of repetitive elements (Newkirk et al., Nucleic Acids Research 2005, 33(22):e191). Sufficient accuracy is achieved to distinguish normal copy number which is generally two for autosomes from hemizygosity or from three or more alleles. This assay allows for the direct analysis of whole genomic DNA (or RNA) using flow cytometry and if necessary can follow routine cytogenetic analysis without requiring large patient sample quantities, additional blood draws, locus-specific amplifications, or time-consuming genomic purification methods. It is notable therefore that copy number determination at a single locus can be carried out within a complex background of sequences consisting of the complete genome. This exquisite level of discrimination achieved by computationally-defined single copy probes can also be used to determine copy number of rare transcripts against the background of the complete transcriptome, or for detection of extremely dilute or low concentrations of specific nucleic acid sequences within heterogeneous solutions of nucleic acids.

In order to develop probes in accordance with the invention, the sequence of the target DNA region must be known. The target region may be an entire chromosome or only portions thereof where rearrangements have been suspected or identified. With this sequence knowledge, the objective is to determine the boundaries of single copy or unique sequences within the target region. This is preferably accomplished by inference from the locations of repetitive sequences within the target region. An important distinction between the method of the instant invention and the other methods is that the target region sequences of the present invention are not compared with known repeat sequences from the corresponding genome, using available computer software. With the instant invention, a catalog of known repeat sequences is, therefore, not a prerequisite to computational recognition of single copy intervals with this software. Therefore, single copy sequences can be derived with the instant invention from any complete genome sequence, so long as a determination of that sequence is completed.

Initially, a genomic or mRNA sequence is identified from which one or more single copy intervals and probes are desired. This test sequence, sometimes also referred to as a target sequence, typically contains at least one repetitive element; however, it is not a requirement that the test sequence contain a repetitive sequence. In the latter instance, the method does not eliminate any sequence from consideration as a potential probe; it simply verifies that the entire test sequence is non-repetitive. This test sequence is subsequently compared with the reference sequence of the same genome from which the test sequence is derived. Using homology search algorithms common in the art, such as, for example, BLAST or BLAT (see details below), this approach will identify matches with at least 80% identity to genomic sequences. Often weaker orthologies with as little as 70% or 60% identity can also be detected, although this typically requires few or no gaps to be present in the sequence alignment. This level of sensitivity is more than adequate for detection of single copy sequences, since highly divergent repetitive elements form heterologous duplexes that are easily eliminated by hybridizing and washing the probe under high stringency conditions (e.g., 0.1×SSC, 42° C.). These comparisons identify at least one region of the genome that matches (or nearly matches, due to genomic polymorphism) that test sequence. The exact and similar matches to the test sequence are termed "hits." When multiple hits are obtained, the test sequence contains one or more members of a repetitive sequence family or one or more low-copy segmental duplicons. In principal, such intervals are not preferred for probe design since a probe designed using such intervals could potentially hybridize to more than a single genomic locus.

There are mitigating circumstances in which multiple hits may still be suitable for probe design, such as, for example, if the two hits occur at nearly contiguous locations on the chromosome. This can be deduced from the chromosomal coordinates of the sequences in the genome that are similar to the potential probe interval. For hybridization by FISH to metaphase chromosomes, these coordinates may be up to approximately 3 million nucleotides apart (it can be more or less than this quantity depending on the level of condensation of the particular genomic region), and the probe signals obtained by FISH will be coincident even at the highest power magnification. For either array-based or microsphere suspension hybridization, however, much higher levels of granularity, i.e., genomic resolution, may be required to precisely localize a genomic target in, for example, a patient specimen.

Typically, 100,000-400,000 by intervals are tested to design single copy probes in a reasonable length of time (i.e., within 1-2 CPU hours on a modern cluster computer), however it can be appreciated by those of skill in the art that this approach could be applied genome-wide, given sufficient computational power. An advantage of genome-wide pre-computation would be that subsequent probe development would only involve looking up relevant single copy intervals to identify the most appropriate primers for amplification of single copy probes using the polymerase chain reaction (PCR) (see U.S. Pat. No. 6,828,097 for details of the PCR reaction to amplify products from deduced single copy genomic intervals).

While it is possible to conduct an exhaustive genome search of every subsequence window in the test sequence, such that the windows overlap and differ by a single nucleotide, this procedure is slow and inefficient. Certain embodiments employ a more efficient approach. The genomic frequency of sequences with test genomic sequence region can be determined to establish optimal parameters of window sizes and displacements based on estimates of the local distribution of repetitive sequences in the test sequence interval. Initially, the test genomic sequence region is prescreened by comparison with the reference genome sequence in order to determine local density of repetitive sequences within the region. This density can vary considerably within local regions across the euchromatic genome and it is not adequate to assume an average density for any particular region. This density dictates the granularity of the overlapping sequence windows needed to comprehensively find all repetitive sequences in a particular region. A higher density of repetitive sequences necessitates that windows of less than this length be used in the subsequent step of defining the precise locations of the repeats. In a preferred embodiment, for a sequence with at least one repeat per kilobase pair in the test region, windows of 0.5 kb sequences are used to determine locations of repeats.

First, end-to-end window comparisons of about 500 by to about 1000 base pairs (bp) are performed across the entire test sequence. This is akin to a pre-screening function. The length utilized in this embodiment was selected because it is consistent with studies indicating the average distances between interspersed repetitive elements in the human genome. The optimal window lengths may be different for other genomes since they would be based on overall repetitive complement in those genomes (determined from kinetic reassociation studies) and the respective genome sizes. This information is available from published sources (Lewin, Eukaryotic Gene Expression, Wiley, 1983). Other factors affecting the selection of a window length include, for example, the degree of resolution desired to determine the boundaries of a single copy sequence, the efficiency (i.e., the amount of time) desired to determine the boundaries of a single copy sequence, the density of repetitive sequences in the genome sequence of interest (i.e. containing potential probe sequences) and the accuracy of sequences in this region of the genome. Accordingly, the test sequence may be divided into test segments (i.e., window lengths) of about 20 by to about 5000 bp, preferably about 100 by to about 2500 bp, more preferably from about 250 by to about 1500 bp, still more preferably about 500 by to about 1000 bp, and most preferably about 1000 bp.

Alternative faster ab initio approaches for detection of repeats have been described based on exact word-matching algorithms based on nucleotide sequences (for example, Healy et al. Genome Res. 13:2306-15, 2003). Here, words are defined as overlapping or non-overlapping sequences of a short uniform length. However such approaches are not comprehensive. It also stated in this paper that this is not sufficient to ensure that repetitive sequences are completely eliminated from the microarray. Follow up approximate homology searching is performed so that the algorithm is carried out on a single human genome reference sequence. Of course, the human genome is highly polymorphic and the word match algorithm does not consider words containing the polymorphic variants. Therefore, a genomic microarray based on this algorithm alone may fail to detect repetitive sequences that contain polymorphic words. Of course, some of the sequences in the patient DNA hybridizing to those oligonucleotides will be repetitive. This will result in incorrect (vastly increased) copy number measurements. Since this is the signature of what they are trying to detect, i.e., abnormalities, it would result in false-positive identification of copy number changes in these oligonucleotides. However, a low-stringency approximate homology search by conventional repeat masking will pick up these sequences. This is why the exact word match procedure must be followed up with conventional repeat-masking (as was done in Healy et al Genome Res. 13:2306-15, 2003; see U.S. Pat. No. 6,828,097) to ensure that single copy sequences are synthesized on the microarray chip.

There are three possible outcomes of the prescreen for repetitive sequences: (1) the subsequence can be entirely composed of repetitive sequence, (2) one or more portions of the subsequence may be repetitive, or (3) the subsequence may contain no detectable repetitive sequences. Efficient methods for comparison of test sequences with complete or near complete reference genomes are well known in the art (BLAST and BLAT). If the genome comparison reveals the presence of sequences with high percentages of similar consecutive nucleotides to the test sequence at multiple genomic loci, this indicates the presence of one or more repetitive sequences within the test sequence.

A detailed description of how the method handles each of these outcomes follows: (1) if the paralogous (related or similar) copies span the entire length of the subsequence, then this subsequence is eliminated as a potential hybridization probe. For this class of subsequences, the objective then is to determine how far upstream and downstream of the subsequence the paralogous repeats extend. The adjacent subsequences within the test sequences are then analyzed to determine whether these sequences are similar to multiple genomic loci within the genome over their entire length. The process of analyzing contiguous adjacent subsequences is iterated until, either (a) the adjacent subsequence is found at only a single genomic location, or (b) only a portion of the subsequence shows similarity to multiple genomic locations, that portion determining the boundary of the single copy and multilocus subsequences; (2) pursuant to (b), such partially repetitive subsequences are again analyzed to determine which portion is contiguous with the relevant adjacent single copy interval. Segments of the subsequence can either be sampled to and compared with the genome reference to determine the approximate locations of repetitive domains which are then fine mapped by additional short sequence comparisons, or a relative series of consecutive, short or overlapping sequence windows are progressively tested against the genome sequence until coordinates that match a single location in the haploid genome sequence are found; (3) subsequences that match only a single location in the genome are considered single copy sequences, however exceptions, for example, including non-polymorphic tandemly repeated sequences of no more than about 10 copies, preferably no more than about 8 copies, more preferably no more than about 3 copies, and still more preferably no more than about 5 copies found at a single location in the genome may be treated as single copy intervals especially in FISH studies, because of their consistent, unequivocal patterns of hybridization to the genome.

Fine mapping of the approximate repetitive sequence/single copy interval within a subsequence is performed on overlapping sequence intervals by iteratively and unidirectionally displacing the sequence window by a fixed, constant length of, for example, 1 to 20 nucleotides. The new sequence is compared with the reference genome sequence and the number of significant matches in the genome (based on length and percent of identity to the new sequence) is determined. After each comparison, the window is again displaced by this length, compared with the reference genome and this process is iterated until the end of the subsequence is reached.

If multiple hits are detected in the genome, then the range of coordinates within the subsequence that contains the repetitive sequence is then refined. This is done by performing a low stringency comparison of the genome and subsequence, preferably with the Smith-Waterman algorithm, however other algorithms may also be used such as BLAST or BLAT. The location of the matching terminal coordinate within the query is determined and this coordinate is recorded. The window is again shifted by 1-20 nucleotides. The length of the pairwise match may increase, remain the same, or decrease. If this length increases, the matching coordinate is again recorded and the window is shifted in the same direction. If it stays the same, the window is also again shifted in the same direction. If the length decreases, then the complete repeat has been found (both boundaries). The final coordinates of the centromeric and telomeric boundaries of the repetitive sequence are then recorded (and the prior intermediate coordinates are discarded).

An optional step that would reduce future computational expense is to bootstrap a catalog of repetitive elements derived from the ab initio procedure. Rather than discarding the sequences found to be present more than once per genome, the interface between single copy and repetitive sequence elements could be defined using the aforementioned procedure, which would determine the coordinates of the repeat, and the repeat sequence then catalogued. This could be accomplished by storing the sequences of the repetitive sequences detected in a separate database for subsequent searches. Similar repeats could then be sorted into families and subfamilies by multiple alignments. Subsequent searches will first compare a new sequence with the repeat sequence database, and then to the genome reference sequence as described above. Although this step is not required, it will significantly improve performance of the algorithm to detect single copy intervals, especially as the repeat catalog grows in size.

Repetitive sequence elements defined by the above method can then be deposited in an electronic database where they can be subsequently retrieved for comparisons with other potential sequences containing single copy and repetitive intervals. Since each matched segment contains an individual repetitive element, the element in most instances will not be identical to the consensus sequence of the corresponding repetitive sequence family representative found in, for example, Knoll et al.'s '097 patent, because consensus sequences are derivative sequences that are compiled by selecting the most common nucleotide at a particular position among a set of elements. Various embodiments can be used to screen sequences contained within current repeat libraries in order to ensure that a repetitive sequence is not misassigned as a single copy sequence. Finally, this procedure may identify repetitive sequences that are not otherwise recognized with the technology described in other approaches reliant upon an established repeat library because the newly identified sequences are not necessarily represented in existing databases.

Defining the boundary of the single copy interval can occur as follows. As the window moves, the repeat sequence boundary should shift by the length of the sequence displaced through each step. When sufficient steps in one direction have been performed so that there is no longer a match to a repeat sequence, this defines the other boundary of the repeat. Definition of the repeat sequence boundaries on both ends makes the repeat sequence eligible for optional deposition into a repeat sequence database.

The resolution of the single copy window is defined by the length of the smallest sequence displacement (i.e., the nucleotide word length) between iteration cycles used in the definition of the repeat/single copy boundary. The single copy interval sequence can be shortened by at least one word at the repeat boundary to ensure that the entirety of the region selected for probe development is single copy.

Single copy sequences defined by this approach can be used to detect chromosome rearrangements including deletions, insertions, additions, translocations, inversions and any combination of these chromosomal modifications by hybridization. Often, such rearrangements are diagnostic for the detection of genetic diseases and cancer.

Accordingly, among the various aspects of the present invention is a method to identify a single copy sequence in a target reference genomic sequence. The method comprises determining a number of matches between at least one subsequence of a first screened sequence and a target reference sequence, wherein the target reference sequence comprises the first screened sequence, the first screened sequence is divided into at least two subsequences, and a subsequence of the first screened sequence with a single match to the target reference sequence or a group of contiguous subsequences of the first screened sequence each with a single match to the target reference sequence is identified as a single copy interval of the first screened sequence; determining a number of matches between at least one subsequence of a second screened sequence and the target reference sequence, wherein the second screened sequence comprises a single copy interval of the first screened sequence; the second screened sequence overlaps the single copy interval of the first screened sequence; the subsequences of the first screened sequence are either (i) consecutive non-overlapping subintervals of the second screened sequence or (ii) overlapping non-identical subintervals of the second screened sequence, each containing one nucleotide homologous to the reference sequence that is not present in the adjacent subinterval; and a subsequence of the second screened sequence with a single match to the target reference sequence or a group of contiguous subsequences of the second screened sequence each with a single match to the target reference sequence is identified as a single copy interval of the second screened sequence; and identifying a single copy interval as a single copy sequence of the target reference sequence suitable for use as a single copy hybridization probe. In one embodiment, the subsequences may be at least about 100 consecutive non-overlapping nucleotides, at least about 200 consecutive non-overlapping nucleotides, at least about 400 consecutive non-overlapping nucleotides, at least about 600 consecutive non-overlapping nucleotides, at least about 800 consecutive non-overlapping nucleotides, or even at least about 1000 consecutive non-overlapping nucleotides.

In one embodiment of the invention, the method further comprises the step of determining a number of matches between at least one subsequence of a third screened sequence and the target reference sequence, wherein the third screened sequence comprises a single copy interval of the second screened sequence; the third screened sequence overlaps the single copy interval of the second screened sequence; the subsequences of the third screened sequence are either (i) consecutive non-overlapping subintervals or (ii) overlapping non-identical subintervals, each containing one nucleotide homologous to the reference sequence that is not present in the adjacent subinterval; and a subsequence of the third screened sequence with a single match to the target reference sequence or a group of contiguous subsequences of the third screened sequence each with a single match to the target reference sequence is identified as a single copy interval of the third screened sequence. In another embodiment, the method further comprises the step of determining a number of matches between at least one subsequence of a fourth screened sequence and the target reference sequence, wherein the fourth screened sequence comprises a single copy interval of the third screened sequence; the fourth screened sequence overlaps the single copy interval of the third screened sequence; the subsequences the of fourth screened sequence are either (i) consecutive non-overlapping subintervals or (ii) overlapping non-identical subintervals, each containing one nucleotide homologous to the reference sequence that is not present in the adjacent subinterval; and a subsequence of the fourth screened sequence with a single match to the target reference sequence or a group of contiguous subsequences of the fourth screened sequence each with a single match to the target reference sequence is identified as a single copy interval of the fourth screened sequence.

In still another embodiment, the method further comprises the step of identifying a subsequence of the screened sequence with at least two matches to the target reference sequence as a subsequence containing a repetitive element wherein the single copy sequence is located adjacent to the repetitive element. In another embodiment, the method further comprises the step of identifying a second, distinct subsequence of the screened sequence with at least two matches to the target reference sequence as a subsequence containing a different repetitive element, wherein the single copy interval is located between the first and the second subsequences containing the distinct repetitive elements.

Another aspect of the present invention is a single copy hybridization probe as described herein. Such probes may comprise at least one single copy interval or single copy sequence identified according to the methods disclosed herein. In one embodiment, the probes comprise at least two contiguous subsequences of a screened sequence, each having a single match to the target reference sequence.

Referring to FIG. 1, a block diagram illustrates a user 102 interacting with a computing environment in one embodiment of the invention. In the example of FIG. 1, the user 102 interacts with a computing device 104. The computing device 104 has access to one or more computer-readable media such as computer-readable medium 106. The computer-readable medium 106 stores one or more computer-executable components. In this example, the components include a first genome comparison component 108, a second genome comparison component 110, and a subsequence component 112. The first genome comparison component 108 determines a number of matches between at least one subsequence of a first screened sequence and a target reference sequence. The target reference sequence includes the first screened sequence which is divided into at least two subsequences. A subsequence of the first screened sequence with at least two matches (and preferably more than five matches) to the target reference sequence can be identified as containing a repetitive element. A subsequence of the first screened sequence with a single match to the target reference sequence or a group of contiguous subsequences of the first screened sequence, each with a single match to the target reference sequence is identified as a single copy interval of the first screened sequence.

The second genome comparison component 110 determines a number of matches between at least one subsequence of a second screened sequence and the target reference sequence. The second screened sequence includes a single copy interval of the first screened sequence. The second screened sequence overlaps the single copy interval of the first screened sequence. The subsequences are either (i) consecutive non-overlapping subintervals of the second screened sequence or (ii) overlapping non-identical subintervals of the second screened sequence, each containing one nucleotide homologous to the reference sequence that is not present in the adjacent subinterval. A subsequence of the second screened sequence with at least two matches (and preferably more than five matches) to the target reference sequence can be identified as containing a repetitive element. A subsequence of the second screened sequence with a single match to the target reference sequence or a group of contiguous subsequences of the second screened sequence each with a single match to the target reference sequence is identified as a single copy interval of the second screened sequence.

The subsequence component 112 identifies a single copy interval as a single copy sequence of the target reference sequence suitable for use as a single copy hybridization probe.

Hardware, software, firmware, computer-executable components, and/or computer-executable instructions such as the exemplary components/instructions illustrated in the figures constitute means for determining a number of matches between at least one subsequence of the first screened sequence and the target reference sequence, means for determining a number of matches between at least one subsequence of the second screened sequence and the target reference sequence, and means for identifying a single copy interval as a single copy sequence of the target reference sequence suitable for use as a single copy hybridization probe.

An exemplary operating environment for implementing aspects of the invention (e.g., the computer programs described herein) such as shown in FIG. 1 includes a general purpose computing device such as computing device 104 executing computer-executable instructions. The computing device 104 typically has at least some form of computer readable media. Computer readable media, which include both volatile and nonvolatile media, removable and non-removable media, may be any available medium that may be accessed by the general purpose computing device 104. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of any of the above are also included within the scope of computer readable media. The computing device 104 includes or has access to computer storage media in the form of removable and/or non-removable, volatile and/or nonvolatile memory. The user 102 may enter commands and information into the computing device 104 through input devices or user interface selection devices such as a keyboard and a pointing device (e.g., a mouse, trackball, pen, or touch pad). Other input devices (not shown) may be connected to the computing device 104. The computing device 104 may operate in a networked environment using logical connections to one or more remote computers.

Although described in connection with an exemplary computing system environment, aspects of the invention are operational with numerous other general purpose or special purpose computing system environments or configurations. The computing system environment is not intended to suggest any limitation as to the scope of use or functionality of aspects of the invention. Moreover, the computing system environment should not be interpreted as having any dependency or requirement relating to any one or combination of components illustrated in the exemplary operating environment. Examples of well known computing systems, environments, and/or configurations that may be suitable for use in embodiments of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more computers or other devices. Generally, program modules include, but are not limited to, routines, programs, objects, components, and data structures that perform particular tasks or implement particular abstract data types. The computer-executable instructions may be embodied in any computer programming language or scripting language including, but not limited to, C, C++. C#, and Perl. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Aspects of the invention may also be practiced in distributed computing environments where tasks are performed by remote processing devices that are linked through a communications network. In a distributed computing environment, program modules may be located in both local and remote computer storage media including memory storage devices. In operation, the computing device 104 executes computer-executable instructions such as those illustrated in the figures to implement embodiments of the invention.

Figure 2:
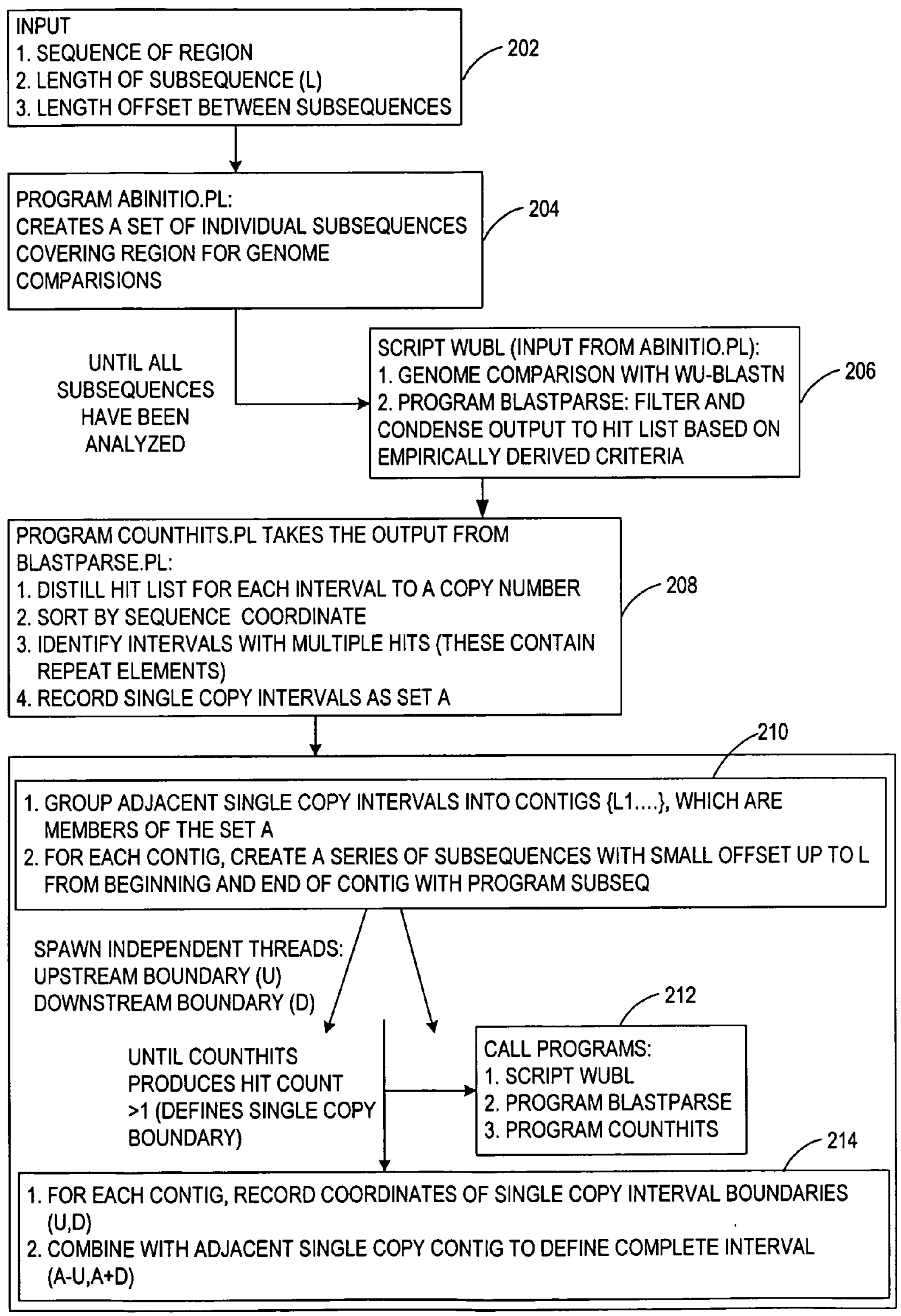
FIG. 2 is a flow chart depicting exemplary operations for deriving the locations of single copy intervals used in probe production.

Referring next to FIG. 2, a flow chart depicts exemplary operations for deriving the locations of single copy intervals used in probe production. FIG. 2 illustrates one exemplary implementation of aspects of the invention using computer-executable instructions. Other implementations are within the scope of embodiments of the invention. For example, the operations illustrated in FIG. 2 may be organized into other components or application programs.

In FIG. 2, an ABINITIO.PL script creates a set of individual subsequences covering a region for genome comparisons. The script takes as input the following at 202: a genomic sequence file, a length of subsequence, a length of window offset between subsequences, a minimum length of match to genomic repeats or paralogs (e.g., for filtering results of genomic comparisons), and a minimum percentage of match to genomic repeats or paralogs. If the length of window offset is smaller than the length of subsequence, the script produces overlapping windows. If the length of window offset is larger than the length of subsequence, the script produces subsequences separated by gaps having a length equal to the length of subsequence minus the length of window offset. If the length of window offset is equal to the length of subsequence, the script produces consecutive windows.

The ABINITIO.PL script outputs at 204 a set of individual subsequences (e.g., files named by subsequence boundaries) to a WUBL script (e.g., a BLAST script) to perform genome comparisons. The WUBL script performs the genome comparisons at 206 on a cluster computer (e.g., a separate parallel job is run simultaneously on a different node). Files indicating the results of the WUBL genome comparisons are filtered by a BLASTPARSE.PL script and condensed to a hit list based on user-provided or empirically-derived criteria. The BLASTPARSE.PL script produces files of filtered output.

The user 102 may confirm that the comparisons with the genome sequence have been completed using an application program, such as qstat, which is a Sun-Grid Engine utility to monitor processor status. In another embodiment, this confirmation operation is automated and the user 102 is notified when the comparisons have been completed.

The files of filtered output from the BLASTPARSE.PL script are input into a COUNTHITS.PL script for summarizing. The COUNTHITS.PL script distills at 208 the hit list from the BLASTPARSE.PL script for each interval to a copy number and sorts by sequence coordinate. The COUNTHITS.PL script identifies intervals with multiple hits as these contain repeat elements and records single copy intervals as, for example, Set A.

One output of COUNTHITS.PL is a count which contains the quantity of hits in the genome found with each subsequence interval. If the quantity of hits exceeds one, the sequence is not single copy based on the parameter definitions that are acceptable by one of skill in the art. These definitions aim to prevent cross hybridization between a single copy probe and other genomic locations that are partially paralogous to the entire potential probe sequence or a portion thereof.

The single copy intervals in Set A are grouped at 210 into contigs {L1 . . . } which are members of the Set A. For each contig, a SUBSEQ program creates a series of subsequences with small offset up to the length of subsequence from the beginning and end of the contig.

Independent threads are spawned with the series of subsequences having an upstream boundary (U) and a downstream boundary (D). The WUBL script, BLASPARSE program, and COUNTHITS.PL script are executed at 212 until the COUNTHITS.PL script produces a hit count greater than one (e.g., defining a single copy boundary). For each contig, the coordinates of single copy interval boundaries (U, D) are recorded and combined with adjacent single copy contigs to define a complete interval (A−U, A+D) at 214.

Appendix A includes an example of the ABINITIO.PL script. Appendix B includes an example of the WUBL script. Appendix C includes an example of the BLASTPARSE.PL script. Appendix D includes an example of the COUNTHITS.PL script. Appendix E includes an example of the SUBSEQ.PL script.

In another embodiment, the operations for deducing single copy intervals use a single program set to analyze a larger sequence and produce a single table that gives the genomic copy number of each consecutive or overlapping subsequence. Via this table, the system automatically detects the transitions between repetitive and single copy intervals. The boundaries may be refined in increasingly higher resolution using a programmable iterative procedure.

The order of execution or performance of the operations illustrated and described herein is not essential, unless otherwise specified. That is, the operations may be performed in any order, unless otherwise specified, and the operations may include more or less elements than those disclosed herein. For example, it is contemplated that executing or performing a particular operation or element before, contemporaneously with, or after another operation or element is within the scope of an embodiment of the invention.

Having described the invention in detail, it will be apparent that modifications and variations are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

The following example illustrates how the probes designed using the instant invention produce similar results to the repeat-free probes described in U.S. Pat. No. 6,828,097. Here we rederive the single copy intervals shown in Example 1 of that Patent with the present invention. First we determined the locations of the repetitive sequences in the human HIRA gene and flanking regions (SEQ ID NO: 1) and subsequently inferred the locations of the single copy intervals therefrom.

TABLE 1

Results obtained using the method described in U.S. Pat. No. 6,828,097

| POSITION IN REFERENCE SEQUENCE | | REPEAT | POSITION IN REPEAT CONSENSUS SEQUENCE* | |
|---|---|---|---|---|
| Begin Coord | End Coord | FAMILY | Begin Coord | End Coord |
| 633 | 653 | GC_rich | 1 | 21 |
| 695 | 859 | (CCG)n | 3 | 172 |
| 987 | 1008 | GC_rich | 1 | 22 |
| 647 | 1061 | MLT2A1 | 436 | 1 |
| 2913 | 3014 | MER58B | 239 | 340 |
| 3053 | 3397 | L1M4 | 2884 | 3209 |
| 3398 | 3698 | AluJb | 303 | 2 |
| 3699 | 3935 | L1M4 | 3209 | 3451 |
| 4002 | 4465 | L1M4c | 1469 | 1003 |
| 4466 | 4766 | AluY | 300 | 1 |
| 4767 | 4861 | L1M4c | 1004 | 910 |
| 4865 | 5081 | AluJo | 5 | 220 |
| 5082 | 5137 | AluSq/x | 86 | 141 |
| 5138 | 5211 | AluS | 76 | 2 |
| 5214 | 5713 | L1MEc | 2392 | 1876 |
| 5740 | 6031 | AluSx | 295 | 6 |
| 6077 | 6206 | L1 | 5015 | 4879 |
| 6291 | 6557 | L1 | 4686 | 4399 |
| 6560 | 6600 | L1M4c | 1457 | 1497 |
| 6602 | 6663 | MLT1E1 | 231 | 293 |
| 6677 | 6743 | MLT1E1 | 417 | 481 |
| 6774 | 6897 | L1PB2 | 91 | 210 |
| 6878 | 7534 | L1PB2 | 1113 | 1767 |
| 7577 | 7655 | Alu | 312 | 234 |
| 7656 | 8290 | L1PB2 | 1771 | 2376 |
| 8291 | 8583 | AluSx | 293 | 1 |
| 8584 | 9844 | L1PB2 | 2376 | 3758 |
| 9845 | 10143 | AluSx | 1 | 298 |
| 10144 | 11262 | L1PB2 | 3983 | 5142 |
| 11263 | 11282 | (TAAAA)n | 3 | 22 |
| 11283 | 11525 | L1PB2 | 5142 | 5378 |
| 11526 | 11659 | AluJb | 1 | 134 |
| 11661 | 11964 | AluJb | 1 | 306 |
| 11965 | 12896 | L1PB2 | 5365 | 6313 |
| 12897 | 13179 | AluSx | 282 | 1 |
| 13180 | 13675 | L1PB2 | 6313 | 6805 |
| 13762 | 14060 | AluJb | 1 | 288 |
| 14136 | 14364 | AluJb | 1 | 229 |
| 14387 | 14502 | FLAM_C | 117 | 2 |
| 14528 | 14584 | L1 | 2931 | 2987 |
| 14586 | 15758 | L1 | 3041 | 4281 |
| 15989 | 16191 | MER1B | 337 | 127 |
| 16191 | 16223 | MER1B | 33 | 1 |
| 16449 | 16582 | L1M | 5265 | 5393 |
| 16728 | 16858 | FLAM_C | 2 | 143 |
| 18149 | 18455 | AluSx | 1 | 307 |
| 18677 | 18964 | L1MCa | 895 | 1178 |
| 18993 | 19286 | AluSq | 293 | 1 |
| 19287 | 19575 | AluSq | 302 | 1 |
| 19586 | 19893 | AluSx | 309 | 2 |
| 20067 | 20241 | HAL1 | 1469 | 1634 |
| 20261 | 20453 | L2 | 2798 | 3023 |
| 20469 | 20569 | AluY | 310 | 210 |
| 20570 | 20852 | L2 | 3043 | 3313 |
| 20994 | 21151 | L2 | 2489 | 2646 |
| 21945 | 22025 | A-rich | 6 | 86 |
| 25263 | 25558 | AluJo | 297 | 2 |
| 28496 | 28708 | AluSg/x | 294 | 82 |
| 29588 | 29670 | MIR | 105 | 191 |
| 30298 | 30367 | MIR | 107 | 34 |
| 32436 | 33041 | L1MCa | 1529 | 2328 |
| 33042 | 33352 | AluSq | 311 | 1 |
| 33353 | 33440 | L1MCa | 2328 | 2416 |
| 33444 | 33753 | AluSc | 1 | 308 |
| 33768 | 33788 | AT_rich | 1 | 21 |
| 33821 | 33945 | FLAM_A | 4 | 128 |
| 33976 | 34107 | L1MC1 | 5912 | 6056 |
| 34108 | 34410 | AluSx | 1 | 295 |
| 34411 | 34513 | L1MC1 | 6056 | 6154 |
| 34523 | 34658 | L1MC1 | 6197 | 6332 |

TABLE 1-continued

Results obtained using the method described in U.S. Pat. No. 6,828,097

| POSITION IN REFERENCE SEQUENCE | | REPEAT | POSITION IN REPEAT CONSENSUS SEQUENCE* | |
|---|---|---|---|---|
| Begin Coord | End Coord | FAMILY | Begin Coord | End Coord |
| 34668 | 34835 | L1MCa | 2559 | 2728 |
| 34843 | 36256 | Tigger1 | 1 | 1358 |
| 36257 | 36551 | 7SLRNA | 19 | 312 |
| 36552 | 36572 | Tigger1 | 1358 | 1377 |
| 36573 | 36868 | AluY | 1 | 296 |
| 36869 | 37248 | Tigger1 | 1377 | 1889 |
| 37253 | 37554 | AluSx | 300 | 1 |
| 37726 | 37860 | MER2 | 1 | 137 |
| 37861 | 38163 | AluSx | 298 | 1 |
| 38164 | 38378 | MER2 | 137 | 344 |
| 38914 | 38938 | AT_rich | 1 | 25 |
| 40144 | 40447 | AluSx | 1 | 309 |
| 40464 | 40735 | AluSx | 312 | 1 |
| 40738 | 41039 | AluSx | 303 | 1 |
| 41814 | 41920 | L1MEd | 1000 | 895 |
| 41961 | 42592 | L1MB6 | 6172 | 5522 |
| 42728 | 43063 | L1MB6 | 5502 | 5156 |
| 43064 | 43363 | AluSq | 301 | 1 |
| 43371 | 43496 | AluJo | 136 | 2 |
| 43497 | 43694 | L1MB6 | 5168 | 4972 |
| 43817 | 44531 | L1MEd | 823 | 59 |
| 44543 | 44777 | AluSq | 1 | 234 |
| 44780 | 44945 | AluJo | 170 | 1 |
| 47718 | 47829 | L2 | 3141 | 3256 |
| 48724 | 48880 | MER104 | 180 | 1 |
| 49052 | 49217 | MIR | 28 | 218 |
| 49281 | 49513 | L1MC/D | 5655 | 5434 |
| 49514 | 49803 | AluY | 306 | 1 |
| 49804 | 49836 | L1MC/D | 5434 | 5404 |
| 49837 | 50139 | AluSg | 1 | 301 |
| 50140 | 50254 | L1MC/D | 5404 | 5256 |
| 50311 | 50596 | AluSc | 288 | 3 |
| 50716 | 50756 | AT_rich | 1 | 41 |
| 51099 | 51415 | AluSx | 306 | 1 |
| 51696 | 51914 | L1 | 4329 | 4067 |
| 51952 | 52256 | L1M4 | 3980 | 3658 |
| 53254 | 53280 | (T)n | 1 | 27 |
| 53417 | 53495 | L1ME4A | 5612 | 5692 |
| 53641 | 53782 | L1ME4A | 5968 | 6125 |
| 54265 | 54528 | L1MA10 | 6182 | 5922 |
| 54529 | 54835 | AluSc | 1 | 300 |
| 54836 | 54877 | L1MA10 | 5922 | 5881 |
| 55140 | 55445 | AluSx | 307 | 1 |
| 57716 | 57845 | MIR | 110 | 250 |
| 60803 | 61122 | AluSx | 1 | 311 |
| 61247 | 61490 | L1ME | 5680 | 5448 |
| 61472 | 61955 | L1ME2 | 5628 | 6132 |
| 61964 | 62271 | AluY | 309 | 1 |
| 63775 | 63814 | AT_rich | 1 | 40 |
| 63849 | 64147 | AluSg | 299 | 1 |
| 66128 | 66369 | L2 | 3031 | 3263 |
| 66726 | 67033 | AluSq | 1 | 308 |
| 69187 | 69478 | AluJb | 1 | 300 |
| 69502 | 69575 | MIR | 157 | 237 |
| 69646 | 69699 | L2 | 3187 | 3240 |
| 70252 | 70300 | AT_rich | 1 | 49 |
| 71084 | 71533 | L2 | 510 | 1029 |
| 71589 | 71784 | L2 | 1815 | 2014 |
| 71790 | 71871 | FLAM | 132 | 48 |
| 71986 | 72419 | L2 | 2275 | 2777 |
| 72700 | 72741 | L2 | 3217 | 3258 |
| 73316 | 73622 | AluJo | 1 | 311 |
| 73820 | 74122 | AluY | 1 | 300 |
| 76503 | 76829 | L1ME4A | 5747 | 6111 |
| 79310 | 79501 | MIR3 | 10 | 186 |
| 79772 | 80074 | AluSx | 304 | 1 |
| 82071 | 82145 | L2 | 3185 | 3266 |
| 82529 | 82563 | Tigger4 (Zombi) | 2730 | 2696 |
| 82555 | 82950 | MLT1G1 | 101 | 587 |
| 82960 | 83036 | MLT1K | 509 | 586 |
| 83328 | 83392 | L2 | 3281 | 3216 |
| 83428 | 83581 | L2 | 3081 | 2907 |
| 83877 | 83905 | (TTTTA)n | 2 | 31 |
| 84088 | 84406 | AluY | 315 | 1 |
| 85204 | 85399 | AluJo | 117 | 305 |
| 85429 | 85604 | AluSg/x | 309 | 134 |
| 85605 | 85643 | Alu | 40 | 2 |
| 85644 | 85998 | L1MB6 | 4209 | 4547 |
| 85999 | 86291 | AluSp | 1 | 293 |
| 86292 | 86804 | L1MB6 | 4547 | 5036 |
| 86805 | 87130 | AluJb | 311 | 1 |
| 87131 | 87414 | L1MB6 | 5036 | 5306 |
| 87415 | 87719 | AluSx | 6 | 310 |
| 87720 | 87833 | L1MB6 | 5306 | 5414 |
| 87834 | 88134 | AluSc | 1 | 301 |
| 88135 | 88725 | L1MB6 | 5414 | 6154 |
| 88771 | 88791 | AT_rich | 1 | 21 |
| 88794 | 88834 | L1MD1 | 5987 | 6024 |
| 88835 | 89139 | AluY | 1 | 301 |
| 89140 | 89415 | L1MD1 | 6024 | 6258 |
| 89418 | 89444 | (CA)n | 2 | 28 |
| 89656 | 89751 | L2 | 2313 | 2413 |
| 89911 | 90214 | L2 | 2995 | 3302 |
| 90533 | 90562 | (TG)n | 1 | 30 |
| 90672 | 90973 | AluJb | 5 | 301 |
| 90982 | 91007 | (CAAA)n | 2 | 28 |
| 91112 | 91213 | FRAM | 52 | 154 |
| 91214 | 91333 | L1PB3 | 6022 | 6140 |
| 91508 | 91808 | AluSq | 1 | 300 |
| 92080 | 92126 | L2 | 2383 | 2429 |
| 92181 | 92463 | AluSx | 283 | 1 |
| 92524 | 92635 | L1ME2 | 6022 | 6134 |
| 92657 | 92747 | (CATATA)n | 5 | 96 |
| 92793 | 93203 | L2 | 2545 | 3016 |
| 93225 | 93631 | LTRI6A | 23 | 431 |
| 93945 | 94017 | (CA)n | 2 | 74 |
| 94573 | 94684 | L2 | 3310 | 3194 |
| 95304 | 95379 | MLT1L | 549 | 471 |
| 95504 | 95590 | MLT1L | 267 | 180 |
| 96194 | 96524 | AluSx | 1 | 299 |
| 97576 | 97749 | MER20 | 219 | 46 |
| 98589 | 98690 | MIR | 124 | 14 |
| 98733 | 98965 | MER20 | 2 | 218 |
| 99158 | 99286 | FLAM_A | 1 | 127 |
| 99626 | 99927 | AluSc | 304 | 1 |
| 100587 | 100676 | L2 | 3304 | 3210 |

The present invention is now shown to provide similar results to the above comparison of a sequence region with a predetermined library of repetitive sequences. The following results were obtained using one embodiment of the present invention.

Initially, the 103 kb HIRA sequence was divided into consecutive non-overlapping intervals of 1000 by in length to determine the density of repetitive sequences across this genomic region. The sequences of each of these intervals were compared with the May, 2004 human genome reference sequence using the WU-BLAST blastn program. The parameters for these comparisons were modified from default values to pick up the weakest similarities in the genome in order to ensure that even poorly conserved repetitive sequences would be detected. The parameters of the search were: –d human, span2, cpus=2 (number of threads), lcmask, and hspmax=100. Each comparison required approximately 5.8 seconds.

The 103 comparisons of 1 kb each required approximately 6 minutes on an 8 node dual CPU cluster computer, which is comparable or faster than the method described by Knoll et al. in the '097 patent.

After filtering the output with a Blast parsing routine (called from the Bioperl implementation of the Perl language; at www.bioperl.org), and counting the number of significant hits detected for each of the 1000 consecutive sub-intervals of SEQ ID NO: 1, the results are summarized in the Table 2. Regarding filtering, we have tested several minimum thresholds for repeat sequence detection in human genomic sequences have and each gives similar results. The preferred minimum thresholds for detection are a pairwise match between the test sequence and its genomic counterpart of at least 100 nucleotides in length and 70 percent identity. Equivalent results were obtained, for example, using criteria of at least a 50 nucleotide length match with at least 65 percent identity, since these filters eliminated all but the actual genomic location of the probe. One of skill in the art could appreciate that these criteria are of sufficiently low stringency so as to identify even the weakest members of a potential cross hybridizing repetitive sequence.

TABLE 2

Results of ab initio repeat detection for HIRA gene region from U.S. Pat. No. 6,828,097

| Begin coordinate SEQ ID No. 1 | End coordinate | Number hits/genome |
|---|---|---|
| 1 | 1000 | 7535 |
| 1001 | 2000 | 20 |
| 2001 | 3000 | 1 |
| 3001 | 4000 | 51045 |
| 5001 | 6000 | 27018 |
| 6001 | 7000 | 901 |
| 7001 | 8000 | 6853 |
| 8001 | 9000 | 5504 |
| 9001 | 10000 | 8337 |
| 10001 | 11000 | 17347 |
| 11001 | 12000 | 20284 |
| 12001 | 13000 | 21380 |
| 13001 | 14000 | 14891 |
| 14001 | 15000 | 30794 |
| 18001 | 19000 | 23772 |
| 19001 | 20000 | 23741 |
| 20001 | 21000 | 19360 |
| 21001 | 22000 | 5 |
| 22001 | 23000 | 1 |
| 23001 | 24000 | 1 |
| 24001 | 25000 | 1 |
| 25001 | 26000 | 17420 |
| 26001 | 27000 | 1 |
| 27001 | 28000 | 1 |
| 28001 | 29000 | 15799 |
| 30001 | 31000 | 1 |
| 31001 | 32000 | 1 |
| 32001 | 33000 | 277 |
| 34001 | 35000 | 47220 |
| 35001 | 36000 | 5639 |
| 37001 | 38000 | 21053 |
| 38001 | 39000 | 42981 |
| 39001 | 40000 | 3 |
| 40001 | 41000 | 23551 |
| 41001 | 42000 | 7546 |
| 42001 | 43000 | 1789 |
| 43001 | 44000 | 22258 |
| 44001 | 45000 | 23320 |
| 45001 | 46000 | 1 |
| 46001 | 47000 | 1 |
| 47001 | 48000 | 1 |
| 48001 | 49000 | 1 |
| 49001 | 50000 | 21609 |
| 50001 | 51000 | 15465 |
| 51001 | 52000 | 12501 |
| 52001 | 53000 | 2 |
| 53001 | 54000 | 2 |
| 54001 | 55000 | 22837 |
| 55001 | 56000 | 23436 |
| 58001 | 59000 | 1 |
| 59001 | 60000 | 1 |
| 61001 | 62000 | 35227 |
| 62001 | 63000 | 23960 |
| 63001 | 64000 | 23119 |
| 64001 | 65000 | 22933 |
| 65001 | 66000 | 1 |
| 66001 | 67000 | 23787 |
| 67001 | 68000 | 6095 |
| 69001 | 70000 | 18850 |
| 70001 | 71000 | 1 |
| 71001 | 72000 | 611 |
| 72001 | 73000 | 2 |
| 73001 | 74000 | 20364 |
| 74001 | 75000 | 19815 |
| 75001 | 76000 | 1 |
| 76001 | 77000 | 3 |
| 77001 | 78000 | 1 |
| 78001 | 79000 | 1 |
| 79001 | 80000 | 23902 |
| 80001 | 81000 | 7712 |
| 81001 | 82000 | 1 |
| 82001 | 83000 | 5 |
| 83001 | 84000 | 1 |
| 84001 | 85000 | 23677 |
| 85001 | 86000 | 23474 |
| 86001 | 87000 | 22801 |
| 87001 | 88000 | 21328 |
| 88001 | 89000 | 21216 |
| 89001 | 90000 | 21128 |
| 90001 | 91000 | 22559 |
| 91001 | 92000 | 44018 |
| 93001 | 94000 | 270 |
| 95001 | 96000 | 1 |
| 96001 | 97000 | 22715 |
| 97001 | 98000 | 129 |
| 98001 | 99000 | 154 |
| 99001 | 100000 | 21398 |
| 100001 | 101000 | 1 |
| 101001 | 102000 | |

Consider, for example, the first single copy interval identified with the present invention—from positions 2001 to 3000. The method of the '097 patent shows that the interval between positions 1062 and 2913 are free of repetitive sequences. The following demonstrates that the method of the present invention confirms this result and independently can identify a single copy intervals delimited by similar coordinates.

The present invention shows that there are sequences with multilocus representation within the flanking subsegments. Within the subsequence defined by the coordinates 1000-2000 there is a match to at least 20 other genomic segments and within the sequence defined by 3000-4000 matches at least 51,045 other genomic sequences. The latter interval contains numerous highly conserved SINE and LINE repetitive elements. The short region containing a small portion of a MER58B repeat (2914-3000) contained within the corresponding single copy interval of the present invention is a highly divergent ember (24.8% of the sequence differs from a consensus MER58B subfamily repeat) that only includes a small portion of the total repeat element (from positions 239 to 340). Hence for all practical purposes, the 86 nucleotide region that is considered to be repetitive will not cross hybridize with other MER58B repeats in the genome, if the hybridization conditions of the probe designed using the instant technology are set to be stringent (final hybridization wash should be 0.1×SSC, at least 42° C.). Similarly, positions 22001-28000 are found to occur once in the haploid reference genome sequence using the method of the present invention.

To precisely define the boundaries of the single copy domain in this region, we then rerun the analysis of the subsegment defined by coordinates 1000 to 4000 of the initial 103 kb HIRA sequence at much higher resolution. This is carried out either by comparing shorter consecutive subsegments or overlapping subsegments from this region of the HIRA gene. The following table indicates a comparison of consecutive subsegments of 200 nucleotides with the genome reference sequence. The criteria for detecting a repeat was that the minimum length match is at least 60 nucleotides and at least 65% of the nucleotides matched.

TABLE 3

Hits in consecutive subsegments in coordinates 1000-4000

| Begin | End | Number hits/genome |
|---|---|---|
| 1001 | 1200 | 50 |
| 1201 | 1400 | 1 |
| 1401 | 1600 | 1 |
| 1601 | 1800 | 1 |
| 1801 | 2000 | 1 |
| 2001 | 2200 | 1 |
| 2201 | 2400 | 1 |
| 2401 | 2600 | 1 |
| 2601 | 2800 | 1 |
| 2801 | 3000 | 456 |
| 3001 | 3200 | 6 |
| 3201 | 3400 | 136 |
| 3601 | 3800 | 1059 |

This analysis indicates that the interval from 1201 through 2800 (a length of 1599 nucleotides) was composed of a single copy sequence (because each of the subsegments in this interval were found to be present once per haploid genome). The centromeric and telomeric boundaries of the single copy interval breaks were within the 1001-1200 and 2801-3000 nucleotide intervals. These results are consistent with the initial analysis of the density of repetitive sequences indicating that positions 1000-2000 and 3000-4000 were partially repetitive.

As an example, we illustrate how the boundary of the repetitive sequence within coordinates 1001-2000 can be even more precisely defined by comparing the sequences of overlapping windows within this region with the genome reference sequence. This is a computationally efficient approach for delineating repetitive sequence boundaries (Vincens et al. Bioinformatics 2002; 18:446-451). The 1 kb subsequences analyzed in the previous step were used to produce a series of subsets, each sequence 200 nucleotides in length, and each beginning 20 nucleotides downstream of the previous sequence (adjacent members contain 160 nucleotides in common). The minimum length pairwise match was 70 nucleotides and paralogous sequences were required to be at least 65% identical. Each of these sequences was compared with that of the reference genome in Table 4. The first two intervals (positions 1001-1200 and 1021-1220) contain one or more members of one or more repetitive sequence families, because these subsegments detect significant length matches to (at least) 50 and at least 118 different genomic locations, respectively. By shifting the centromeric end of the subsequence a further 20 nucleotides in the telomeric direction, the interval defined by positions 1041-1240 of the sequence matches a single genomic location with 100% identity (Query=1041_1240_HIRAcg; Min length of match=70; Min percent identity=65; Number of total hits=3; Number of qualified hits=1; Hit=ref|NC_000022.7|NC_000022, Length=200, Percent_id=100, Start_hit=17692626, End_hit=17692825). This indicates that the single copy interval is expected to begin approximately at this position and this finding is confirmed based on the method of the '097 patent (Table 1; see below). The degree of error in specifying the precise coordinate of the single copy interval is dictated by the amount of nucleotide displacement of each window, which in this case, is 20 nucleotides. It will be evident to those of the art that the coordinates of the 3' or telomeric boundary of this single copy interval can be refined using precisely the same procedure as was used to define the 5' or centromeric end of this interval at 200 nucleotide resolution.

TABLE 4

Detailed refinement of 5' centromeric boundary of a single copy interval in the HIRA gene

| Begin | End | Number hits in genome |
|---|---|---|
| 1001 | 1200 | 50 |
| 1021 | 1220 | 118 |
| 1041 | 1240 | 1 |
| 1061 | 1260 | 1 |
| 1081 | 1280 | 1 |
| 1101 | 1300 | 1 |
| 1121 | 1320 | 1 |
| 1141 | 1340 | 1 |
| 1161 | 1360 | 1 |
| 1181 | 1380 | 1 |
| 1201 | 1400 | 1 |
| 1221 | 1420 | 1 |
| 1241 | 1440 | 1 |
| 1261 | 1460 | 1 |
| 1281 | 1480 | 1 |
| 1301 | 1500 | 1 |
| 1321 | 1520 | 1 |
| 1341 | 1540 | 1 |
| 1361 | 1560 | 1 |
| 1381 | 1580 | 1 |
| 1401 | 1600 | 1 |
| 1421 | 1620 | 1 |
| 1441 | 1640 | 1 |
| 1461 | 1660 | 1 |
| 1481 | 1680 | 1 |
| 1501 | 1700 | 1 |
| 1521 | 1720 | 1 |
| 1541 | 1740 | 1 |
| 1561 | 1760 | 1 |
| 1581 | 1780 | 1 |
| 1601 | 1800 | 1 |
| 1621 | 1820 | 1 |
| 1661 | 1860 | 1 |
| 1681 | 1880 | 1 |
| 1721 | 1920 | 1 |
| 1761 | 1960 | 1 |
| 1781 | 1980 | 1 |

TABLE 5

Analysis of Intermediate subsequence (minimum 50 nucleotides, 65% identity)

| Begin | End | Number_hits |
|---|---|---|
| 2001 | 2100 | 1 |
| 2101 | 2200 | 1 |
| 2201 | 2300 | 1 |
| 2301 | 2400 | 1 |
| 2401 | 2500 | 1 |
| 2501 | 2600 | 1 |
| 2601 | 2700 | 1 |
| 2701 | 2800 | 1 |

TABLE 5-continued

| Analysis of Intermediate subsequence (minimum 50 nucleotides, 65% identity) | | |
|---|---|---|
| Begin | End | Number_hits |
| 2801 | 2900 | 1 |
| 2901 | 3000 | 1 |

This moderate resolution (i.e. 100 nts) subsequence analysis at low stringency of the interval containing positions 2001-3000 confirms that the entire region is composed of single copy sequence. We then proceed to analyze the next 1 kb subsequence at moderate (Table 6), and then finally at high (Table 7) resolution.

TABLE 6

| Definition of telomeric breakpoint at moderate resolution | | |
|---|---|---|
| Begin | End | Number_hits |
| 3001 | 3100 | 1 |
| 3101 | 3200 | 1 |
| 3201 | 3300 | 1 |
| 3301 | 3400 | 1 |
| 3401 | 3500 | 2081 |
| 3501 | 3600 | 529 |
| 3601 | 3700 | 1 |
| 3701 | 3800 | 1 |
| 3801 | 3900 | 163 |
| 3901 | 4000 | 1 |

The results shown in Table 5 suggest that the telomeric boundary of the single copy sequence interval resides between coordinates 3400 and 3500.

TABLE 7

| Detailed refinement of the 3' telomeric boundary of the single copy interval in the HIRA gene using overlapping windows (same interval as that analyzed in Table 4) | | |
|---|---|---|
| Begin | End | Number hits |
| 3001 | 3100 | 1 |
| 3021 | 3120 | 2 |
| 3041 | 3140 | 7 |
| 3061 | 3160 | 4 |
| 3081 | 3180 | 2 |
| 3101 | 3200 | 1 |
| 3121 | 3220 | 1 |
| 3141 | 3240 | 1 |
| 3161 | 3260 | 1 |
| 3181 | 3280 | 2 |
| 3201 | 3300 | 6 |
| 3221 | 3320 | 11 |
| 3241 | 3340 | 67 |
| 3261 | 3360 | 63 |
| 3281 | 3380 | 20 |
| 3301 | 3400 | 39 |
| 3321 | 3420 | 36 |
| 3341 | 3440 | 150 |
| 3361 | 3460 | 610 |
| 3381 | 3480 | 1936 |
| 3401 | 3500 | 2081 |
| 3421 | 3520 | 2987 |
| 3441 | 3540 | 3626 |
| 3461 | 3560 | 330 |
| 3481 | 3580 | 3479 |
| 3501 | 3600 | 529 |

TABLE 7-continued

| Detailed refinement of the 3' telomeric boundary of the single copy interval in the HIRA gene using overlapping windows (same interval as that analyzed in Table 4) | | |
|---|---|---|
| Begin | End | Number hits |
| 3521 | 3620 | 3473 |
| 3561 | 3660 | 819 |
| 3581 | 3680 | 1406 |
| 3601 | 3700 | 2044 |
| 3601 | 3700 | 2351 |
| 3641 | 3740 | 1281 |
| 3661 | 3760 | 1610 |
| 3701 | 3800 | 22 |
| 3721 | 3820 | 57 |
| 3741 | 3840 | 140 |
| 3761 | 3860 | 19 |
| 3781 | 3880 | 8 |
| 3801 | 3900 | 157 |
| 3801 | 3900 | 163 |
| 3821 | 3920 | 709 |
| 3881 | 3980 | 19 |

The results of the detailed analysis of the subsequence covered by the positions 3001-4000 subsequence indicate that the end of the first repetitive sequence can be found between positions 3100 and 3120 (positions 3021-3120 was present in 2 copies, whereas 3001-3100 is found only once per genome). Comparing with the results obtained in Table 1, we find that the telomeric boundary determined with the instant invention overlap highly divergent members of the MER58B and L1M4 subfamilies. The element contained in the HIRA derived subsequence respectively 24.5% and 22.8% (with 13.2% insertion/deletion) different from prototypic members of these families. Because of the level of divergence from the consensus elements in the genome, and the limited length of the match to these elements (101 and 47 nucleotides, respectively), probes containing these sequences should not cross hybridize with other genomic locations.

In this example, we have shown that the instant invention enables the definition of a particular single copy interval spanning coordinates 1041 through 3100 within the 103 kb HIRA complete genomic sequence. A probe prepared from this interval would be of adequate length and suitable for use as a genomic probe (for FISH, microsphere, microarray, MAPH, or Southern hybridization) using the method described in U.S. Pat. No. 6,828,097.

Although the non-homologous genomic location is still a very divergent copy, it nevertheless meets our minimum criteria for a repetitive sequence (65 nucleotides in length, and at least a 70% identity). Such a stringent criterion is necessary in order to eliminate the possibility of spurious cross hybridization with divergent repetitive sequences in the genome. This potential sequence similarly may not pose a problem of cross hybridization in actual laboratory experiments, however due to the cost and labor associated with carrying out those experiments, it is recommended that this sequence not be included in the probe. The match to the non-homologous sequence is indicated below:

```
>ref|NC_000017.8|NC_000017 Homo sapiens chromosome 17, complete sequence
Length = 81,860,266

Plus Strand HSPs:

Score = 189 (34.4 bits), Expect = 0.54, P = 0.42
Identities = 63/87 (72%), Positives = 63/87 (72%), Strand = Plus/Plus

Query:      12 CTAACTAAAATAATTG-AGTAAAACTCATAGGTCAAAGGGGAATTCTAATTAAGTGAAAT 70 (SEQ ID NO: 4)
         |||| ||| ||| ||    || | |||| |||||||||||    ||| || ||    |||||||||
Sbjct: 19011641 CTAAATAACATACTTTTAG-ATAACCCATAGGTCAAAGAAGAAGTC-AA--AAGTGAAAT 19011696 (SEQ ID NO: 5)

Query:      71 TAAAAATGACTTGCAAGAGAATGGTAA 97 (SEQ ID NO: 6)
         ||||||    |    ||    ||        ||||    ||
Sbjct: 19011697 TAAAAAGTATTTAGAACCAAATGAAAA 19011723 (SEQ ID NO: 7)

Score = 171 (31.7 bits), Expect = 3.5. P = 0.97
Identities = 63/87 (72%), Positives = 63/87 (72%), Strand = Plus/Plus

Query:      13 TAACTAAAATAATTGAGTAAAACTCATAGGTCAAAGGGGAATTCTAATTAAGTGAAATTA 72 (SEQ ID NO: 8)
         ||| ||| |||| | | |||    | ||||||||||| ||||    |     |        ||| | |||||||
Sbjct: 12941025 TAAGTAATATAAGTAAATAAT-C-CATAGGTCAAAGAGGAAAT-T-TTATGGGAAATTA 12941079 (SEQ ID NO: 9)

Query:      73 AAAA-TGACTTGCAAGAGAATGGTAA 97 (SEQ ID NO: 10)
         ||||    ||    ||| ||    ||||    ||
Sbjct: 12941080 AAAACATGTTTTG-AACTGAATGAAAA 12941105 (SEQ ID NO: 11)
```

Note that there are limitations to this precision of the breakpoints that can be defined by this method. In order to detect repetitive sequence elements that are highly degenerate, it is not appropriate to continue to reduce the length of the search sequence to extremely short segments because the algorithms used to detect repetitive sequences are sensitive to the lengths and composition of divergent genomic copies of such sequences. Repetitive sequences in the human genome often differ significantly both in homology and length from one another and consensus sequences derived from these repeat families, and this degree of sequence divergence challenges the sensitivity of most algorithms to detect repetitive sequence. Sequence comparisons between short test sequences and the genome using most of the common alignment methods can fail to detect shorter intervals (e.g., 50-75 nucleotides) containing members of repeat sequence families that are divergent from the majority of family members and thus the performance of the instant invention can be compromised by comparison of short subsets of sequences. The degree of similarity between a test sequence and other related sequences in the genome can vary widely across the length of the test sequence. Particular subintervals with low percentage identities can falsely indicate that a sequence is present once per genome, even though the overall subsequence (which contains this interval) is actually present multiple times in the genome.

To demonstrate this phenomenon, we attempted to divide the 1000 nucleotide subsegments from HIRA into consecutive, non-overlapping sequences as short as 50 nucleotides and search these sequences with the human genome. Most of these 50 nucleotide sequence were found by both BLAST and BLAT only one in the human genome reference, despite evidence showing that these sequences were subsets of known repetitive family methods. Thus, it might not be obvious to one of ordinary skill in the art that short contiguous sequences cannot be used to search the genome with high efficiency, since recognition of limitations on the length of the search interval are dependent on characteristics of the specific repeat sequences that are being detected. There are many eukaryotic species with genomes with families of repetitive sequences that are highly heterogeneous and contain short repetitive elements (e.g., SINE elements in the canine genome, which are often polymorphic in terms of their presence or absence in different animals). The alternative strategy of using precise word matching methods to identify repetitive sequences are themselves insensitive to weak homologies between related family members and that lack of sensitivity is only amplified when the sequence being search is particularly short.

Based on the results in Table 1, the boundaries of cataloged repetitive sequence family members flanking this interval at the centromeric and telomeric ends occur at positions 1061 and at 2913, which are completely consistent with the findings indicated in Tables 3 and 4. The minimum length of this single copy interval, i.e., 1599 nucleotides, would be quite useful for probe production for a variety of applications including fluorescence in situ hybridization, microarray hybridization, Southern analysis, and microsphere suspension array hybridization.

This same procedure was then repeated for each 1000 by subsegment that was found to be present in single copy in the initial screen that determined the overall density of repetitive sequences across the HIRA gene region. These presumed single copy subsegments and the immediately flanking subsegments which contain repeat sequences are again selected for more detailed delineation of the boundaries of the single copy intervals. These regions would include intervals defined by positions 21001-26000, 25001-29000, 28001-33000, 44001-50000, 55001-62000, 64001-67000, 69001-72000, 74001-77000, 76001-80000, 80001-83000, 82001-85000, 93001-97000, and 100001-102000 (intervals derived from Table 2).

Upon identification of the single copy intervals with the present technology, DNA products derived from these intervals are then amplified, extracted or purified from genomic DNA or from recombinant DNA clones known to contain these sequences. The derivation of such products and their hybridization to other nucleic acids (from patients with chromosome abnormalities, for example) by either Southern analysis, fluorescence in situ hybridization, attachment to microsphere suspensions, microarrays or other solid phase surfaces are entirely conventional and well known by those of skill in the art. Examples and procedures for synthesis of such probes that have been developed from computationally defined sequences of single copy intervals and hybridization applications of the instant invention have been carried out by the inventor in the ’097 patent.

Example 2

HIRA Gene

The same approximate 103 kilobase pair length interval comprising the 100,836 by HIRA gene and flanking sequences (SEQ ID NO: 1) was extracted from Genbank accession NT_001039. Position 1 of this interval corresponds to position 798,334 of NT_001039. This approximate 103 kb interval was analyzed using the method of the instant invention. The following indicates a comparison of results obtained for design of single copy probes using the method of U.S. Pat. No. 6,828,097 versus the ab initio method of the instant invention. The coordinates provided correspond to the 103 kb interval from which probes were previously derived.

Unless otherwise noted, initially the sequence region to be tested for repetitive and single copy sequences was separated into consecutive 1000 by intervals, each of which were tested for similarity for other sequences in the genome using WU-BLAST as described in Example 1. These were divided into 100 nucleotide (nt) intervals usually overlapping one another by 10-50 nucleotides and each tested for repeats by determining the number of genomic copies of each 100 nt subsequence with matches >70 nts in length and >=70% identity.

1. Previously determined Single Copy Interval Boundaries in U.S. Pat. No. 6,828,097: Positions 55445-60803

The initial low (1 kb) resolution survey of the 103 kb region defined a single copy domain by positions 56,001-60,000 is present in single copy in the genome. The repetitive sequences adjacent to this interval were identified as follows: Centromeric boundary: $1^{st}$ iteration localized to positions 55001-56000; $2^{nd}$ iteration to 55393-55484 (because 55442-55541 is single copy and 55393-55492 is present in 1086 copies per haploid genome); $3^{rd}$ iteration to 55,424-55,434. This single copy interval boundary is within 11 nucleotides of the boundary determined with the method of U.S. Pat. No. 6,828,097.

Telomeric boundary: Boundary iteratively defined with increasingly narrower intervals. Intermediate resolution ($1^{st}$): positions 60,001-61,000; Higher resolution analysis ($2^{nd}$): we find that the interval from 60,687 to 60,786 is unique in the genome (1 copy) and the interval from 60,786-60,884 is repetitive (33 copies); Highest resolution ($3^{rd}$): positions 60,767-60,777. This single copy boundary is within 26 nucleotides of the boundary determined by the method of U.S. Pat. No. 6,828,097.

2. Previously Determined Single Copy Interval Boundaries in U.S. Pat. No. 6,828,097: Positions 44937-48722

Centromeric boundary: $1^{st}$: Intermediate resolution analysis shows that the 5' most repeat ends between positions 44991 and 45000. $2^{nd}$: Fine resolution analysis shows that the boundary is between 44911 and 44921. The interval downstream of 44937 (boundary within an AluJo repeat defined by method of U.S. Pat. No. 6,828,097) is single copy. The ab initio boundary is within 16 nucleotides of the ’097 boundary.

Telomeric boundary: An L2 repetitive element was shown to begin at 47718, the boundary of the single copy interval defined by the ’097 patent. With the instant invention: the intermediate resolution (1st) analysis shows that a repeat begins in the interval defined by positions 47601-47700. Fine (2nd) resolution analysis shows that a repetitive sequence (with 80% identity) present four times per genome beginning in the interval defined by 47651-47661. This boundary is 58 nucleotides upstream of the boundary disclosed in U.S. Pat. No. 6,828,097.

3. Previously Determined Single Copy Interval Boundaries in U.S. Pat. No. 6,828,097: 76829-79310

Centromeric boundary: Intermediate resolution analysis (1st) delineates single copy boundary between positions 76801-76850. Fine resolution (2nd) analysis of nucleotides 76701-76900 indicates that the boundary of a repetitive sequence occurs between 76880 and 76900.

In other words, the ab initio detects a low copy divergent repeat (30% of the nucleotides are discordant) within the interval between positions 76829 and 76880 that is not found by the method of the U.S. Pat. No. 6,828,097. While this indicates that in some instances, the ab initio method may be more sensitive for detecting single copy intervals than the previous approach, one of skill in the art would recognize that divergent repetitive sequences with this level of sequence divergence do not usually produce cross-hybridization to other genomic locations under typical laboratory hybridization conditions.

Telomeric boundary: Intermediate resolution (1st) analysis (using a threshold of detecting repetitive sequences of 65% nucleotide identity) indicates boundary between positions 79400 and 79450. Fine resolution analysis (2nd) narrows this interval to between 79400 and 79410, which is 90 nucleotides from the boundary detected using the method of the ’097 patent. The ab initio approach fails to detect a portion of an extremely divergent MER3 repeat element which begins at position 79310 and ends at 79501 (which is found using the method of the ’097 patent). This element differs by 33% from the consensus MER3 sequence and contains insertions and deletions comprising 13% of that sequence. Because of the weak similarity to other related elements, divergent repetitive sequences of this type would not cross-hybridize to other genomic locations under typical laboratory conditions. Therefore single copy probes containing such sequences would still hybridize to a single location in the human genome under moderately stringent post-hybridization wash conditions.

4. Previously Determined Single Copy Interval Boundaries in U.S. Pat. No. 6,828,097: Positions 21423-25270

Centromeric boundary: At intermediate resolution, the ab initio method finds the boundary between a centromeric repeat and the adjacent single copy sequence within the interval defined by positions 21101 through 21149. At high resolution, the boundary is more precisely delineated between positions 21119 and 21139 using the default conditions for repeat detection. However, using a lower threshold of detecting repetitive sequences of 65% nucleotide identity, a weak, highly divergent repetitive sequence (with 67% identity to one other element in the genome) is detected within positions 21301-21399. Under typical hybridization conditions, this unlinked repetitive element would not cross-hybridize with a probe derived from this genomic interval. Application of the method used in the ’097 patent indicates that the repetitive sequence at the single copy boundary is an L2 element which ends at 21151. The single copy boundary found by the ab initio method is thus 12 nucleotides from the boundary demonstrated in the ’097 patent.

Telomeric boundary: At intermediate resolution (1st), the boundary found with the ab initio method between single copy and repetitive sequences falls between 25199 and 25297. The high resolution (2nd), this boundary occurs within the interval delineated between positions 25280 and 25300, which is 10 nucleotides away from the interval boundary determined in the '097 patent (position 25270).

CDC2L1 Gene

The previously determined boundaries of single copy interval based on the method of the '097 patent used to develop probes are positions 8145-17744 of GenBank accession AL03182 (SEQ ID NO: 3).

Ab initio analysis of consecutive 1 kb intervals in AL03182 (SEQ ID NO: 3) shows that positions 9001-17000 are single copy in the human genome. The sequences adjacent to this interval each contain repetitive sequences. Sequences from positions 8001-9000 are present in 117 copies per genome and sequences from 17001-18000 are present in 1672 copies.

To more precisely define the boundaries of the repetitive sequences centromeric and telomeric to the single copy interval, each of the flanking regions were further analyzed by comparing overlapping genomic intervals with increasingly shorter displacement.

Centromeric boundary: The 1st analysis localized this boundary to positions 8151-8200; the 2nd analysis to 8170-8180. The minimum distance between the boundary of the single copy interval determined with the ab initio method and the boundary determined by '097 patent is 25 nucleotides.

Telomeric boundary: The 1st analysis localized this boundary to positions 17651-17749; the 2nd analysis to positions 17662-17672. The minimum distance between the boundary of the single copy interval determined with the ab initio method and the boundary determined by '097 patent is 72 nucleotides.

This 9.5 kilobase interval was divided into two overlapping single copy intervals in order to develop probes that could be easily amplified for hybridization. As in the '097 patent, the interval sequences were used as templates for essentially conventional PCR primer selection methods, as described in the '097 patent. The resulting probes from these two intervals substantially overlapped the sequences comprising the probes of the '097 patent and when labeled by nick translation, produce an identical genomic hybridization patterns previously obtained with FISH. Differences between results produced by the current invention and the '097 patent only occur for short probes (~100 nt) whose sequences fall at or close to the deduced boundary between the single copy and repetitive sequences (for example, for single copy probes of 100 nt typically used in microsphere hybridization assays). Probe design should avoid using probes comprised of deduced single copy sequences that are located close to the position of the single copy-repetitive sequence transition.

NDN (NECDIN) Gene

Three single copy probe intervals were derived from Genbank accession number: AC006596 (SEQ ID NO: 2) from the NECDIN gene on chromosome 15.

1. Previously Determined Single Copy Interval Boundaries in U.S. Pat. No. 6,828,097: Positions 68031-75948

For the first interval in the NECDIN gene region, the previously determined single copy interval boundaries (given in U.S. Pat. No. 6,828,097; amplified by PCR primers corresponding to SEQ ID NOS: 437 and 438 of the '097 patent) are bounded on the centromeric end by position 68031 and at the telomeric end at position 75948 of AC006596 (SEQ ID NO: 2). Sequences between these coordinates are considered single copy and are not similar to known families of repetitive sequences.

At 1 kilobase pair resolution, sequences between 69001 and 75000 were found to be present at only this location on chromosome 15 as a single copy sequence in the genome. The adjacent intervals consisting of positions 68001-69000 and 75001-76000 contained repetitive sequences based on initial copy number analysis of these sequences. Using the method of the instant invention, we first localized the centromeric boundary at intermediate resolution between positions 68051 and 68101. This interval was then refined to between positions 68051 and 68061, which is within 20 nucleotides of the previously determined centromeric single copy repetitive sequence boundary (in the '097 patent). The telomeric boundary was first determined to occur between 75949 and 75999 and subsequently refined to the interval between positions 75971 and 75981 using the ab initio method, which is within 23 nucleotides of the previously determined boundary using the method of the '097 patent.

2. Previously Determined Single Copy Interval Boundaries in U.S. Pat. No. 6,828,097: Positions 76241-78441

The second interval in the NECDIN gene region (corresponding to sequences for PCR amplification (SEQ ID NOS: 441 and 442 of the '097 patent)) has a centromeric bound at position 76249 and a telomeric bound at 79221 of the same Genbank accession number. Applying the ab initio method iteratively as shown in the previous examples, these intervals were found to occur between positions 76241-76251 at the centrometric end and between 78431-78441 at the telomeric end. Thus, the 10 nucleotide window containing the centromeric bound of the repetitive sequence defined by the ab initio method contains the boundary determined using the method of '097 patent, i.e., they are essentially coincident. The ab initio method locates a highly divergent repetitive sequence (70% sequence identity) that was not detected using the method of the '097 patent, which accounts for the 800 nucleotide difference between the respective boundary coordinates. This divergent repeat would not cause cross-hybridization under the laboratory conditions used for probe hybridization. In any case, the interval defined by the ab initio method is more conservative than the one found using the method of the '097 patent. Using typical laboratory chromosomal hybridization conditions (described in the '097 patent), one of skill in the art will understand that probes derived from this interval will produce hybridization to a single genomic location.

3. Previously Determined Single Copy Interval Boundaries in U.S. Pat. No. 6,828,097: Positions 94498-99152

The third interval in the NECDIN gene region (region (corresponding to sequences for PCR amplification (SEQ ID NOS: 439 and 440 of the '097 patent)) has a centromeric bound at position 94498 and a telomeric bound at 99152 of the Genbank AC006596. Applying the ab initio method iteratively as shown in the previous examples, these intervals were found to occur between positions 94661-94671 at the centrometric end and between 97691-97701 at the telomeric end.

The probe interval obtained using the ab initio method is more conservatively determined than the single copy interval defined by the method of the '097 patent, suggesting that the ab initio method identifies unrecognized repetitive sequences not detected with the '097 method. Indeed the instant invention detects a previously unrecognized highly divergent repetitive sequence which is present 23 times in the genome and shows an average 71% identity with the interval 97651-97750 in the Necdin gene region. This divergent repeat would not cause cross-hybridization under the laboratory conditions used for probe hybridization. Using typical laboratory chromosomal hybridization conditions (described in the '097 patent), one of skill in the art will understand that probes derived from this interval will produce hybridization to a single genomic location. At the telomeric end of this interval, the ab initio method detects several contiguous simple repetitive sequence composed of imperfect runs of polynucleotides ($G_n$) or polydinucleotides ($[TG]_n$). These are detected as well by the methods of the '097 patent; however because these sequences are relatively short interrupted runs of imperfect homopolymers, they will not cause cross-hybridization under the laboratory conditions used for probe hybridization and can therefore incorporated in most probes developed using the '097 invention. Nevertheless, the ab initio method does recognize even these short, divergent sequences as repetitive sequences.

As demonstrated above, the ab initio method of probe design can recapitulate in most cases the single copy probe intervals deduced using the method of the '097 patent. In those instances where the two methods differ, in nearly all cases, the ab initio approach is more sensitive detecting even weaker similarities (of less than 70% identity) to known repetitive elements in the genome than that found with the prior method. The ab initio method may in some cases produce purer single copy sequence compositions than the methods of the '097 patent. In the laboratory however, these weak sequences similarities are not relevant, since under even moderate stringency post-hybridization wash conditions, any duplexes formed with such sequences will be disrupted and eliminated, thus preventing cross hybridization between these highly divergent repeats at other genomic locations and the designed probes.

All references cited above are hereby incorporated herein by reference.

APPENDIX A

The following script is an example of the ABINITIO.PL script.

```
#!/usr/bin/perl
# gets subsequences of defined length and increment from input sequence
# P Rogan 2005
#
use Bio::SeqIO;
use Bio::SeqIO::fasta;
use Bio::PrimarySeqI;
use Bio::SeqFeature::Generic;
# command line arguments:
# (1) Name of genomic sequence
# (2) Length of subsequence
# (3) Length of window increment
# (4) Minimum Length of Match to repeats
# (5) Minimum Percentage Match to repeat
system("date");
system("pwd");
#   get name of sequence
$ARGV = shift @ARGV;
chomp $ARGV;
if (-s $ARGV) {
   print "processing $ARGV ...\n";
} else {
   print "Params: (1) Name of genomic seq, (2) Length of subsequence, (3)
Length of increment, \n(4) Min length of match and (5) Min percent match
to repeats\n";
   exit; }
$seqin = Bio::SeqIO->new('-file'=>$ARGV,
      '-format' => 'Fasta');
#initialization of subsequence extraction
$begin = 1;
$end = shift @ARGV;
chomp $end;
if($end<2) {die "subsequence too short"};
$incr = shift @ARGV;
chomp $incr;
if ($incr < 1) {die "beginning and ending nucleotides of subsequence are
identical"};
$minlen = shift @ARGV; chomp $minlen;
$minperc = shift @ARGV; chomp $minperc;
#   $seqout = Bio::SeqIO->new('-format'=>'Fasta', '-file'=>'>
#   output.fa');
#   print $ARGV," ", $end, " ", $incr;
while(( my $seqobj=$seqin->next_seq( ))) {
#length of full sequence
```

APPENDIX A-continued

The following script is an example of the ABINITIO.PL script.

```
my $len = $seqobj->length;
#print "length", $len;
  while( $len > $end ) {
#   print "seen sequence ",seqobj->display_id( ),"start of seq",
#                             substr($seqobj->seq,1,10),"\n";
  if($seqobj->alphabet eq 'dna'){
     $subseqin = $seqobj->subseq($begin,$end);
     $id = $seqobj->display_id( );
     $idsub = $begin . "_" . $end . "_" . $id;
     $nameseg = $begin . "_" . $end;
     open (OUT, ">$nameseg");
     print OUT ">",$idsub, "\n", $subseqin, "\n";
#   print ">",$idsub, "\n", $subseqin, "\n";
# insert system call for qsub of wublast job here
#   job runs the wubl script and then a perl program that has blast parser
      for each blast run.
Results are
#   appended to a table
     $fpresults = "~/Documents/" . $nameseg . "_results";
     system("qsub -cwd -o $fpresults -e /dev/null ~/Documents/wubl
~/Documents/$nameseg $minlen $minperc");
#   for example: qsub -o ~/Documents/test wubl ~/Documents/101_200
     close (OUT);
     $begin = $begin + $incr;
     $end = $end + $incr;
  }
    }}
#   $seqout->write_seq($subseqin)
$date=system("date");
print $date;
```

APPENDIX B

The following script is an example of the WUBL script.

```
if [ "$#" -ne 3 ]
then
   echo "form: wubl sequence_file min_length_match min_percent_
match"
echo "sequence name (fasta format): "$1
echo "Minimum length of match to repeat: "$2
echo "Minimum percent match to repeat: "$3
blastn -d "human" -span2 -i $1 -cpus 2 -lcmask -hspmax 100 -warnings
-errors -o $1_results
blaspars.pl $1_results $2 $3 >> blastparse
```

APPENDIX C

The following script is an example of the BLASTPARSE.PL script.

```
#!/usr/bin/perl
use Bio::SearchIO;
use Bio::Tools::BPlite;
# this program is called within the wubl script
#
# command line parameters : name of blast result file, min length of
match, min percent identity
$minlen = 100;
$minperc = 70;
$ARGV = shift @ARGV;
chomp $ARGV;
$minlen = shift @ARGV;
chomp $minlen;
$minperc = shift @ARGV;
chomp $minperc;
   my $in = new Bio::SearchIO(-format => 'blast',
                        -file => $ARGV);
   print $ARGV "\n";
   while( my $result = $in->next_result ) {
   print "\nQuery = ", $result->query_name, "\n";
   print "Min length of match = ", $minlen, " Min percent identity = ",
$minperc;
```

APPENDIX C-continued

The following script is an example of the BLASTPARSE.PL script.

```
print "Number of hits = ", $result->num_hits, "\n";
  while( my $hit = $result->next_hit ) {
    while( my $hsp = $hit->next_hsp ) {
      if( $hsp->length('total') > $minlen ) {
        if ( $hsp->percent_identity >= $minperc ) {
          print "Hit= ",        $hit->name,
            ",Length=",        $hsp->length('total'),
            Percent_id=", $hsp->percent_identity,
            "Start_hit=",   $hsp->start('hit'),
            ",End_hit=",     $hsp->end('hit'), "\n";
          }
        }
      }
    }
  }
```

APPENDIX D

The following script is an example of the COUNTHITS.PL script.

```
#!/usr/bin/perl
#counts number of qualified hits along a windowed sequence
# 1 commandline argument: name of blastparse output file
# parameters
#min length of match
$minlen = 100;
#min percent identity
$minperc = 70;
$ARGV = shift @ARGV;
chomp $ARGV;
open (BLASTSUM, $ARGV);
open (COUNT, ">count");
$num=0;
      print "Begin        End        Number hits\n";
      print COUNT "Begin        End        Number hits\n";
while (<BLASTSUM>) {
  chomp;
  if (/Hit*/) {
    $num++;
     $coords[3]=$num;    }
  if (/Query*/) {
# count the number of lines with hits
.
#print out the number of hits for the previous query:
  if ($num>0) {
     print $coords[1],"\t", $coords[2], "\t", $coords[3], "\n";
     print COUNT $coords[1],"\t", $coords[2], "\t", $coords[3],"\n";
  }
   s/Query = /_/;
   @coords = split(/_/,$_);
   $coords[3]= 0;
   $num=0;
   }
}
```

APPENDIX E

The following script is an example of the SUBSEQ script.

```
#!/usr/bin/perl
# gets subsequences of defined length and increment from input sequence
# P Rogan 2005
#
use Bio::SeqIO;
use Bio::SeqIO::fasta;
use Bio::PrimarySeqI;
use Bio::SeqFeature::Generic;
# command line arguments:
# (1) Name of genomic sequence
# (2) Length of subsequence
# (3) Length of window increment
# (4) Minimum Length of Match to repeats
```

APPENDIX E-continued

The following script is an example of the SUBSEQ script.

```
# (5) Minimum Percentage Match to repeat
system("date");
system("pwd");
#   get name of sequence
$ARGV = shift @ARGV;
chomp $ARGV;
if (-s $ARGV) {
  print "processing $ARGV ...\n";
} else {
  print "Params: (1) Name of genomic seq, (2) Length of subsequence, (3)
Length of increment, \n(4) Min length of match and (5) Min percent match
to repeats\n";
  exit; }
$seqin = Bio::SeqIO->new('-file'=>$ARGV,
     '-format' => 'Fasta');
#initialization of subsequence extraction
$begin = 1;
$end = shift @ARGV;
chomp $end;
if($end<2) {die "subsequence too short"};
$incr = shift @ARGV;
chomp $incr;
if ($incr < 1) {die "beginning and ending nucleotides of subsequence are
identical"};
$minlen = shift @ARGV; chomp $minlen;
$minperc = shift @ARGV; chomp $minperc;
#                     $seqout = Bio::SeqIO->new('-format'=>'Fasta',
#'-file'=>'>output.fa');
#   print $ARGV," ", $end, " ", $incr;
while(( my $seqobj=$seqin->next_seq( ))) {
#length of full sequence
my $len = $seqobj->length;
#print "length", $len;
  while( $len > $end ) {
#                             print "seen sequence ",seqobj->display_
#                             id( ),",start of seq",
                              substr($seqobj->seq,1,10),"\n";
  if($seqobj->alphabet eq 'dna'){
    $subseqin = $seqobj->subseq($begin,$end);
    $id = $seqobj->display_id( );
    $idsub = $begin . "_" . $end . "_" . $id;
    $nameseg = $begin . "_" . $end;
    open (OUT, ">$nameseg");
    print OUT ">",$idsub, "\n", $subseqin, "\n";
#                                        print ">",$idsub, "\n", $subseqin, "\n";
# insert system call for qsub of wublast job here
#   job runs the wubl script and then a perl program that has blast parser
     for each blast run.
Results are
#   appended to a table
    $fpresults = "~/Documents/" . $nameseg . "_results";
    system("qsub -cwd -o $fpresults -e /dev/null ~/Documents/wubl
~/Documents/$nameseg $minlen $minperc");
#                                   this works: qsub -o ~/Documents/test wubl
                                      ~/Documents/101_200
    close (OUT);
    $begin = $begin + $incr;
    $end = $end + $incr;
  }
   }}
#                     $seqout->write_seq($subseqin)
$date=system("date");
print $date;
```

What is claimed is:

1. A method to identify and produce a single copy sequence in a target reference complete genome sequence by successive division of the target reference genome sequence into subintervals and comparison the subintervals to the target reference sequence, said method comprising:

determining a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence is divided into at least two subsequences, and a subsequence of the first screened sequence with a single subsequence occurrence in the target reference genome sequence or a group of contiguous subsequences of the first screened sequence each with a single subsequence occurrence in the target reference genome sequence is identified as a single copy interval of the first screened sequence, wherein an occurrence is defined by at least about 50 consecutive nucleotides of the subsequence of the first screened sequence or the group of contiguous subsequences of the first screened sequence displaying (i) at least about 60% homology to the target reference sequence; (ii) at least about 70% homology to the target reference sequence; or (iii) at least about 80% homology to the target reference sequence;

determining a count of the number of times a subsequence of a second screened sequence occurs in the target reference genome sequence, said screened sequence being at least one subinterval of the target reference genome sequence, wherein the second screened sequence comprises a single copy interval of the first screened sequence; the second screened sequence overlaps the single copy interval of the first screened sequence; the subsequences of the second screened sequence are either (i) consecutive non-overlapping subintervals of the second screened sequence or (ii) overlapping non-identical subintervals of the second screened sequence, and a subsequence of the second screened sequence with a single subsequence occurrence in the target reference genome sequence or a group of contiguous subsequences of the second screened sequence each with a single subsequence occurrence in the target reference genome sequence is identified as a single copy interval of the second screened sequence, wherein an occurrence is defined by at least about 50 consecutive nucleotides of the subsequence of the second screened sequence or the group of contiguous subsequences of the second screened sequence displaying (i) at least about 60% homology to the target reference sequence; (ii) at least about 70% homology to the target reference sequence; or (iii) at least about 80% homology to the target reference sequence;

identifying a single copy interval as a single copy sequence of the target reference sequence suitable for use as a single copy hybridization probe; and producing the single copy sequence as a nucleic acid molecule.

2. The method of claim 1 further comprised of the step of determining a count of the number of times a subsequence of a third screened sequence occurs in the target reference sequence, wherein the third screened sequence comprises a single copy interval of the second screened sequence; the third screened sequence overlaps the single copy interval of the second screened sequence; the subsequences of the third screened sequence are either (i) consecutive non-overlapping subintervals or (ii) overlapping non-identical subintervals, and a subsequence of the third screened sequence with a single subsequence occurrence in the target reference sequence or a group of contiguous subsequences of the third screened sequence each with a single subsequence occurrence in the target reference sequence is identified as a single copy interval of the third screened sequence, wherein an occurrence is defined by at least about 50 consecutive nucleotides of the subsequence of the third screened sequence or the group of contiguous subsequences of the third screened sequence displaying (i) at least about 60% homology to the target reference sequence; (ii) at least about 70% homology to the target reference sequence; or (iii) at least about 80% homology to the target reference sequence.

3. The method of claim 2 further comprised of the step of determining a count of the number of times a subsequence of a fourth screened sequence occurs in the target reference sequence, wherein the fourth screened sequence comprises a single copy interval of the third screened sequence; the fourth screened sequence overlaps the single copy interval of the third screened sequence; the subsequences the of fourth screened sequence are either (i) consecutive non-overlapping subintervals or (ii) overlapping non-identical subintervals, and a subsequence of the fourth screened sequence with a single subsequence occurrence in the target reference sequence or a group of contiguous subsequences of the fourth screened sequence each with a single subsequence occurrence in the target reference sequence is identified as a single copy interval of the fourth screened sequence, wherein an occurrence is defined by at least about 50 consecutive nucleotides of the subsequence of the fourth screened sequence or the group of contiguous subsequences of the fourth screened sequence displaying (i) at least about 60% homology to the target reference sequence; (ii) at least about 70% homology to the target reference sequence; or (iii) at least about 80% homology to the target reference sequence.

4. The method of claim 1 further comprised of the step of identifying a subsequence of the first or second screened sequences with at least two occurrences in the target reference sequence as a subsequence containing a repetitive element wherein the single copy sequence is located adjacent to the repetitive element.

5. The method of claim 4 further comprised of the step of identifying a second, distinct subsequence of the first or second screened sequences with at least occurrences in the target reference sequence as a subsequence containing a different repetitive element, wherein the single copy interval is located between the first and the second subsequences containing the distinct repetitive elements.

6. The method of claim 3 wherein the second, third, or fourth screened sequence comprise (i) a centromeric end that overlaps the single copy interval of the first, second, or third screened sequence, respectively; (ii) a telomeric end that overlaps the single copy interval of the first, second, or third screened sequence, respectively; or (iii) a centromeric and telomeric end that both overlap the single copy interval of the first, second, or third screened sequence, respectively.

7. The method of claim 6 further comprising the step of determining whether the extended test sequence extends in the direction toward the centromere of the chromosomal arm containing the subsequence.

8. The method of claim 3 wherein the subsequence is (i) at least about 100 consecutive non-overlapping nucleotides; (ii) at least about 200 consecutive non-overlapping nucleotides; (iii) at least about 400 consecutive non-overlapping nucleotides; (iv) at least about 600 consecutive non-overlapping nucleotides; (v) at least about 800 consecutive non-overlapping nucleotides; or (vi) at least about 1000 consecutive non-overlapping nucleotides.

9. The method of claim 1 wherein the target reference sequence is about 100,000 nucleotides to about 400,000 nucleotides.

10. The method of claim 1 wherein the target reference sequence is a sequenced genome of an organism.

11. The method of claim 9 wherein the target reference sequence is a sequenced genome of a human.

12. The method of claim 1 wherein the overlapping subintervals of the screened sequence are displaced by at least about 20 nucleotides from adjacent subintervals.

13. The method of claim 4 further comprising the step of (i) storing a sequence of a single copy sequence or (ii) storing a subsequence of a screened sequence that displays more than one match to the target reference sequence or (ii) storing a sequence of a screened subsequence containing a repetitive element.

14. One or more tangible computer-readable storage media having computer-executable components for identifying a single copy sequence in a target reference complete genome sequence, said components comprising:

a first genome comparison component for determining a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence is divided into at least two subsequences, and a subsequence of the first screened sequence with a single subsequence occurrence in the target reference genome sequence or a group of contiguous subsequences of the first screened sequence each with a single subsequence occurrence in the target reference genome sequence is identified as a single copy interval of the first screened sequence, wherein an occurrence is defined by at least about 50 consecutive nucleotides of the subsequence of the first screened sequence or the group of contiguous subsequences of the first screened sequence displaying (i) at least about 60% homology to the target reference sequence; (ii) at least about 70% homology to the target reference sequence; or (iii) at least about 80% homology to the target reference sequence;

a second genome comparison component for determining a count of the number of times a subsequence of a second screened sequence occurs in the target reference genome sequence, said screened sequence being at least one subinterval of the target reference genome sequence, wherein the second screened sequence comprises a single copy interval of the first screened sequence; the second screened sequence overlaps the single copy interval of the first screened sequence; the subsequences of the first screened sequence are either (i) consecutive non-overlapping subintervals of the second screened sequence or (ii) overlapping non-identical subintervals of the second screened sequence, and a subsequence of the second screened sequence with a single subsequence occurrence in the target reference genome sequence or a group of contiguous subsequences of the second screened sequence each with a single subsequence occurrence in the target reference genome sequence is identified as a single copy interval of the second screened sequence, wherein an occurrence is defined by at least about 50 consecutive nucleotides of the subsequence of the second screened sequence or the group of contiguous subsequences of the second screened sequence displaying (i) at least about 60% homology to the target reference sequence; (ii) at least about 70% homology to the target reference sequence; or (iii) at least about 80% homology to the target reference sequence; and a subsequence component for identifying a single copy interval as a single copy sequence of the target reference sequence suitable for use as a single copy hybridization probe;

and wherein the results achieved from the computer-executable components of the computer-readable storage media are outputted in a user readable format.

15. A computerized system for identifying a single copy sequence in a target reference complete genome sequence, said computerized system comprising a computer-readable storage media, said computer-readable storage media comprising:

means for determining a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence is divided into at least two subsequences, and a subsequence of the first screened sequence with a single subsequence occurrence in the target reference genome sequence or a group of contiguous subsequences of the first screened sequence each with a single subsequence occurrence in the target reference genome sequence is identified as a single copy interval of the first screened sequence, wherein an occurrence is defined by at least about 50 consecutive nucleotides of the subsequence of the first screened sequence or the group of contiguous subsequences of the first screened sequence displaying (i) at least about 60% homology to the target reference sequence; (ii) at least about 70% homology to the target reference sequence; or (iii) at least about 80% homology to the target reference sequence;

means for determining a count of the number of times a subsequence of a second screened sequence occurs in the target reference genome sequence, said screened sequence being at least one subinterval of the target reference genome sequence, wherein the second screened sequence comprises a single copy interval of the first screened sequence; the second screened sequence overlaps the single copy interval of the first screened sequence; the subsequences of the first screened sequence are either (i) consecutive non-overlapping subintervals of the second screened sequence or (ii) overlapping non-identical subintervals of the second screened sequence, and a subsequence of the second screened sequence with a single subsequence occurrence in the target reference genome sequence or a group of contiguous subsequences of the second screened sequence each with a single subsequence occurrence in the target reference genome sequence is identified as a single copy interval of the second screened sequence, wherein an occurrence is defined by at least about 50 consecutive nucleotides of the subsequence of the second screened sequence or the group of contiguous subsequences of the second screened sequence displaying (i) at least about 60% homology to the target reference sequence; (ii) at least about 70% homology to the target reference sequence; or (iii) at least about 80% homology to the target reference sequence; and means for identifying a single copy interval as a single copy sequence of the target reference genome sequence suitable for use as a single copy hybridization probe;

and wherein the single copy sequence is outputted in a user readable format.

16. A method to prepare a single copy hybridization probe from a target reference complete genome sequence by successive division of the target reference genome sequence into subintervals and comparison the subintervals to the target reference sequence, said method comprising:

determining a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence is divided into at least two subsequences, and a subsequence of the first screened sequence with a single subsequence occurrence in the target reference genome sequence or a group of contiguous subsequences of the first screened sequence each with a single subsequence occurrence in the target reference genome sequence is identified as a single copy interval of the first screened sequence, wherein an occurrence is defined by at least about 50 consecutive nucleotides of the subsequence of the first screened sequence or the group of contiguous subsequences of the first screened sequence displaying (i) at least about 60% homology to the target reference sequence; (ii) at least about 70% homology to the target reference sequence; or (iii) at least about 80% homology to the target reference sequence;

determining a count of the number of times a subsequence of a second screened sequence occurs in the target reference genome sequence, said screened sequence being at least one subinterval of the target reference genome sequence, wherein the second screened sequence comprises a single copy interval of the first screened sequence; the second screened sequence overlaps the single copy interval of the first screened sequence; the subsequences of the second screened sequence are either (i) consecutive non-overlapping subintervals of the second screened sequence or (ii) overlapping non-identical subintervals of the second screened sequence, and a subsequence of the second screened sequence with a single subsequence occurrence in the target reference genome sequence or a group of contiguous subsequences of the second screened sequence each with a single subsequence occurrence in the target reference genome sequence is identified as a single copy interval of the second screened sequence, wherein an occurrence is defined by at least about 50 consecutive nucleotides of the subsequence of the second screened sequence or the group of contiguous subsequences of the second screened sequence displaying (i) at least about 60% homology to the target reference sequence; (ii) at least about 70% homology to the target reference sequence; or (iii) at least about 80% homology to the target reference sequence;

identifying a single copy interval as a single copy sequence of the target reference sequence suitable for use as a single copy hybridization probe; and preparing a single copy hybridization probe comprising a single copy sequence.

* * * * *

UNITED STATES PATENT AND TRADEMARK OFFICE
CERTIFICATE OF CORRECTION

PATENT NO. : 7,734,424 B1
APPLICATION NO. : 11/324102
DATED : June 8, 2010
INVENTOR(S) : Peter K. Rogan It is certified that error appears in the above-identified patent and that said Letters Patent is hereby corrected as shown below:

Column 309, line 24 – Column 310, line 67, delete claims 1-16 and substitute therefore the attached claims 1-16.

Claim 1. A method to identify and produce a single copy sequence from a target reference complete genome sequence by successive division of the target reference genome sequence into subintervals and comparison of the subintervals to the target reference sequence, said method comprising:

(A) determining a count of the number of times a subsequence of a first screened sequence occurs in the target reference genome sequence, said screened sequence is at least one subinterval of the target reference genome sequence obtained by division of the target reference genome sequence, wherein (1) the target reference genome sequence comprises the first screened sequence, (2) the first screened sequence comprises at least two subsequences, and (3) a single copy interval of the first screened sequence is identified as (i) a subsequence of the first screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or Signed and Sealed this Fourteenth Day of September, 2010

David J. Kappos
*Director of the United States Patent and Trademark Office*

(ii) a group of contiguous subsequences of the first screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence;

(B) determining a count of the number of times a subsequence of a second screened sequence occurs in the target reference genome sequence, said screened sequence being at least one subinterval of the target reference genome sequence, wherein (1) the second screened sequence comprises a single copy interval of the first screened sequence;

(2) the second screened sequence overlaps the single copy interval of the first screened sequence;

(3) the subsequences of the second screened sequence are either (i) consecutive non-overlapping subintervals of the second screened sequence or (ii) overlapping non-identical subintervals of the second screened sequence; and (4) a single copy interval of the second screened sequence is identified as (i) a subsequence of the second screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member having a single subsequence occurrence in the target reference genome sequence, wherein an occurrence is defined by at least about 50 consecutive nucleotides of the subsequences with
(i) at least about 60% homology to the target reference sequence; (ii) at least about 70% homology to the target reference sequence; or (iii) at least about 80% homology to the target reference sequence;

(C) identifying a single copy interval as a single copy sequence of the target reference sequence suitable for use as a single copy hybridization probe; and (D) producing the single copy sequence as a nucleic acid molecule.

Claim 2. The method of claim 1 further comprising a step of determining a count of the number of times a subsequence of a third screened sequence occurs in the target reference sequence, wherein (A) the third screened sequence comprises a single copy interval of the second screened sequence;
(B) the third screened sequence overlaps the single copy interval of the second screened sequence;
(C) the subsequences of the third screened sequence are either (i) consecutive non-overlapping subintervals or (ii) overlapping non-identical subintervals; and
(D) a single copy interval of the third screened sequence is identified as
  (i) a subsequence of the third screened sequence with a single subsequence occurrence in the target reference sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or
  (ii) a group of contiguous subsequences of the third screened sequence, each member having a single subsequence occurrence in the target reference sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence.

Claim 3. The method of claim 2 further comprising a step of determining a count of the number of times a subsequence of a fourth screened sequence occurs in the target reference sequence, wherein (A) the fourth screened sequence comprises a single copy interval of the third screened sequence;
(B) the fourth screened sequence overlaps the single copy interval of the third screened sequence;
(C) the subsequences of the fourth screened sequence are either (i) consecutive non-overlapping subintervals or (ii) overlapping non-identical subintervals; and
(D) a single copy interval of the fourth screened sequence is identified as (i) a subsequence of the fourth screened sequence with a single subsequence occurrence in the target reference sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the fourth screened sequence, each member having a single subsequence occurrence in the target reference sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence.

Claim 4. The method of claim 3 wherein a subsequence is (i) at least about 100 consecutive non-overlapping nucleotides; (ii) at least about 200 consecutive non-overlapping nucleotides; (iii) at least about 400 consecutive non-overlapping nucleotides; (iv) at least about 600 consecutive non-overlapping nucleotides; (v) at least about 800 consecutive non-overlapping nucleotides; or (vi) at least about 1000 consecutive non-overlapping nucleotides.

Claim 5. The method of claim 3 wherein the second, third, or fourth screened sequence comprises (i) a centromeric end that overlaps the single copy interval of the first, second, or third screened sequence, respectively; (ii) a telomeric end that overlaps the single copy interval of the first, second, or third screened sequence, respectively; or (iii) a centromeric and telomeric end that both overlap the single copy interval of the first, second, or third screened sequence, respectively.

Claim 6. The method of claim 5 further comprising a step of determining whether an extended test sequence extends in the direction toward the centromere of the chromosomal arm containing the subsequence.

Claim 7. The method of claim 1 further comprising a step of identifying a subsequence of the first or second screened sequences with at least two occurrences in the target reference sequence as a subsequence containing a repetitive element wherein the single copy interval is located adjacent to the repetitive element.

Claim 8. The method of claim 7 further comprising a step of identifying a second, distinct subsequence of the first or second screened sequences with at least two occurrences in the target reference sequence as a subsequence containing a different repetitive element, wherein the single copy interval is located between the first and the second subsequences containing the differing repetitive elements.

Claim 9. The method of claim 7 further comprising a step of (i) storing a sequence of a single copy sequence or (ii) storing a subsequence of a screened sequence that displays more than one match to the target reference sequence or (ii) storing a sequence of a screened subsequence containing a repetitive element.

Claim 10. The method of claim 1 wherein the target reference sequence is about 100,000 nucleotides to about 400,000 nucleotides.

Claim 11. The method of claim 10 wherein the target reference sequence is a sequenced genome of a human.

Claim 12. The method of claim 1 wherein the target reference sequence is a sequenced genome of an organism.

Claim 13. The method of claim 1 wherein the overlapping subintervals of the screened sequence are displaced by at least about 20 nucleotides from adjacent subintervals.

Claim 14. A method to prepare a single copy hybridization probe from a target reference complete genome sequence by successive division of the target reference genome sequence into subintervals and comparison of the subintervals to the target reference sequence, said method comprising:

(A) determining a count of the number of times a subsequence of a first screened sequence occurs in the target reference genome sequence, said screened sequence is at least one subinterval of the target reference genome sequence obtained by division of the target reference genome sequence, wherein
  (1) the target reference genome sequence comprises the first screened sequence,
  (2) the first screened sequence comprises at least two subsequences, and
  (3) a single copy interval of the first screened sequence is identified as
    (i) a subsequence of the first screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence;

(B) determining a count of the number of times a subsequence of a second screened sequence occurs in the target reference genome sequence, said screened sequence is at least one subinterval of the target reference genome sequence, wherein (1) the second screened sequence comprises a single copy interval of the first screened sequence;

(2) the second screened sequence overlaps the single copy interval of the first screened sequence;

(3) the subsequences of the second screened sequence are either (i) consecutive non-overlapping subintervals of the second screened sequence or (ii) overlapping non-identical subintervals of the second screened sequence; and (4) a single copy interval of the second screened sequence is identified as (i) a subsequence of the second screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence;

(C) identifying a single copy interval as a single copy sequence of the target reference sequence suitable for use as a single copy hybridization probe; and (D) preparing a single copy hybridization probe comprising a single copy sequence.

Claim 15. One or more tangible computer-readable storage media having computer-executable components for identifying a single copy sequence in a target reference complete genome sequence, said components comprising:

(A) a first genome comparison component for determining a count of the number of times a subsequence of a first screened sequence occurs in the target reference genome sequence, said screened sequence is at least one subinterval of the target reference genome sequence obtained by division of the target reference genome sequence, wherein (1) the target reference genome sequence comprises the first screened sequence, (2) the first screened sequence comprises at least two subsequences, and (3) a single copy interval of the first screened sequence is identified as (i) a subsequence of the first screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence;

(B) a second genome comparison component for determining a count of the number of times a subsequence of a second screened sequence occurs in the target reference genome sequence, said screened sequence is at least one subinterval of the target reference genome sequence, wherein (1) the second screened sequence comprises a single copy interval of the first screened sequence;

(2) the second screened sequence overlaps the single copy interval of the first screened sequence;

(3) the subsequences of the first screened sequence are either (i) consecutive non-overlapping subintervals of the second screened sequence or (ii) overlapping non-identical subintervals of the second screened sequence; and (4) a single copy interval of the second screened sequence is identified as (i) a subsequence of the second screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence; and (C) a subsequence component for identifying a single copy interval as a single copy sequence of the target reference sequence suitable for use as a single copy hybridization probe;

and wherein the results achieved from the computer-executable components of the computer-readable storage media are outputted in a user readable format.

Claim 16. A computerized system for identifying a single copy sequence in a target reference complete genome sequence, said computerized system comprising a computer-readable storage media, said computer-readable storage media comprising:

(A) means for determining a count of the number of times a subsequence of a first screened sequence occurs in the target reference genome sequence, said screened sequence is at least one subinterval of the target reference genome sequence obtained by division of the target reference genome sequence, wherein (1) the target reference genome sequence comprises the first screened sequence, (2) the first screened sequence comprises at least two subsequences, and (3) a single copy interval of the first screened sequence is identified as (i) a subsequence of the first screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence;

(B) means for determining a count of the number of times a subsequence of a second screened sequence occurs in the target reference genome sequence, said screened sequence is at least one subinterval of the target reference genome sequence, wherein (1) the second screened sequence comprises a single copy interval of the first screened sequence;

(2) the second screened sequence overlaps the single copy interval of the first screened sequence;

(3) the subsequences of the first screened sequence are either (i) consecutive non-overlapping subintervals of the second screened sequence or (ii) overlapping non-identical subintervals of the second screened sequence; and (4) a single copy interval of the second screened sequence is identified as (i) a subsequence of the second screened sequence with a single subsequence occurrence in the target reference genome sequence, wherein an occurrence is defined by at least about 50 consecutive nucleotides of the subsequence with (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member having a single subsequence occurrence in the target reference genome sequence, wherein an occurrence is defined by at least about 50 consecutive nucleotides of the subsequences with (i) at least about 60% homology to the target reference sequence; (ii) at least about 70% homology to the target reference sequence; or (iii) at least about 80% homology to the target reference sequence; and (C) means for identifying a single copy interval as a single copy sequence of the target reference genome sequence suitable for use as a single copy hybridization probe;
and wherein the single copy sequence is outputted in a user readable format.

SEQUENCE LISTING

<160> NUMBER OF SEQ ID NOS: 11

<210> SEQ ID NO 1
<211> LENGTH: 102780
<212> TYPE: DNA
<213> ORGANISM: Homo sapiens

<400> SEQUENCE: 1

```
gctgcctcac ctgcacagca agtctctggc tcttcattcc ttaagagtcc cacttgcagc     60
ctggcttttt atgtgtacac acacacacac tcacacaaac tatcctggct ttatttggca    120
tgaacacatg cctgggtctc atccagccac ttgacatccg agtgagacat ggagtggaat    180
ggctgctagg ccagagatca gtggtcagtt accccggcct ctgactccaa gtccaaggct    240
ccttctccag gctcagaccc acacactggg tggtggtgac aaagatcagg acccaggagt    300
gggtggtact cagccctcac tgtgcttaaa gattctgtga ttctgtttct tctcctgtag    360
atcaacgtct ggatcacttt ctaataaaat tccaactttg ctgataattc tccaatatac    420
ccaagactgt aaatactgat ttcctttcat gaaattgtcc aaacagctgc agcccttggt    480
gcacagtatg atctggacct ggggcacagc aagaccagaa ccatgaacca ccatgaacca    540
tgactcctca cttgtgagat gacgtgtgca aggtgaccta tggtgcttca tgaccacaga    600
agtgaccact ctacactgtg aaatgaattt ctgcatgggg ggtatattag ggttctctac    660
agggacagaa ctaatagata tatatgaaag tttattaagt attaacttac acaatcacaa    720
ggtcccacaa taggccatct gcaagctgag gagcaaggag agccagttcg agtcccaaaa    780
ttgaagaact tgggagtccg atgtttgagg gcaggaagca tccagcacgg gagaaagatg    840
taggctggga ggctaagcaa gtctcatctc ttcacatttt tctgcctgct ttatattcgt    900
tggcagctga ttagatggtg cccacctgat taagagtggg tctgccttcc ccagcctgac    960
tcaaatgtta atctcctttg gcaacaccct cacagacaca tccaggatca atattgcatc   1020
cttcaatcca atcaagttga cacgcagtat taaccatgac agggggggaat gagatgacac   1080
aaaggatccc ttctggctct catgttctgt caccatctac ttcaggagag agatgcactg   1140
tgtggggagg atgaaagtta gaaggaaaag gcaagagaaa tcaggagggt ttggtattca   1200
atgcgtgttc atttatttta cacttacaaa agaaatcgcc cacccctttg ccccattccc   1260
ccaaaacagt ctctttttac aaacatttaa aaattaaaac caaatgaaga tagacaagtt   1320
aatttcagta caattatttt tcagtgtagc tgtcataatt agagtttaaa tttcctacaa   1380
gtgaccaatg tccaagtgac ttatagggaa atcctgatta tcggccaaag gaaattcaat   1440
attacaagtt agcaaattct agtacaaaaa tagtccgtgt gttggaacag ctttcctttt   1500
acataggtct taggtcagtc tgctgtaata cctaacgctt ccggattctc tctcacaaat   1560
ggctcaatcg tcactgctga agcagcatgg tgcctgcagc agcaggggct agtgtccacc   1620
ttggggccgt gctggagacg gcaggcctgg gactgccttg ctggccccag ggcacctggg   1680
cagagctcca gccctagctc cgcatcgggg gcttggaggg agggatgagc ttccccctcc   1740
tgaggcaatg tcagacccag gacacagggc acatctgccc agggagctgg gctggcgctg   1800
gtgcaggaca gcacatctcc tgccagtgtc tcctccccct acagcctggt caggtgagag   1860
gcggtcctgc atgtcatcag cggcgagagt gtggccctgc ccttgctgca gccagggcag   1920
gctggggcag gctacttgtc cctcaggatg tcgagctgtt cctgacactc ggtgaagagg   1980
cgctggaatc ggaggttctg cccgatgact ggtagcagct ccttcagcag ctccctcttc   2040
```

-continued

```
cgcagaccct gtggacacag agtgacagct gagtgcaagt gtcagtgaag agacctagat   2100
tgtggggact ttcctggcct ggcagagaac cttgtgtctg ctcacgggag aaggaaagaa   2160
caattcctct gcaggtgaga aactgtgaga gagctgtggg gcaaatgtgc aggatgaagt   2220
ggcaggtgga atgggagcaa cacagtgtgg ggataaagga ggatgaggcc aatgcagggt   2280
ctgctcctcc atccgtgggc acagccactg ctgaccttat agtgactgag cagttccctg   2340
accatccagg gcaggatgag agtagaacaa ggctgagggt caggtggctg gccattcagg   2400
aggggctgtt ccctcatgct gatgtttgcc aggggtttga ggtcaagccc cagggcaagg   2460
atgcacctgg ggggcagtga ctggctttag ttttccagca acacaaatga ggtgccagta   2520
tcccctgatg tggaggatgt tcggatgctg accaaactat gcttagttgc ctaaacatcc   2580
tccacgtcag gtcatattgg caccacagtc tgaaacaagc attgccagtt ggggtctctg   2640
ctgcacagac caaaagagca gactcctgag cagtacggct gctccaaagg gaaaactacc   2700
agccagacaa ctttaacact ggacgagaag gtctaagatc ttgaattaac ggtgacagat   2760
atacctgcaa caagtctaga agtgacagta aagaataagt gtaactatta ggtttgagta   2820
acacagaagt tgttagagat gggataagca ggagaatggc tgctgttggc gaccaagttt   2880
gatggaggag cagcccacac tccaacaggg aggctctgac accagagtgc catagtcaga   2940
acagagatgg tatggatttg caaaggctga aatgtttact atctggtcct ttacagaaaa   3000
gtttgtcaac tcctaaaata gatcatgttt tctaactaaa ataattgagt aaaactcata   3060
ggtcaaaggg gaattctaat taagtgaaat taaaaatgac ttgcaagaga atggtaaaaa   3120
aaaaaaacca acacaaaata ctccaaaagt ggtaagattc agcaaaagtg ggcactttag   3180
aggcatttag aaacaacagc ttatactgta ttagagaaca tgaaagaatg acaagccaag   3240
actccaacct aaagccatca ggggaaagga aaaaaaaaaa gactaaagaa aaaaaggaca   3300
tgagaaaaaa acattttttt taaaaaaagg agataataaa aattgaaata aataaaatag   3360
aaaacaaaga tttaatagag aagatttaga aaaacaattt tattttatat atttttttga   3420
gacagggtct agctctgttg cccaggctgg agcgtagtgg tgcaatcaca gctcgctgca   3480
gcctcaacct cccaggctca agtgatcctc ctgcctcagt tacccgagta gctgggacta   3540
taggtgtgtg ccaccatgtc tggctaattt ttatatattt agtagagcgg ggtttcacct   3600
tgttggccag gctgatctca aactcctgag ctcaagtgat cttcctgcct tgttctccca   3660
aagtgctggg attaaaggcg tgagccacta tgcctggcaa aagtcatttc ttgaaaagac   3720
taatggacaa acgtctggca ggattaatca agaaagagag agaaagctta aagaaataat   3780
attagaaata aaaagagaca taactacaga tatagaagaa agaaaaagat atgattacta   3840
tcaactttat gctaagaaat ttgaacattt agagaaaatg gagaaattcc tagaaaaata   3900
taatttatca aaactagctc aaaaagaaat agaaaggaaa agttaattat taccataaag   3960
aaaacatcag gaatactatt ttaaaactga catcaaggat gagattttct ttgtctttcc   4020
tttcccacag tttgactaat gtgtctcagt gcaggttcct ttgggatttt cctacttaga   4080
gttcactgag gctcttgtat tagtagaccc ccgtctttcc tcaaatttgg aaaatttccg   4140
ccagtatttc ttcaaataag ctctctactc ctttctctct cttacacttc tagaactccc   4200
attatggatt catgggtata cttggatggt gtctggtaag tctcttagac tctgtttgct   4260
tttcttcatt ctattttctt tttgctcctc atacttgata atttcaaatg acctgttttc   4320
aagtttgctg atttaccctt ttgtctattc gagtctgctg ttgaaccctt ctagtgaact   4380
```

-continued

```
tttcaattca gttattgtat ttttaaactc cagatttctg tttagctctt tttttggaat   4440
ttctatctcc ttgttgatac tctcattttc tttttttttt tcttgagatg gagcctcgat   4500
ctgtcgccca ggctggagtg cagtggtgtg atctcggctc actgcaagct ccgcctcctg   4560
ggttcacacc attctcctgc ctcagcctcc cgagtagctg ggactacagg cgccggccag   4620
cacgcctggc taattttttt gtatttttag tagagatggg gttccaccat gttagcaagg   4680
atggtctcga tctcctgacc ttgtgatccg cccgccttgg cctcccaaag tgctgggatt   4740
acaggcatga gccactgcac ccggccctca ttttcttcat atatagtttt cctgattttg   4800
tttagttgtc tgtattctcc ttgagcattt tttaagacat ttattttaaa gtcttatgtc   4860
tgatgggcac agtggctcat gcctgtaatc tcagcacttt gggaggccaa ggcgggcaga   4920
tcgcttgagg ccaggagttc gagaccagtc tggccaacat ggcgaaaccc catctccact   4980
aaaaatacaa aaattaggcc aggcgcggtg gctcacgcct ataatcccag cactttggga   5040
ggctgaggcg gctggatcac ttgaggtcag gagttcgaga ccagtctggc caacatggcg   5100
aaaccccatc tccactaaaa atactaaaat tagccagtcc tgacctcagg tgatccacct   5160
gccttggcct cccaaagtgc tgggattaag gcatgaacca acgcacccgg cagtcctttt   5220
acttttaagc cattgtgtta ttacatgtaa gctgggtttc ttataagcag catacagctg   5280
gttgttatta attctaatct gataatctat gccttttaga cctatattta atgattattg   5340
atatattagg gtttaaatct accatcctat gtatgttttt ctgccttctt ttgaatgaat   5400
gtattatttt ctatcattca attttatcta tttgttagtt ttttagctac gattcttttt   5460
actgctttgg gatttgtatg tgtatgtgca tgagttttat tttttggttt tggtggttgc   5520
tctagggcat ataacataca gtatatgcct ttacttatca tagtctgtct tcaagtatta   5580
tatcactttg cataatgtgt aaaaatcttt taatggtata ctttcatatc cccactcctg   5640
gcgtctgtga tactgctgtc atgccacttc acttctacat atgttataat tacaaactac   5700
attttcatta tttggcttaa aaaggcagaa ctttttgact tttttttttt ttgagacagg   5760
gtcttgcgct ctgttgccca ggctggagtg cagtggcgtg atcttggctc actgcaacct   5820
ctgcctctca ggttcaagca attcttgtgt cttcgcctcc tgagtagctg ggactacagg   5880
catgtgccac cacacccggc taatttttgt atttctagta gagatggggt ttcgccacgt   5940
tggccaggct ggtcttgaac tcctggcctc aagtgatctg tccacctcgg cctcccaaag   6000
tgctgggatt acaggcgtga gccaccgcgc cgaacgagaa ctttttttaca ttttgacatt   6060
tagatgaaca cttttgacat ttaattctta accctttgga ggtatatttt tatgaactga   6120
agatctgctt ttacttagtt acatataaat aaccagtttc ctaaactcca tttattgaat   6180
agccccccct atttttccca ctgtatctgt tttgtcttct ctctcatata gcaaagtatc   6240
taaattactc cggcttcata ataaacccaa atatctggta gcatagtgaa tgtcttaact   6300
attcttggct ttttactgct ccatataaat tgttgaatta gcttgtcaag tttcattgaa   6360
acctctagtg ggcatttgat tagagaggca ttgagtcagt aggtctgttt agaaacggtt   6420
ggcgtctttt actgtactgc actttctcat cgtttgtcca ggttttcttt aatgacttta   6480
agtaaacgtt tataattctt agcatatagg ctatgtacat cctttgttag atttattctt   6540
agatacttta taattctcaa aagagacaat cttgaaagtg gcaaaaaaaa agtgactcat   6600
gagagggatt tgaagtttgt gaagaactac acgcacaatt gctggcttaa agatggagga   6660
ggcaggtgga aagctaacaa ggaaatgaat tctgctattc caataacgac tgagcttgga   6720
agaggacctt gaaccctagg tgatctcatc tggccagtaa tttgagtaga gaattcagga   6780
```

-continued

```
accactgcaa aagcacacca ggaagaccga aagaaatcac agatcctttg aaagaagtgg   6840
caggctgctg caaattccac aagacaggtg aaaaactctg gtgctctctc aaaagtgcca   6900
tctcctggct ggaggccaat taactcagga cattacagca attcataaca gaacaaccct   6960
gctccaagga aggagaaaaa caacagctaa ttccactgcc tgcaacatcc tttctaacca   7020
gtggtcctga gtgtgtccac atgatgactt cactggtagc ataaccagca tttgagaaag   7080
cctgcacact aaacatatct acaaacaagg actctcacag agtctacgcc attcccctgg   7140
caccaccacc acagcaggtg ctggtatcca cagctgggag atctgaagat ggatcacatc   7200
accgggttct ttgcagacgt tccccagcat gggcccagag cctggtagcc ccactgggtg   7260
gctagaccca gaagggcaat aataatcacc gcagtctggc tcataggaat ctccatccct   7320
aggggaaggg gaagtgcacc aaatcaaggg atcaccctgt gggacaaaat aatctcaaca   7380
gcagcctctg agttccagat ttttccactg aactagtcta cccaaatgag aagtaatcag   7440
aaaagtaatt ctggcaataa tgacaaaaca aggttctata atacctccaa aagaccacac   7500
tagctcctca gcaatggatc caaaccaaga ataattacaa agtacatttt cattatttgg   7560
cttaaaaagg cagaactttt tggctttttc tttttctttt ttttttgaga cagggtctcg   7620
ctctgttgtc caggctggag tgcagtggcg tgatctctga attgccaaag aattcagaag   7680
gctgattatt aagctactca aggagatacc aaaggtgaaa atcaacttca agaaatttta   7740
aaaaatatat aggatatgga tgaaaaatgc tccagagaaa tcggtatcat aaagaaaaaa   7800
tcaaaaaatc aaaaatcaaa acttctggaa ataaaagaca cacttagaga aatacaaaat   7860
gcactagaaa gtttcaacaa tagaatcaaa gaagtagaag agagaacttc agaattcaaa   7920
gacaagactt tgaatcagac aaaaacaaag aaaaaataat tttttaaaaa aatgaacaaa   7980
gcctccaaga aatttgggat tatgttaaat ggccaaacct aagagtaaga ataaatggtg   8040
ttcctaagaa gagaaatcta aaagtctgaa aaacgtattt gtggggatag ttgaggaaag   8100
cttccctgac cttgctagag atctagacat ccaaatacaa gaagctcaaa gaacacctgg   8160
gaaatttatc acaaaaagat catcacccag gtacacagtc atcaggttat ctaaagtcaa   8220
gacaaaggaa agaatcttaa gagctgtaag gcaaaagcat caggtaacct atacacgaaa   8280
gcctatcgga tttttttttt tgagacagag tcttgctttg tcatccaggc tggagtgcag   8340
tggtgcaatc ttggctcact gcaatctctg ccgccctggt tcacgcaatt ctcctgcctc   8400
agcctcccaa gtagctggga ctacaggccc ctgccaccag gcctggataa tttttgtatt   8460
tttattagag gtggggtttc accgtgttgg ccaggctggt cttgaactcc tgaccttaaa   8520
tgatccaccc accttggcct ccctaagtgt tgggattaca cgaatgagcc actgcgcctg   8580
gccagaatac ctatcagatt aacagcagat ttctcagcag ataccctaca agccagaagg   8640
gtttgggttc ctatttttag cttcctcaaa caaactaact gccagccaag aatttagtat   8700
ccagcaaaat taagtgtcat atatgaagga ggcataaagt ctttttcaga caaatgctga   8760
gagaatttgc caccaccaag ccagcactac aagaaatgct aaaaggagtt ctaaatcttg   8820
aaacaaaacc ttgaaataca ccaaaataga acttccttaa agcataaaac tcacagggtc   8880
tataaaacaa taacaaaatg aaaaaaaaaa aaccaacaaa aaaagaaggt attcaggtaa   8940
aaacaagcat ggtaaataaa acagtacctc acatctcgat actaacattg aatgtaaata   9000
gtctaaatgc tccacttaaa agatacagaa tggcagaatg gatacaaatc caccaaccaa   9060
atatctgcta acacatatgg actcacataa gttgagggta aaggggtgaa aaaagatatt   9120
```

-continued

```
ccatgcaaat acaaaccaaa agcgagcaga aatagctatt cttatatcag acaaaacaga   9180
ctttaaagca acaatagttg aaaaagacaa aaagggacat tacataatga taaaaggatc   9240
agtccaacag gaaaatatca caatcctaaa tatatatgca cctagcacgg gagctcccaa   9300
atttataaaa caattagtac tcaacgtaag aaatgagata cacagcaaca cagtaacagc   9360
ggggacttca acactagaca ggtcatcaag acagaaaagc aacaaagaaa caatggactt   9420
acactatacc ctagaacaaa tggacttaac acatatttac agaacattct acccaacaac   9480
tgcagaatat acattctttt catcagcaca tggaacattc tccaagaaag accatatgat   9540
aggccacaaa acaactctca ataaacttaa gaaaatcgaa attatatcaa gtaccctctt   9600
agaccacagt aaaataaaat tggaaattaa ctccaaaagg aaccctcaaa actatacaaa   9660
tacatggaaa ttaaaaaata tgctcctgaa tgatctttgg gtaaacaatg aaatcaagat   9720
ggaaattaaa aagttttatg aactgaataa tgacacagct tatcaaaacc tctgggacac   9780
agcaaaagtg gtgctaagag gaaagttgat agcattaaat gcttacatca aaaagtatga   9840
aagaggccaa gcacggtggc tcgtgtctgt aatcccagca attttggagg ccaaggcagg   9900
aggatcactt gaggtcagga gttcaagacc agcctggcca aaatgccaaa accccgtctc   9960
tatcaaaaat agaaaaaaat tagctgggtg tggtgacgca tgcctgtagt cccagctact  10020
tgggaggctg aggcctgaga attgcttgaa cctgggaggc agaggttgta gtgagccgag  10080
atgcaccact gcactccagc ctgggcgaca gagcgagact ccgtctcaaa aaaaaaaaaa  10140
aaagatccaa ttaagctaaa ttagaaacaa aatgaaagat attacaactg ataccacaga  10200
aatagaaaag atcattcaag actactatga acacctttat gcacacaaac tagaaaatct  10260
agaggaaatg gataaattcc tggaaatata taaccctcct agattcattc aggaaaaaat  10320
agaaactttg aacagaccaa taataagtag caagactgaa acagtaattt aaaaattgcc  10380
aacaaaaaaa cagtctggga ccagatggat tcacagctga attctattga acattcaaag  10440
aagaatttgt accaatctta ctgaagctat tacaaaagac agagaaagag ggaatctccc  10500
taaatcactc tatgaagcca gtatcaccct aataccaaaa ccaggaaagg acataacaaa  10560
aaatgaaatc tacagaccaa tatccctggt gaacatagat gcaaaaatcc tcaacaaaat  10620
actacctaat cgaatcaaat ggtgtatcaa aaagataata caccatgatc aagtgggttt  10680
cataccaggg atacagggaa gacttaacgt acacatgtca ataaatgaga tacatcacat  10740
aaacagaatt aaaaacaaaa tcatatgatc atctcaatag atgccgaaaa agcatctgac  10800
aaaatctagc atgccttcga ttaaagccct caggaaaacc gtcatagaat ggaaatacct  10860
caaggtaata aaagccacta tgacaaactc acagttgact ttataccgaa aagggaaaag  10920
ataaaagggt tccccctgag aactctaaca gacaaggatg cccactgtca ccactgctat  10980
tcaacattgt actggaagtc ctagccagag caaacagaca agagaaagaa ataaagggca  11040
tccaaatatg taaaggggaa gtcaaaatat cgctgtttgc caatgatatg atcgtatacc  11100
tagaaaaccc taaagactca tccaaaaagc tcctagatct aataaatgaa ttccgtaaac  11160
tttcagggta caaaatcaat gtacacaaat cagtaacact gctgtatacc aacaatgacc  11220
aagctgagaa tcaaatcaag aacctcttgt tacaatagct gcaaataaaa taaaataaaa  11280
tacttcggaa tatacctaac caaggatgtg aaagatctct acaagaaaaa ctgaaaaact  11340
gattgctgaa agaaatcata gacaacacaa ataaatggaa acacatctaa agctcatggt  11400
aggtaaaatt aaaaatgacc atactgctaa gagcaatcta cagattcaat gcaattccca  11460
tcaaactacc atgattattc ttcacagaac tagaaaaaac aaccctaaaa ttcacaagaa  11520
```

-continued

```
accacagcag ggtgtggtgg ctcacgcctg taattccagc actttgggag gctaaggtag  11580
gcagatcact tgagcccagg agttcgaaac cagtctgggc aacatggcga aactctgtct  11640
ctacaaaata tacaaaaatc agctgggtgt ggtggctcac gtctgtaatc ccagcacttt  11700
gggaggctaa aatgggcaga tcacttgagc ccaggagttc gagaccagcc tagacaacat  11760
ggtgaaaccc tatctttaca aaacatacaa aaattagccg ggtgtgctgg cacatgctgt  11820
agtcccagct actcaggagg ctgaggtgca ggatcacttg agccttggag gcagagtttg  11880
ccatgagccg agattgtgcc actgcactcc aacctgggtg acagagtggg accctgtttc  11940
aaaaaaaaaa aaaaaaaaaa aaaatcatat ggaacaaaag agcccaaata gccaaagcaa  12000
gataaagctg gaggcatcac attacccgac atcaaactat actacaagga tatagttacc  12060
accaaaacag catggtactg gtataaaaat aggcaaacag accaatggaa cagaatagag  12120
aacccagaaa taaagccaaa tacttacagc caacagatct tcaacaaagc aaacaaaaat  12180
acagagtggg gaacaaacac cctattcaac aagtggtgct gggataactg gcaagccaca  12240
tatagaagaa tgaagctgga tcctcatctc tcatcttata caaatatcaa ttcaagatgg  12300
atcaaagact taaatctacg atctgaaacc acaacaattc tagaagataa catcggaaaa  12360
actcttctag acattggctt aggcaaatag ttcatgacta cgaacccaaa agcaaatgca  12420
acaaaaacaa ggataaagag atggcaccta attaaactta aaagcttctg cacagcaaaa  12480
gaaataatca gcagagtaaa cagacaaccc acagagtggg agaaaatatt tgcaaactat  12540
gcatctgaca aggactaat atctggaatc tacaaggaac tcaaacaaat cagcaagata  12600
aaaacaaata accccattaa aaagtggaca aagaacatga atagacaatt ctcaaaagaa  12660
gatatacaaa tgaccaacaa acatatgaaa aaaatgctca acatcactaa ttatcaggga  12720
aatgcaaatc aaaaccacaa tgacatacca ccttactcct gcaagaatgg ccataattaa  12780
aaaataaaaa aaatagatat tagcatggag gtggtgaaaa gggaacactt ttacactgct  12840
ggtgggaatg taaactagta caaccaccgt ggaaaacagt atggggactc gttctggaga  12900
tggagtctca ctctgtcacc caggctggaa tgcagtggca cgatctcggc tcactggaac  12960
ctctgcctcc tgggttcaag tgattctcct gcctcagcct cctgagtagc tgggactata  13020
ggcatgcgcc accatggttg gctaattttt tgtattttta gtagagacag ggtttcacca  13080
tgttggctgt gctggtcttg aactcctgac ctcaggtgat ctttccgcct cagcctccca  13140
aagtgctggg attacaggca tgagccactg cacctggcca gagattcctt aaagaactaa  13200
aagtagaact accatttgat ccagcaatcc cactactgtg tatctaccca gaggaaaaga  13260
agtcattatg tgaacaatac acttgtacac acgtttatag cagcaccatt tgcaactgca  13320
aaaatacgga accagtctaa atgcccatca accaatgagt ggataaagaa aatgtggtat  13380
atatacacca tggaatacta ctcagcctta aaaaggaatg aaataatggc attcacagca  13440
acctggatgg agttggagac cattattcta agtgaagtaa ctcaggaatg gaaaaccaaa  13500
cattatatgt tctcacttat aagtaggagc taacctatga ggatgcaaag gtataacaat  13560
gatgtaatgg actttgggga ctcaggggga agggtgaaga gggtgagtga taaaagacta  13620
cacattgggt acagtgtaca ctgctcaggt gatgggtgca ctaaaatgtc aaaaaaagaa  13680
aaaaagcaac tcatgtaaat aggatattca ataagattat cagcatagtc agtgggatga  13740
catattcaaa agaaagaaag aggccaggtg cagtggctca cacctgtaat cccagcactt  13800
tgggaggctg aggtaggtgg attgcttgag ctcaggagtt tgggaccagc ctgggcaaca  13860
```

-continued

```
cagcaaaatc ccacctctac caagaaaaaa aataaaaata aaaaatttgc caggcatggt  13920
ggcgcacatc tgtggtccca gctactcagg aggctgaggt gggaggccca cttgagcctg  13980
ggaggtggag gttgaagtaa gtcgagatta caccaatgta ctccagcctg ggtggcagag  14040
tcagactctg tctccaaaaa tctacaacat cgtggaagtt ggaaaacaca ctgttatttt  14100
aaatttcatg tatttttata aaaacagatg gagttggttg ggtgtggtgg cttacacctg  14160
taatcccaac actttgggag cctgagacgg gtggattgat tgagcctagg aatttgagac  14220
cagcctgggc aacatggaga aaaccccatc tctacaaaag atacaacaat tagttgggtg  14280
tggtggtgca cgcctgtaat cccagctact cgggaggcag aggcaggagg attgattgag  14340
ccagaaggtt gaggccacag tgaggggaaa aaaaaaaaag agagagagag agagagtctt  14400
gctatgttgc tcaggctggt ctcgaattcc tgacctcaag tgatcttccc acctcagctt  14460
cccaaagtgc tgggattaca ggtgtgagcc accacgcctg gctgaaaaaa cacactatta  14520
aacaaagtga gacaaatgaa aatgaaaata caacatacca aaacttacag tatgcagtga  14580
aagctgatct caaatcaata atctaacatt acaccttaag gaactagaaa aagaactata  14640
cctaaagcta gcagaagaaa ataataaaga taatgggaca agataaatgg aaaataatag  14700
agataatcaa tgaaaccaaa agttgattct ttgaaaagat gaacaaaatt gacaaacttt  14760
tagctagact acataataaa aagagagaca agatccaaat aatgaaaatc aaaaatgaaa  14820
gcagggacat tacaaccaat gccacaaaaa taaaaaagat tataaataag agaacagcat  14880
gaacaactat atgacaataa atctgataac ctacataaaa tggaaacaac ttaccaagac  14940
tggctcataa agaaattaaa aatctggacg gatctctaat gagcaagaaa actgaatcaa  15000
taaaacaaac cctctcataa agaaaagcct aggatcatat agcttctctg atgtattcta  15060
ccaaacactt agagaattaa caccaatcct ccttccaaaa taggtaggaa cacttcctat  15120
ttcattctat gaggacagca ttaccctgac aaagctagac aaagatacta caagaaaact  15180
attagatcaa tatcctttgt aaacagtgac ccaaaaatcc tcaacaaaat gccagcaaac  15240
agaattccaa agtacattaa aagaattata caccatgacc aagtgggatt tattccttga  15300
atgcaagaat ggtttaacat atgaaaacca atcactgtaa tacatcacat taatgaaata  15360
aaagaaaatt ttaaaatgac acgatcatct taatgcagaa aaagcatctg agaaaatgca  15420
acattctttc ttgataaaag cactcaacaa actaggaatg gaagaaaact atctcgacat  15480
agtaaagacc ataaataaaa agcccacagc taacatcgta cttaatggta aaagactaaa  15540
agcttttcct ttaatatcag gaacaagaga aggatgcctg cttccagcac taatatttaa  15600
cgtagtatta agagtcctag acagatcaat taggcaagga gaagaaataa aaggcaacca  15660
aattgggaaa aaagaagtaa aattatttct gttcacagat gacatgatct tatatatgga  15720
aaaccctaaa gattcagcga aaaactacta taaacaaagc aaaacattct gcctgcctgt  15780
ggtactagga agaagctgca agaggacttg ccctctggcc tgaaggcaat gtaaagagca  15840
gccaagtatt attgatattt cctcaccctt cggctctcag taaaggatgg tttttccact  15900
ctttcaggat gcgatgtata gctctttgta cagcctgcaa cacacaactt aatcaccacc  15960
tctctggcca ctgccacagg tcttacagca gcagtcccca accttttcgg cacccaggac  16020
tggttttttt ttatggacca gtgggggagg ggaagacggt ttcaggataa aactgttcca  16080
cctcagatca tcaggcatta gattctcata aggagcacac aacctagatc tctcatatgt  16140
gaagttcaca atagggtttg tgctcctatg agaatttaat gttgctgctg actggtctgt  16200
ggcccagagg ttggggaccc ctgtcttaca ctgaagacca cagcaaaggg aggcttccta  16260
```

-continued

```
agaacagggc ctggctgggg aggctggagc cagaacaaag cccaggaacc tgaaaggtgt  16320
ttgcttagtg ccccaacctt ctgcttctca ttttcctccc atgcacactg aaccatgcaa  16380
aggatccttg aagttgaaag aaatctgaac ctttggtgtc cctgtggtgc actggcagct  16440
caaatcagag tatataaaga gctcctataa tatacataga gttcctacaa accattgaga  16500
aaaacaaatg gcaacaagta tttcaataga tagttcaaaa aagggaaaca caagcggctc  16560
ttaagcatgt gaaatgatgc tctcctaaca agccttcttg ggagggctgc tgagtcagca  16620
tggctggttg gaagtccacc ctccaaccac agctatattt tcccagttat ttgaaggatc  16680
agttccactt gaatgaccaa ttctcaccat aaatgttgat aaataaggcc aggcacggtg  16740
gctcacgcct gtaatcccag cactttggga ggctgaggtg ggccactgca ttccacactc  16800
cagcctgggt gacagagaga gacttcgtct caaataaaca cataaataaa ataaaagagt  16860
gttgataaat aaacccaaga agagcacaga aggctcatgc tcactcatct cctctgcccc  16920
aacatctaga tgaaaagaca gtaaacatac agaaaaaaag gaacaaattc agaatagtgt  16980
tgagatcagg agaggacctg gcagaagaca ctgggattgg ctatgtctac gtctgctcta  17040
aatcctcttc tcttacatat tctttgtaca gagggagaaa acctgctcat tttcccagcc  17100
tcccttgcag cagaggtggg tgcccaagtg atttaatggt tgcctgtgag gcacagacta  17160
gtttctggga gagcgtttct tttctgatga gagggtgaat gttgctgttg ccagatttct  17220
cctgttctct ctccttccct gatcttggac atggaagcca ccttgtaacc atgagggaag  17280
ggctaggaga cctttacaga gggtggtaag cgggtggtac atactgacag gtgactctgg  17340
gaggggaacc acagattctc ttaggcagag cctcagtgaa gtgtcctgtt tggagttggt  17400
aagaataatc agcaggaagg aggggagaag aagaaatcat ggccatcaaa tggtagcctg  17460
tttgtggctc cttctgtcta taccaccacg gcccagagtg cttactttca ggctgagaaa  17520
gagaactact atggtgagct ttggcgggca tcttgggcta aggctgacag aatgaagctc  17580
cacaacctgc ccatgagggg gactcactgg gcaggtttct gcctgcctcc cactctagta  17640
gatggctcat cggcctgtcc tggaggtgag atgtgctaag ctgtgctaag cgaacagctg  17700
tactcttgaa aaggaaacct gaggccacta tcaatctggg ttcttcactt gtaactacaa  17760
cctgataacc aaggatttcc acatagggta aaatgtcctc aagtaaagac cgcaatgaac  17820
aaatcaaaga ttgaacccag aaaagccaga taattcaggg aacaaattat tttagaaaat  17880
gttagcatct gcagctgata tctgagaaga tatcacaagc ctttccttcc attaatagac  17940
catgcaattc agaacagcct tcctcactga caacaaagaa aaaaaggtgg acaaatagca  18000
gcaaacttct gagagctaat gtgttaatga taaatgactg agccatgctg tggggaagac  18060
agagatccaa agagggatgc ctttgctttg gaaatattta tccatgagga agaagctagg  18120
cagaacttct accaaacttg agggcctggg ttgggagcgg tggctcatgt ctataatccc  18180
agcacttcgg gaggctgagg tgggtagatc acctgaggtc aggagtttga gaccagcctg  18240
gtcaacatgg tgaaaccccg cctctactaa aaaaataaaa attagctggg tgtagtggtg  18300
tgtgcctgta attccagcta cttgggaggc tgaggcagga gaattgcttg aacccaggag  18360
gcagaggtta cagtgagctg atattgtgcc actgtactcc agcccgggtg acagagcgag  18420
actccgtctc aaaataaaca aacaaaacaa acaaacaact tgagggccta gggggaccat  18480
agcaggggct agggccctgt taacttaccc ctcctttgtc ctggtattcc aaaggtacgc  18540
aacctagaat aagcgtcaac tggaagtaaa ctagcctcta taccagctgg cacccagctt  18600
```

-continued

```
tgagttccag gcagcctaga aaacctcagt ccctgaacgg gatcatggag tccctacagt  18660
gctactccca agaagttggc agaagcaaat agaagtgttc tgtagaagaa gataacatca  18720
tcttaggcct caaactattt ctacaataaa tttttcaaat actatgtcca ccagatagta  18780
aaaaataacc aggtacataa ggagataaga caatctgaat gagaaacagc agaaatattt  18840
ataggcaacg gaaatagatc tgcaaaggct cctgatacta gaattatcag acataaaact  18900
ttaaaataac taagattatt atgctaaagt agataaaagc ctaaattaaa aatctggtga  18960
agaattgaaa gcatgaaaaa tgatacagct gatttttttt tttttgagac agagtctcac  19020
cctgtcgcct gggctggtgt gcaatggcgc gatctcggct cactgcaacc tccgcctcct  19080
gggttcaagt gattctcctg cctcagcctc ccaagtagct gggattacag gtgcccgcca  19140
ccatgcctgg ctaatttttt gtatttttag tagagatggg gtttcactaa gttggccagg  19200
ctggtctcaa actcctgacc tcatgatccg accccccttgg cctcccaaag tgctggaatt  19260
acaggagtga gccaccacgc ttggcctttt tatttttttat tttttgagat ggagtttcgc  19320
tcttgtcgcc caggctggag tacaatggcg tgatcttggc tctgcctcct aggttcaagc  19380
gattctcctg cctcagcctc ccgagtagct gggattacag gcacatgtca ccaagcccag  19440
ctaatttttt tttttagtag agtcggggtt tcaccatgtt ggctgggttg gtctcaaact  19500
cctgacctca ggtgatccgc ccatcttggc ctcccaaaag gctgggatta taggcatgag  19560
ccaccacgcc tggcctgata cttgatttta cttttttttta aattttcctt ttcttgagac  19620
ggagttttgc tctgtctccc aggatggagt gcagtggtgt gatcttggct cactgcagcc  19680
tcctcctccc ggttcaagcg attctcctgc ctcagcctcc ccagtagctg ggattacagg  19740
agtgtgccac cacacccagc taatttttat ttttagtaga gacgggattt cagcatgttg  19800
gccgggcagg tcttgaactc ctgacctcag gtgatccacc catctcggtt tcccaaagtg  19860
ctgggattac aggcatgagc cactgtgccc ggcgatacag ctgattttaa aaagagagga  19920
tattacatct ctcagatgat ggggaaaatg aaagggaaga aataatcaaa taggaaaacc  19980
gaagaaaatc actggtctct gtctctgttt ctacagaatg aatgagcttt ctgaatcttc  20040
aaaacaccaa gataggatcc caaagtactt acaaagcaat ggaaattaga tttacaatag  20100
atttttttag caataacact ggatgcaaag tctatggaac aatgccttca gggacttaag  20160
gggatttgac tttgaaccca ggattcaaag tacctagtca attaaggtac accacagtca  20220
aatttaagaa tggaataaaa aattaggcct ctgtacacac caaggcctgt gagggctgac  20280
cctctggcct tttgatgtca actcctttca cccttctgct accatcccgt tgggctgttc  20340
cttttaaact ccaagctctc ccacctcagg cctttgcact ttccctctgc ctggatgttc  20400
ttctcccaaa tatatgcatg gtttcatccc tcacctttttc tggtctctgc ttatctgttt  20460
gtttggcctt tcctttttct tttctttttt tttttttgag acggagtctc gctctattgc  20520
ccagactgga gtgcagtggc gcgatcttgg ctcactgaaa gcttagcctg gcctttctta  20580
attgcccagc atgaaatagc agcctgccag tattctatat ctccctgccc ttttaatttt  20640
tttcccatgg catccatcac cactcaagac actacagata cctcttctca tttgcttagt  20700
ctgtctctct ccataagaaa gcagatccat gaatgcaggg actcagtctg ccttattcac  20760
tgctgcctgc cccattcact gctgcctgcc ctatgcctat aacatgcctg gccaggggag  20820
gtgccccatc agtaattgct caatgattga atgaagctgt gagctaactc ttagatccat  20880
accttctccc atcccccacc aacctgttac cttcttgatt taatgaatgg ttctggcatc  20940
catttttgc agctgaacct ggaggtgcca catgttcatt atgcttttttc cttccacatc  21000
```

-continued

```
caaccaccca tcaaatctta ttggttctgc ctccaaaata catcttgaat ctgtctcctt  21060
tcccctctcc atggccacca cactgatcca agtcaccttc atctcttcct gggactgtta  21120
cagaagatac tccctgactg tttttctatt ttagttcatg acacctctgt gccaactctg  21180
ccaagaagaa aacgctagct cctgtaaagg tctctgtggt ccacctcctg cctcatttca  21240
caccaccctc tccttttgcc ttctatgtgc cagccacagt ggctccaaac agatcaagca  21300
ctccttgctt ttactctcac ttctactagg aaacactttc tccaggtctc tgtatggctg  21360
tctcactctt ctccttgggt ttcatccgca gtgtcctctc acaaggcctt cctggtcact  21420
ccttcccagg cactctcatc tgaagaccct gcttacttcc ttcttagtct gaatctagtc  21480
tgaaaatatt ttgttgacct aactgcctcc ctgtttatgt gtgcatccct accagaccga  21540
gctccacgaa ggcagggaag taccttccgt cttttgtctt cacaaccaag cccagagccc  21600
ctgcaggcag cctccctcag cacaggcacg tggcggagca ctccgtggct cctgatgtcc  21660
agggcccagc tcctgccagg ttgtggaggg ccgtcggcat gtcaccctct cactgatgct  21720
gggacctgag gctgggtgct ggagaagtct aacgggacac aatttcaaag cactttggct  21780
tatttaaaaa atctccacct tcatgtttca agaaagaatt cttgcagcaa caatgaaaga  21840
agcacctacc actactgttg actcccactg gcttccagtg gagtagtgaa ccggacccag  21900
taagtccttg catatttctc gaagtcggta ttcaaaccct aattacagaa aaacaaacaa  21960
acaacaacaa caaaaaacaa aacagaaata ggaacacatt acaaaaagaa ataaaatcaa  22020
gaatatgttg ttgtgtctat caaatcagaa taaacacatg cgtattttat tgcctactat  22080
gggcaagacg cccctgcatg tctctcagcg gggggcactg agacccataa tcacagattt  22140
tcactcactt gctcactccc ctgacatctg tagtgcctcc tctgtgtgtt gggcccagag  22200
gaaaaacgag atatggccag ttctgtgata aactccttaa ggtgatggga agatatggga  22260
aattgtgggc tggtgagatc tgtctttgag aagatgcgct ggcagctggt gttgagggga  22320
ggtcaggagg gtgggacggc cagcccgcag gaggtaagag atggcaaagg catgactgaa  22380
gaggggcaac tgagtggagg gggcataggt ccattaactc aagggttatg ggcaccaccc  22440
agtagggctg ctagaaaggc tggaggtaga gtgtcggggt ttgtcagcac ttggggcagc  22500
taaagcaata gggaatggat taaactgtcc aaagaaaagg gtggagtaag agagatgaaa  22560
ctggaatctg aggaattttg gaagtgaatg gggtccactt ttatactaga ttcctccttt  22620
tacagccaag gaaacaaggg acagaatgga gggtgggtaa ctggtgtatg gacactagaa  22680
caggcaggtg gaagatggag aaagagaagc aagcagcaga agtcatccca agatgggtgg  22740
cggggcggag aggaggtggg gacttgatgc agggcatcag agcaagtccc agtcaacacc  22800
caggatgaag caaaccagag tggagtaaga ggaggggctc ccagggaaga cgtgactaga  22860
gcaccacagg agaggtatga gagcctggga aggctgagta ttcagaaaag ctggggacca  22920
cacataatgg caaccacata gacctggtgg gaagagtaaa catcaaattc atcatcgtgg  22980
tctgcaggga gggaggggag gcttcaagtt gatcagtaat atttgctgtc gtttacaagt  23040
gtatgtacac acacacacac atacactcgt atttacacag ccagaggcac atgtgacatg  23100
ttagttctgg gaattacatc cgtgaaggtc tgattatgat tttctctgtc ttttctgtac  23160
ttaaattttt ttctaaatta taatcaaaat ggggagggtg atgacaaaaa taaagcaaaa  23220
agcccaggaa gctgcacaga gagagctctg ggagggcctg ccccatgccg caccctgaag  23280
gctgcactca agtgggagga aaagttggta aggctattgg agtcactgtg aggacagtgc  23340
```

-continued

```
agccacctct tccagcacac ctggctttct gcaagggagg cagcagagtg agagctctgg  23400
cgggaagtgc cagaaatgga gggcctcagt aagtgcagga catcaggcaa gcctgtccag  23460
ggcaggaagg gctgggagga ggaagagaac cactgctaca agatgccctc actgattagc  23520
agcactgcca agttgtggtg cagggcagga gccagaacat agaatctgct ccttcagacc  23580
atgtctttcc acccaggcat ctattcctcc gtcctgctgc ctgtcctgct gcttctctgc  23640
gggaacaccc tcagggtcac tctattcaga gcctcagagc ctataagggg ctgggtgcct  23700
gctgagctgc cttgactgca gctcaggctg ggaggtagag gctgctgggc catcacatct  23760
tttccctgat ttcacaggga ctaagtgagg cctgggagga tggaggggca gaaggagaag  23820
gctgctcagg gctgccagga gcctcacctt cgtttacgag gtaccgtgcg tagacgagga  23880
gccaatggcg gtactcgtgg ctggactgca gggtgagtgc tgctgccacc tggttctcta  23940
ggtaggccag ggtggtctct tgctgcacca catgaggcac ggagaagagc cgggcagcct  24000
gccttcccga gctgcagaga ccaggagagt ttccatgatg ggcagcaggg cactacacag  24060
agtcaggaac tgcccccgtg tgcaacaggc aaggagctgg caggaggcag gcaccagggc  24120
tgccaaggcc tcccgtccac tagccagtct gttggcagat gccagatctg ttgtctgccc  24180
atccccacgc cccagccatg tgcctcctgg cacccttggg gtatctcacc cagcacctgc  24240
catctgggcc cctgaagtga cagggccagt gattgctgcc cccaacccca agatattacc  24300
tgatgcagga ccactaccct cagcacccct agtccgtcct gcccagcctg cctgtgctga  24360
ccagcacctg gggcacaggg gaagggcagg tggagaccag gcctgggcag ggactgtgcg  24420
tgcactgacc caggcacttc cccagggcag gactaaggac agtggccatg gcattcaggt  24480
cacgtacttg gaggtgcggc cctggattat ggctaacggt cctgagcaca gcatggcgtc  24540
ctgggatggc aggctgctcc taaagtctgc acactgagcc agtgagtcct gcttgtcaga  24600
aaccaggttc ctggggaggc aaaggcagga gcagagctca ggaaaaccaa gagatctggt  24660
tggcctcttt gccaaccaga gaaggctggc aaagaggcca cagagaagca gcccctgccg  24720
acacagaaag ccagtagagg ctgagcgccc ctgcacttcc gcacaggcgc ctatcactga  24780
caggtttcat ggtaatgggt ctgatagatc actgttccaa aggaaaaatg agtgaagtga  24840
aggctgtgga tagggccctt gctgggaaca cttcagctcc atatgttggt tcctgatgac  24900
tgcaggcctc tgtgtgcagt gtgctctgat gctcagctca aacactgcca tggtctgccc  24960
acagggccac atggcctggg ccctgtagct agcgagcaat gccaggcctc tacctgcctg  25020
tatttctaca actatcccag actggcagtc cttccacctt ctctggaccc ttctcatcct  25080
tgtgaagaag actcttcaca cacttttaga acagctagat gtctttgtaa atgtgtccaa  25140
aatacaaaga tgcctacaga gagtcaatat ttctcttctt aaataatcag cttatttcca  25200
ttattacagc aatcatatat aatagacaac attttgcaat ttgggggagc aggcagtgga  25260
gatttttttt ttcctttgag acagggtctt actctgctgc ccaggctgaa gtgcagtagt  25320
gtgattacag ctcactgcag cctcgacctc ctgggctcaa gggatctcct gcttcagctt  25380
cccaaggagc tgggactaca gatgtgtgcc actgcacctg gcttatttaa aatttttttt  25440
ttttggtaga gacagggtct cactatgttg cccaagctgg tctcaaactc atgggatcaa  25500
gcaatcctct cagcctccca cagcgctggg attacaggtg tgagccatcg cacccagcag  25560
attttttttt tccaaattca agaaagaagt ctcagtgtga atgtagactt ctgcatggca  25620
gttcttaaca gaaaaggggc taggaggtag caagctttgg ttcttaagga ccaaaggtat  25680
agacagaaga aaagaacttg gagtggctgg aacacaacgt acataattca cgtgtctggg  25740
```

-continued

```
ttaagagctc tgatgtataa attattttgc aagtacaaaa aagggctcca aattcctgag  25800
tggacagagg aaaagtacag accatcatgc ctgggtaagt ggataagcat ccttactaat  25860
tcactgagga agtctgaagt gcttactaag ctcacagaaa ttgactagtc ctgttaaggc  25920
tcctgtaaag cccactaacc tatgctcatg gtggctaagg gggccacagc aaaaaccata  25980
aaaattttgg ggctttttca aaaagtgcct cctgaaaata atgcaggagg acagtgctcc  26040
tgcacacagg ctctgagggc agaggccata ggctgcagtg tcctgctggg acaggggagc  26100
atgcacagat agtcaatgca gcctgcactc cagggcctga ctctcaggaa aagcagggct  26160
aggcagccct gtaggccacg accctttgct ctgctgtcta gagcagacag acactcttcc  26220
agggaatagg actgggggtc agcttgctta ccatgtggaa agtgacggat taaagcagta  26280
cgccttccca tcggacaggt tcattactgg gattccatgc tgcgtcagca agatctgtga  26340
taccgtcata tcacttcctg aggacagcat gggaatgagt tctgggtgtg ctctgatcag  26400
caagtgtttt caaacatatc aaaggagaaa tctgtactct aggctcccac agtcccagca  26460
gcaaatgcat caacactgcc ttggcaaata gggagggcaa gccattctcc ttgccacaca  26520
ccaggctttt gtcacctctt ggggacccat tcaaacatgc ccccaaaaag tgtgtgtctc  26580
ctgcagcgta accacacctc ctgcctcact gagagccctg ggctgaggcc agagcctggc  26640
tctctgagcg gggcccttct gcagcatcag acatgaactt gggcccccaa aagagtaggg  26700
acagcctgtt gcctgcatta cctgccagga tggagtgtag agactcttct ttcaccacaa  26760
ccacctgtct gtgaacatcc ctaggaggga gacagggaac agtttactca ccaacccagg  26820
taaacacatc agagtgtgcc ttggctgctc agacaccctg gccctactgc atgcgaccct  26880
aaccctggcc tctcctagtg agaggggctc tgggctacga gtggcttctg ctctccatgt  26940
gccactacac tccctctgca ttaaggctgc agcacaaagc ccaggcaaca gagccatggg  27000
gaaccctcag cgcccacacc actttggggg aagccaggcc acagcagcca catcaggaac  27060
atggccacat tctgccagct aagactccat ttctgatgaa tcttgcatag gaccctggca  27120
gtgcaactgg tcgcatgggc tgctccagta aggaaataat cgagcaggca agctgcctcc  27180
atccccccttg cacactaccc ctcagccctc agcctaccca gggcacccaa cacaagcaat  27240
atcactaact gctcagggcc tcttctgggg cctgatggcc agccttgtcc actgccttcc  27300
ctgcccctgc agtgaggtgg ggcctacaca gccctgtcct gccctggctg aagcccaccc  27360
caccctgtgc ctgcctctca ccagacagag agtgtggctg cagcggtgag cgccatgacg  27420
taggagcctg tgcaatgcaa agtagagatc ggggatggca ggaggatggg agagaggaga  27480
cggcgaccac aggtggagaa cactgacagc atcctttttt cacaggcgac acacaccacg  27540
tcactgagaa ggcagagtgg gggcaggtgt catgggggct gagtgctgca gccaagacag  27600
tagccctgga agtgtgggcc ttccctctgc ctgggcccaa caagggcctc ccctgagcag  27660
gtacagccag aagggaaggt ggattgggtc agggtagggc tggtggggct gttggagcct  27720
ccctgagatc ttggatgaaa gaggcttctg tcctatttcc acaggctgcc tgcgctttcc  27780
tgagctcatg ctgatgctga ccaaggggtg tgggggcttt ggagagccaa tgcctctgat  27840
gatcacccag gaaacatgcc ttgctcatca gataaggcca catagtaccc acaggacagt  27900
ctcctggctg caactagtca gaccagtcct gagaaggtct ctaacaaggc aggctaagag  27960
aagtatgggg atgacagcat gcacctctgt gtccaggggg ctgtctggct ggcgtgggag  28020
atgtgtgtcg ctcccaaaca aggagtgcgt tacagaacag tctggacact gtccagcttc  28080
```

-continued

```
tcccgagtga ccaccaggcc cctgggtggg ccctgcacga gcaggctgct gccttcccag  28140
acagagcccc ctaaggcaca gccacaggcc cagggtgagg ctggagctca gacgcaggca  28200
ggggtagcag atgtacagcc agtacagtga gatcctggcc acagtaggcc acccagagcc  28260
ctgctttgtg tcacttctat cctggtgagc cagtcactcc agcaggctca aggaggtcag  28320
ttaaggaagg agctctgcca actgccttcc taatgagcca ctattgctac tggctccaaa  28380
aagggagagg caagtgagat gcttttgttt acaaatgttt acttggagag tatgaatcag  28440
agaacactct aagcagcacg ggcaacaagg agctctctgc agtgctgtga ctgaattctt  28500
atttttctg agacagagtc tcggtctgtc gcccaggctg gagtgtagtg gcgtgatctc  28560
ggctcactgc aacctccgcc tccccagttc aagcgattct cctaccttag cctcccgagt  28620
agctgggatt acaggcacat gctaccacgc ctggctaatt tttgtatttt tggtagagat  28680
ggggtttcaa tatgttggcc aggctggtac tgtgactgaa ttctatctgc ccatctctgg  28740
tggtcagagc ctggctcaag ccagcccact gcaaagaaag ccatcatttt tgggctgtaa  28800
cactggggaa caggtctgca ggctgggcct gaactgggca ggactaagca ggaggagagg  28860
tcccacgtgg tccagcaggc ttgccccaca gctgccatgt cactgtggga gaggctgtgc  28920
cgacacccct tagccctcag ctgggcaagc cacctgcctt gaggggaggg acagagagtg  28980
ggagcctgtg gaagcatctg atacacaggt gcctgggact gggaatttaa atggctcatc  29040
tggaggggga atttgaggga ggaacagaac aaacagtggg gtcccctagg cctaaaaaca  29100
caaaactcac tcagggccca cgagaattgt ggtctaagac ctaaggccat gtgctttgac  29160
acaagtaaaa gcatttacat gggacctcat ggcagatgat taagggtgta attatgatga  29220
ctgtatctgg tcctgactgg gatgctacat cagacaggaa cctgaggaga aacattggtt  29280
ccccttccac attgaacaca ggtagggaca gggctcacgt acagttctag gaacccaggg  29340
gaagatactg ggtgactaat cactgaatca aggtccccct cacagtgcag aatctggcat  29400
gggctgggat ggggacttca gggacagtca gaaatccatc ctgaccaact tggatggaaa  29460
tctgggatcc aaaaaaggaa ccagcccagg tcaaggtgag ccaggcacac ctcagtgtgg  29520
aattcgagac tttggggatc tggctggaca agggaatcag gccatcaggt tcaaagcttg  29580
gcctgggtaa ccctcaaggg ctcagtttcc ccatctgtaa cacggggata ctgatgctga  29640
ccttgctggg tgctgcaggg actgagatga caagcacata tgcttggcct ggagtgaagc  29700
ctggtgtgag tctctgtggg agctggtgct cccagggtca tgcacctccc ctagacaggc  29760
ccaggcccag aatgatggca tgtgtgcctg tgtcacctgg gccggctaag gacctgccca  29820
cccttaccag ctgcccgcag cagtgaggat ccggctggtg agtaccgtct cccactcctt  29880
cccttcccgg ttgcacttca ggcggctcag cttcacgccc cccaccactg tcacttcatt  29940
ctccacctca atgtacatgg aaggatcgga gctgacctgg atgaagtaaa cacacgggtc  30000
tgctcagaca agggccgcag cccaggtgac atgctccaag gctctgtagc ctggggcccc  30060
aaggcagcag caggatacag aggcagactg gctggccaag agaggagagg gagggcaggt  30120
agggcaaagg ggctgagcgg gaggcccaga gggccagaca tgtggccccc aaggcaggga  30180
gaatgctggg agctggtttc taccctgtca tttgtgtagt tgaacagcca gagaagagaa  30240
gcagtgccag ggttaaagac cccaaagtct cccaaccctg ccacttcatc tcacaaggga  30300
gtaacgtgcc caaaagcaca ctgcaaagga ccgagctggg agtgagactt gggtttctag  30360
cctcctactt gaagaatctt caaagatggc agtgtttggc aagattagag accatgtcag  30420
tgcttggagg gaatgtttag aaaacccccca aaggggctct ccagttcctg tggtggtgag  30480
```

-continued

```
acttggtctg ctcaactgag actaaactgg caggggtgtt tatggcacag catgtatgaa  30540
aagcacctaa ttcagtgtct ggcaccaaat gggctcagcc acacgcgtgt gtggggagct  30600
gaccaacaga ttttccctgt ggtaaaatag gcagaaccac caaacagtct gtgcttgtgt  30660
ggccactcaa gtgggtgagc tgggccgagg gctgactgcc cccttcacag acccagaaat  30720
gacagtccca agcagtgctt ggagggcaag atgcctaggg gaagggctgg aggagtttgg  30780
gagagttctg tgctgagaag cagggcaccc aggagggaac ctaagtcaga acacctctga  30840
gtgcaagagc acgtctgaac gctgctgacc actggagggc ccctgcctcc gttcacacca  30900
gcaataagaa caaaccctat gggttcctac cctttggctt ccctgcttca ttcctctgca  30960
ctgtggccca gaaggaccta tggtaggaag ggctgacgcc tgctctctgg tgccctgtga  31020
ggaccaacct gggctcagag cagtgtgtag ccagtgggaa gtgacccgca agcagggtcc  31080
aagaaggctg ctcgaggaca cgcacctgag ctgaggtaca agggtatgca gagaggcagc  31140
agtgtgtgtg acggcaccat ggcaggagag gcctagatac tatgctgggc caagtgacca  31200
ggagggctct gggtataaag gattatttac tccagaattg tgttttggat aaccacatgc  31260
ttacaagctt ccattccaag agctcaaaca actctgatga ttgactgtgc cagacactga  31320
gaagacaaag ctagcaggat ggttgggaga tagattatga ccacacattc ccacagacac  31380
caagcctgag gctgcccagg gctgtgtgtg gaggtggagg tggcttccag ccaggacacc  31440
tgagaggagt cctgaagagc accagaacat gtggtggtaa tggcagcccc agcagctgga  31500
atcccaaggg caaagccaga cagaggctat gggtgagtga gagtggaggc tggcaatttc  31560
gctaagagtt ggtgggtacc ccgatctgct atgacttctc ccagaaggtg atggagagcc  31620
actggaaacc aatctccaag gaagtgacaa gataggattt gtatgcagta ggggacagag  31680
aatgtctggg tgtgcctgag ggagaactgg cagggtccta gaacttacct ggagggtgaa  31740
tgctctctgg gggcttggaa ttggcagctt cagtgcaagt gctggtgcag acagacacat  31800
ggcctccttc tctgcggtta gggcagctgg agactggaag agccagaaac gttcctgagc  31860
cttgctctaa cactacgggg tagcatttgg taaaggcagg tcacccagaa gtgaggctga  31920
gcctgcgacc agagcatttc caccctggga gggaggaagc agaggggaat gctacaagga  31980
tcctaacctc atggacaagc cagttgatgc cagggaacct gctcaagggc cctgggtgag  32040
tcaagggcac atctgaggga gagcgtggcc tccatgctac attccagggg ctgcatgtct  32100
aagccagctg gttcccaagg tgacccaccc agctgaggct taccatgcac acagggcctt  32160
caagctctaa gtacagaaag gtgggctaaa gaaggcagga tgggcccact ggcctcacct  32220
ggacagacag agacacaggc atgagacgag agtccttccg aggccgccct ttcttcttct  32280
tctctactgt ctctacctca agctcaagtt ttcgcttgga cagtgaggaa gccttagcca  32340
aagggacttt ctcatcgctg tcactgctgc tctccaggag gtctcggggc ctcagctctt  32400
tcacaaggtt ctgctctttt aacctgcaca aaaacattac atcacacttc ccttcagaaa  32460
ccattcatgc aagaaagagt gaagtgaaat atttaaagtg cttaaacaaa cctcttgcca  32520
acctagaatt ctgtgtccag tgaaattatg cctcaaaagt aaaggagaaa taatgacttt  32580
gtcagacaaa aataaacaaa gagacaccgg aatctgttgc cagaagacct gccttgcaag  32640
aaatgttaaa agtctttcag agagaagata aatgatgcag gccagaaact cacatctgca  32700
tgaagaaagg aagagtgatg ttagagaaaa aaaacaatga acataaaata gaatcttttg  32760
tatttcatat tcccaactga tctgagagac aactttctgt tcaaacaaat aacagccacc  32820
```

-continued

```
atgtcttgaa ttactatagt ttatgaatga gtgaaataag tggtaccaat gtcatagggc  32880
atggaaggaa agagtgggga actctttcta ctacccatga agtggtataa tattatttga  32940
aagtagagtt aggttataaa tgtttattgt aaactctaga gcaatcacta aaaaaaattt  33000
tttaaagcat aattaataat gctgagagga gagaaaattt atttttattt tattatcatt  33060
tttttttgg agatggattt tcactcttct cgcccagcct ggaatgcaat ggtgtgatct  33120
tggctcactg caacatccac ctactggggt caagtgattc tcctgcctca gtctcccaag  33180
tagctgggat tacaggtgtg tgccaccacg cctggttaat ttttgtatta ttagtagaga  33240
cagggtttca tcatgttggc caggccagtc ttgaactcct gacctcaggt gacctacccg  33300
cctcagcctc ccaaagtgtt gggattatgg tcgtgagcca ccatgcctgg ctgagaaaac  33360
tgaatcatat aaaatactca gctaaaacca gagaaggcag aaaaagaaga taaaaagaag  33420
tgaagattaa aaaaaaagaa taaggccggg cacggtggct cacgcctgta atcccagcac  33480
tttgggaggc tgaggtgggt gaatcacctg aggtcaggag attgagaccg tcctggccaa  33540
cacggtgaaa ccctgtctct actaaaatac aaaaaattag ccgggtgtgg tggcgtgtgc  33600
ctgtagtccc agctactcgg caggctgagg cagggcaatt gcttgaaccc aggaggcaga  33660
ggttgcaggg agtcaagatc gtgccactgc actccagcct ggtgacaaag tgagattccg  33720
tctcaaaaaa aaaaacaaaa aaaacaaaaa aaagaaatgg gtttatgttt ttaaaaattt  33780
aattttaact acaaaagaca aagacagatt aatagtaggt ggacacagtg gctcatgcct  33840
gtagtcccag ctacttggta ggctgaggca ggaggactgc tcgagcccag aggcttgaga  33900
gcagcctggg caaaataatg agaccccatc tctaagaaca aaaaataagt aaataaataa  33960
atacaagaaa aggggtgatt ctaactatat gacaacctgg aacaggcaaa accatggaga  34020
caataaaaag atcagtggtt tccaggggtt ggggaaagga aggtaactat atgaagcaca  34080
gaatttttaa ggcattgaaa ctattctggc tgggtgtggt ggctctttcc tgtaattcct  34140
acactttggg aggccaaggt gggcagatca cttgaggtca ggagtttgag actggcctgg  34200
ccaacatggt gagaccccat ctctactaaa aatacaaaaa ttagccacgt gtggtggcat  34260
acacatgtaa tcccagctac ctgggaggct gaggtaggag aattgcttga acctgggagg  34320
cggaggttgc agtgagccga gatgcgactg tgccaccgca ctccagcctg ggcaatagag  34380
cgagactctg tctcgaaaaa acccaaaaaa ctattctgta agatatataa tgatgaatat  34440
atgtcattat acattggtta aacccgtaaa acgtacaaca tcaagagtag acccaaatgt  34500
aaactttggg tgacggtgtg ccccactctg gtgggggatg ctgaaagtgg gggatgctat  34560
gggtatgttg gggaggcggg catgtgggaa ctctttgtat ttcctgttca atttagctgt  34620
gaacctaaac tgctctaaca aataaagtct attaaaaaaa aaaagcgagg actggagaaa  34680
gacatgccat gataacacta atcaaaaaaa ggtggtgtag ttacgtaagc aaagcaggca  34740
tcagagacag taaagttatc aaggataaag agggacatta cacagtgata aagatgaagg  34800
agtcaattct tcaagaagac agaacaattc tgaataagta cacaggcata ccttgtgtta  34860
ttgtgcttta cttcactgtg cttcgcagag actatgtttt ttttacaagt tgaaggtttg  34920
tggcaaccct gcatcaagca agtctattgg cgccatttcc ccaacagcag gtgctcattt  34980
cgtgtctctg tgtcacattt tgataattct cacaatattt caaacatttt cattcttatt  35040
gtatctgttt tggtgatctg ccattagtga tctttcatgt tagtattata actgttttgg  35100
ggcactgtga accacaccca tgtaagatgc tgaacttaat caataaatgg cgtttatgtt  35160
ctgactgctc caccaactgg ttgttctcct gtctcccttc ctctccccag gcctccctat  35220
```

-continued

```
tatctgagac aaaacaatat tgaaattagg ccaatcgata accctataat ggcctctaag  35280
taagtgttaa accaaaagct aaaaatgatt aagcttaaag aggaaggcac attgaaagct  35340
gagacaggcc aaaagctata ccttttgcac cagttagcca aggtgtgaat gcaatggaaa  35400
agctcttaaa ggaagttaaa agtgctactc cagtgaacac atgtttgaaa agaaagcaaa  35460
acagccttat tgctaatatg gagaaagttt tagtgctctg gatagaagat caaaccagcc  35520
acaacactcc cttaatccac agcctaatcc aaagcaaggc tctaactatt ttcatttcta  35580
tgaaggctga gagaggtgag gaagctggag aagaaagtct gaagctagca gaggttggct  35640
catgaagttt aaggaaagaa gctgcctcta taacataaaa cggcaaggtg aagcagcaag  35700
tgctaatgta gaagttgcag caaggtatta gaacatctag ctaagatcat ggatgaaggt  35760
ggtaacacta aacaacagat tgtcagtgta ggtaaaacag ccttctatca gaagaagatg  35820
tcatctagga ctttcctagc tagagaaggg aagtcaatgc ctggcttcaa agtttcagaa  35880
gacaggctgg ttatcttatt gaagtgaatg cagctggtga ttttaggtgg aagtcaatac  35940
tcattaacta ttccaaaaat cctagggccc ttaagaatta ttctaaatct ataaatgcaa  36000
caagaaagcc tagatgacag cacatctgtt tagagcatgg tttactgaat atttgaagcc  36060
caatgttgac acctactgct tggaaaaaaa gattcctttc aaaagattgc tgctgactgg  36120
caatgcactt ggtcaaccaa gagctctgac agagatgaat gttgttttca taccaactaa  36180
cacaacacac attctgcagc ccatgaacaa ggagcatttt catctttcaa gtttcattat  36240
ttaagaggta catttttgcc tgtggtccca gctacctgga ggctgaggca ggaggactgt  36300
ttaagtccag aagttctgag ttatagtgcg ctatgccaat tgggtgtcca cactaagttt  36360
ggcatcagta tagtgacctt ctgagagcaa gagaccacac caggttgcct aaggagaggt  36420
gaactgccca gtttggaaac agagcaggta aaaactcttg tgttgataag tagtggtact  36480
gtgcctgtga ataacactgc actccagcct gggcaacata gcaagacact atctcttaaa  36540
taaattaaaa ataataatta aaaaattttg tgggccaggt gtggtggttc ccgcctgtaa  36600
tcccagcact ttgggaggct gaggcaggca gatcacaagg tcaggagacc gagaccatcc  36660
tggataacac ggtaaaaccc cgtctctact aaaaatacaa aaaattagcc aggtgtggtg  36720
gggggcgcct gtagtcccag ctacttggga ggctgaggca ggagaatggc gtgaacccgg  36780
gaggtggagc ttgcagtgag ccgagaccgc accactgcac tccagcctgg gcgacagagc  36840
gagactccgt ctcaaaaaaa caaaaaaaca ttttgtaagc tatatcagat tcctctggca  36900
gatctgggca aagtaatctg gaaagtattc accattctag atgtcattaa gaacatcagt  36960
gattcatggg atgtcaaaat atcaacctta acaagagttt ggaagaagcg gattccaacc  37020
ctcatgaatg actttgaggg gttcaagact tcagtggaaa aagtcattac acatgtggtg  37080
gaaacagtaa gagaactaga agtaaagcct gaagatggga ctaaattgct gcaatctcat  37140
aaaaaacttg aacaaatgag gaggtgctag ttagggaaga gcaaagaaag tagtttctta  37200
agatggaatc tcctggtgaa gatgctgtgc atattgttga aataataagg gatttattta  37260
tttttatttt gagacagatt ctcattctgt tgcccaggct ggagtacagt ggcacaatct  37320
cagctcgctg caacctccgc ctcctgggct caagggattc tcatacctca gcctccccga  37380
gtagctagga ctacaggcat gcaccgtgac aaccggctaa ttttttgtat ttttaataga  37440
gatggggttt caccatgttg gccaagctgg tcttgagctc ctgacctcag atgaaccacc  37500
cacctcggcc tcccaaagtg ttgggattac aggtgtgagc cactgcacct ggcctttatt  37560
```

-continued

```
ggcatacatt gaaatatcat gccatcgaaa tcctttttgt aaggttggta ctaatgcctc  37620
ctttcatttc tgattgtatt tatttatata ctaatcatac tttaatacaa ctgtatgtcg  37680
ggcttttttc aaataacatt ccatctgaac tatttttcca tagtacagtc atcctttggt  37740
atctgcatgg ggattgattc caggaccccc aggagatatc aaaatccaag gatgctcaag  37800
tcccgtatat aaaatgattt agtatttgca tataatgtag gcacagcttc caatgtacca  37860
tttttttttt tttttgaga cggagtctca ctctgttgct caggctggaa tgcagtggtg  37920
tgatcttgga tcactgcaac ctctgcctcc caggttcaag tgactctcct gcctcagcct  37980
cccaagtagc tgagattaca ggcacgcacc accacgcccc gctaattttt gtatttttac  38040
tagagacgaa gttttgccat gttggccagg gtggtctcga attcctgacc tcaggtgatc  38100
tgcctgcctt ggcttcccaa agtgctgaga ttacaggtat gagccactga gctgagcccg  38160
gccagcctcc tatatacttt aaataatctc tagatcacgt atacatagta caatgcctaa  38220
aaataacttc atttgcatgg attcaaagta gtacttggca tgtagcaaat tcagtttttg  38280
ctttttggaa ctctgtggaa tttcttttcc caaatatttt tgatccatag ttggctgaat  38340
ccatagatgt ggaacccatg gatacagagg ggcgcctgta ctttggtcct tataaacatt  38400
aaagagaggc acaacataat gaatagctta cttcctcaac acctctcttt tgaagaagtt  38460
ggtaaatgtt tctcataatg ctgtgttaaa catctctaaa tatgacagac tccctggatc  38520
acaggtgcta tcactgatct tatttcctca aggagttcac catgagtgaa ctcctgtcta  38580
gtatccaaga gccctcatcc ctgcctgcct tcccactgct aaccagcctc tggcctgtta  38640
gcccctcctc tgggcactgt cttcagctgt tttccctgct agtcacctgg gtcaaagaaa  38700
tgtgggcaga tacacacacc agcgtgtaga atcctggatt cttttcattt gtatccatgt  38760
gaaaaactgg gaagacaaga ggcccatgac gctgctctgt gaaactgaag tgtctgttcc  38820
cctttcttct aatgtcctac aacagggcaa agcatccatc tgtgggtgta gcttaatatt  38880
ctggaagtcc tgagtcagtg ctcctcaaaa tcctttaaaa attttttttt ttttaaatgt  38940
cagacatttg cctcttcaaa gagcttgttt tactatgttg taaaaatcag atcatgtaca  39000
ttttcatatt aaattttttg ttaaataagc ttttggaaca gtcaaaaatg ctttctctca  39060
gatgttctga atatggaaat ggaatattag cttgttctaa tttttctaa catgaatttt  39120
cctggttcag actgatctga aagggtttca tgtattaaaa tgagagaatc ctattgtgaa  39180
acatggaaaa aaagtcagac ttttatgtaa ctatcgtttt gtaaaataca gcgagaatgt  39240
cacagcaacg tccaactatc atctaagttt ctaaggcggg cggtggcttc ctgagctcac  39300
cacagcactg gcccatgaca tacacttgct tggcactgcc gagctccagc tgctccaccc  39360
tctctggttg ggacccctga gagcccttag gagtctcccc acctcctgcc tctgccagat  39420
gccccattca gggactctgg ggccagtggc ccactgggaa ctgcacctcc ccagcctgca  39480
tgtgggcttg tatcagttgt tacaatatcc ctgggagcac caggtaaatc gatctacagc  39540
agttgcccaa tgggtctaga catctgtgaa gcaagagcac agctggccag ggctgccccc  39600
cttacaaatg ggctccatcc taggttctgt ctgctcaggc ctacttgccc tgtagtcact  39660
tacctcaggt ccctacgtgc ttctgcctga cacctggcct taggagaggg tggagcagaa  39720
gacccacagt ttcacccagg gctgctaccc tgtacctggg atgctagcat ttggctccca  39780
atccacctga ggctcttggc taggaagtgc cagtcaggtt gcaggggtct cactgcccaa  39840
ccactgtgac gcacaatgaa ggaacaacag caggagctga catgtgctgc tcaccgtgag  39900
gcaaggacca agatacggct ttacaggcct aaggttaagg gatacctcct atgaggagag  39960
```

```
ttttcctggg aggtccattc tgcctgagag gagatggact cagaaagacc atgtgtctca  40020
agattatccc tcctccctct ctgaggaagt gggggacctg ggcctaactt gcaaggtgta  40080
ttactttgcg caccacccct aaccactgca tgacactgtg cctcaaagaa aatctccact  40140
gaaggccagg tgcggtggct cacacctgta atcccaacac tgggaggccg aggtgggcgc  40200
atcacttgag gtcaggagtt caagaccagc ctggccaaca tggtgaaacc ccatctgtac  40260
taaaaataca aaaattagcc gggcgtcatg gcatacacct gtaatcccag ctactaggga  40320
ggctgaggca gaattgcttg agcctgggag acagaggttg cagtaagcca agactgcgcc  40380
actgcactcc agcctgggcg acacagcgag actctgtctc aaaaaacaaa caaacaaaca  40440
aagaaaatct ccactgatgg gtgttttctt gtttcgtttt gtttttgttt tttgagacaa  40500
gtcttgttca ggctggagtg caatggtaca atctcggctc actgcaatct ctgcctcctg  40560
ggttcaagcg attctcctgc ctcagcctct cgccactaca cttggctaat ttttgtattt  40620
ttatagtaga gacggggttt caccatgttg gccaggctgg tctccaactc ctaacctcag  40680
gtgatctgcc cacctcggcc tcccaaatta caggcatgag ccaccacgcc tggcctgttt  40740
tgtttttatt cttgttttga gacagggtct cactctgttg cccaggctgc agtggagtga  40800
tttctgctta ctgcaacctc tgcttcctgc gtttaaggaa ttctgctgcc tcagcctcct  40860
gagtagctgg gactacaggc acgcaccacc atgcccagct aatttttgta ttttcagcag  40920
agatggggtt tcaccatgat gaccaagctg gtctcaaact cccggactca agtgatccac  40980
ctgcctcggc ctcccagaat gctaggattg actacaggca tgagccactg caccaggcct  41040
ccagtgatgg gtgttttaaa gggctcctcc tggttttcat tgagaatcaa tacaagaaaa  41100
cagccacatc aagaaagtat ctgcattttc tgtaaggcct ttgttaaaga tactgggact  41160
tgttttattt cattttcctc atataaggat ccaacccaac ctgagaattc agcaccaggc  41220
tcctagaagc tcactatact cattctggct ggaaagcagg aagctcagcc ccaagtgaat  41280
gctcactcac tgccactttc aagtgagaaa ctgaggatga caaatgtgat ggtggcccct  41340
tattatacag atcttgctac agctgtattt atggctggac ggtcttgtga gaccctgtgg  41400
acatagctgc tgaggaacca acccttgtgg caccaggacc caggatatac agtcaagatt  41460
ctgtctccag aagccaatct aagggctatc ctcctggctt ctcattcagg gtatgcacta  41520
catgagagat aagggccaca gaaagccaca aagcaaacat gagtgtcttc ctcaataagc  41580
aggactgtct gtggcacact gtagtttctc tcaggtgggg aattcatttt atttattttg  41640
ttcagaactt gctccatttc aaaatctgag gtttcttcac cttctggtaa gcctcttaac  41700
tccctcttga caactacccc gcagcacatc ctcctggggg gactcctctc tattgccctg  41760
tcttcagctc cacctcctca cctctgtgcc actctggcca attttgtaga ctgaatgttc  41820
ttttcagctg gttctgatct gctctctgaa atgcttgttg acttttaaac tgcaatgatt  41880
attatttttc ttttctaaaa gtattttttt tggttcattt ccaaatctgg tttttttttg  41940
atagtgtatt attcttttaa tttttattga gatatatata tcataaactt cgccacttta  42000
aagtatagaa tcattagctt ttagcatatt cataaggtta agcaaccatc atcactatct  42060
aatgccagaa cattttcata attccaaaaa caaactctgt acccattggt actcactcct  42120
tatcctccct ccctcagacc ctggcaacca ctgttactct actttcttta tggattttcc  42180
attctggaca tttcctatca atggaatcat acaacctatg atcctttgtg actggcttct  42240
ttctcttagc ataatgtctt taaggtttat cgttattgta gcacatgtaa gcattccatt  42300
```

-continued

```
cctctttatt gttgaataat attctattgt atgggtaaac catattttgt ttattcatca  42360
cctgatggac ttttgggcta tttccacttt ttggttatta tgtacagatg tgaacattca  42420
tgtatgagtt attgcatgga tatatgtttt caattctcct gggtatgtat ctaggtgtgg  42480
gaactgctag gtcagatgat aactctatat tttaccattt gaggaacttc cagactgttt  42540
tccaaaggtg ctaaaagact ttacattcct accagcatgt atatgagggt tccctttaga  42600
gctaattttt gtttacagaa tagagtatta atctttcctc acattttgtt ttagctttca  42660
tgtccttcaa gacttaagca tactttatag tgccatctga caattctatg atcacaggtt  42720
tataggacca acacttatta tctgactatc tgatctttta attacagacc tccaaatggg  42780
tatgaagtat ttcattgaag ttttgctttg tatttccctg atggctaatg atgttgattg  42840
aatttttatg tacctgtgct ttgtatatat tctctgcagt ttctcttcag atcttttgct  42900
catttttaag ctgtgttatt cgtcttttta ttgttgaatt gtaaaagtta tttatataat  42960
ttaaattctg gactttaatt agatgggatt tgcaaatatt ttctcccatt ctgtaggttg  43020
tctttcaatt ctgatagtgc tttggaagca aaaaagcttt taattttttt tttttttttt  43080
tgagatggag ttttgctctt ttgcccaggc tggagtgaag tggcgtgatc tctgctcact  43140
gcaacctctg tcccccgagt ttaagtgatt ctcttgtctc agcctactga gtagctggga  43200
ttataggcgc ctgccaccat gcctggctca tttttgtatt tttagtagag atggggtttc  43260
gccatgttgg ccaggctggt cttgaactcc tgacctcagg tgatccaccc acctcagcct  43320
cccaaagtgc taggattaca ggcgtgagcc accgtgcctg gccaagcttt taatttttaa  43380
catggttttg taaagatgag gtcttgccat gttgctcagg ctggtctgaa ttactgggcc  43440
ttctgtctcg ggcttccaaa gtgctaagat tataagcatg agccattgtg tccagccaaa  43500
agttttaaat tttgatgaag tccaatttat cgattccttc ctttagttgt ttgtgcatta  43560
ggtgtcatat ctaagaaaca gttgcctaat ccaaggtcac atagatttct atctatattt  43620
tcttctaaga gttttatagt ttttgctctt acatttagtt ctttgttccc ttttgagtta  43680
atttttgttt atagaataca gtattaatct ttcctcattt tgttttagct tttgttccaa  43740
ttttgtttta gctttcatgt ctttcaaaat ttgttccaat tttgttttag ctttcatgtc  43800
tttcaagact taagcatatt ttatagtgcc atctgacaat tctatgatca caggtttata  43860
gaaacctaag tctcccagta agtatgtctc ctgacatttg tgcatgacag gctctttctt  43920
cttgtgactg tggattttat gatcatctaa acagtgcttt atcagtggta atgctgtaca  43980
ccctggccca aggaatgtca ctgcatggtg gatacgcatc tctgccaagt gcctctgaac  44040
gtcaattaga ccaggatttc gtttgtgttc atttctcggc ttggcgattt ctatacaaca  44100
caagtagtat taaactggcc ctgaatccac atgagggcag acctgtggtt acacagtctc  44160
aagggaagac tgttatccca acccaaaaac aggctgagac attccaactt ctctgctagt  44220
tcttgtgctg tcagttgggt tttcccaggt ctgcctcagt cctttttaa gcagcttgac  44280
tttatgctgg tgacttaatt ccaactccta catggcttag accccaggcc ttgtctcaag  44340
tcgatgtggt cattaaaact caaggtcctc agtcaagacc cctagccttg cacccatggt  44400
gcagttctgc tcactgctct ggcttttttg ttcactctta gattttagac tctgggtact  44460
gctctttcct gtgaactagt tattcatttt agggacgagg gttgcattta atccagcatt  44520
tcaaagtatt tagaagcatg gagaccgcgc gcggtggctc acgcctgtaa tcccagcact  44580
ttaggaggct gaggcgggtg gatcacctga ggtcaggagt ttgagaccag cgtggccaac  44640
atggtgaaac cccatctcta ctaaaattac caaaaattag ccaggtgttg tggcaggcgc  44700
```

```
cagtaatccc agctacttgg gaggctgaag caggggaatc aatcaaacct gggaggcgga  44760
ggttgcagtg agcagagtgg ctaggacaat agacataagc cacaacacct ggataatttt  44820
tctggtagag atacgggtct cactatgttg cccaggctgg tctcaaactc ctggcctcaa  44880
gcgatcctcc tgtcttggcc tcccaaagca tttgggatta caggcatgag ctatcgcatg  44940
tggcctgcat tgagttaatt atgaaacaag catgattaga ttacagagca gactacaaga  45000
ttccacacca agtttataga tacagcatca aacttgcaga aagggtcctc ccatgctagc  45060
ttccaggaac tgttttccaa ggagaataaa tcctgtccag acatgcagtt ctggacaggg  45120
cttttcataa gcaaagcccc agaggtagca tgctgtggct ttagctccaa atcaccatct  45180
actgcaagga caggtcacat acaaatgctc ctttcattgg gcacctgctg gctgtgtggc  45240
tactgcaagt ttctgaccag tgtccttgta cttggctgat ggtggcacag gctagggtgt  45300
gtctgcccag ggctgctgag ccctataaac ctcgcagtgg ggtgcaactc ttaagggaca  45360
gctcttaagc cccaaagtc cagcccacat ctgcctctcc tctcctaggc tctgactcac  45420
tgggatgtga acttagctcc ttgtcaagct aggcttggag ggagggggccc tctcaggagg  45480
cagagaactt cagtgccaat ggcagaggct gcagacattc gctctggcca cctcaggagg  45540
atgcactact gcaaaactcc aagaaataaa gaactacaac ctgcgtgatg tcacagctgt  45600
gtttgagggg agacccagag aatggataag cagcatagtg tccacaagag ctcagaagcc  45660
aatctgactt gacaaagacc tcacttacat catttttatt gcagctctct acctctggtc  45720
agtttctgag tggaaggccg tcacttccat gatgtatcaa tatcagagtc ttccacctct  45780
ccaactaatc tcatgctctc ttccgtgcaa actctgggct ccatccaaac accattattc  45840
tcagttcagc ctctgcactg accaatcctt gtgcctttga ccttgtggtt cttttgccgc  45900
gtcctccccc atgactcctt ccagccacct tcccacttca aggaaccacc tctttctcct  45960
ggtggctcac taagggctct gcagtcttgc tcccatgtat tgagtggcta gagtcttttc  46020
cccaacagga aggcaggttg cttggtggga acactgccac tgtgctgttg acccatgcct  46080
gcaccctgcc tggtccttca gggtcctgca gctaccacct acctttccac agctgtcgga  46140
gtcatgctgg tcagggcagg agcacctggt gtggctttgg accgctctgt gaaccgggag  46200
tcaaacgctt tcatgggttc gatcttggac ggggtcgtta acacagaagg tgacaatgca  46260
gcaggagtag aggtagcatt catactgggg tgaagaagag gggaggcatg tcaagcgcaa  46320
tcctgaaagg atctggaggt ctagtatttg cattatttgg agcctactaa aaaaggcaca  46380
aatatcaaac ttccataaac acaaaaaatg tcaagataca atctactact cccatttctt  46440
taaaattttc atgtgtcaaa attatggaca cctagaaggt tgtgagcaaa tgcattcaca  46500
tttccccctt tgcactgttc tgagagcttt tgcgggtaga atgaggccta gaacatggtt  46560
cttacaaccc ttttctctag tcacactgcc ctatctccac aacttaaata cagcacctct  46620
accccaaacc actccagcca ctcacctttc ccactttgac aatgagtctc atgagataag  46680
cctgcacctg gggtcctgaa gccatggtct gcttttaccc ttagtcaggc atcctccatc  46740
ctgagcggcc cctcccatat ctccctgtga cagtgtcaca ttcttagcat tatgctccaa  46800
gtgctcatca cacaactttc atcttctatt ccacagagaa aggagaggcc aggcagaagc  46860
ctgcctggtc catccttcat gtccaagccc acaccacacg ctttgggacc atggccactg  46920
gacctcctcc taagcacacc caggctaaca ccttccactc ctatctgccc agacaccaca  46980
ccacatgcct ggtagtcacc ctggacagcc ccattcttct cctccatgat ctgtggccac  47040
```

-continued

```
tagaatgggc catccccaca gagttctcag atctggcatg gtctgtcctt cccaggctcc  47100
cttcgtcctg gcatgctttg cttcctcact ggtcttgctg ctcagtcttc tcttcctacc  47160
ctctcagggt ccccccaggg cagtgaccta atgtttgggc atgccttcac agccatggtg  47220
ctagcaccca gaagtaggag gctgaagtaa cataagactc cattccacca atggagaatt  47280
gctctgacgg tatcagctgt atcccagaag caggggggctg cagtaacaca agactccatt  47340
ccaccaatgg agaatcgctc tgacggtatc agctgtatgt gccagggagt ggcctatttg  47400
gggcaccacc gcctaacaga gtcactttcc taaaatggag atctcaaagc cttctacgtc  47460
tccactctgg ggaaaagccc agactacctg atccagcaca gacaccttgg ccttctccct  47520
cttcttggcc ttcctcaggg gactgggggg ctgctgcccc taatccccag gcctcatccc  47580
ctggtaggcc tgtatgagtc ctgtggaggg taccctctga ggcacctccc tgatccctga  47640
gataccagcc cctctttgga tggctagcca tttctatcca ggggacctga ggggccacct  47700
gcaaccctgt ggctacctct cccccaccag cctacacact ccctgaggat gaggacccac  47760
ccattaagcc cctgcgatgc ctggggccta gcagggtgta taacccagag caggtgctga  47820
gcaaacgttc actcctggct ttcatttgtg cttgcctggt tctttctgat ttctaatttg  47880
gtttccaagt aacaatgggt gaggacacag gctctgtgag tgaatataat tctgagagta  47940
taaggggagt ctgtgccctc ccacaggaga accctgccta agatgaatgc tgtgtgatgt  48000
gctcagcaga gtgaagtgga agctgaggcc ccagaaatgt gaagcacctc cagtgtagag  48060
ctgccaggtg gggctgaccc tgcagcacgt agcatttcac tggtagttcc cacccttagc  48120
agcctgaccc tcggtcagcc ttgatacact ctgtgaaatc ctcaacagtc ctgtgcatca  48180
gagactcact gaacaagtcc tcccctctga gaagtcccca tttcaaatca cgcatttttt  48240
tctttctttt ttgattgaag gggccacaaa gtgcaaacag aataaaattc tctgtcctca  48300
aaactatgtg caaacctgaa ctttccccag ggacaggaac aagccttggc acccactaac  48360
ctgtctttat tgacagaatc gcctgcaggt ctggcactgg cagccaccac aggctctgtg  48420
caaggcttcg aggcgccgaa ggagttaggg gtactggagt ccagtggcag tagctgtgga  48480
ctgctatgag aagagagcat ggtgcccgcc agggagcccg agagggggat gctgttaaag  48540
aatgccgtgg agaagtccct gtcatcaagt aagaacaaaa gtcagccttg aaagtcaggt  48600
gccacatcca gtactttata cattcaaata acttttttct aggtccaaag gcagtatgtt  48660
ttcatgatag aaaatctgca aagttacaga aaagtaaaaa gaaaattaaa gccacttaat  48720
atactatatt taattgaatc taggatttac aggttctata tgtactacta agaaagaaaa  48780
caatgctact aattgtcaga tgccattgac tgtacaacac acccaaatct cagaggtgtt  48840
aaactgtgca aacacatgtc ttaggaggaa tgaaatgcag caatacagaa agggcctccc  48900
tttcatgaag ggccatgggg catgccacta gatgggtgtg ccataatata cctaacccag  48960
cctctactga gggaccacaa gactgtctcc agctttttct agaacagatg ctgctgcacc  49020
aggaagcaag gtattgcagt gtcagaactg aggattctgg gacagccagg tctgactcct  49080
ctgccatttg ttagcttgtg acttgctcta actactcttg tgcctccagt catgtctgca  49140
aaatacaaag tgccaggact ctccccatgg ggttgctgtc aggactaaag cagttggtgt  49200
aggacactct tagaacacac attggctgct caaagaatta tgaaattcta ataattgtca  49260
ttacacctaa gattcacata atatatggga taaattctta gaagtggaat tgtagcagca  49320
aatgaaatgt tcactgatga tttggaataa atatttctaa agtgccctcc tcagaggttt  49380
aaattacaag ccatgtatga gagcgcctat ttctccacat aggtgcttag taacactttt  49440
```

-continued

```
atcaaatttc ttgacactta acaatctgac agaagaaaaa tggtatctta ttttgatatg  49500
agtgacgttg acattttttc tttttctttt ttttttttga gacagagtct ctcccgccgc  49560
ccaggctgga gtgcagtggc gcgatctcgc ctcactgcaa gctccgcctc ccgggttcac  49620
gccattctcc tgcctcagcc tcccgagtat cccgccacca tgcccggcta atttttttgta  49680
tttttagtag agacggggtt taaccgtgtt agccaggatg gtctcgatct cctgacctcg  49740
tgatccgccc gccttggctt cccaaagtgc tgggattaca ggtgtgagcc accgtgcccg  49800
gccggcagtt tttcaaagta gaaatacttg atttccggcc aggcgcagtg gctcatgcct  49860
gtaatcccag cactttggca ggccgaggcg ggtggatcac gaggtcaaga gttcgagacc  49920
agcctggcca acatggtgaa accccgtctc cactaaaaat acaaaaatta gccgggcatg  49980
gtggtaggcg cctgtaatcc cagctacttg ggaggctgag gcaggagaat ctcttgaacc  50040
agggaggcag aggctgcagt gagttgagat cacaccactg tactccagcc tgggcaacag  50100
agtgagactt cgcctcaatt aaaaaaaaaa aaaaagaaat acttgatttc tttttttttt  50160
tttttgtgaa ctgcttgttc atatgctttg tctactgttt tgttattggt ctttattact  50220
gatttgtaaa aatcatttac atattaaaaa aattccttat atggtaggaa atattttacc  50280
tgggatgttg tgtttcaact atttatggcc tttttttttg agacgaagtc tcgctgtgtc  50340
gccaggctgg agtgcagtgg cgcaatctcg gctcactgca acctctgcct cctgggttca  50400
agtgactttc ctgcctcagc cttccaagta gctgggacta caggggcgtg ccaccacgcc  50460
cagctaattt ttatattttt tagtagagac ggggtttcac catgttggcc aggatggtct  50520
tgatctcttg accttgtatc catctgcctc agcctccgaa agtgctggga ttacaggtgt  50580
gagccaccac gcccagacag cctatctttt aaatgcacta aaattttaaa atttttgtgt  50640
actctaaatt gtcatttaca gaaaacactt ttttgacctc tgagattata aaaaatattc  50700
ttccagggaa tcttctaaaa ttttaaacaa aaatatttta aataacaatt taaaaagaaa  50760
caaactataa gctgtttaga atgtatgtaa tgataagtta tgaggctggg acccaacatt  50820
gtttctagga ggtgccatgt agtcctgtct tccatttacc gaattagcca atgttttatc  50880
actgatgtga aatgctacct ttaaaattcc cataaatatt cgggcctgtt tcctcatatt  50940
ctatcatatt ccactgcact atctactcat gtgtcagtat ctcactgttt tgagttatga  51000
cagcttttaa gtcttaattt ctggtggggc tagtcttccc tggctaatct tctttttcag  51060
aaatatttcg gccattccta tttatttttc cagataactt tattttattt atttatttat  51120
ttgatacaaa gtctcactct gtcacccagg ctggagagtg gcactatctt ggctcactgc  51180
aacctcccag gttcaagcaa ttctcctgcc tcagcctcca agtatctggg atacaggtag  51240
tagctacagt agctacaggt gggcaccacc actcccagct aatttttata tttttagtag  51300
ggacggggtt tcaccatgtt ggccaggctg gtctcaaact cgtgacctca ggtgatctgc  51360
ctgcctcggc ctcccaaagt gctgagatta cagttgtcag ccactgtgcc cagtcgattt  51420
ttccacataa ctttatagtt accttgtctg attcccaaaa ttcctacggt tatttgtact  51480
ggttaaattt ataggctaca agagagctga catctttatg atgccatcct agctaatcaa  51540
tggtatgaat ttctagttat ttctttgagt tttctttgaa gcctctcagt agggttttta  51600
attttttcttt cattaagata tgcatctctg gttgcatcct agttatttta tttgtgaata  51660
tgacttattt ctttatgtgc tctgagggta gttggtgcta cctgacttca tgttgattgt  51720
atcctgccat gtgactatct tctttcattg cctatggcag cttttccagt tgattctctt  51780
```

-continued

```
ataaaccata tcatccttaa ataattatcc tttccaattt gttctttcct ttgactaact  51840
acatgggcta ggacctatag aacaatgtta aattatagtt gcaagagtag gcatttgttt  51900
agtttttgaa cttaatttga aataagataa tttatcaagt taaggaagca tccacctatt  51960
cccatttaac tgagttttaa aacaacgttg aattttacca aaacgcctat taagcatcga  52020
tgagagatca tataattttt tttcttttga tctactgata cgtagaatta aatagttacc  52080
taaaatttga acctccttac tttcccaaaa caaacctcac ttggtcatgg tatattagcc  52140
ttttaacaag cagtaaggtt ctgtttgtta ctattttact taggattttg cactgacatt  52200
cagaaatgag aatgatcttg aatttattat gttttatcct tgtaagattt tgatatatta  52260
tgttcatttc aaaataaaaa tttgcacatt tcttctccat gcactagaat atttaaaatg  52320
gtattaacag ttacctgagt tacctgttcc ttaaaagttc ctgaagtttc cctgtgaagc  52380
catcttagtc cggtggcttt ggtggggtta actctgtcct ctatttcttc cacaataatt  52440
tttcactttt agtaatttta ttttcttcaa aaaccatcca ctttctgtgc aaatttattt  52500
gcacagagtt cagcaaagaa gtctctcatc tttttgattt gtctattatt tctcacttat  52560
acctactttg tatatttatg ctttttctct tctttcttga ttagctaagc taataaggac  52620
ctatcctgtt gctacgtgtt agaacgtggg aatcaggagg gcaaaaagct tttaatacca  52680
aaaggatcag gtcctgatgc tagaaatatg catcctatgt cagaaagttg gccccagacc  52740
agttaggaag ccacctacac cttctcacca ggtaacgcct ggaaggatcc acagaacaaa  52800
gtgtcaccat caccaccacc acctccccat cccacaggcc cagtatgttc agagctcaac  52860
cacacactgg gtctcacttg gtctcaataa aaggtaggta ggggcattac cccctacagg  52920
gtcacaatag gaaaaagact tagtcaaaag aaaatgagtg ctctgtgggg agccagcaga  52980
cctggttctt gctctactcg tggggacctc agagcctgca catctaacat gaggagactg  53040
gatctgtaca ctgtacgagt gaaggtttct ttagacacca aggaagattt ggaatagctc  53100
gtggatggac aactgcaaaa cgcagaggcc taaagtgtgt ggcctccatg aagggcttac  53160
aaatgccctg agcagataga cggaatgaga ataaaaccca gagtgaactg ccttgacagt  53220
gggggtctat ttctttcaca cagtgcttta tcatttttct ttcttttttt tttttttttt  53280
gaatcaacac acatcatttt gggaagatta accaattcaa aaacaatctt cactatatac  53340
actgggacaa cagcaagtgg tgaatgagtc tcttccccct tctctgtccc ccacagggaa  53400
atatgtttgg gagccctact ctctgcccag taattccact tctagaagtt atcctgagag  53460
aacaaccaca ggtgagctca aagactcatt tataatcacg agaaactgga cacaaacaca  53520
agtctacagt gagctggcta agcaaatcct aggatgggaa tctggataat cagatagcaa  53580
acacctcaga ggactagtta ttaaaatgga tgaatgggca tgaaacagta acgagtgggg  53640
aaaaaaaaga ctggaaatac agatataaaa acattaacag tgactgtatc tgattatgga  53700
taatgttttt ttcttctttg ggcttttact attttctaaa tttaaccatg tgtaaatata  53760
cctttcataa tcataaaaat aactttatga aagaaaaaaa agaaaaaaaa aatcagcctg  53820
actgactgct ttccttgtgc gtcctctggt gccctggcaa cagtgaagtg cagcagatgt  53880
gctggccgcc ttagcactcc cacccctcac atgattcagg tgtgcacaag ggctccagga  53940
ggagtatggg ctttgagact gcgggaagct gagcttcact tccttgcttc catgttctac  54000
cagtcaggtt gtgaaggacc cgtgaagatc ctcactgtga aagtgttaac cgctgaaaga  54060
agacaggaag atctcgccag ataagaccat gaaaggggaa tgaaccagta cccagtgtcc  54120
agctgtgcta tgcagagagg cgtgattctt ctccggccat ctgctgtccg agtctcaact  54180
```

-continued

```
tgtttcttca aaagattctg gcaaagcaga gttacataaa tgaatgcaaa agttttggcc  54240
aactatttcc aaatattaaa aaataaagtc tcttttttc ctggtgataa gaacactaag  54300
cataagatcc accctcttag caaagtttta agtatgcaat atcatattgt gaactgtagg  54360
cactatgctg taggggagat ttctaggact tattcatctt ctataactta aactttatac  54420
cctttggcta ataactccca ttttcctctg accccagtat tcaccattct attctctgtc  54480
tctgtgagtt tgactatttt agattcctca tataagaggt atcaggcagg ccaggcacgg  54540
tggctcacgc ctgtaatccc agcactttgg ggaggccgag gtggacagat cacaaggtca  54600
ggagatcgag accattctgg ccaacatggt gaaaccccgt ctctactaaa aatacaaaaa  54660
ttagctgggc gtggtggtgt gtaactgtaa tcccagctac tcaggaggct gaggctgagg  54720
caggagaatc gcctgaacca gggagtcgga ggttgcagtg agccaagatt gcgccactgc  54780
actccagcct ggtgacagag cgagactcca tctcaaaaaa aaaaaaaaaa aaaaagagag  54840
atatcatgcg gtatttgtcc ttctgtgtct ggcttatcat taatttgtac acactaagta  54900
tgtataactt tttatatgtc aattgtactt caacacggta ggtttaaaaa taataaggct  54960
tctaaggaaa tgtattctaa attgccctcc tggtacaact aaataagaca cccaagcaaa  55020
gaacaagcag tgggtacatg ccacactggc cgcctcgcac aacagccatg ggaccaatga  55080
aagggctaaa ggactgagct ctgtacccgt gaaccacaca tctgtcacta agctagggat  55140
tttctttctt tctttttttt ttttgagaca gaatctcact ctgtctccca ggctggagtg  55200
cagtggcgca gtctcggcac actgcaatat ctgcttcccg ggtttaagca attctcctgc  55260
tcagcctccc atgtagctgg gattataggc atgcaccacc atacccggct attttttttt  55320
tttttaagta gagacaaggt ttcaccatgt tggccaggct ggtcggaact cctgacctca  55380
agtgatccgc ctgcctcagc ctcccaaagt gctgggatta caggggtgag ccactgcgcc  55440
tggcctgagg tagagatttt caaactgact ttcaaaatag aatccttcct tccacagaaa  55500
gcttgtaact aggggttttc tctcatactt tatatctgaa ttgcctggag gaggtttgtc  55560
agcctacaca ggctcctgga gatggtttat actccccagg caataacgtt ccctacccttt  55620
ttcccgcccc atttccaacc ccttcccatc aaacatggct tccagatgaa gaagggggag  55680
cccatagaag tctcctaagg gcagagcctg aaatccactg ttgttagcat ctaggatttt  55740
tagaaagacc agaaggataa aattcgtaag ttcttacaag agatgacctc ctctgggctc  55800
ctggggataa ggaggccttt gataaagagg atccaggccc cattactgca tcatgcagca  55860
gtgggcaagg ggccaacagg cccgaggctg gctaacccac agatcccgta ccactctaaa  55920
caaacccctt ccttaccacc actggtgtct gcccctcacc ctgtccctgg gcatatgtcc  55980
atgtctttag cgccaccagg cagggctctc accttcctga tatcttcaag actctccccg  56040
ttgacaacgc ctgcgactga ggtggctgag cccatctccc tggtcgcagc actcttctgg  56100
tccagctgct gctgctgctg ccttcgctgg tacttgagca tctcagggtt ctcaatgacg  56160
gctgtggaga gctgggcctc ggtcatgatg gctaggctct tgccataggt ggactggtga  56220
atgcggctct ggggaagcaa ggagaggcat gacatgccag catgagtgcc agtgtggcca  56280
gtgctgccca ccagcaggca aactacagca gggctctcct ggctctgagt ggagaaggga  56340
cccaaggcca actccccatc gcctcccatc ctattctgcc tgtccctcat tcgacagctc  56400
tgttgatgtc tcatgcccac ccttgatttt tatggcctcc cttgtatctg tagctgggat  56460
gacagtaaat gagacagcca acaagacaac acctgcccca cagtctggtg gagaacaaat  56520
```

-continued

```
gacaatccac agtgcttcag tggaaaggaa gatactcaag gtgctaactt aaggctctta  56580
aatcactcct aggacccaaa tgattttggg aatcagatcc tagaacaaaa gtctactttc  56640
acagctcatc tgcagccata agccctgtgg ttggaagtcc ccattggcct gcttagtgtc  56700
tctaagagta tgggaaggcc tggcacagca gggctgggga gcctccttta ctcccacccc  56760
tcctagtatg tcatcatact cccctccttc taggccctca tagtcttgtg ccctaacaag  56820
ctagacagga gcctcatgag agcagagatg gtgtccccag cacactgtag tgactgctgt  56880
acatgaaagt gcatgaggaa cacacttcca tgggatgtgc aaatgtccaa tgtgggattc  56940
tgctcaagaa cagggactgt ggttaacagg acatctgctt tacagcagag catgggttga  57000
gaggcagcgt tccaagagag gtgccttggg acctgctcct gcagggcttg aatgtggcca  57060
ggaacctcct tttcttgcca tcttggctcc tgcccttctc tcctgagtct atcccctgga  57120
atctcgaagc agaattcagt gtttggccag ggtttcccta gtgttcctcc aacatggagt  57180
cccagcctga cttgggaaat ggtaagcaga tgggttatta ggctcccaga gtgactccaa  57240
gggagtgcat agtgatccca ggtacctgat gacagtgaca aggttggagg aggacctgag  57300
gcctctgaga tactcattcc ttcatggaaa aatgatgggg tggcaggccc cattctaagt  57360
gtagtcatta aggcagacct ctcccccaaa ggggttcaca ttttagtggg gaggtcacac  57420
tgtaggttaa gaggaagctt ccaccagcaa ataaggtcat gaggagagct gccagcctgc  57480
tctgggcttt cacagagctc ccttcagaca catacacaca acccaccaag tgggggcagg  57540
tttctaagcc tctggtaggt gaagcagggc ttttctcaaa gcctggcaga agggcagaga  57600
gaccccatca ccccagcaga gcacagaggg gaggcagcct ggcccagagg cagcaggcct  57660
tgttcactct tctgacctaa gggtcacata cagtctgggc aaagagccat gctattttct  57720
gaggcttagt ttccatatcc acgaaatgga tgagccttgc cttgaagggt tttgtgcaat  57780
ttaaatgaaa tcatatgtgc aaaacacatt cccagagcct ggcagacaat gcgttctaag  57840
aaatgaccaa tattactacc atgaaggtga aagtgacatg agcaggggcc cctgaggagt  57900
cacttcagct ctttcccagg gcaaaaacct cccagtggat ggcctattat cagctcaaaa  57960
agagatgcct aaaatagttc tactcttaac tccaggactt atttctgaaa tggggactcg  58020
ttttttaatt aatctatttt gtaaagaagg attacaagat ataaaagatg aataccccat  58080
tacatgttaa gaaatgactt gtctgtgtat ctcacaagaa gagggtgtag tcaaaggggt  58140
ctctcagagc tattgtggca atggccacag agcacccagc agcacaagag ccgtcagcct  58200
accttctcct cctcgctcag gggatcgcca agctcatcct gggagaagtc gaggaatgcc  58260
acagagccgt ccatagagca taccaagatg cccagcccat tcagagtcct gaaagacatg  58320
gccatcagca gcctggtagc aagagcccca ggcagacaca tgtgccgcag tagctggcct  58380
gtgaggatgg tgggcagtgt tctagggaga tgctggaaac tcctggttcc cttctgtggc  58440
ctggttccct tctttggcct gggcgggggg gggagggggc gacaattgta tcccaaaggg  58500
ccctggtgtt ctttagctct aagcaggtgt acaaaatatc tcctttacca tatgttctgt  58560
aagaatttttc aattttactt atcttacttt tgaaactatt aaaataaaaa aaacttgaca  58620
aagtatacat ataaatcagg tcactgagaa gcagaaagtg tgcttctgac tttggttcat  58680
gcactgacgg agtaaagtgg aacatactag gatcacgtca ttctcctcgt cttagacaaa  58740
tcctgaaaag gcattttcca gtggcaaatt ctacacaggc aggacattct cgcagcagca  58800
ggtacaccgc tgccagttcc caaatcacgt gcaaacagca ctcttggtct gcgctactat  58860
gacacctggg gaggggccac tggccacctg accctagtca cacccagaag gcctcatgtt  58920
```

-continued

```
ccaatgtgtg gcttctcctt tcttaaccta ttcctgtaag tagaatccac cttaccagga  58980
aatatccatg atggatttgt caaacagttc atggatgacc accagcggcc gtttcagaca  59040
tgtgagctgg aaggaaagac acagtcaagg ttaatgaaat tactgaaatc cccttctgta  59100
ttcagctcag ttaacataac caacctagaa gcctgggtca aagtggctgc tgatatttaa  59160
ggcatcttca actctattca aactgcagct gcagagatcc caaactgtgg gaaccaaagc  59220
ctgccaaaaa tgtgcatgct acctagagtg gaccctgcct ccagggcttg ctgtggtctg  59280
acaggggaaa tagctttata cacagataac tagcaacaga gaaggcagag tgggagtggg  59340
tttctgaagg gctatggtcg gaggagaggg acagccccag ggtggacctc tgagagggtc  59400
tatggagcag gagacacgat gccaaagcct agacagggga tgaggcaccc tgagagagaa  59460
cacaacacat cttccctggg cccaagggac tctggtacac atttatccaa ggctcattct  59520
acactatgtg taggtagtac agaaatacac acctgggccc ttaatctggg cctagttacc  59580
gactattaat actttgatga attattatct tctattttgt gcaaatattt attttattct  59640
tcaaagtaag aatttatttt attcttcata gttgtgtctg ttttttcatt taacacacaa  59700
taagtatgtc attaaatatc ctgtaaaagt ctcttctgga tgactgcata gcatgcactg  59760
tgcatattct ctatcgagtc actcaattgc tggcatacac tctgactcca cgttcccaca  59820
actatggtag gcctttccac ttgtgcacaa gtgcctggct accctgctgg ctggccctga  59880
actgcaggac aatgggcagg gaagaaacac acttcctcac gggatggtgg gctcccatag  59940
gtgctgctgc agcttctggg aggctgtggg gctgagcgtc ccagtgcagc ctgagactgc  60000
tatgtgggga aggagaagct gtgtctaccc tagtggtgga gagggggctg aagtctgaac  60060
gatctggaac ccacattaag aatctcgcct ccaccttaat tccacttcta gaaaaagctg  60120
ccttgtccct cctctcataa atgtgcctac agacccctca gaaatctaca ggccgtgtga  60180
ctgcctaacc tgagcattct aagaaatatg ggcatcacag tcagtgatgt tttggttgca  60240
gcgccacaaa cagggcctct ggctgggagg aaacagggaa ggtcccctga acggcaatct  60300
gtggtactgt ggttcaggtt ccagaatggg tgttaagtga atacttggcc taaaaaaaaa  60360
aaaaaaaatc acaacgcaca cagtaatata tttctctata ccaaactaat aaatgcagcc  60420
agaggataac cttcaaaccc agaacttcca acttgctctg cttataggga cactttttta  60480
caaaatgaaa aaaaaaaaaa attaatgtgt gtgcactttg ctttatcaaa ctttaaatat  60540
attggcacct tgatgctcag caccaagact gctccctgca ctgcatgcgg aggtgtctct  60600
taccacacag tcaggtcaca gcacaccagc ccctggcagt gagaaactta acccttcagg  60660
agccctcact tagaaaccgc cacagttctt acccttgggt tctcactcgc caactaccat  60720
tgagtatatc tgctgagaac ctgctctgta gagggcactg agttaggaag gtgaggggaa  60780
caatgaaact gaagacacat cgggctgggt gtggtggctc acacctgtaa tcccagtact  60840
ttgggaggcc aaggcgggcg gatcacctga ggtcaggagt ttgtgaccag cctggacaac  60900
atggtgaaac cccatcttta ctaaaattac aaaaaaatta accgggtgtg gtggcctgta  60960
atcccagcta ttcaggaggc tgaggcagga gaatctcgct cgaacccagg aggcagaggt  61020
tgcagtgact caagaagcca agattgcacc actgcactcc agcctgctgg gcaatagagg  61080
gagactctgt ctcaaaaaaa aaaaaaaaaa aaaaaaaaag aagctgaaga catcgcctca  61140
tctcagggga tccagcgagt gaggagtact aggctcacaa ccttacccat cacagcatca  61200
cccaggggtg aaatggacta ataaaggcgt cagctttctg tgtgtctttt tctgtggaca  61260
```

-continued

```
taagcactta tctgtcttgg ttgtatgcct aggagtggaa gtgctctagg tcatatgctt  61320
agctgtggta gaaactgcca gacagttttc ccaagtgctc atgccagcgt aaacacctgt  61380
cagcaacacg tgtcagcaat gtatcagttc cagcttatca tgtccttgct gacacttggt  61440
actatttttt tgtttttttt tttaatttta gaactctact cataggtatg tactcataaa  61500
tgaaaacgta catccacata aagacttata caagaatgtt catatcagct ttagtcataa  61560
tatctcaaaa ctggaacaat cttaatgtcc atcaacagga gactgtataa acaaattgtg  61620
gtgtattcat acagtggaat gctacaccga aattataagg aataaaatac tgttaagtgc  61680
agcaacatac acgaatctca aaaacactgt gccaagcaaa agaaatgaag acacaaagaa  61740
gcaagtacca cacaattgca tttatatgaa gttcaagagc aggcaaaact catcagtgta  61800
acagaggcca ttagagtggt tgctttggtg gtgagggagg tcttgactgg ggagggacaa  61860
agggacaaaa aggagtgctc taggcagtga tgacactggt gtgtaaacat gtatgacaac  61920
tcaccaaact gtacctttca ggtgaataca ctttatataa agatttttct ttttcttttt  61980
ttttttttt tgagacggag tctcgctctg ttgcccaggc tggagtgcag tggcgcggtc  62040
tcagctcact gcaagctctg cctcccaggt tcacgccatt ctccgtctca gcctcccgag  62100
tagctgggac tacaggcgcc caccaccacg cccagctaat tttttgtatt tttagtagag  62160
acggggtttc actgtgttag ccaggatggt ctcgaactcc tgaccttgtg atccgcccac  62220
ctcggcctcc taaagtgctg ggattacagg cgtgagccac cgcgcccagc catataaaga  62280
tttttctaat aggaagcaag cccaacatgc tgctcatggc attgaccact gagggtgctg  62340
cctgagtctg gacacaagag ctggtctagg tgggggtcaa ggtggcctct cctggctggg  62400
cacagaccca gtcttcagca cttccttctg ggagagcagg agagcctgtg agcttccaag  62460
gaggggctga ccccaggtgc agaatagaaa tacactctta gcatcaccca aagcaggtct  62520
ctttcctcca cttgctactt taccaaccta cacctcccgt cctgcaacaa aagctcagga  62580
tagcaggctc acccagacag aaagcgagcg gtccttgctg ccaacagcac agcagcagta  62640
cgggcagcta ggcttcgcag aactcccatt cttctgcttc tttttgaaga tttttgggtt  62700
gaatttctaa agccaaataa cagatgttaa aaataattaa tcaagcatca ggcatgtccc  62760
ctgtgcccaa gtcccagccc actgaaggga gtctcccaca gacattctct gagcccaggc  62820
actgagcatg catttcatct tcccgaccac ctatgaggca tctggctgat gatggaaagg  62880
aagcttaggg aggtcagaaa gtatgtgcgg aggcaccaaa tgagtaagct gggaaatgca  62940
gatttgaaac tagagctacc aaactctcca tttctggagc ttgccaagta gaagggatgc  63000
gtagctactg aaactagcct tctcaattcc ctctggccag gcagggccag ccctaggacc  63060
tgcagaaaag ctgagcctgc aagggggctt cagaaacaaa gacctactca ctccctatct  63120
cctaagggag gccaagggga tgggcaggag gggtgtgaat ctctgaattc cttattgcct  63180
cactgcattt gttgttcagt cataaccgtc tagcagagat ctgctcagtc agagagtcat  63240
ttgtgatctc cctgggccag tgaccatggc aatatcacac aaaggtgctt ggttggctgc  63300
ttagtccagg gaactacccc gagagtaact tgtctttgtt tctgcaaagg atgaaagcac  63360
tcactgagct cccagacacc ctcctggatt taaaggggtg ggcgctctgg gaatccccaa  63420
cctaggacaa ctgagggcag aagaaggagg gttcctgaaa gcctggtgtc aggtagccta  63480
gagatgtttt aattccagag ggcaggcagg aatggccggg gtgcacagag actggagaag  63540
atggaactca gaggcgtgtc cctgggcttg ctgtctctaa caccaatgag gctgcagggc  63600
cttaggagct ctgtgagcca taggcaggcg tcgtgatctc ccagagctgc taataaagtg  63660
```

-continued

```
gttgtgagga ctgcatggga gaatcacgta gagcactaac catgaagcac tgatttccaa  63720
agactttagc aacaaagctc tggttcaaac aaaaccctac atgaactcca aaacaaaaaa  63780
atttaataag taatatttta ttcatataaa atttgtgttt taaggtacaa tatatgatac  63840
ttattatctt tttttatttt tatttttgag acggagtctc gctctgtcgc ccaggctgga  63900
gtacggtggc gcaatctcag ctcactgcaa cctccgcctc ccgggttcaa gtgattctct  63960
tgcctcggcc tcctgagtgg ctgggattac aggcgcatga caccatgccc agctaatttt  64020
tgtattttca gtagagacgg ggtttcatca tgttggtcag gctggtcttg acctcctgac  64080
ctcatgatcc gcccaccaca gcctcccaaa gtgctgggat tacaggcatg agccaccgtg  64140
tccggccgat acttattatc tatttaaaca cgggcaaaag tgagtctatt ttcatcaggg  64200
tcttggatga tccttcactt ttatcaacct tagtccacca atctgtttat tttatttggc  64260
tgcccagtgt tgagaaaatc ctggttctca cagattattc gcaactactt aacagcttgc  64320
cttgggctct gtcaggacac tatttaatta aagtcatgga gaagcataag acgagtggcc  64380
agacaactct catgcctaag gactgacagc agttcacgcc tctgagctct tcacctgccg  64440
cagcaagatc tggcagcagc tcccaactca gtgatccatg gcatggcctt gcacctgtgg  64500
ttgatgctgc caggtgtggg gacaagcaca gtgcttggtg ggtataccag aattgtacct  64560
gtattcactg gagccaggtg agggtggcac cgtgcttggg caccccaagc atacctgagt  64620
gtgtaaaagg ctgatgtgga gctacgatgt tcctaaccca agactgattt tggtgatgtt  64680
cacatgtaaa gtttgccaat aaatcaacca agtacatact ctattttgta aaattagctt  64740
ttaaatattt aagtataact attcaaaata aaccaagaat taatatttgc tgaatcttgg  64800
agcccatctc cctttagttc cctgggcact caccacgaca gtcacagctt tccggtgccc  64860
aacaaagtcc atgttggtct tccatccctc ccgttcgatg atctgggcag tggggcctga  64920
gttgttcatg gcatgggcag acaccaggta atgcccatca ggtgaccagc tgagccgcaa  64980
cacatgggtc gttcctccac actgaaagaa gcatctgcac ttgaaaggag ctcaaggcca  65040
cctttgtgac caaaactctg gcctcgagga taaagttaaa cttcaattta taaatgtgtg  65100
atggtggagc atgcacccca agcttctggc tacactgaca gcttctgtct caccagatgg  65160
cccaaccaaa aagggctctg tgaaatgaat ttggaaactg cagcatccta cactccccca  65220
gaggagctga acaaagaaat atagtacaga agtgtatgcc ctgaggagat ctgcaggaag  65280
gctacctgtt tgaaccatag cctctgcatg ggccaaatct ctctggccac tgacccaatt  65340
cttctgtgta gcacctgtta acccacagca tggcatctgc acagcatcct caagatatac  65400
tctggtggag aaaaagccct ttttaaccca ggagcctggc agaagcctgt gtctgtaatg  65460
tagctgatga ctgtgaggca ccacctactc tcttgagcct gttgcctcac ccaaagggtg  65520
gtgaggatac ccgcaaggga gaagaggttt gtaacatcct tataaactat aaaaggaaca  65580
gtagaaaggc actgctcccc cagtctggac tgggggctga ggcagagcat ccctccacat  65640
tatccctcct gcaaaaagag atgacatggg tccagagcca gctccttgaa gctcaaggtg  65700
ggcccagggc agctctaaag acttaagggt taagatcatg acctcacagc tctagagcag  65760
gacatgacaa accagagcct gagtatagtg aaatcaccca cctcagctct cagcctaggt  65820
gacagaacca ccccctacct ggaaggatgg gcccacccag tagaggctga agagtactac  65880
cacctcctgc tggtactcaa gacactccta aagccgtccc taggagtcca cctcatggga  65940
ccccactgcc tggcagtcag agccctgagg aactccagaa ggagcaaaag ctccttaggg  66000
```

-continued

```
caagactaag taaggtaaaa accagtactc atatacctag cccaggagct ggtgttgtgc  66060
gggaagaact gaacatatga ctatcacttt acttttgcag ccatcctgac cagtgggcaa  66120
atgcgtgctc ttcctgcaaa ccttccctca tgtgtccctc gctctgtgaa gtctttcctg  66180
atgcactcac ctctcctggg ctgtttctgc actctggaca actccattat catgcaacta  66240
atgggaatgc ctgtctttcc tatggggctt taagcttcaa gaggagagac tccatctcaa  66300
tccactttta tttccctgtg cccagttatt gccttctata cagtagacac ttaataaatg  66360
tctaatgaac aatggtgatc ttgagctctc attccatttg aaatcagaac tcaaataacg  66420
gaagagagat taaaatacca gagaagctac tgcagtctga tctccaaaca tgtgcaaact  66480
gtactgctaa ctccagccag gaaaaaaggc ccctgaactg cagggtgcat atcaacaagc  66540
acagcacagt cgaggatggc acaagagtct cctccatcct ccccaacaag ctgctctgcg  66600
ggaggctcag agtaaactcc gcactataag aagcagtttt atccacgtct gtgggagtga  66660
gctgggtgac agaatgatgt ggagacatct ctaaggttca cttcaacttt aaacctataa  66720
atccgggcca ggcgcagtga ctcatgcttg taatcccagc actttgggaa gctgaagcgg  66780
gtagatcacc tgaggtcagg agttcgagac cagcctggcc aacatggcga aaccgcatct  66840
ctgttaaaaa tacaaaaatt agctaggtgt ggtggtgggc acctgtaatc ccagctactc  66900
aggaggctga ggcaggagaa tcgcttgaac ccaggaggcg gaggttgcag tgagctgaga  66960
tcgtgccact gcactctagc ctgggcaaca agagcgaaac tctgtcgcca aaacaaagca  67020
aaaaacaaca aaactataaa tcccttttat ttcaaagttg gaaattaaac agcgtctcag  67080
aaatgaagga ttctgtatta tctgactctt agggccagag tcccacccca gagagccttg  67140
gtgaatccgc tcaggccccc ggactctgtg cattccccag gtggcctggc ccatggccag  67200
ctccctctct gtacacagaa gtcaggaaga ggctggggca gctgcggggg ctcagctccc  67260
tgagctgtcc ccacttacct catcaaaagg cttggtgatg ctggtctcca actgccagtc  67320
cagcgtcctc cacaccttta ggctgcggtc atcagcttga gaagctatgt atttaccaac  67380
agggtcccat gtcaaccctt tgaccaagcc agaatgacct ctcagagtag ctagaatttc  67440
tgtgaagaaa aaaggaatgt ggagaggtgt tgtctgaggg aaacatgacc tgcaatccat  67500
gggccatggg atggatatgc aagagagggg actcagcagt ctgccatggc cagccccccac  67560
accagacaga agcagaaggg cctcctcatt tgatctccac caaggcaaaa gccaattgaa  67620
gaaatgacag catcaaggag gcaggcacca aggggctagt tctgatccag gtcttatctg  67680
tatctagcgg ccctgcctat ggctgccctt cctgggctgt gacaccagca cttctgacgt  67740
tagcctccct ggtagctccc tgataaggag gaggcctact agctcaaagg gcctgactgt  67800
ggctgagtct tttataagtt atggctgaag acaaaggtgt gtacgacggt accccatata  67860
gatctgtaat ccaaatgcta ctccggtctc taaagcttcc ctctccatag ccagactgag  67920
tgtttccaca catgctggtg gctttcaaag agttaaaatg acctggatcc ataaggaaag  67980
catacttcaa atacagagct gaaatatgag aagaatttta ctagttataa actgcagcac  68040
tgtgccaggt tatgccatct gttgtgactt taaacacaat gaataagaaa aatcaatctt  68100
ttgcaaaact gggtttgtgt tagcccgtat ctgctcaagg gtttcacaga ggagatggtg  68160
actgagctga gcccagagcc cagtggtggg ggtgcacaca gcaggtttag gagcatcagg  68220
gtccccaaca acagctgccc atccattacc ctcctgatct gtggcatgcc atgctagcac  68280
tcagttacca tttttcttaa gcatgaatct ctttttaaag cttaaacaaa tgtaactgac  68340
aaagaaaaac tgacaagaca cataaatcct aggccactgt gacacatctg ttgccaccaa  68400
```

-continued

```
gactaaggag acagcccaac ccctgctcca gaaactgaca ggcagtactg cttgctgtta  68460
accagtcaga ggaggcccca gacctgggaa ctttacagca ttccagatga cgacagtgtt  68520
atccacgctg catgaggcta gccaggcatc gtggggagac catgctacat ccatcacatc  68580
tgaaagaaga cagagggttc tggtgagatc tcttacctgg tgatgccctt gtctattagc  68640
ttggccagtg cccctgggac ctgggaccat cataaccact ctggtatttt ttaaccaacc  68700
tgaaaaaact ccccccagaa tttttcaatt ggtcataaat ttaaagcatc taaccgaccc  68760
cagtgcctca ctccttttac agacgaagca actgagggcg tggttcagag cttgggcacc  68820
atatggcacc acacccatgc atgagagcct gctacttcgt gggtctgtgg cctggagcat  68880
gctcctcagc cctgctgact tgctttgcca atcataacag ggccttcctc cgagagcctt  68940
ctgagcatga gacacagtgg gtaaagcaca tggcagaatg cctggcacag tcagaactcc  69000
agggctgctg acaactgaac acaagtcatc ttgaggccct cgtctggttc atggactggg  69060
tctcatctcc cagaccctga caggagtacc ccttcactat ggagcctcca aacagaatta  69120
ttcacattca cttctttgtg actccatttt atcatttgtt aagtgcagat taaaaaacaa  69180
aatctaggcc aggtgcaggg actcacgtct gtaatctcag cattttggga ggctgaggtg  69240
ggcagatcgc ttgagcccag aggtacaata ccagcctagg caacatggca aaaccctatc  69300
tctacaaaaa attggctggg cttggtagca catgcctgta tccccagcta cacaggaagt  69360
tgaggtggga ggatcacttg agcccaggga ggttaaggct gcagtgacca tgattgcacc  69420
actgcactcc aggctgggca acagagtaag accctgtctc aaaaaacaaa caaaaaaacc  69480
aatgaaacaa aaaaccccaa aacctatcct catagggtca ctgtaaggat taaatgtgat  69540
aaactgctgc aacaccatgc caggcacaca ccaaggcatc gatgagggtc cgctgtgacg  69600
atggtgccaa ccttgcctat cctgccatca ggggtgaagg gcgcagtctt agttatttct  69660
ctaacctcag cgcctggtgc agtgctaggt atacagaaga atgattggtg agttgaagaa  69720
acaaacatag cagcaaggta atagctatca agtcctttct ttgtacaaga ggtttaagca  69780
aaatattcca aatatctatt gtatttttc cagttaaaaa aaaactatag taacagctta  69840
acaggttttt tttttttttt caaattgtct cacatgctgt ggttcacatt ttgtattcta  69900
aatgcctatg tgatcttcac agcttctttc ctttttgcc ctgcattcta tgtggttgag  69960
agtattcact actattaatt gacctaattt aacactgaag attaactgga ttctggtttt  70020
ttgggcccgt gtgtatttgt cactctccat actccagatt attactctga gacgcatacc  70080
ctagagtggg aatcctgggc agaatatctg agcatcctca taggtctgga ttctcataaa  70140
actgtagact gcttttccaa gatccctgtg gttttacatt tctacatgca gactgtttgc  70200
ttcaaaactc ccttattagc attgaggatg atgacttttt ccccttccga cttatttatt  70260
caatacaatt ttatatttaa aatttttaat tagattatta gtgaaagcgt ttgtctctta  70320
tctaatgtgt ttttggactg atttgctgac ttattgtgac catttactgg gaagtgtttc  70380
gggcagtggg tctaacaaca taaatgcagt gcctacaaaa atgaagaaaa caacaacttt  70440
ctctagtaac tgagagtcct ggaggggcac acatgcaaac gccaggacag caggggagtg  70500
cccacatcct agaacagaga atatgtggtt aggtgggagc ccagaaagga gaagggattt  70560
tcttagcaat ctccacagac acatataatg cagctattaa ctgcaaattt cacctctcta  70620
ctttttata ctgtagtagt tttatggagt aaagtctgtt attctccttt gtgatttctt  70680
ctattgcctt gttaaccttg aaaaatattc tctctgctag aggtctggta aatattcaat  70740
```

-continued

```
tctatttttt ccttgtgtag ttatttagaa tgtttctctc tttagtatct ggtttggtgt  70800
gtgctgtatt tggtgaggat tgaaattaat ttctcctcac taactgctta acagttacta  70860
tgctccatgt gaggaagaat ccattttgat aagcgatgcc tcctttcaca acacaccaac  70920
ttcttaggta tactgtagcc tctttcagtg ttacgagttt accctcaaac ccatgatgtt  70980
tctatcactg gaactttgaa tgttttcatc cgtaacattc ttatccttcc agatacgatc  71040
ctttagaatc actgctgagt aaatccacat acatgacata attttctcct aaactcccag  71100
tttggagttt ctgtcttcag actatatagc acctcctttt tatggtgcat ctacacacac  71160
aggagaccct cccctcactt gtagatttac atttctggcc actgttctca ccatcattct  71220
tggtgactcc aagaggatga ttcttctaac actccaggct cttggttcct taaattcctc  71280
cttcccttct gatgaccgtg gcttccacta ctttcacccc acggtcatgt ccagaggcct  71340
tccatgacaa atcactgcaa tctgtctcaa ttccaacctt cccacaggcc aaccatcagc  71400
cccgtgctcc tagctcaccc tcagctccaa cagcactttc acgccaccag gaactccgat  71460
ctactgatgc tgccgtcccc tcaccacttg ccaaccacct ggtccttacc tctctcctcc  71520
agctgagagc ccaccaccac tccccctttt cttctcctcc atcttcctac acgcctgaca  71580
aagctcagct cctctcctag tgttttttga gtactctcca atgacacctt tggcccaatg  71640
acaccacatg aatattgcac ttgcctaggc ccccagcacc ctccatgctg tcaagcccag  71700
cagtctatcc ttggtcttca ctttgcccct cagcaataag caatacgctg cctgttcccc  71760
tctccttcaa atactctctt cactgtccgt tttgttgttg ttgctgagac agggtctcgc  71820
tatgatgccc aggctgttga gctactggcc tcaagtgatc ctcatgcctc gcttcttttc  71880
actgtcttaa ctggcctctc cttctagctt ctttttctgg tttcagctct ccaatcccta  71940
ggctcatcct tggactctgc tcatacccag aacctcatat ttccaagatt catatttcca  72000
aatgtctaca cagtatgtcc atttacactg gcaaacttaa catatccaaa accaaactct  72060
gaaaacactt cccttaacaa acatttctgt cccacctgca gacttcctgc ttcaggttac  72120
agccactgca tcctttccac tgtttggacc atagtccggg aagccatcct gactcctctg  72180
cttatctcac atcccatatt caatgcacca ggaaatccgc ctctgatcac ttctcaccac  72240
ttctgtgtta tgactccaaa ccaccattgt ctctcccttg tttttcggag cggctccttt  72300
actagtcttc ccagtgcagc cctgagaccc ccatggtaga atccacactg ctgccacagg  72360
tctcaactcc tctgcctaga tccctgcgga gacttcatat tcttgctcag agaagagcct  72420
ctgccacggt ctcaaaggca cactgcctcc cgcaccctcc tcccccgccc cagctcccag  72480
gggttcactg ggcacagtaa gcacatgtcc atgctccaag gccttcgcac tggctgtccc  72540
ctcactgccg tccagtcttc cctcaaatgt catctcctca ctggccccca gcactcatct  72600
tccaactcct tacaggactc tgccttctag gctcatcttc aaatctccta tactactcac  72660
tcgtctgtct cttttacaag aacaaatctc cttgagagaa gaacagtgcc tggaacatgg  72720
caggcactca ataaatgttt ggtatgtgga caagtaaata ttaatttggg aaaaaatgta  72780
tttcatctag cctttcaatt taggaagcca ttttctatct ctcaatgtca ttttgtatct  72840
taaaacgttt gtgatttaag tcttacaaaa ctaattcatt tcttggtaag attacttatt  72900
cctggatatt tataactttt gatcccactc tgtataattc tctttttatc attagatatt  72960
ctaattggct attagtagca aaagaccaat aatttaaaat tgttctgtta tgaggccaat  73020
ataaagactc attttattag ttctaagtat ttttcagtgc tttatttgtt ccaagagctt  73080
tatcccccta tggtttttcc taatatgaaa taatgtcacc ttcatttcct ttttgcctta  73140
```

```
ttttccagtt tctatttaac tgtgttgcag aaattccaga gcaacaaatt aaatgacagc  73200
acccatcatt gtcttttctt gatataaacc gcaaccaggc ttaactgtga actgtaatat  73260
ttgccactgg tttgaaaaag actaaggact ctaccatgtt aaggaaatag ctttaggaca  73320
ggtgtggtgg cttatgcctg taatcccagc actttggaag atgcaggtgg gaggatcgct  73380
tgagcccaag agttcaagac cagcctgggc aacatagtga aaccccatct ctacgaaaaa  73440
aaaaatcagc caggtatggt gatgtacatc tgtagtccta gctactcagg aggctgaggc  73500
aagaggatca cctgagccca ggagttcaag gctgcagtga gccgtaattg caccactgca  73560
ttttgcctgg gtgacatagt gagacacagt ctcaaaaaaa aaaaaaaaaa gaaaaagaaa  73620
aagaaatatc ttcctatggg cattttaaaa aaagcatttt taataggaac tgatgttgaa  73680
ttgtctaatg ttccttttaa aacacctaag atgactgtag cttttcccat ctaacttcct  73740
agtatgtaaa gttatattaa tagattccct tgtactacac ttacaagtca catttaatca  73800
taataaatta ctattttctg gccggtcatg gtgactcatg cctgtaatcc cagcacttcg  73860
ggaggccagg acaggcagat cacgaggtca ggagatcaag accatcctgg ctaacacagt  73920
gaaaccctgt ctctactaaa aatacaaaaa aaaagtggcc gggtgtggtg gcacgtgcct  73980
gtagtcccag ctactcagga gtctgaggca ggagaatagc tggaacccgg gaggtggagg  74040
ttgcagtgag ctgagatcgt aacactgcag tccagcctgg gcaacagagc aggactctgt  74100
ctcaagtaaa taaataaata aatgagtaac tgctttcaag tgttattata tttactagta  74160
ttgtttctga tttttctatc tttattcata ttattctatg cttttgttac attatttttc  74220
ttaggttttc ttgtattttc cagatacaat aaccctggct tatatcttcc tttcaattat  74280
aaatattgct attgttctgt ataatttttc ttaaaagctc aaaacaatgc acctacaact  74340
aatttagaac caagaagcat ttctgaagac agcctttcat ttcttcattg gttactattc  74400
tgttcagttt ttcctaatcc tatggtatca attatgaaag ttcctatttt ctagaaaatt  74460
attttttagt attttgttct ttagcttaat agtacaaaca ttatattgta ctgtttgatg  74520
atttttttct gtctgggtta aatgtttttc tagatcttta aactctaatt ttgtctaggt  74580
tttttcttcc caacccccaa ttaaatatac caagtatata tttctcacac tttgcttttc  74640
aaagatccgg ttctttctta ttcatttact tctgcttttc attgattttt cttcttgaat  74700
ggttctgcct gcacctgcta ccaggaccag tgagtaatga gtgtcaggtc cccagctgaa  74760
ggtggtcaac tctacttgtc tggtaaagga gccccactgg gcggtgggta ggaaagagaa  74820
tgcaaggctc tggttagggc cttgtaaaag tcctcacttg aggcctaccc cacacttggg  74880
caccctcata gacatgtgca ccaagttcca gaaaagtcca actagacttc actgttagta  74940
ctgtgacaca agtaagggcc aattacacaa tttaattatc aaacaataac acaacactaa  75000
ccgtttcagc tttcacaaat gtggactcaa tctatggccg ccaccaagat gggtttgttc  75060
tccttttaac agtctacagg gaatctgcta agcatacact aacaatggat tatagctgat  75120
gccacctccc acacctctca ctcctgccct gtcctcgccc agagctccag gctcaatttg  75180
aaggtttctt gacatttctt cccctacccc tcaagccagg ggcaactcca ttctgaactg  75240
gtatccgtcc ccataagcct gttgtcctta gggtctcagc agaggtgata cctctgacta  75300
tctaggcatc cagccaagaa tctatctcat acctctctgt gccctatcct aagtattccc  75360
aaatcaatct cctcttctct acctcaatta tcacaggcct agctcaggcc ctgacagtgt  75420
ccatctaaac gactggaaga acctccactt cactgagctg tcacaatgac ctctctgttg  75480
```

-continued

```
tgcttcaaag cttttagtgg ctccctatct cttccatgac aagggactcc ctcagtaaca  75540
gggagcacaa gctttccatg atccgactct ggcatacctg accagcctca ctttgtgctg  75600
ctccctgcct tgtctataaa gatccagcca tggtgaaatg cctccaaatc cccattcaca  75660
ccaagacttt ctcacttatg ctgtaccacc ctgcctggaa aaccctttgg tccattcctg  75720
gaccaaacgg actcagactc ctaagtcaag tctaaattgc actcaacctg gtatccttga  75780
cacctgagtg tacagtgcat gggcaacctt ccccctcagt ctaaattcat aaaatgtgct  75840
tctttccatg ccaagtttat ttaaaacact gcaaacatac tcaaggtcaa gttgagaaac  75900
ttttcaatgg gcatctgtga gctgatttct ggggaataaa caaagtgtgc ttacggactt  75960
agtgatccgc tgatgaaggt actgattctg ttcagcagga caaacagcag aacgtgggaa  76020
gttctacatt aaagatataa acatataccc catgagggca agagtgggga gactgaatgc  76080
agctggagac aggtagtgga cccggtgact gcacagatct taagggacag gcagggtgtg  76140
actgattgtg atggggtggg acagcccaga catagggctg ctttaaggac caaacagtcc  76200
cacaggggac gtggcggtgc tgctgatctg agccaggtgt caggggccca cccaccccaa  76260
caggcagtcc cactcaccgc ctgaatgatt ccggaggata gagacacacc gccactgctc  76320
cacattggca agcttaccac tggagccgaa cacggtgctg gggccgatgt acctgtgtga  76380
gaaaggggcc aaaaaggcac tcatggagtg ctctgggcac tgcatagaaa tgctccctgc  76440
agccagctta tcagggcaca cagaacaaag caaaaacaaa caagaactgg aaagcactgg  76500
gttgttgaat aaaaggggct ggttaggtga attatgatcc atgcacttga tgaaatacta  76560
cacagccatt acaaatcttg catgggaaaa cgttcacaat aagtgaaaga agcaggccac  76620
aggacatcac atacaatatg atatcactta tgtaaaggaa aaaaaaccac atgacatgga  76680
tagcatctat gcatggaaaa tggattagaa ggacacacat cccaaaatgt caaaatatta  76740
actgtagctt tctttaggtg gtgtgatgag ggatattttt tcttttgtat ttttagtttt  76800
ctaaattgta tactaaatgt tacttatgtt ggctatttaa agaagcaaaa tcaacagtat  76860
tttattttta agcatctcac aatgaatcaa atggctttga catctgaggc agagaaacca  76920
cgcgatctat aggtactagc ccccaccaca ggagccagag gagcatcaat cacctggggc  76980
ctggtggagg cagtgctgac acaccgatga tcagagcctc tgataacacc ttttgctctt  77040
gtagagctca tcacaaatcc acagaaagag tgtgctgaga tagccaagta ggctgaagag  77100
acagcctctg cctctgctct tgaagccaca gccacagggc cactcttggt gagcaatggt  77160
gcagggtctg gtgccccaga ctgactggcc cagagacctg ggagcaatag ttttccaggt  77220
gatggttagc tccttttgag agtagagcag aggctgcccc aggtggggac caacagagaa  77280
taaagtaatg gcaaagaggc tggactctgg atcccctgcc ccagatcctg ggcaagaacc  77340
agagcaccct gacttttaac cattttgtat attgggcttc catgtgaaat ttcacttgaa  77400
aaaacaaaag caacgaagcc ccacccacat cggcactaga agagatcaga ctttcctttt  77460
caggtgagag cctgcagtcc tgtgaggggg cagctgacca ggtctcctga attcctggtc  77520
aggctccacc tgctcctgac ctacatgcac tttccactac ttatgaggtc agggctatgg  77580
gaacttcagt gacagggtag ggaaaggtga ctttgataaa gaccagcaaa gcagcttcta  77640
aaaataaaat gtgaagaaag gaaaatgatg cttacgtagc ccgcttccac accataatca  77700
gtttgtcatc tcccccagaa gctaaataca tcccactgtt tgaccaccgc acacagttca  77760
cacatgctgg gaagaaaaaa aaataaggtg atgaaaatcc agtagtcatg cccatttgct  77820
ttatgtagag tttggcaaga tgtaaagggt ttataaaatc taatctatct aatctattta  77880
```

-continued

```
aggcatctac tgtgtgagag ccccagaaaa acaattcagt ttaagcacta acctacttgt  77940
gctataaaaa caaattacca gaacagtctg gagggggaaa aatatacatt atctgagaat  78000
cgttagtgct gaatgacata gtcaatagaa ggcttctttc taagaaaatc aaaaaatgat  78060
aaccaaatct cattatttca aaagggtcat ctattaatga gacacatttc tgagtagaga  78120
ttattctcaa aaaaagagta cgtgctaaaa agggtcagat gctttttcta gatttttcag  78180
atgaacagtc tgttacagta taaaactctg acttcatctc atctgtcaga gccagccctg  78240
tcacattcgg attttccaaa ctcgccagca ctgcagattg actgactctg cgcttataag  78300
ctaagatcag cagaaattcc cccaggcccc tgatgggcca gagcctccaa gagcactcac  78360
aacttggcct ttggaagacc tgaaagatgg ctatcaaagt tgtagccccc acatggcccg  78420
tgagtaacat gctccaggtc tgaagacact gagaggcatg ttgagaggac aagaacacac  78480
agaggaaagg aaggagctga tgtccaaagg ccagtgactg ttcattaagc atctcagggg  78540
tgggaaacta aggcactaca gcaggaaagg aaaccatcac actgtctgat ggccaaaagg  78600
gtcctggcag agagcctcag agtgacacag taacaacctg agatgttttg gcaaattgtc  78660
tcttgcgcac ccttccccag aaccctactg tgtccaggtc gctggcccca aagccccatg  78720
gaatcaggca gtaacgactc atgagcagga aatcaccaga ggtacctgca gactgtccaa  78780
agatggttct gtgggcgggc cgagtcttct gctgaataac tcacccaggt gtgcagccaa  78840
catctgtgcc ttcagacagc aggccgaggg gagttaccgc cgcacggggc cttatctttc  78900
taattacaaa cacatgtgct aaccttgggc actctgccaa cacgcaaagc ctgcaaaggg  78960
ccactctgta atacctaagt gattgtccat ctggcaaagc atcttgggaa tattttcatc  79020
cttctcgtca tcctcctgga ggactggaga catattccag atcacaacct tcccagaatc  79080
ctgccctgga acaaaggagc agaaatggct gaatgtgcaa ggagtagaaa tttgatatta  79140
atatttaatg tcaaattaaa ttaggagaag tcctcactta gcttccataa acaataatta  79200
actagatcta aggagactga atttaaatta ctaatttaag ttacagaaaa gatgataagt  79260
actcatgggg acgaaacgga gcggacttag cagtcagcag aagtcaacct gactttacaa  79320
aaagaacttt agactagcaa tcaggaggga actgagctct gatctggcct ctaacacgga  79380
tccaccaggg gtccctaaaa ggtcttcatc cctgcccagc acctagactc cgactccttg  79440
actcctcatc tgtgaaatga ggagaaggga aagtcaatgt cataagacct tttctgttct  79500
gtgtacaccc taaaaagcaa acagaaaagc acaccctagt ggggtttccc tccccttcca  79560
ggtgctgcct ggaatttagg ctgttccaga gccgactgtt ttgagaccca aatgtaccct  79620
gaacacagga aaaatggctc attatcttgt tatccaccct ttgcagttac ctacagacga  79680
gagaccacca aaagagggga tttagggctc ccgtggtcat gagttgatgt attgctcggc  79740
taaaaaatat acccatgcct tttagtaatg atttcttttc tttttttttt tttgagatgg  79800
agtctcactc tgtctcccag gctggagtgc agtggcacga tctcggctca ctgcaacctc  79860
cgcctcgcag gttccagcga ttctcctatc tcagcctccc gactagctgg gattacaggc  79920
gaacaccatg acacctagct aatttttgta tttttagtag agacggggtt tcgccatgtt  79980
ggccaggctg attcgaactc ctgacctcag atgattcgcc tgccttggcc tcccaaagtg  80040
ctgaaatcac aggcgtgagc caccgtgccc agccttagta atgatttcta agctttccat  80100
cactgatatc taacgaagtt tagcccctca cttaattttc ctattataat agggccaaat  80160
ccaatgaaca tgccaaaatt accataaagc atgtttgaaa ctgcctcttg gccaatatgt  80220
```

-continued

```
aaaagtattt ccaaaacatc tctgctggac caaggtggca aaatgtgtgt cttctgggta  80280
caggtgcgaa ccctctgatt ccttcagcta agtccatgtg ttctctctca tgtgctgcac  80340
ctcctcctct cgggtgcagt ccacagcatg gaaggagaga aaggcttccc tgcccacagc  80400
ttccctacac tcccttccag ctccttgatt ctgggtggaa gcatctgctg gaaacccacc  80460
ctgcagcacc tggcctgagg acctagagct cacaaaggca ctctctaagt gctgcctggg  80520
gaggcctggt tggagggagg ccccgctctg gggtaaagat gacagagggc tgggctctgt  80580
ggaatgctac attgtgtcac tatatataca tcttggtatt gtggcatgaa gaacagctct  80640
gtctttccaa atagaaccat gcaacattgc aaaagatgct ggctgaagca taagggcaat  80700
actaccaata acagtttcaa atggtgtggg ctttcttact tgcccacagt gtgctttctc  80760
tttaacctaa ctgaattcct ttgacgagaa aatgggccta ataactacac gattgcttta  80820
gaagcttaaa ttaccctcat tccctttttt cagatgagaa aaatgctgac agagcccttg  80880
tctctggggc tgggctttgc ccactggacc acctaccgct ctcgatgctc tacaagtttg  80940
gggatacaaa ctgattttaa tattaactca ataaacagaa attagaatga tacatccgct  81000
gccaaaatac ttacagagag cacactaaag ccataaaagg attttgattt tattcattca  81060
gataacacat tataactgta cattttaaac agcgttgcat ccatcctgaa aaatagcaag  81120
tattccctct acagctaaat ggacagcagg agaagagcaa ggtggcaggg ctgttaagct  81180
ttccctttct ttattccata aacatacctt gtcctccagt tgcgaacttg gtcccgtcag  81240
ggtgaatatc aactgaaaaa atcggcttgc ctggaaacaa agaaaaaaaa atacagtatc  81300
taaattggct tttattcatt gaagtgtatc aaactcaaca gattcagtta aagtctaaac  81360
tgctagaaga ttctccaaac atcagacaac tgaaagtcca acagtgggag aaagcattcc  81420
atcactgaga atggctgagc ccataggatg cctgggcatt tgtctgccat cttgtaggga  81480
tgtgtgtttg taatggctat gagctgttca tgattgaagt tctgagtctc aggtacttag  81540
tgaaaagggc acacagctgt aactccagac atctccctat tgcatggatc tgcacttgac  81600
tggcagccta gacagaagga ctgctatttg tcttttctgg ctgacagctg agcaggacca  81660
gcgctggctg caaccaagga gcattgcttc gcttgtcata cttctgcttc caaacagccc  81720
tcttttgttt gtgctgtgaa gttcccatac cgtctgccat ctcagcatct cctctggctg  81780
aacctccttc acagtttgta ctctatgtta aattagctgt tcaattcctc caggagaaag  81840
gactgtggct attagttctt agaagcccca aagagcccag tatgggccta ggcttgcact  81900
aggatcccat gaagctagct ggctggctgg gtgggtggat cagaccggca aaagcactgt  81960
aggagcttga aacccagcag accatagaag gcactcacgc ctggtgggca tttgtccagc  82020
tccctgcttc taggacaaag gtttaagagc tacaagtggc atgtcagttg ctgttgagtt  82080
catcacatct tcagcctcta gcacagtacc cagtgtacag tagcgcagta atatttgttc  82140
attgacaaag gagatacatg acaatgatct gagcatcaac aattgctgat atagatgggc  82200
tgttgccaag agtctcttaa ttgaacatgt tctgtctctg tcacccaaga ggaggcaatg  82260
tggacacagt accagagtca ccagccctag aatcactcag caagtactgg gatcaggagt  82320
gtgtgggcag gcagtggctg tctgagaact gtgaagtcct gccagggctc ccatgcaagt  82380
gtgaaaatta aatgctggtg cccaaaaggc actgcccagc atgggaccca ggcagcaccc  82440
agctgtggag agccgcagcc atgtagtcaa atcaagcatg aacttgagat aaaatacact  82500
ttccttctta ctggtcacta tgtagtatag gttgagtatc ccttatctga aacacctggg  82560
acccgtttta accaaaggga aatgacagaa gtaatgttgc tccagttcca ggtgtaggcc  82620
```

-continued

```
ttaagagtct agcagttcaa ctttggctct ctggagaaac ctagttgtca tgtgagaagt  82680
ccaagtaccc tgagaccacc atgttttgaa gaggcccaag ctggccacat gtagagcatc  82740
aaagagcccg gacaagtgag aatcaaggtc acagacacag gcctggtgag gtgttctatc  82800
cccaagctat tcgagccatc ccagcagatt ccatagagcc aagatgagct gaacctgcta  82860
agtcctgaca agctgcagaa ttatgagcaa ataataaaac tgttattggt ttaagccagc  82920
aaatttaggg gtttgtcata taagagataa accaaaatgc caattcattt gcttttctgc  82980
ttaagccagc ttgagctggg catttgtcat tttaacaaaa aatgttctag ctgacagctt  83040
tggtcttgac gggcaatcag ggcggaacat tcccctcccc ttggagtgct tttcagttcc  83100
ataagtctgt gagacattgt attacatcag tcccctcaag aagcacacca gaaaccctta  83160
cctgcaagtc acagttcccc tgactaccca agagcacgta caggctgagc caggctgtgc  83220
tgagggctca gctgcacaag taaccaatta cagcccatgc gctttagatc atgcccactc  83280
acagcatcaa ctgcatgttt tctcactcag tctctgtttg cagatttcta ctatgtgcca  83340
ggcattaggc taagcaatga gaaagtaaag atacataatc atacaaactc ccctagtaag  83400
atgtccactg atggacactt cacaagcaga aagccacctg actcagcctc gggcttcctg  83460
cagaaataat aactgaattg ggtcccaagg gttgagtaag agttagccag aagatcgggt  83520
gaaggagagg gttttcaggc tgaggggacg cacggcatgg aatcaagaaa taggctgatg  83580
taatgttgca gagcagactg caggtagaga gtgtgagaaa gaagaggaga cagagatggc  83640
tcagcaagca tcagtaagga gctgagacat ttctctaaag gtactttcaa ggcagggtaa  83700
tgccaaggtc agattcacat tctggctcca caatagcagt gtggaaaatg ggggtggggg  83760
cctcaaggct ccaggggaag gcagggatgg aggctggcaa caagtttggg ttttggcatt  83820
aaacatcatg ggctgaatct ttagccctgc cacttaccca gctacaaagc cttgagattt  83880
tattttattt tatttttatt attttgagaa ggcgtgcctg gttcattggc accaggtttc  83940
ctttcctagt gctatgcaga ttagatgaaa tatggtaggg gacctacaca gataccagcg  84000
cagtgctggc tccccgcctc cttacagcac taggcctttc catcccaagg aaagcagtca  84060
ctcacattcc attagtggga atgaaactat ttatttattt atttatttat ttatttattt  84120
atagacagag tttcgctctg tcgcccaggc tagagtgcag tggcgtgatc tccactcact  84180
gcaagctccg tctcccaggt tcacgccatt ctcctgcctc agcctcctga atagctggga  84240
ctacaggtgc ctgctaccac gcccagctaa ttttggtatt tttagtagaa acagggtttc  84300
accatgttag ccaggatggt ctcgatctcc tgacctcatg atccgaccac ctcagcctcc  84360
caaagtgctg ggattacagg ggtaatcccg gccaccgtgc ccggccagga atgaacctct  84420
tctaaagggc tctctgaggt ggagctaagg aaagggacct tctggctgag ctagttagac  84480
aactcttcct gtggcacagc atgatgatga caaagatgag ttcccaacta cctccagtgt  84540
ctggcctttc tttgtaatag agacagaaag aaaagacaaa ttaacacacc ctagactcta  84600
gagacaccaa gcaatcacct atccttagat caaccccaga tcagaatgtt gtccctgcac  84660
acccaataca cagccaatat agtcagccac tgtctactgt ctggggattt gctgatttga  84720
caagagcagc acaaatgctt tccacctggc agggaataaa gaatacatta aggaagctgg  84780
gattatgaca gggcatgctc aggtagaatc gtaccctcct tcacactagg ggaaagattc  84840
ctagaagagg actaaacatg ggaacttaaa ctctgagcac agagaggtgg ccagaggcaa  84900
agcagagagg gcacaatgga gagctgctgg cccttccctc tcagcagtcc cacagacctt  84960
```

-continued

```
tggtttggct ccaaaaagtc tctgggcttt tatgttctga tagttcattg ggtagagctg  85020
actggaacac atgtgcatat gtccttttgg aatgaagctt gggaaagttg aggcttttgc  85080
ccagtgaatg ttgctcctgg gaacacttcc tgcactgccc aatagaactt ggttttaacc  85140
aatgttgaca aatttagaat taaaaataag aaaatgtttg aaacatttat taaatgaaac  85200
agttacagaa caatactaaa atataaggtg gggccggtca tggtggctca cgccggtaat  85260
cccagcactt tgggaagcca aggcaggtag atcacttgag gtcaggagtt tgagaccagc  85320
ctgaccaaca ggcgcaccat tgcactccag cctgggtgac agagtgagac tgtctcaaga  85380
aacaaaacaa aacaaaaaat atataaggtg ggtgcaaaca acacaaactt atttatttat  85440
ttatttattt attttgagac gaaatctcac tctgtcaccc aggctggagt gcagtaacgc  85500
aatctcagct cactgcaacc tctacctcct aagttcaagc gattctcctg cctcagcctc  85560
ccgagtagct gggactatag gtgtgtgcca ccatgcctgg ctaaaaagtg ctggaattac  85620
aggcttgagc caccccgccc agctacaaac aacataatct taaatgtaga aaaccctaaa  85680
aattccacag aaaaactatt agtgctaata atgaattcag caaagttgca ggatacaaaa  85740
tcaacaaaca aaagtcatct gcatttctat acaccaacaa tgaacaatct gaaagggaaa  85800
ttaagaaaac aattcaattt acaacagaat caaaatgaat aaaatttgta ggaataaact  85860
tagcccagga ggcgaaagac ttgtacactg aaactataaa atataaaaca ctgctgaagg  85920
aaatcaaaga cacaaataaa tgaaaaaaca ttatatatgt actcatggac tagaagattt  85980
aataacttta agatgttagg ctgggcacag tggctcatgc ctgtaatccc agcactttgg  86040
gaggctgagg tgggtggatc acatgaggtt gggagtccaa gaccagcctg atcaacatgg  86100
agaaaccctg tctctactaa aaatacaaaa attggccgga catggtagca catgcctata  86160
atcccagcta cttgggaggc tgaggcagga gaattgcttg aacccgggag gtggaggttg  86220
cagtgagcca attttgtgcc attgcactcc agcctgggca acaagagtga aactccgtct  86280
caaaaaaaaa agatgtcaaa actcttaaaa gtgatttgta ggcttaatgc aatccctatg  86340
aaaatcccaa tggtactttc tgcagaaata aaaaaaaaaa tcgatcccaa aattcacatg  86400
gaatcttaag ggactctgaa cagtcaaaag aatcttcaaa aagtacaaag ttgaggatct  86460
cgcatttcct tatttcaaaa cttactacaa agctacagta atcagaacag tgaagtacag  86520
gcatagacag acacctagaa caacagaata cagagcccag aaataaactg ttgtgtatat  86580
gatcaaatga ttttgacaag gggccaagac cattcaatgg ggaaagaaca gtctctttta  86640
caaatggtgc tgcgaaaact gcacatgcaa aagaatgaag ttggatccct atctcatacc  86700
atatacaatt aactcaaaat ggatcaaaga cctgcatata tatcttagaa ggaaacatag  86760
gggaaaagct tcacaagatt ggatttggca gtaatttctt tttctttttt ctttctttct  86820
tttctttttt tttgagacag cacctcattc tgtcgcccag gctggagtgc agtggtatga  86880
tcttggccca ctgcagcctc aaccttccag gctcaagcaa ccctcccacc tcagtctcct  86940
gagtagttgg ggactgaggg cacaaccacg cctggtgcgc accaccacgc ctggctaatt  87000
tttgtatttc ttgtagagat ggggtttcac catgttgccc agactggtct caaactcctg  87060
agttcaagcg atctgctacc tttacgtccc aaagtgctag gattataggc gtgcaccact  87120
gcatctgacc atgaatttgg caataatttc ttagatatga gactaaaggc acagacaata  87180
aaagaaaaat aaactgaact ttatcaaaat taaaaacttt tgtgcatcaa aggaaaatat  87240
caacagaata aaaaggcaac ccatagaatg ggagaaatat ctgcaaatta catatctgat  87300
aagggattaa tgtccagaat atatagagaa atcctgaaac tcaacaacgt gactcaaaat  87360
```

```
tgggcaaata acttgaacag gcatttctcc aaagaagata tacaaatgag gcacggtgca  87420
atggctcaca tctgtaatcc cagcactttg ggaggctgag gtgggtggat cacctgaggt  87480
aaagaattca agaccagcct ggccaacatg gtgaaacccc atctcttcta aaactacaaa  87540
aattagccaa gcgtggtggt gggtgcctgt agtcctatct actctggagg ctgaagcagg  87600
agaatcactt gaacccaggg ggcagaggtt gcagtgagct gagatcgtgc cattgcactc  87660
cagcctgggc gacagtgtga gactctgtct caaaaaagaa aagaaaagaa aagaaaagat  87720
acacaaataa ccaacaagca catgaaaaga tgtcaacatc agtaaccagt agagaaatgc  87780
aagtcaaaac cacaattacg tattacctca catccattaa gatggctact aacggctggg  87840
tgcggtggct catgcctgta atcccagcac tttgagaggc taaggtgggt ggatcaagag  87900
gtcaagagat caagaccatc ctggccaaca tggtgaaacc ccatctctac taaaaataca  87960
aaaattagct gggcatggta gcgtgtgcct gtagtcccag ctactcggga ggctgaggca  88020
ggagaatcac ttgaacctgg gaggcggagg ttgcagtggg ccaagatccc gccactgcac  88080
tccagcctgg agacacagtg agactccgtc tcaaaaaaaa taaataaata aaaagatggc  88140
tacttacaaa aaacctcagg aaataagtgt tgatgagggt gtacagaaat tgtaactctt  88200
gttaaaaata taattaccat atgacctggc aattatactt ctgggtatat aaccaaaaga  88260
aagggtcttg aagagctatt tgtacaccca tgttcatagc agtactattc actacagcca  88320
agaggtggaa gcaacccaag tgtcccttga ccgatgaatg gatgaacaaa atgtggtata  88380
tatccataca atggaatatt atttagcctt aaaaaggaaa gtagttctga tgcacactac  88440
aatgtggatg aacctcaaag acattatggt aagtgaaaaa agacaaatgt cataggattc  88500
cacttatatg agctatctat gaatagtcaa attcatagaa acacaaagta gaatggtggt  88560
tgcctacgtc tgagttgagg ggaaaatagg gagttgttgc ttaattggta taaaggtttg  88620
caagatgaaa atgttccgga gactggctgc acaataatgt gaattgtgac agtactgaat  88680
tacatactta aaaatgatta agatagtaaa ttttatattg tgaatatctg accacaattt  88740
ttaaaatgct aataaaaacc aaacaaaacc aaaaataaaa ataaataaaa tggaggagtg  88800
taggagggag gtgggtgtaa ttataaaaat tgttggcggg gtgcggtggc tcacacctgt  88860
aatcccaaca ctttgggagg ctgaggcggg tggatcatga ggtcaggaga ttgagaccat  88920
cctgactaac acggtgaaac cccgtctcta ttaaaaatac aaaaaaaaaa aattgccagg  88980
catggtggtg gcaggcgcct gtagtcccag ctacttggga ggctgaggca ggagaatggc  89040
atgaacctgg gaggcggagc ttgcagtgag ccgagatcgc gcctgttcca gcctgggcaa  89100
cagagcgaga ctctgtctca aaaaaataaa aataaaaaat atataaaaat tgttggaact  89160
gttcagcatc tcgactgcag tggtagatac atgaacctgc acaggtgaca aaattgtata  89220
gaactaaaca tacacacgca caaataagta caaacaaaac tggggaaata aattttaaaa  89280
aataggtagc atatgtcaat gtcaactata gttttgcaaa atgttaacat tgggagaaac  89340
tggactaagt ccagaagtac cttctcagta tttcatacaa ttcggtgtga atctataatc  89400
atctcgataa gaaataaaca cacacacaca cacacacaca cacaaggcct gtttttaaaa  89460
aacgatatat atgtgtgtgt actaatatat aaggcagtag aggtaaatat ccaaacacca  89520
gaggttaggt cataataaaa atgattcttt tcatgtgcag gtgacaatat gcacactcta  89580
taacaagcaa tccctctgga gaaactcatc agccaaacac actaatgtga cctatatgca  89640
agtaactcct atggctgact gccttctaga cacctcaccc tgatcttctc tataacggtc  89700
```

-continued

```
tgatctttcc aagaaacctg ctctacccac tgtctgcccc aacacagtta aggccagacc  89760
ttgagaggag aggccaacaa tccttgcaca atggccaccc cgcccccacg acttttctga  89820
cctcatctcc tactaacccc caccatcgct ggtcttcctc ttttcttgga ctgtaccagg  89880
tgcgctccta tcttgggcct tgtactgact cttccttgcc tccttcaggt ctttgctcaa  89940
tgtcaccctc acattgaggc ctactctaac aactttaatt taaaggatta tttccccaat  90000
gtggcacaac aaatcccctt agtcctgatc tatttatttc ctcgggaatt tcttacatat  90060
taatttcctt tattgtatgt ctgtctactc tgcccactag aatgtaaact ccagtaagta  90120
gatcagctct tttgtctgtt ttattcacta attcatcctc aggacccaga gctgtggctt  90180
ggcacataac aggcacaaca ataaaaactt gttgctgttg aatggctgga gaaagctcat  90240
gacagaagca ctacattcaa acaccttcag tatcactggt gtaacaatct ttggaaggca  90300
ggctcctgat ctactgctgt ggggactcag atttcgccaa ctgcctgcag gtgggaagca  90360
caccccttggc tggttcacag ccatctgctg ctgttatctc taccactttc gaccacaaaa  90420
acttatcccc atcttcttta gtaagcatga cacaatgaca tctcataggt gtcagatgcc  90480
taagagattg aaaacatagc acaggaagga agctgttgca ccatacaacc attgtgtgtg  90540
tgtgtgtgtg tgtgtgtgtg tgcacgcgcc acaaactaaa gtggaaaagt gtcacaggta  90600
tatcatttag gagaccttaa tcacttctcc tgaagcatct gccaacatat aatcaacaaa  90660
gttttgagat tgggcgcagt ggctcactcc tgtaatccca gcactttggg aggccaaggc  90720
aggcagatca cttgctctga ggaattcgag accactttag gcaacatggt gaaccccatc  90780
tctacaaatt aaaaacaaaa aacaaaaatt acccagtagt ggtggtgcaa gcctgtagtc  90840
tcagctactc aggaggctga ggtgggagga tctattgagc tcgggaggtc gaggctgcag  90900
tgagccgtga tcacgccact gcactgcagc ctgggcaaca aaaaaaactg tctcaaaaaa  90960
aaaaaaaaaa aaaccaaacc aaaacaaaaa acaaacaaac aaacaaaacc ccaaaaaaca  91020
aaaaagtttt gacgaaaggc atttctgttt cttaatactt ctttcccccc tcattttgca  91080
aaacagaggt attccctaaa aagtatctgc acaggaggat tgcttgagcc caggagctca  91140
aggctgcagt gaactatggt catgccactg tactccattc tgagcgacaa agtaagacct  91200
tgtctttaaa aaaaaaagtt atctgcaagg gtacaatgta tattattcag gtgatggttg  91260
cactaaaagc ccagacttca tcactaagca atatatccat gtaacaaaac tgcacttaca  91320
tcccttaaat ttaacaacaa aaagttatct gcaaaatgta ctcctataaa tctagtccct  91380
tccacctact tccattagaa aattaaaagc tacatttcca tagtgggaaa aatctgctag  91440
ctcaacaata accacaatta agaagacaac aaacctacaa tactatttaa gtgaaaaatg  91500
cacagcaggc tgggcgcagt ggctcacgcc tgtaatccca gcactttggg aggtcgaggc  91560
gggtggatca cctgaggtca ggagttcaaa accagcctgg ccaacatggt gaaaccccat  91620
ctctactaaa aatacaaaaa atttattggg tgtggtggca agtgcctgta atcccagcta  91680
atcggaaggc tgaggcagga gaatcgcttg aaccctggag gcagagattg cagtgagccg  91740
aggttgcacc attgcactcc agcctgggca acaaaagcga aactccgtct caaaaaaaaa  91800
aaaaaaaatg cacagcaaca ttttagctat gccagttatc tgtacaatgc aaggtctgta  91860
agggaggcta cacaccaaag acattggatt tgctatggtg actgatgggg atttggttaa  91920
agtcttaaaa aaattcagac acttgtataa tgtgcataca ctaaatgcgt cttctaaaat  91980
cacaaaatca cccagttgtt tttttccaaa tggtttgaaa gaccacatta aaagttttaa  92040
caatgtgttt tcctttgtgc attttctaat ttttcctaac ttctttcaca gtcttactga  92100
```

-continued

```
gctcagtaga tagcaactct gcccttagac tggaactcat ccttctgttc tctcttaact  92160
cttttgtgtg tgtgtgtgta tgagatggag tcttgctctg tcacccaggc tggaccgcag  92220
tgatgcgacc tcagctcact gcaacctccc actctgggtt tcaagcaatt ctcctgcctc  92280
agcctcccga gttgctggga ctacaggtac atgccaccac acctggctaa tttttgtatt  92340
tttagtagag acgcattttt gccatgttgg ccagactggt cttgaactcc taacctcaag  92400
tgatctgcct gccttggcct cccaaagtgc tgggattaca ggtgtgagcc accatgcccg  92460
gcctgttcta tcttatctca taccccatat ttgaccctac cttcccaaca tacccataac  92520
ccaaactttc aggagagatg caaatgttcc ttaactttat cagggaacag gttacaaagt  92580
acattaactt gtcaaaagtc aacacattat acatttaagg tctggacatt ttatttatac  92640
ctgaaaagaa tgtgtttata tatacacaca cacacacaca cacacataca catatatata  92700
tatacatata tatattacat atacatataa acacatatat acatgtaatg tattacataa  92760
acacacacac acacagagtc tcccccacca gctccaacca tttcttgcca tcacagccat  92820
caccatcctg atccagacca tctcttgctt ggattactac cagtagttgg cattataact  92880
ggtctcctgg ctcctccctc cctctggtcc cccacaacca atctagtctc cacgtagcag  92940
tcagaaagat ctctaaaact cacgtcagat cacagtagtc ctctgctccc cttgcagtga  93000
gaatcaaggc cttctagtag cctactaggc tctcccaatc agtctgctat tcactctctg  93060
gcctcctctc tcacagccct tgccttgctc caaccacaat gacatctgtg ctactgctca  93120
aaccctccag gcaagttcca gctcttcttt ctgcctggaa tgctcttccc tcagatggca  93180
ccttcctcat ctccatgagg cctgcagcga atgctgtggt atcatgccca ggtccctacc  93240
ctccagggac taaagcacac tcccatagct atctgtggag tgttggcagc cccaacagct  93300
ccctgtagtc ttcctccagg tcagacctgc cctcagtgga agcactcttt tggcagggtc  93360
aggtctcctt tccaaaagag cctatatcca ggctgtggac acgggagtaa agggccctgg  93420
tctcccaccc caatccacga caattctgaa gggcctcccc agctacagaa ctcccagcag  93480
ggctggctgc ggctttctct gtgcttacat catagcttgc cttctccctc tgtctggtgc  93540
tgcttccttc actccttcaa tggtgtggat cccgagagcc ctccccaata atcctgcatg  93600
caaaaatctg cagctcagaa tctgactcct gcaacaaggc ctttgctcaa atgttacctt  93660
ttcactcagg ctttgccaaa gcgtcccact taaacccgtc tatcccccgc ctctgcctca  93720
gcattcctca tctctaagtc tgctgtttct ccaattcaca ggatcttgtt tgtgattccg  93780
ctatgtgtct caccaggaag ctcccctccc acatctcctc ttttccactt acacaggaaa  93840
cccccagcag atcccatccc agtctcactg gccaggatgc ataacaggct gctcctcaag  93900
agcctggcat gctgcttggt tcactgctgt tttaagagct gaaaacatac acacactgac  93960
tcacacacat gcatacacac acacacacac acacacacac acacacacac acacacatat  94020
tttcagctct taaaacagca gtgaatttat caactgtttt ttccatgtga gaccttctgt  94080
tagaggatgc agcagacctg gagtctgctc caacgtaggt ctatccctgg acctcaaata  94140
aggcctgctg tcccttctgt ctggtcttca ccacagtggc ttttgccagg gtagcctccc  94200
agggaattgg cctaccctag gtttgttaat gcatcgaggc agacaatgct tttaggagca  94260
acaaatgtta atctaaatgg gtttttcttt tgccaggagt gttttaaaac catttgctat  94320
ctgtttcatc cacttccttt cctaaaatgg aaggctctag aagacagaat catgtaaatg  94380
aactccttgg gtaaggcttg ggcagaatgt ttcccctcat cattggaatt gccagcagat  94440
```

-continued

```
tccactagaa agagccagcc aggatgaaca agaagtttat ttgcagtaca tcaactctac  94500
cagccaagga caacagacac tgttagctgc ccatccatca gccactttcc atcaccaact  94560
tccagcactc agcactcctt caacatttac tgagtgacta ctatggtgtg taccaagtac  94620
cattcctggc cctgggaaaa gggcatgagc aaagacaaag tctgttttcc aggagcatat  94680
gctcccccag ggaggtgtct aatagaactc cagttttatt cagatatcca ctctgcccgt  94740
tatgtaagcc agtaggcaac gatgattgat gcaagagagg gcacatgacc tagttggacc  94800
aatcagccaa tggggaagac ccaaagtcca aggctggggc acagacctct cccttctgct  94860
tctcactgaa aacattctcg ataccccaca accagagaac tcttgaaaat caaatgccag  94920
aaaaggctca ccaagcacat ttcaagagaa acctaccagg ttagaagccc caaggcactc  94980
agaatggcta cagaagcagt cagaggacaa gctccaggga ccagactcct ggtcccatgc  95040
tgtaccacgt ggtttctgaa agctgtcctt ctgaggagga aatgggcctg aagctctcca  95100
ggacggagtg gccagcctca gcacaaagac cagtgcttag caaattagaa agagtaagtc  95160
tgggcttggg ctggagtcta agtgtgactc tcaacacatc tccatcacat ctagtggaat  95220
cttggtgcca gggggtcacc tcatctcact cagcctaagt ttccatctgt gaactgtaat  95280
gctgcaagtc atagagaatt tcgagggtaa tcttctatcg tatataacaa gtcctgagat  95340
aggtcagctt cagggtgcat taatttagca acttaaagag acgtgtccct ctgtcttcct  95400
ctcctgtcat cagtgtcggc cctgttccaa gctggctttt acacgcagac ctagtaaagt  95460
ccagcagaag agactagcct gtcaagcatc tcctcttatt taattcccta ggaggtccca  95520
gcagacgtcc cctcctagtc tcaagggcca aaatggcatc acatggctgt tcctcaacaa  95580
atccttggca tttacccaca catcagctta gggctatcag caggttggcc tgcagaaggc  95640
agaccaaaaa aattggggtt ctgctaacaa ggaacaaggc aggcaaccct acaatatttg  95700
caacactccc tttgtgctat ttgacaatat gcacaatgtt cacaatccca ctcacttcta  95760
ggtgttgttg ctgactctgg caggatgata aaatgtgctt tgcataaatt tttggtcccc  95820
agggctcatt ccatacctct ggttcatgtg ctagacactt ctgcagtcca taggcaaaca  95880
ccccggatga acagaacatg ctagcaacct ctggggaaag ggaggggtca agccagacac  95940
agagcatcct cttcctggtc accgacagga cccaagatca gcacagtgga agcaggtctc  96000
ctacttggct tcagtggtca aggccagacg ctcctcagaa gtccctccca gctgtgtaac  96060
tatgattctg ctcataaagt gaaaatagtt ttcaaccact tcttagagta aaacaaatgt  96120
ttaagaaaat cccatttcct ggccttcatc catattcttt ctgcagcata ttaaagaaat  96180
aaattcagag agaggctggg agcggtggct cacacctgta ataccagcac tttgggaggc  96240
cgaggcgggt ggatcacctg aggtcaggag ttcgagagca gccaggccaa cgtggcgaaa  96300
atgtgtatta aaaatacaaa aacactaaat accgaatact aaaaatacaa aaattagcca  96360
ggcgtggtgg catgtgcctg taatcccagc tactcgggag gctgaggtag gagaatcact  96420
tgaacccggg aggtggaggt tgcagtgagc tgagaccatg ccactgcact ccagcctggc  96480
ctgggtaaca gagcgagact ctgtctcaaa ataaataaag aaaatatata agtaaataaa  96540
tacattcaga gtggcccaaa tctacagtca cctgcctaca tggccaagtc ccattaattc  96600
tacctctacc ctgtctttag tgcctctcta tttctcacct ccatcacctg tgatctccct  96660
gtctccctga gcatctcacc aagactagaa attcctaact cctctagggc ctgcctaaga  96720
cacaggttgg gtgtttcatc cagcttcctc agaagcctca atgttctcct ctctccccta  96780
accccaagaa ggaagttcaa gctgctggca aggctctgcc tcccagcccc attctccctc  96840
```

-continued

```
ttgccctgtt tagcctccct cctaacatgt tctatgtctt tccctaaatg ctttcaccct  96900
ctgggccttt tctcctgatg gtctcatgtg ctgtagcgcc ttctctgcca tcacaattct  96960
agtcacgtca aggttcagtc caaggacaca tccacaaacc cgactctgct ggtgaagtgc  97020
ccttcctcct tgggctatca cgcttattcc tctagctcct gtttcccctg ccctgcattc  97080
tagaatacgg tttgtatgtc aatctctctc atctatcttc cacacagctt tctgttcaga  97140
gagagagcct tatttacctc tggtccccac agaactctta ccagaaaggt tcaatgtttg  97200
ttgcataaat cagtgaaaaa tccacagcaa aatctcaccc agttttcttc tgactcttca  97260
gatgtactct ggttattttc ctaaatcaac ctactgtctt caggcataag tcaggagaga  97320
aattgctgag agaatttgca ttttctgagc taccacatgg agcaggtgag gcaagaatta  97380
ctgacttcat gaacagatta ggaagagatg gaaaaacttt ttatgtcaca tatttagtaa  97440
gcagcagggc acagagactc cagagcagga tatctgattc caaaaacaga agacaaaatt  97500
cttgtcctca agaaacttac agtctagtcg gaactgtaag acaaatacac caaaaggcaa  97560
ataacttatt cagagcgggg tttctcaccc ttagcactat tgatatttgg ggctagataa  97620
ttctccatga gtgggctgtc ctgcatgcta tacgatgttt aacagatttg tcccctaccc  97680
acttgatacc agtagcacgt accctgccca accctgttgt gacaaccaca aatgtctcta  97740
gacattgccc tgtagaacca ctgatctaaa gcaactgcca tgtttatctc tcaaccactg  97800
caatcatata acctcaccat taggatcctt tccctgccaa ttctcagaca taggtctgca  97860
gtgccctccg gcagcaggct ggaccttacc cacccactcc taactttatc attatatgat  97920
tctgcctaca ttttcccttc aagctgaatt atttaatttt catgctgatg tctcagtagg  97980
acagcttcaa atccttttca gaatgacaca aggtaggggt aaaaataatc caatcgcagg  98040
acaggagaaa atacacacca taaggccatg tgattaccag caaattaccc tgttcttgaa  98100
aatttcccaa atccctttc ataacactgc catcaaagtg tgaaccaaag gccaaaggtg  98160
gacaagagct ctttcagtcc tggccctctt ggttagaact ggcttcacca aagagctgag  98220
cataagcgct gtctgcccag gcatgagaat tccagaaaaa actcaggagc aaaggcccag  98280
agttgggaag agccatgaat ctcaacgaga ttttctaaac atacaaactc catatttcta  98340
caaactttaa aaccagaaac ctagttgttt ttactttctg accttaacct aacttagaaa  98400
taaagcttat tttggtcaat tctaaaataa aatatataga gaatactgta tccaagaaca  98460
cgaagtaaaa tgtgtatgta tgaacaataa ctgacacatc ttctatataa atgatagcta  98520
ttatatttca atttaacaat cttttatatt tggtcccagg ataaaatgga agaggtaagt  98580
cttattttac caaggcccag aagtagagtt ataagtccaa gaatttacag ctagtaaatg  98640
atgcagtttt gaacccagtc tgattccaca ttcaaggctc atttcactac aacgtgacaa  98700
cttcaagatt aacttattga taaccttaga caagtgcttc tcaattgggg gtgattttgg  98760
ctaccaatgg acattggcaa tgactggaga tatttttggt tgatacaact agaagttgta  98820
tcaacttact ctaagaaggt gtttgtgaag tgctactggc atctggtggg tagaggccaa  98880
ggatactaga aacattctat aacatagatg acaatcacac aattttatgg cccaaaatgt  98940
caacctgctg aagttgggaa accctacctt agaggtgtct ctattatcag ccaagaaaat  99000
gaagaccaaa gtacacccac atttcaataa atacttcttc tcctgttcta gctaccctct  99060
ccactttgaa tggattccct gccacaccag agaaaaatgc tgagctgtct gctacttccc  99120
cctttagact ctcgaaaaac agaaaaagta tgttcatgct gggtgcagtg gctcacgcct  99180
```

-continued

```
gtagtcccag ctactcagga tgctgaggca ggaagatccc ttgagcccag gtatttgagt  99240
ctagcctggg caacactgca agatcccatt tctattaaaa aaaaaagtta tgtttgtgct  99300
tcacaaaatt ggagacatga atatagaaca aggaagccag aaagtgcaat gatggcttta  99360
caaaagcaag cacaatttta ctggccacta cccacccctc aggcttccgg ctgagcagcc  99420
cctgctccca gcagccacca atactcctac agtatttaaa ggcctgctcg gtagtgattc  99480
agaccagcat catctcctcc agggcagtgg taatttacct cttgacagtc cttctgaaca  99540
ttccatgaga ttttaaaaga aaggaaattt aacaaagaac aagtttaaaa gaagttaaat  99600
cccatcctgc cagagttgcc atatcttttt tttttttttt ttttttttt gagatggagt  99660
ctcactgtca tcaggctgga gtgcagtggc gcgatctcgg ctcactgcaa cctctacctc  99720
ccgggctcaa gcgattctcc tgtctcagcc tcccgagtag ttgggactac aggtgcgtac  99780
caccacgccc agctaatttt tgtattttta gtagagacgg ggtttcacca tgttggccag  99840
gatggtctcg atctcttgac ctcgtgatcc acctgcctca gcctcccaaa gtgctgggat  99900
tacaggcatg tgccaccgtg cccagcctct ttttattatt acttattatc tcagatttct  99960
aaagcactta acagtttggg gagcattttt atatctacgc tcccaactga gtatcacaag 100020
catactatga agtggttaga gtagatatta tcatgctcca ttctagggct gtagagaggc 100080
cctcagcaat aagggccact gttgtgcttg ctctgccagg ctgatgcact tggctgctga 100140
tctgagtgta gtctcttatt catttgtacc tagttcgtca cttaagcatc ttgacttact 100200
tatgtttaca tagcataaaa cttttggcct acaaaggagc ttatcaaaaa ggaacaagtt 100260
atatgacagt agaagagagg ctggagaagg gtaggctatt cacaaaaact gatttaggta 100320
aagcatttta aaataaaaat tctatcagac cttcacacag taaactagtt cataataaca 100380
tttttccttt cctaatcaca agcatcataa ttcataatta caatatttgt ccagttctcc 100440
agggaaagat ctgcacagta cacatcagga aatgctcttg gagatcaaca ggagaaatga 100500
aactaaaact caaggcttcg gctttcatgc acagtaaacc taacttcatc ttgataaatt 100560
atgaaaacct cagctttctt acctgtttta gccaatattt atcacatacc catcatgtgg 100620
aagaggttgt tcaatgcagt agggcataca gaagggactg aggcagtccc taccctgggg 100680
gcatatggaa agtaccctca caccttccat gccaggcaaa acacacagac agtgatacag 100740
cacatctacc ggggtaactc aggatgaaca gtttcaaaag aaacacgtga acctagtccc 100800
tgaaaaatgg gaaagatgtc acacaagatg gaaggagaga gaggtggcag gaggagaaca 100860
cacacatgat cagttcagtt tagttgtggt agtagagagc atcctgggac caaattcaaa 100920
acgaaaaagc cacatgttaa aatatctatt ctcgctccta aagaaaacgg tagcaccctg 100980
tagtcgcact gcaaagtaga aatgaggaac aagacagcat cagggtgacc ctttgcctgt 101040
caacagtcag acaggccaga atcaggccct gggctggagg agtctccctg ggttgatttc 101100
tgtgctacag tgctgtcagc agagtggggt gggggagggg gaggcgcgct tttttcatct 101160
acccggggag caaacaccaa ctcctgcagc agttctgcca acaaggcaga actatgacga 101220
aactgattac cactagcctc tctgtatcag agtcaagata tggggtggat gagtccgttc 101280
cccaagggtg tgctttggag ccactgccac agagctaaga agcccctctg ctagaacaca 101340
cctgtgccct atctgcccaa ccctagttca ccctgatgtc ccagctcagc attaatcgtg 101400
gatccttcgc gggggcccgg ggcccccaaa ccctcctatt tagggaccac aattccccaa 101460
ctgggggcac tgtccccaga tccagagggg cagtaacagt ccctcttgca gatttcggat 101520
cttcatcctg ccactgaaag gccacaaggg ggatttcatc ccggtttcac cttcaggacc 101580
```

```
gtctgagcac ttctcgggcg atgcagacca gtggaaggca ctggctggca ccaaggcccg 101640

ctcctgggag ccaggccgcg gcccctccaa ggaccacagg tgggcagcgg aagactcaga 101700

gcaagagcca ggggcgaaga tggccctcgc tgcggtcaac ccggagcacg tgctggggct 101760

caccagcctc tccgcgctga ggacaaagtc cgctcccgcc ggcttcttgg cttgggcacc 101820

gggtaccggg cgtcaggggc gagacaggca ggacttgcgc gcgccccgac tcgactccag 101880

accccgaccc gactccgggc tcggcctccc gcgacccctg cgcgcactca ccattgtggt 101940

tgacccaggt cggcttcagg agcttcattg ttcggccgcc gccgccgccg ggctgaggcg 102000

agcgccgggt ccctcagcgc gcccgggcca tggagccacc gccgccgctt cctcccgcgc 102060

cacccgccct ccggccgccg cccgccccgc gccctcaggg ccgccgcgcc atcgccggcc 102120

cgcgcccccc tccgccgcca cagccgccac ccgcgctcgg ccgccgccgc cgccaccaca 102180

gccgcatccc ctgcgccgct cctcctcagg cggctcccgg gcaacgccgg aagtcacggc 102240

gcgcacctgc caaatcgccc cggcgggaaa ccgctcccca cgcggactgg gccgccccgg 102300

ctcctccgct ggcaggggct tcgggtcggg cccgggcgcg ggcgccccag aaagggcggt 102360

tcgcctggac ggcggacagc gagcggggcc tgcagttgca acccgggccg cccgcagagg 102420

caggcggggc ccaggtggcg tggaccgccc gtcaccagct ctgcctcgcc agtctgagtc 102480

cgacttatta actagcttcc gtcattcatc aacacgcgct attgggcatc ttgcgagcgc 102540

cgggctccgc gccggcgccg gaatgcgatc cgggcttcgg actcgaacga atgcggggga 102600

cgagccaacc ctggtggggg aggctggggc ggacgcgttt attagaagat cggggccgtt 102660

tgcctagaca tgaacatttg gactcggagg agcagaggga cgccccctcg gccgctccgg 102720

ctgcactgcg gagccgaggc ccgcgcgagg gcgcagaccg accaaccggc tagggcctga 102780
```

<210> SEQ ID NO 2
<211> LENGTH: 103863
<212> TYPE: DNA
<213> ORGANISM: Homo sapiens

<400> SEQUENCE: 2

```
atggtggata agctttttga tgtgctgctg gattcggttt gccagtattt tattgaggat     60

ttttgcatca gtgttcgtca aggatattgg tctaaaattc tctttttgg ttgtgtctct    120

gcccagcttt ggtatcagga tgatgctggc ctcataaaat gagttaggga ggattccctc    180

tttttctatt gattggaata gtttcagaag gaatggtacc agttcctcct tgtacctctg    240

gtagaattcg gctgtgaatc tatctggtcc tggactcttt ttggttggta agctattgat    300

tattgccaca atttcagatc ctgttattgg tctattcaga gattcaactt cttcctggtt    360

tagtcttggg agagtgtatg tgtcgaggaa tttatccatt tcttctagat tttctagttt    420

atttgcgtag aggtgtttgt agtattctct gatggtagtt tgtatttctg tgggatcggt    480

ggtgatatct cctttatcat tttttattgc atctatttga ttcttctctc tttttttctt    540

tattagtctt gctagtggtt tatcaatttt gttgatcctt tcaaaaaacc agctcctgga    600

ttcattaatt ttttgaaggg ttttttgtgt ctttatttcc ttcagttctg ctctgatttt    660

agttatttct tgccttctga tagcttttga atgtgtttgc tcttgctttt ctagttcttt    720

taattgtgat gttagggtgt caattttgga tctttcctgc tttctcttgt gggcatttag    780

tcctataaat ttccctgtac acactgcttt gaatgcatcc cagagattct ggcatgttgt    840

gtctttgttc tcattggttt caaagaacat ctttatttct gccttcattt cattatgtac    900
```

-continued

```
ccagtagtca ttcagcagca ggttgttcag tttccttgta gttgagcggt tttgagtgag    960
attcttaatc ctgagttcta gtttgattgt actgtggtct gagagatagt ttgttataat   1020
ttctgttctt ttacatttgc tgaggagagc tttacttcca actatgtggt caattttgga   1080
ataggtgtgg tgtggtgctg aaaaaaatgt atattctgtt gatttggggt ggagagttct   1140
gtagatgtct attaggtccg cttggtgcag agctgagttc aattcctggg tatccttgtt   1200
gactttctgt cttgttgatc tgtctaatgt tgacagtggg gtgttaaagt ctcccattat   1260
taatgtgtgg gagtctaagt ctctttgtag gtcactcagg acttgcttta tgaatctggg   1320
tgctcctata ttgggtgcat atatatttag gatagttagc tcttcttgtt gaattgatcc   1380
cttcaccatt atgtagtggc cttctttgtc tcttttgatc tttgttggtt taaagcctgt   1440
tttatcagag actaggattg caacccctgc cttttttttgt tttccatttg cttggtagat  1500
cttcctccat ccttttattt tgagcctatg tgtgtctctg cacgtgagat gggtttcctg   1560
aatacagcac actgatgggt cttgactctt tatccaattt gccagtctgt gtcttttaat   1620
tggagcattt agtccattta catttaaagt taatattgtt atgtgtgaat ttgatcctgt   1680
cattatgatg ttagctggtt attttgctca ttagttgatg tagtttcttc ctagtcttga   1740
tggtctttac attttggcat gattttgcag tggctggtac tggttgttcc tttccatgtt   1800
tagcgcttcc ttcaggagct cttttagggc aggcctggtg gtgacaaaat ctctcagcat   1860
ttacttgtct gtaaagtatt ttatttctcc ttcacttatg aagcttagtt tggctggata   1920
tgaaattctg ggttgaaaat tcttttcttt aagaatgttg aatattggcc cccaccctct   1980
tctggcttgt agagtttctg ccgagagatc cgctgttagt ctgatgggct tccctttgtg   2040
ggtaacccga cctttctctc ctctggctgc ccttaatatt ttttcctcat ttcaaccttg   2100
gtgaatctga caattatgtg tcttggagtt gctcttctcg aggagtatct ttgtggcgtt   2160
ctctgtattt cctgaatctg aatgttggcc tgccttgcta gattggggac gttctcctag   2220
ataatatcct gcagagtgtt ttccaacttg gttccattct ccccgtcact ttcaggtaca   2280
ccaatcagac gtagattcgg tcttttcaca tagtcccata tttcttggag gatttgctca   2340
tttcttttta ttcttttttc tctaaacttc ccttctcgct tcatttcatt catttcatct   2400
tccatcgctg ataccctttc ttccagttga tcacatcggc tcctgaggct tctgcattct   2460
tcacgtagtt cttgagcctt ggttttcagc tccatcagct cctttaagca tttctctgta   2520
ttggttattc tagttataca ttcttctaaa tttttttcaa agattttaac ttctttgcct   2580
ttggtttgaa tgtcctcctg tagctcggag taatttgatc gtctgaagcc ttcttctctc   2640
agctcgtcaa agtcattctc cgtccagctt tgttctgttg ctggtgagga actgcattcc   2700
tctgaaggag gagaggtgcc ctgcttttta gagtttccag tttttctgct ctgttttttc   2760
cccatctttg tggttttatc tacttttggt ctttgatgat ggtgatgtac agatgggttt   2820
ttgatgtgga tgtccttttct gtttgttagt tttccttcta acagacagga ccctcagctg  2880
caggtctgtt ggagtaccct gccatgtgag gtgtcagtgt gcccctgctg gggggtgcct   2940
cccagttagg ctgctcgggg gtcaggggtc agggacccac ttgaggaggc agtctgcccg   3000
ttctcagatc tccagctgcg tgctgggaga accactgctc tcttcaaagc tgtcagacag   3060
ggacatttaa gtctgcagag gttactgctg tctttttgtt tgtctgtgcc ctgcccccag   3120
aggtggagcc tacagaggca ggcaggcctc cttgagctgt ggtgggctcc acccagttcc   3180
agcttccctg ctgctttgtt tacctaagca agcctgggca atggagggcg cccctccccc   3240
agcctcgctg ccgctttgct gtttgatctc agaaggctgt gctagcaatc agcgagactc   3300
```

-continued

```
catgggtgta ggaccctccg attcaggtgc gggatatgat ctcctggtgc gccgtttttt   3360
aagcccgtcg gaaaagctca gtattcgggt gggagtgacc cgattttcca ggtgccgtct   3420
gtcacccctt tctttgacta ggaaagggaa ctccctgacc ccttgcgctt ccctagtgag   3480
gcaatgcctc gccctgcttc cgctcgccca cggtgcgcgc acccaccgac ctgcgcccac   3540
tgtctggcac tccctaatga gatgaacccc gtacctcaga tggaaatgca gaaatcaccc   3600
gtcttctgcg tcgctcacac tgggagctgt agaccggagc tgtttctatt cggccatctt   3660
ggctcctcct caatggagtt cttaacactg aaggaacatg atcaatgtca aacatttgaa   3720
tgtaggcaaa taggtaagag ttttggaaac agaataaata caggtaaatg aaaccttttt   3780
ttcttatttt tatattctga cacataacct gcattttaaa gcaaaaatag taaccatgtt   3840
ttatctgttc atagcatata tatataaata attataaata taaacatatt catagcatat   3900
atatagcata tatataattt atagcatata tataattcat agcatatata taatttggat   3960
ttaataaaag attatatata aactatatat ataatttgaa ggcaattata tatatacaat   4020
ttataatgat tcatagcata tatataattt ggattcagaa tatatataat tatatatata   4080
aacaatatat atgtaattca tagcatatat atagttcata gcatatatac atactcctat   4140
atataaaatt atacatatat tatcaaaaat tatatatatt tgtaaacata tgacaataat   4200
agcacaaagt caatccaaag tgatactggg agggagagat tggaaattta ctgtcatgaa   4260
gtctttatat gacatgtgaa gaggtataat attatttaaa agtacactca gattacattt   4320
aaatgtatac tgtaaacccc aggacaacta gttttgtttc ttttaatgga agtcaacttc   4380
tggtttacaa gtgacactga agtcatcatt cctattctta caaaaagagg aaaacttaca   4440
atcaataact tttcttagac ccatcagaga tgtgaggtcg caggagaaag tgccacctga   4500
aatctgaaga gactggtgaa cacagagaca cagctgagct ctcacacctg gagcagaagc   4560
cactggagcc gtaatctggt aggaattctt aaacggtaat tttagtgaat ttctggacag   4620
tgaatttgga ctagcataga gtaaaaagct cctggaggtc agagtcttga ggggccctcc   4680
ccgacctttg tgggtttacc tctacctcta tgaacctcat tgttacctgg tgtaatggct   4740
acatgacata actgaatttc taccccaccc aaatgctgct taaaaagaat acctgttgga   4800
tactatgctt attacctggg taactaaata atatgtacac caaaccccca caacatgcag   4860
tttacctaca tagtaatctg gcatatgtgc ccctaaacct aaaattagag ttataaaaag   4920
aagaagacac atgcagtaca aagttctctc tgtaactaca ccagccaaaa ctggctggaa   4980
cctagatagc tgactgaatg gcttcaaaaa gttctcaggt ttcattataa tttcatttct   5040
gtgttaaatg acacttccac cagcaccatg acagttgacc atcgccataa aaacaactgc   5100
aagaagccac agaaggccaa aaaagaaggc ttcactctgg ttccaagttc actgcccatt   5160
tctggaaaag acataactat ttatcctatc acttttaatg tccagtccct ttgtttatat   5220
tgacgcccta tattttaacc tcctcacccc cgactagtag agaagctgat ttgtgacaaa   5280
catccctgct tcttcatttc ctggccatga atagctctgc ttgatgctca ctttcggttg   5340
cttattggct ctgtgacacc aaatggggac agagcccatc ttttcaggct accaacttta   5400
ttggttaaaa aatggcaact ggctgggcac ggtggctcac gcctgtaatc ccagcacttt   5460
gggaggctga ggtgggcaga tcacgaagtc aggagatgga gaccatcctg gctaacatgg   5520
tgaaaccccg tctctactaa aaatacaaaa aattagctgg gcacagtggc gggcgcctgt   5580
agtcccagct actcgggagg ctgaggcagg agaatggcat gaacatggga ggtggagctt   5640
```

-continued

```
gcagtgaccc gagatcgcgc cactgcactc cagcctgggc aatgagcgag actccgtctc   5700
aaaaaaaaaa aaaaagaaaa gaaaaaagaa aaaggcaact gtgacaggac tgtggaatag   5760
atagttcact tccctgtttg ggaagcctcc ttacctcctc agagactggg aaactggtgc   5820
ccaacaacac tggccagcaa aggatatgca tgcccatttt ctttccagct tgagtttctc   5880
ccctttttggg aaatgcccct tccaccactc ctccttgcct ttggtcagtg gcagccactg   5940
ccctccattt aaaagagaca gagaagttaa cctttgggca atccctaacc atctggactc   6000
cccattaccc agaccctcat aaaggaaagg ggggcagaat gactgtcccc aggcagggct   6060
ctccagtaac acataatgct tattgataac cctcacataa cttttttctt ttttgagagg   6120
gagtctcaca gtgtcaccca ggctggagtg tagtggcgcc atcttggctc actgcagcct   6180
ccacctttca ggttcgagcg atgctcctgc ctcagccacc tgagtagcca ggactacagg   6240
cacacacccc aacacctgtc taattttttg tatttttagt agatacagtg tttcgccatg   6300
ttggccaggc tggtctcgaa ctcctgactt caagtgatct gcctgccttg gcctcccaaa   6360
gtgctgggat tacaggtgtg agccaccgca cctggccgac ccacataacg ttgaaggtgt   6420
gtaacatctt gaagccagac atcctctttc catatgaaga cagtcactta tctcttgact   6480
gcttaggggt gatggaggaa gtgtacccta gtggaccaga ccataaaagt gaacctgtta   6540
aaaattctaa agccaagatc ttcactgatg ggcacagcta tatgctggag ggacagtgga   6600
gggcaggata agctatggtc cttctcagtg gggttgcaga agctggtgct catccaccaa   6660
gatgctattt gtatctgtaa taaacaagcc caggtggcag taatccattg ctacagccac   6720
cagaagggtg ttgttgaagt agttaaagaa aataataaag ctgatctcct gtcaaatcat   6780
gtggctttag ggaagatcac ttttcaaatg ccactttttc ctcccccccc atgccaatcc   6840
tacttttttta ccccacttta ctctcgaaag gaatgggaaa ccgcctccaa atggggatat   6900
accaaaagtc ttaccatcca ggagggttaa tcaaccctca tggacaactt ttcccagaag   6960
cagttgcatt gcaggctgtt aaaaagccca tacaaatgct cacttttgtc aggaggccct   7020
gtgtaactgg cttttccaga gcatgactgt cccaaacttc agggagctaa tcaaagaggc   7080
ggttgagact tgctccacct gctatgttaa taaccctaac atccacccca caggggagtg   7140
cagagggggc cattcagctg gtccagtacc aaagtagata accagggaaa gattgacaaa   7200
ttgattccgc agttatgtcc agagccttgg tacctcctgg tcctcactga tagcttttct   7260
ggatgggtag aatttttgcc accctcactg agatggcacg tgaggtagca aaggtgctgt   7320
taaaggaaat tgttcccaga ttcaggttgc ctcagccaat ccaaagtgat accagaccag   7380
cattcatatt ttccattact gagggtactt cttgggacct agaaataaaa cggtgctcac   7440
atgtcccctg gagaccacag tcttccagta cagtgggcta gccagaccct tgaaaggacc   7500
ttagttaaat tacgccagaa aactcatctc ccatggattt cattactctc catggcactg   7560
ttaagaataa gaatagctcc aaaaggaaag atcaaactga gcccttacaa gctgatatat   7620
cgccaatggg tcccagtctg gctaggtgac caggaggtcc tcagagctgt ggggaaaaaa   7680
tatggtatgc cacccaaatt ggaggagtaa tgaaggccct tcaggcctat ggaaatcaat   7740
cattactttc gccatctgac ataaccctcc atcctttcca actcagggat tgggtttact   7800
taaaaaccta gagagaaggg gaaccgcagt catttagaac ctaaatggaa gggcccatat   7860
cttgtggttc tcacaaaaaa attctgcctt aaaattacag ggagtttgcc gggcacagtg   7920
gctcatgcct gtaatcctag cactttggga agccgaggca ggcagatcgc ttgagctcaa   7980
gagttcaaga ccagcctggg taatatggtg aaacccccat ctctactaaa aatacaaaaa   8040
```

-continued

```
aattagccag gcatggtggc gcacgcctgt agtcctagct acttggaggg ctgaggtggg   8100
aggatccatt gagcatagga ggcggaggtt gaagtgagcc gatatcacac cactgcactc   8160
cagcctgggc aacaaaacga gactctagtt caaaaaagaa aaaaaaaata cagggagtga   8220
cgccttggat acaccacatc tgggtcaagg cagccatgga acctaaggaa aaaagccgca   8280
tgtacccagc taaaccactc tcagatctaa aattcctgtt gaaaaagaca gacttatccc   8340
cagccagatg agcaacctta ggcctacatg catttcctgc caggacttag tctattagcc   8400
ttgcttatag gtattctcat cttactccat caagaaccta cccctattt agggatttgc   8460
ctcctcctat cagtcactac catattcacc ttaaacctca tctgtgcaca cctgggaact   8520
acagcgcagt ggtgcattta tcaacatgcc ctgttcttcc tattgctatg ggttgagata   8580
tggggagagt tatcagaata atggagtgaa aataaccttg ttaaaattat agctattata   8640
gctaaaggtt cattaactgc tggatttccc atctacaccc ctaagcccaa tctccttggc   8700
ccatagcttg atcaacagcc tgaccaataa ctgtgatcaa tcatctaact ttaatccatc   8760
ttgcctggac ccacctgaag tcccattagt gatcttcctg gaacaagact ttttattatc   8820
ttggccttgt gtaaacctca ctggcaatgg aatctgggtc agtctccctt taacctgtca   8880
aaaggatggc tatattaaag taatctatga tcaggccaag tgtttatacc aatttaaccc   8940
ttccagggcc ctgtagcttc taccctgat ttcttggccc tgtctcctaa atttctggtc   9000
ttgtttgtgt ctaagcaaac tgaggtcgta caactacaaa tgacagttac tcagggatat   9060
aaacatctgg gcttgcaccc aggagataac cagtcctagc taagaccagc tagggaaaaa   9120
attcaccctt ctaatgggcc ctatatcaac acccaaattc agcttgaaga agctatagaa   9180
gacagacctt ggcctgtcag cacccttcaa gaatgaggag tgaatataaa gataggggag   9240
atttgttacc cagtgtaatg cctacatgac agctggattt ctaccccact ctgactgctt   9300
atctttaaga aataggatgt ctaccttaaa aagttccctt tgtaaccaga ccagctgaga   9360
ctgtctaaaa ccaagatagc tgaccgaatg acttcaaaaa gacctcaggc ttcattataa   9420
tctcattccc atgctaaata acaattctca acagtgccat aaccattgac aaccaccatg   9480
aaaacaactg gaagaagcca taaaaggaga gaaaggaaag cagcactcca gttctgagaa   9540
gatcactgcc catttctgga aaaggcactt ttaaggctga accccttcat tatagaaacc   9600
ctatatttta accccctctt ccctactagc agataagttg atttatgagc cacactccca   9660
cttctccatt gtttggccat caaataaagc ttactctgct tgacactcac tttcagtgag   9720
tgtactggct cagtgtcacc caacaagaaa atattctatc ttttagggtt actgagttta   9780
ctggtaacat aagagtctca tggcaaaaag ccaagaaaat gtccctcata gctccagcag   9840
atggaaagga aaagtaactc tttcctgagt tactgagaaa taactgagaa ttgtatatta   9900
aagattcaaa tggaaaaagt agtcaacttg caagagcaaa tgcataatgt gagcagaaat   9960
atggaaacta taatatacat gtaaaaaatg ctagcaatca aagcactgta atggaactga  10020
agtgtgcctg tgatggaatc atctgtagat ggaacatggt tgaagaaaga attactgatc  10080
ttgaaggcat gtcaacagaa gctactcaaa ctaaaatgca aaaagaacaa tgggaaaaac  10140
acaatagaac atttgagaat tggtggacaa agttaaaagc tgtcatatac acatagttgg  10200
aatacaagaa aacaaagaga caatggagca gaagaaatat ttgaaataat agttatcaag  10260
agtttacaaa attaatgaca aacaccaaac catggatatt agaataaata ctaaaaaatt  10320
cacatttagg cataccatat taaaattgag agaaccaaag acagagaata ttctgaaaga  10380
```

-continued

```
agaaagagag gaaaaagcat gctagctata gaggaacacg gatcagaatt acactggact  10440
tttcatcaga aatcacgcaa gcaagtacaa gaagagagta gaatgaaaca tgtaagatag  10500
tgaatgaagc tgggtggggt ggctcacacc tgtaatccta gtactttggg aggcagacca  10560
aacctcgagc tcttcatctc tagagtctca gaagcaaaga atgggtatac aactgaaaaa  10620
gtatctgaaa agttcatgtc attacccttt ctaaatttgg aaaaatacac aagtatatga  10680
gttcacgatg ctaagaaaac ctccagaagg aaaaattcaa agaaatccat acccagttac  10740
atcacaatcc atttatttga aaactaaagg gctgggcatg gtggctcacg cctgtgatcc  10800
cagcactttg gaaggccaag ttgggtggat cacttgaggt caggagtttg agaccaacct  10860
ggctaatgtg gtgaaacccc atctctacta aaaatgcaaa aattagttgg gtgtggtggc  10920
aggcacctgt aatcccagct acttgggagg ctgaggaagg agaatcactt gaacccggga  10980
agcggaggtt gcagtgagcc aagattactc cattgcactc cagcctgggc gacaagaggg  11040
aaattcagtc tcacaaaaaa aaaaaaaaaa aaaaaagaag gcagggcgcg atagctcacg  11100
cttgtaatcc cagcactttg ggaggccaaa gagggtggat cacgaggtca ggagatcgag  11160
aacatcctgg ctaatatggt gaaatcccat ctctactaaa aatacaaaaa attagccagg  11220
catggtggca ggcgtctgtg gtcccagctg ctcaggaggc tgaggcagga gaatggtatg  11280
aacccgggag gcggagcttg cagtgagcca agatcgcacc actgcattcc aacccaggcg  11340
acagagcaag actccgtccc cactcgccaa aaaaaaaaaa ggaaaaggaa agaaaagaaa  11400
aagaaaacta cagatgtaga aaaaggtctt gaaaataccg tggatttcta tgtgaaacca  11460
tggagatcag aaggaagggg aacgccagtg aaaatatctt tcagaaataa aggtgaaaga  11520
catacattcc cacctaaaag aagtgataaa ggaagttcca cagacagaat ggaaggaaga  11580
taaaaacaga aggaaatgtg cagcatcacc aattagacaa gagtagtata aagatttaag  11640
gaataaacca cacacacaca ctcacacaca aacacacaca cacgaaccaa tctaaaagag  11700
ctgccaaggg ccaaagctga agtaacttaa acaacaaaat aaatttcaca tgtgttaatt  11760
tataacccaa aagataaaat aagtatccat gagtccatac tgatataaat gtatgcttga  11820
ataaattaac aaatgaggag aaaaagacaa atcttatgca taaaagaatt ttatttaata  11880
aatgtagaaa aatatatgac aacagaaaac caccactaaa ataccacagt aaaaaatgct  11940
gcaggcaaga ctcatgatac atgataaaat tcctgggtga gactttaaaa agaaatagaa  12000
taacaggtta ttcacatggc ctcgaataat tttcactaaa aaatgtatca gttaatgtgg  12060
ttattttaat atatgtccat acatactttc atatcattcc ctccaataag tgaaacttag  12120
ttcctagtca ttgagtgtgg tctggagtta gtggtttccc tctaccaaat ggaaagagaa  12180
aatagtaact ttacagtcaa gaatccagca gacatcatcc tatgtgattc agcttaatat  12240
tagcaataga taaagttgat aacacataca ttctaatatg atatggtgag aaggacacct  12300
gacttccatg ttattcttcc ccaaaatcca tggccaaagc ataatcatga gaaaacatca  12360
gatgaatata agtgggtaga tattcttcaa aatgcctcac ttggaccctt caaatgtgtc  12420
acagtcacat aggagaagtg cagactgaga aactgtcaca gatgggggct aagaagaaag  12480
ggtgactgac gcagtgtgta tccttgatta gactccgaaa tgaaaaaaga cattagcaaa  12540
agaatacaaa gtggatgaaa tatgtataca gtttttagtt ttgttattag tatttcacca  12600
atattaagtt cttagtttgg gtaaatgtgg catgattatg taagatgcta gccttagggg  12660
aaacgcggtg aagggtgtac tcaaattcac tgtactatcg ttttcactct tctgtaagtc  12720
taaaattatt tcaaaataaa aaaattaaaa ttgcaaacat tgtcagattg gatataaaaa  12780
```

```
gcaagattca accatatgtt acttatgaac ataatacttt tttttttttt gagaccgagt  12840
tttactctgt ctcccaggct ggagtgcagt ggtgcaattt cagctcactg caatctctgc  12900
ctcctaggtt ccagcaattc ttgtgcctca gcctcccaag taactgaaat tacaggcatg  12960
atccaccacg tccggctaat ttttgtattt ttagtaaaga cagggtttca atatgttggc  13020
caggctggtc tcaaactcct gacctcaagc gatcagccta cctcggcctc ccaaagtgct  13080
gggattacag gcctgagcca ccacaactgg cccaaacata atactttaaa tataatgaca  13140
taaataagtt aaaaggaaag gatggaaaaa tatagattcc atgctagtac taagtaaaac  13200
aaaactgtgg tgcctatttc aatattggac aaagtcgatt tcagaggaga gaaaacttcc  13260
agaagataat tttacaaata caaacataaa tacaaatata aatatactat ttatccagaa  13320
aacaaattaa cccaagatga gaatctgcaa gaggacatgc ataaaactat atttataatt  13380
gacaatttca atatttttct ctgaataatt gatggaaaaa gcagacagac aaatatccaa  13440
agtacaaaaa gcattgaata acattataaa ccaaattgac ctacctgaca tttatataac  13500
atgtcatcaa ataacaccaa catttctatt atttcccaaa acacatttaa catgtgcaag  13560
ggtccttgtt ctgggccatt aaaaaaaaaa aaaaacagga ttcaagaagt acaaagtatg  13620
gttattctct gacctcaagg gaattaaatt aagaattcac aatattccct actcttttta  13680
aaagtaaatc ccacacttct aaataaccat gggccacacc aaacaaatat caatggggaa  13740
aaatcaaaat gtatgggata tcattcaaga agtctttggg aggaatatta tagaactaag  13800
tgcctatatt atgaataaga agggtctcaa atcaatgacc ttagcttagg aatacaaaaa  13860
aggaatagca aattatacac ttagaaagta gaaaaaatga aataataaat gtcatgaaga  13920
acactcaaaa acaatagaga gtgtcaatga aacaacaaaa aaacaaaaac ctggtttctt  13980
gaaaaattaa gaaaattggt aattatctag tcaaactgct cagcatcaaa tcagagaacg  14040
atcaaataat attaccaatg tcaataatga ggaaggcagc agcactaaag gttcaaaatt  14100
attaaccgga tcgtaatgac ataaaatgaa taaacttcac aattaagaga tggacaaagt  14160
cctagggtga caaacactcg taaaccctac tcagcatacg cccatatata tatgtatata  14220
tccattaaat aagaagaatt tttagttaaa ataattccga ctaaggaaac tgttagagat  14280
caataagaga gagatatctg taaggttttt gtaacatttg aaaattgatt aatgtaaccc  14340
acattagtaa caaagtaaca aagaaacaaa atcatcccag tagggcagaa aaacacgata  14400
cttaacggtg aaagcttgca tcatctctca taatataata gtggtgaaat aataattttt  14460
ttaacagggt gaacttgatt cataactaat attttataca aaattttatc aaaaatagat  14520
aattatgaat gtactatgtg cattgtaatt gtacccaaat attcaagcta aaactacaaa  14580
atctctcaag gaaaacatag gagatattct ttgagacttt gggctagcaa aatatttttt  14640
agctatggca tcaaaaggca aaatacatta atgtacacat tgttgaattt tatcaaaata  14700
gaaacattct gctctcaaaa tatactgcta agggaatgac aaggccacaa attggaataa  14760
aatatttgca aagcacattt caccaaagat tatatgttca tgatgagaag cacacgaagg  14820
gttgttcaat atcattagcc ataaggtgaa tacaatcaaa ctttgaatga aatgccacta  14880
ctatcctatt aagatggcta agattaagaa aattgactgt atccactgtt tgtaagaatg  14940
tggaggaagt agaactctca ttcatttctg ttggatttaa aattttacaa taactttgag  15000
aaaaaaaatt ttttttagtt tctttaagag ttaaaaattc acccaccata tgatccagcc  15060
atttgatttc tagtaagaga aataaagaca tttttccata cagagtattt tacatgaatg  15120
```

-continued

```
ttcttagcaa ttttatttgt aatagctcca aagtggaaac aatcaaaacc tcatcaatag  15180
aaaaatggca aacaaactgt ggtatatttc tacaatgaaa tactgctcag caataaaatg  15240
aataactctt agtatatgct atgacatgaa agagtcttaa aataactatg ctgagttaaa  15300
gaagccagat aaaaaagatt aagcactgta ggatttcatt atataaaatt ctagaaaatg  15360
cacactactc aattgtggca gagagcagat cgctggttac tgaaaaagta ggatagagtg  15420
ggtgggggag aaattacaga ggggcatgag gaagcatgtg gggtggcga acatgttcat  15480
tatcttgatg ggggtaatgg ttgcatggat ttatatgtca aaagttgtca aattatacac  15540
attaaatatg tgcagtttat catatatcaa ttacacctca ataaagctgt taaaaataag  15600
ctctggagct tcacctgtgg gaagtgtcag tggtgaagaa agtaagacac aggaaagtca  15660
aggttttcaa tggtatatat taaacagcat ctatgcctgt ttatctctgc cctgtaatga  15720
atgaacaggg ttccaatgcc cctaagggag atgtgtggtt ctagaccctt atgttctatg  15780
aatagtaaag tctcttctct gttgggaaca ggccctcaaa tctggccata aactggcccc  15840
aaaactggtc ataaacaaaa tctctgcagc actctgacat gttcgtgatg gccatgatgc  15900
ccacgctgaa ggttgtgggt ttactggaat gagggcaagg aacacctggc ccaccccggg  15960
tggaaaaccg cttaaaggcg ttcctaagcc acgaacaata gcatgagtga tctgtgcctt  16020
aaggacatgt tcctgcttca gataactatc cagagcccat ccctttgttt cccttaagga  16080
atacttttag ttaatctata atctatagaa acaatgctta ccactggctt gctgtcaata  16140
aatatgtggg tcaaactctg ctcggggctc tcagctctga aggctgtcag ccccctgatt  16200
ttccactctg cactctgtat ttctctgtgt gtgtgtcttt aattcctcta gcaccactgg  16260
gttagggtct ccatgaccaa gctggtcttg tcaaggggtg cccataccta gggctggaac  16320
ccgggtcgaa gggttgctgg agcgatggtt ggagaaggtg gaactaagct ggaggacacc  16380
cgagtactct taagcaatcc ccatggtgag taagaagggg agcttggaag catcagggta  16440
acaatgggac aagtgtggga tctggttcgt tccacctggg aaccttttca cactgatgag  16500
gaggaggaag gaaagtataa ctaagtaaaa gaagaggtaa cagagaaggt ttgtttccca  16560
gctaaagcta aagcggcaaa ggaggaagag attcatccct acccttctgc accccctcat  16620
tattttgaag aaaaagagtg gcctgaccct ccagatcttt cttttccgga ggacacgggg  16680
tgaaaggtgc cccagtgact gtttgagcag tgcctcgagt accgctctca gttctattca  16740
ggcaggaatc cagcaagcta gatgtgaggg tgatatagag gcttggcagt tccctttttgg  16800
gatacacccc ccagatcaac agggaaatat tatagctaca tttgagcctt ttcctttaa  16860
aatacttaaa gaatttaagc aagcccttaa tcaatatgga ctatgttctc cttttgtaat  16920
gggactgtta aagaatgtta ctgtctccgg tcagatgttg ccagtggggg caataggatt  16980
acgtctaggt atatatagtt taaatttatt tatttattta tttttgagag ggagtctcac  17040
tctgtcaccc aggctggagt gcagtggtgc aatctcggct cactgcaagc tccacctcct  17100
gggttcacac cattctcctg cctcagcctc cacagcagct gagactacag gcacccgcca  17160
ccacacccgg ctaatttttt gtatttttaa tagagacagg gtttcaccgt gttagccagg  17220
acggtctcga tctcctgacc ttgtgatccg cccatctcgg cctcccaaag tggtgggatt  17280
acaggcgtga gccacagtgc ctggccatca aggttaaatt taaaaggagc acaaatacat  17340
acaggagtaa ttgattcaga ttacaatggg gaaattgaaa ttgttatatc tactgttccc  17400
tggaaagcag agccaggaga gcatatagca cagctcctga ttgtgccgta tgtggaaatg  17460
gggaaaagtg aattaaatga acaggaggat ttggaagcac aaatcaacaa ggcaaagcag  17520
```

```
cttattgggt gaatcaaatt actgataaat gtcctacctg tgaaataact attcagggaa  17580
agaaatttaa aggtttgata catacaggag cagacatttc aatcatttct ctacagcaat  17640
ggccgtccac gtggccaatt caatccactc aatttaacag agttggagtt ggtaaagccc  17700
ctgaagtata tcagagtagt tatattttgc actgtgaagg gcccaatgga caaactggga  17760
ctattcaacc aattgtaact tctgtaccta taaatttatg gggagagat ttattacaac  17820
aatgggaagc acaagttcta attccagaac aattatatag ccctgaaagt caacatatga  17880
tgcatgaaat ggggtgtgtc cctggtatgg gactagaaaa tatttgcaag atttgaagga  17940
accacttcaa gtggaaagac aaagttcccg ccaaggttta ggatatcatt tttgatggca  18000
gacattgtta agcctccaga acgtatacct ttaaaattgt taacagataa gccaatttgg  18060
atagaacaat ggctgctaag taaagagaaa ctggaggctt tagaggactt agttactgaa  18120
caattagaaa atggacacat agctccaaca ttttcccctt ggaattctcc agtttttgta  18180
attaagaaaa aatcaggtaa atggagaatg ttacctgact taagagccat taattcactt  18240
atacaaccta tggggacatt acagccagga ttgccttctc ctgctatgat tccgaaaaaa  18300
tggcctttca tagtcataga tttaaaagac tgtttcttta ctatcccctt ggctgagcaa  18360
gactgtgaac agtttgcatt tacaaaacct gcagcctgct aagcgtattc attggaaagt  18420
gttgccacaa ggcatgttaa acagtccaac aatttgcgag atgtttgtag ggcaagcaat  18480
tgaacctact catacaaaat tttcacagtg ttacattatt cagtatatgg atgatatact  18540
ttgtgctgcc cccacttgaa aaatattact ctaatgttat gatcacttgc aaaatttgat  18600
ttctcatgct ggtttaatta tagctcctga caaaattcag actactactc cttactccta  18660
cttggggacc ttagtaaatg acactaccat tgtgctacag aaagtaacca tacgtaagga  18720
tcaattgaaa acattaaatg actttcaaaa attactaggg aacattagtt ggatacgacc  18780
tgctctaggc attcctacct atgccatgag taatctattt tctatcctta gaggagatcc  18840
tagtctcact agtccttgac aattaacaaa agagcctgag gcagagttac agctgcttga  18900
aaagcaagtc cataaggctc aaataaatag aacagatcca gagaagactc tagatttgct  18960
aatttttca actcatcatt cacccactgg tgttattgtc caagagcagg acttagtaga  19020
atggcttttt cttccacatg ctaattcatg gactctaact ccttatttgg atcaaatcac  19080
tactatgata ggaaatggga gaactcagat tgttaaatta catggatatg atcctggata  19140
aattatagtc cctctcataa agacacaaat acagcaagct tttataaaca gtcttacttg  19200
acaaacccat ttagctgact gtgtgggtat tctagataat cattttccta aaatgaaact  19260
gtttcaattt ttgaaattaa ctaattggat tctccctaaa attactaaat ttaaaccaat  19320
tgaaggtgct gagaatgttt ttacagatgg gtctagtaat gataaaactt cttattctgg  19380
ctcaaaaggt aaagtttttc agacacccta tacttcagct cagaaagcag agcttgtagc  19440
tgtaattgag gtatttactg cttttaatat acctattaat gtgtttctga ttcttcatac  19500
atggttcatt ccacacaatt agttgaaaat gctcagttat gatttcatac agatgaacaa  19560
ctgatgactt tatttaccca attgcaaaca gcagtctgga gtagaatgca ccctttttac  19620
atcactcaca ttagggctca tacacctctt ccaggacctt taactgaagg gaatcaaatg  19680
gctgatcgcc tagttgctac tgcaatatat aatgccagac acttttacaa tttaacccat  19740
gttaatgcct ctggtctcaa acgcagatac agcattacct ggaaagaagc taaagctatt  19800
atccagcaat gcccaatttg ctaaatggta cattcctcat ctttcacagg aggagttaat  19860
```

-continued

```
cctcgaggat tggaacctaa ttctctttgg caaatggatg tcacacatgt tccctcattt  19920
ggagactagc ttatgtacat atatttgtgg acaccttttc tcactttgtc tgggctacgt  19980
gccaatcagg agagtcttct gcctgtgtta aacatcatct tttgcagtgt tttgcagtga  20040
tgggcattcc agcttgtatt aaaacagata atgccccagg ctatactagc aaagctcttg  20100
ctacatgttt ctctatatgg aatattaaac acattactgg tatcccatat aattctcaag  20160
gacaagcaat agtggaatga atgaatctct ccctgaaaca gcagttgcaa aagcaaagtg  20220
gggggaaaca gggactgtgg gacaccccat atatgcaatt gaatctagta ttattgactt  20280
taaatttttt gagcctgcct aaaggccaga tgctatcagc agctgaacaa catctacaga  20340
aaccagctgc aaagacagaa gcagaacaac tggtttagtg gagagacccg ataacaaaaa  20400
gttgggaaat aggtaaaata ataacttggg gtagaggtta tgcttgtgtt tctccaggcc  20460
aaaaccagca gccgatttgg ataccatcaa aacacctgaa accttatcat gagccagatg  20520
ctgaggaaga gattccagga ggattctgag gacccccctgg ttgcagccat gtcgagactg  20580
atgctgagaa ggaccccaac tgtcatgagc aacatctgtc aaacacagcc acctatctgg  20640
ggacagatca agaagctgtc acagatggtg gaagaaaacc tgaggaaagt gggacaacca  20700
gtcacaacga gtaatttaat tgtagctatg atagcggtga tcaccactgc catgagtatt  20760
ccttcaatga gggctgacac agagaacaat tatacttatt gggcatattt atcaatcttg  20820
aatggcaata atgcctggat gtaatcactc tataacacag ttacacatgc tttctgatct  20880
cagtatttac cataataaat ctgctcctat aattgaggga taccaccctc aaaaacctat  20940
ttgtaaacag aattggacct gaccagaaat aatgaacgtg cttgtttggg aagatttcat  21000
tgcagaacag gcagaggtgc tggcaacgaa tcctatggaa tcattattga ttggtcccct  21060
aaggggatgt ttagcttgaa ttgcacctct cagtctgcgt cccacgacca cactatgttc  21120
agctggtcta aacaaaatgg tcagatggta gaaatggtaa gaaacacggc aagagttcct  21180
attatctgga aacatggcag tatagtggca cctcaacttc aaatgatatg gcccgctgta  21240
ggagctaaac ataagaattt gtggaaacta ttaatggcac ttaataagat caaaatttgg  21300
gaaagaataa aaaatcatat agaaggacac tctacaaact tgtctttaga tactgcaaaa  21360
ttaaaagaac aaatatttaa agcatcccag gcacacctga ccattatgcc aggaactgga  21420
gtgcttgaag gagctgcaga tggattagca gctagtaacc caataaaatg gataaaaaca  21480
cttggaggct ctgtgatttc aatgatgatt gtgcttttaa tctgtgttgt ttgtctttgt  21540
atagtctgca gatgtggatc ccaattcctg caagaagtag ctcactgtga taaggctgcc  21600
tttgtccttt tatcatgttg caaaagcaaa aagggggaat gtgttgggaa caggccccca  21660
aatctggcca taaactggcc ccaaaactgg ccataaacaa aatctctgca gcactgtggc  21720
atgctcctga tggctatgat gcccatgctg aaggttgtgg gtttaccaga atgaaggcaa  21780
ggaacacctg gcccacccag ggtggaaaac aacttaagga gttcctaaac cacaaacaat  21840
agcatgagcg atctgtgcct taaggaaatg ttcctgggac agataactag ccagagccca  21900
tccctttgtt tcagcccatc cctttgtttc ccataaggaa tacttttagt taatctataa  21960
tctatagaaa taatgcttat cactggcttg ctgtcaataa atatgtgcgc caaactctgt  22020
tcaaggttct cagctctgaa ggctgtcagc cccccgattt cccactctgc actctatatt  22080
tctgtgtgtg tgtctttaat tcctctagtg tcgctgggtt agggtctcca tgaccaagct  22140
ggtcttggcg cttctcagct ttcctttgag ggtacaaact tctgtccaaa ggagcctaca  22200
gtaagcatca aatagaggaa gctagaatac caggaagcag ggtggataaa ttcaagtcat  22260
```

```
cttatcagag cctgtgttac aataaaaaat ttacctgatc tttgtcctaa gttccttgct  22320
tataaccttt ggaatttctt gagtgatagg agtgtctttg ctatgctaat aaggtaactc  22380
atgatggatc aatacaaaac tttaaaatgg ggctggtcac aagactaaat atatgattac  22440
agagttggga cttcagttgc ctgaccttct gagtagtaag gggacctggt ggctgagttc  22500
aatcacatgg cccatgattt aagcaatcat gcctacatat gaagccccag taaaaactct  22560
gaacaatgta gctcagtgga gattcctggt ttttgtgaac aaatggatgg tcctagagag  22620
tggcatgccc tgatcccaca tggagaggtc ataaatctct gctgttcctc caagaccccc  22680
tcccaaacat gtttcttttc taagaaagtg ataatcataa gtacagcact ttcagtgagt  22740
tctgttagtc agtatagcaa attattaaat ctactagggt catgggaatc tccaaatatg  22800
taggtagtta gttggaagtg tgggtgtcct gagggcccct gaagtacagc tggcattgga  22860
agaacattct tgttgggggt cacacacttc agcttgtagg atctgcacta aatttgtgtg  22920
attactgtaa gatttgaatt atggtacacc cagttggacc ataattcaac aaagtagaaa  22980
tgacgcaata aacttaaagc agaatggagc tcatttattt ccctaattga cacattagta  23040
ataactgggg gggggcatat aaggccatga ttataaaaat tatttcacat aattttatgt  23100
aattataaaa aattaatccc tgacaacatc agcaggtgga agcaactaac aagtctgatc  23160
caactgggga tgatggggtc ccatcttaat gaacctaaga gccttccata ttccaaaagc  23220
tggtacctga atgcatgctc ctgacttttc aatggataag tgggatttga ggctattttt  23280
catgagactc cagaatatag ccacctgaac ctaacaatat tgaaacagca aacatccttt  23340
ctcttgagac cagcctattg tggatcaata tgactgtgct gtaccagtaa ccaggaagtt  23400
aggagaaacg ctagaattgg actttattta gcagtctttt ccagcctcat tgactatgaa  23460
tgtgaaaaac cctgtggtta cttagaaatc ccacagtact ctatgccatt tgtgaagatc  23520
cttgtgaaga tgggtagaga ttggagttat tttgctacca gtcaaggaat gccagaagcc  23580
tctagatggc aggaagggca ggaacagatt ctcccttaaa gcctttggta ggagcatggc  23640
caaaccaaca ccttgattta aaacttctgg ctgccaaatc tacaagagaa tacactcctg  23700
ttattttatg ccacccaatt tgtggtgatt ttttatggca gccttaggaa acaaatatgg  23760
gagaaatgtt ttaatttcag aaaatgtact ggtttcagtg tgcaaagtaa actgcagtga  23820
ataaactagt gagaaggcac agagggtgtc cacggtggtg atccaattgt gaaagagcgg  23880
tggaatatag tcgtggatgg cagtaagtgg cttacagaag gtgagaatta tgtgattatc  23940
tagatatgaa ggatacagga gaatcagtgg tgtcctcttt tcttcctcag gaccctgggt  24000
ggacagctat gccatgtact gtgaggtagg gaacacactg gcagcagaag gtttcaggca  24060
gacactgatg aagtagagta aaatgttgaa tttaaaactc agactgggtg tggtggctca  24120
tgtctgtaat cccagcactt taggagtctg aggcaggtgg attagttggg tccagcagtt  24180
caagacaagt ctgggaaaca tggtaaaact ccatctctaa aaatatgaaa atttagccaa  24240
gcgtggtggc acacacctgc agtcctgcta ctcaggaggc ggaggtggga aaataacctg  24300
agcctggggg attgaggctg cagtgagctg agattacacc attgcactca agcctgggca  24360
atcagaagga gactctgtct caaaaataaa ataaaataaa ataaaataaa ataaaataaa  24420
actcaaaggc acaatgttaa gatgacattt aggcagttgg atatccagtt atataacata  24480
aaagagacat ctgagtctgg agaaatgaat tttggactca tttgtgtata gatgtaaaat  24540
tcaagctctg ggagatggtg ttgctcagaa tacaaggtga caggaacaga agaggtgaga  24600
```

-continued

```
taggaccacc agaaacttca acttttagag gatggctgga gaaagatatt tcaaaagatc  24660
tgaaaaggtg aagagagttc tcagcaatcc ctgaagtcta tggtataccc tgaggactca  24720
gggctatctg gaggaatagc catgacatgg gtggtgcatg tgtgtgtgtt gcgtatttgc  24780
acgtgtgtgt tcccaatata gataaggaac ccaagactgc ttggtagata attctatcat  24840
taaaaggata acaagaaata cgcaaacacc aggacacaca taaatttgac aaattagatt  24900
aaatggccag atatggtttg gatttgtgtt cctgcccaaa tctcacctct cgtgttggag  24960
gaggggcctg gtgggaggtg attggatcat gggttggtga ctggacttcc tccttgctgt  25020
tctcctgata gtgagtgagt tcttacgaga tctggctgtt caaatgtgcg tggcaccttc  25080
ttcttggctt tcctcctcct gctctggtta tgtaagatgt gcttgcttcc ccttttcctt  25140
ccaccatgac tgtaagttcc ctgaggctcc ccagtcatgt ttcctgtaca gcttgcagaa  25200
ccatgatcca atgaaaccac ttttctttat aaattcccca gtctcaggta gctctttata  25260
gtaattccag aatgaactaa tacatgagcc aacaccctaa gaccacaaag taccaaaacc  25320
catccattat gaaaagataa tctgaatagg cttacaatta aaacaaatag ttacaaacta  25380
tctgaaaaag aaaacttcag gcactgatgg tttcactgaa aattcctacc aagcatttga  25440
agaagaaata aaaacaattc tacacaattt attccataaa gctgaagaga aggagggacc  25500
agtagtttta tgaggttata atgtcaaaac cagatacaga cattacagaa agtgaaaact  25560
atagaccaat atcactgttg agcatataaa taaaaactct cagctaaata ttaccaaatt  25620
aaattcggtg acatgtaaaa ggaataatac aggacaaact ggaacccaac atcttcttga  25680
atagagttta tcttagagaa gagtgtttaa gatgaggcaa gctattttaa tatgtcccag  25740
aaatagctcc aattggatgg tcataggata gtctgcaaag aggcttaaat cacctgggcc  25800
tattgctatg cctgtctctc ctcactcctc tctgcttgtt attttctgtg gttctcagtt  25860
ggggaccgcg ctgcccataa aagggctttt ggtggtgtgt gggcatggtt ccttttctct  25920
tttctccact ttcctgttag ttttcccatg tctggagggc atttatgtgt gcatgtgaag  25980
ggagacagcc tctgtggcat gtgctatgtt ctcacacaat gaaacattac gccattctca  26040
gatcattaaa gagccctgct ccagacactc tcagggtgat gtgatttatc ttctttacct  26100
tccaaactta actttccagt gcaggcgttt ttgctgagtt gtgtcaatcc agatatccgc  26160
tgggtaagac cgttcggtct tcccagaatc ttctggtcct tctctctgca tggtttcagg  26220
aaatggcacc tgaatctcat agctgcactg tcctgctcaa ttggctgcct gagacagaat  26280
cctggatgtg cctgttattc acagtctccc ctccccttcc attgctgttt atatcttttg  26340
aacctggcat ttctattgaa cctcggctcc ctctgtccca ctcttggtga taatattgct  26400
tcacaatatg catcataaca tatgatttga tcaggcattt gttttctctt ttaacgctct  26460
ttttctccac cactttccct cagtacagat tacagagacc atgtctcttc tcattgtatc  26520
cccaggcaca aggcctgaaa tgtaatgtta gtaaacagtt ggcgaatgaa gatgaaatgc  26580
aagccatcac ccattttcac atggagtcct gggaagggac ccctaatgag actccctgcc  26640
tctgcttgtc cacctgcccc aaactctaat cttactctgt atgcaggtga cttttcagaa  26700
gacaccctag actccttaac tatctgagag agctgctcct tggggctgtg cagaacagaa  26760
aattctccca tttcagtgca tgcgatggac cttgaatgga tgagcatgag cagtggcccc  26820
ctagggaggc tggggatgag gggccagggt ccagtccctc cctacaccct cccaactttg  26880
gaaagcagca ctgcctgtcc taacttctta atgttttcta acaaaaaaag gggcccagct  26940
gccatgggtt tttccctcag actgagactt ttctgaaatg caaatatttc aggcacatga  27000
```

-continued

```
cggatattgc tcaatatttg ctgaacacat taaagtgaat tccgtttaag atccttggcc  27060
tgaaaggcat ttggggccca tttaggggct acaaggtgga ggttgctgcc tatgtggaca  27120
gggaagagcc agaggattca catttcatcc agggcctctg ggcccctgca ctgcgagcat  27180
gcgcacttcc cactagaggc tctggggtga ccccccttcc tccgttcact atggaaacca  27240
aggctgggac tggcctctcc tcctgttcct gggtctgcca agaacagcct attccacagc  27300
tgtgtaatct gttccgtatt acagagttcg aagtaaccca ccagcaaaac tgtctgctcc  27360
agaatatttt aagttacagc ttctccgtat attttctgtg tctattcaca gaacttctat  27420
ttacagaatt ttgatttaat gagtagttga gatatatttt tgtagtcttc acacttttct  27480
actaagctgc tggccctgag aggacttatt gcccaactca aataggggcc cccctggaga  27540
cacccagcaa gatttattat ccccatgact ctcaggacag cattagagct ccatcccaga  27600
tcttgagcct tgggtcaagg tagttgtgga tgccttccaa gtactagctt cgtctcattt  27660
ctcacagtgt ctttggtcct ttttgttatt actctgaagg tcggaatctc tggttcgtgg  27720
gcacacacct tattaggcag ccatcaagct actgacccgt ctatcccatt gcacctgcgc  27780
atgtgtgctt tccccactaa caggctatcc caggctttat tttgtcccac taccccacct  27840
acccaaactt ctactcccag taatttgatt ttgggggga attgaacctc ttcattcttc  27900
aggaagaaga tgatatcatt ttagcaggtg tacagttggg ctccaggtct agcctgtgct  27960
tcatttcaga cttgtgcatc agacctaagg ctttaagcct tccaagtgta atctctcagg  28020
gtggtcttaa tcgacaggcc ctggtacagc attggacaac ccttctgtca gaagtgtagt  28080
gtgttgtgtg ctgcaggaga ggccttctgc acagtctgct tgatgctggc aacttcacta  28140
gaatgaagtc caggtagaag ttatccagtc ctgcccaggc agcaactgaa gtccaagcag  28200
ctctctggcc agagcgctga tactcacttc agcagagcca ccttttattg ttgtcatgcc  28260
ccaagcctgc actttaattt caagaatcca ttacatctcg gagggtgaca tgtgagaatg  28320
cagttttaat gagatcacaa tgttaaaaac catagcctat ggccaaagcc aagttgagat  28380
ttaaatagta ggttcaaaca cttttcttat taaaaaatat atcaaatgaa ctaaatattt  28440
tatttcttta tttatttaat gtttgagaca gtctcgctct gttgcccagg ctggagtgca  28500
gtggcatgct ctcagctgac tgcaaactcc acctcccagg ttcaagcgag tctcctgcct  28560
cagcctgcca agcagttggg attaagggtg cccaccacca cacccggcta atttttgtat  28620
ttttagtaga gacggggttt tgccacgttg gccaggctgg tctcgacctc ctgacctcag  28680
gtgatctgcc cgcctcacct tcccaaagtg ctgggattac aggcgtgagc caccgcacct  28740
ggcctaaata ttttatttaa atagttagaa aataatacat acccaaacaa aataaagaat  28800
aatattgatg gagatttaaa tgcaataaat gaggattata tttatgaagc atgggggtaa  28860
taagtctgtt caagagacat tcttaaaaac aatgaatata attagcatat ttctgtaaga  28920
tgttcccaag aaaatggtag atatctataa atagaagaag gagaaaaagg agaagtagat  28980
ggagaggaga aggaggaggt ggaggagggt gaggaggagg agaaaagtgt tgaaataatt  29040
ccaactaaga ctgatatcta ggaattaccc tggtgaagtg ggaagcttaa gagtcctgtt  29100
ggagggactg gtgtggtaat ggctctgcca aaagtgttat gtgcgtgcaa acccaaagag  29160
agaaagcaca gaaaaccttt caacatcaac ctgcttgagg aaaaataaag tgggaaaaga  29220
tacatactca cagtgaggac tctagacatg tcaagacaat ttttaaatat gcttttggct  29280
tcgagtggca ataactagat tcaagacagc atatttaaga agctgctgat gagaagaaac  29340
```

-continued

```
ccgggaagag ctgaaggacc acatcagccc agaccaagga tgctgaagca gcattaaggt  29400
ccctggtttc agatgctcag gcaatgaccc tttttttcat ggagagcctg taggagtgac  29460
agttttgtct ttgcccactg ggaatctgtt ttccatacct ggaaaacagg gttacctatg  29520
tttcccctgc taccctttgg tcatctcaga gacactacca gatattaccc atgggaccta  29580
ttttttttt aaatctcagg aaagacttgg gtgtggcttc caacgtggag gactcagtag  29640
cttcagagag ggtcctgaga gaaggtgaat tgaagaatga gggtgctggg cagagggaaa  29700
agacattatc atacaagttt gtgctaaaag atatagcaat ccttctgcta tggactaagt  29760
atggaaaaaa ataaaatgga atcaaagtta cccaaaggaa gtgtaaaacc caaatttatg  29820
cccgttaaag cattaatgat gctctaagtc cactgcctac ttaaaaagtt catagttcac  29880
atgggttgat aggaaattac gttaacgaca cactgcattt ccccttttct tatagcctat  29940
ctgatttggt agggagtcga tcattttta ttggaatttc tcaggattcc aacctcagac  30000
atccacttta cagtttacac attttcttgg acaagcccga ctgttcctct cactggttcg  30060
cataaagctc atgtttacaa agccgcccag acctttctct gggactctca tatttaactt  30120
aattctggat atacccaggt aagcgtttcc caagaaactt gaccccaaca tcccaaaaac  30180
ttaaggtatc tttcccttaa actggcccct tctccagtac gcatccatct cacttctctc  30240
ctgccctaga tcttctcagc ccaaacagga aaccccggga tcgctctccc agcaggtgaa  30300
gcctcgccat ggaccctccc cgtcggggcc ccgcgctgcc ccgcccgccc ccagccgctg  30360
gccaaggccg cggtcgcgca ggcgcagtgc cgcgtcccgc cgccgccccg ccctgcccgt  30420
cgctgcggaa ggcgccgcgc gcagcaacgc gcacttcctc tccaggaatc cgcggaggga  30480
gcgcaggctc gaagagctcc tggacgcaga ggccctgccc ttgccagacg gcgcagacat  30540
gtcagaacaa agtaaggatc tgagcgaccc taactttgca gccgaggccc ccaactccga  30600
ggtgcacagc agccctgggg tttcggaggg ggttcctccg tccgcgaccc tggcagagcc  30660
gcagagccct cctctaggcc cgacggccgc tccgcaggcc gcgccgcctc cccaggcccc  30720
gaacgacgag ggcgacccga aggccctgca gcaggctgcg gaggagggcc gcgcccacca  30780
ggccccgagc gcggcccagc cgggcccggc accgccagcc ccggcgcagc tggtgcagaa  30840
ggcgcacgag ctcatgtggt acgtgctggt caaggaccag aagaagatga tcatctggtt  30900
tccagacatg gtgaaagatg tcatcggcag ctacaagaag tggtgcagga gcatcctccg  30960
gcgcaccagc ctcatcctcg cccgggtgtt cgggctgcac ctgaggctaa ccagcctgca  31020
caccatggag tttgcgctgg tcaaagcgct ggagcccgag gagctggaca gggtggcgct  31080
gagcaaccgc atgcccatga caggcctcct gctcatgatc ctgagcctca tctacgtgaa  31140
gggccgcggc gccagagaga gcgccgtctg gaacgtgctg cgcatcctgg ggctgcggcc  31200
ctggaagaag cactccacct tcggggacgt gcggaagctc atcactgagg agttcgtcca  31260
aatgaattac ctgaagtacc agcgcgtccc atacgtggag ccgcccgaat acgagttctt  31320
ttggggctcc cgggccagcc gcgaaatcac caagatgcaa atcatggagt tcctggccag  31380
ggtctttaag aaagaccccc aggcctggcc ctcccgatac agagaagctc tggaggaggc  31440
cagagctctg cgggaggcta atcccactgc ccactaccct cgcagcagtg tctctgagga  31500
ctagcaaagt ctggaggcag atgaatggtt tctgaccctc accagggctg tggaagggtg  31560
ggggtgggtc attatagtat tcaggattta cagtgcagta ttcacgtgta acttttaagt  31620
tttcagtaca gtgcttttat acctttaatg caatgttgta ttcatttggg tactattgtg  31680
tagtatttag gatgtatgca tgtttgttta tatgtaagct tggttggtgc tttcgctttt  31740
```

-continued

```
gtgctacctt tcttggattt ttgtaccaga gatgtgctaa actgatgaaa tacattgaga  31800
aagtttccat cttattcttt tatatgggac tgatgatgtg tgttggggta gactgctcct  31860
gcagagtttg gaagaagtca ccagcaaagc cggcctaacc aagaaaagtc aaggcccttc  31920
atgaccttgc tgggcacaga aaacaccctc gtggagtaca ctaatttgaa ctggactggt  31980
ctcagtgtga gcacttggca cactttacta aacacatata caaccccacc gtgagtcaac  32040
tttaaagtaa acattaaaga ttcttgtgat acaatcattt ttggaaaagt gtactttatc  32100
atttaacaa agcagtatgg ttgggaatga gacaattctc tattttacag tgtatacaga  32160
tacaactatt tcccctaata gggtgggaaa aatcgctact catgattact cctaaatttg  32220
tgaagtttat agttctattg tctttaaatg taactcatgt ttatttcaaa aacattcaca  32280
aatatagaaa agtatacaaa acaaaacagt aagattgtct gtaatcacat catatgggaa  32340
taaaaaacaa aaataatttc cttcccttaa gtttctacat tttatcaaaa ttaatagatg  32400
tcttgtgaca tctattaata tacatataac atatttataa tataaaagag tgagacattg  32460
tgctaagccc taacatgtat ttttctcctt taatccttgc aacaggcctg tcaggcaggc  32520
acctactgcc tctgcaccat ggaggaaaca caggaataat gtaggtaatg aactttccat  32580
agctcataaa ggttaataag agaaggagct aggacttgaa ctcagaatga atccagagcc  32640
cacatttgtc tccacctgcc tacgactgcc ctataccccg tggcttttag gttatttatt  32700
tttaaattta tttttacatt ttatgtggga gcctacaatc acatgggttc atgggccaca  32760
catacaaaaa ggctaggaat tttatttttc taattctcat gatattttgg agaaagcaat  32820
atcattctga ttgtgcaaat taagaaactt acttttggag aggttaatta acctaacaaa  32880
gtgatattcc tatttagcag tgaagctagg atttgaaaca atctctcctg agggttggag  32940
gtgaaggcac cttctctgac aaacacacaa gacacctgag agagggaggt gggttgtcca  33000
tcaggatgtc tgtggccttg cagcccttca gttgcggtga gccactaggt aatcctcaga  33060
ggatggggtg ggctgcgggt gggcattagg ggcaatgcct gaagaaaaat ctcactgtga  33120
atttttagtc ctgcaagggg tagcggggag aaagggggct ttaataagac tagaagtcct  33180
ttaaactaca aaagagtggg aaagaccatt tggccaaagc cagaaacttt tctgtggaag  33240
atggataatg aagaggacac atgtcacata acaccccaaa gaagtaaact gggagtccta  33300
ttagggtgag ggaattataa tttggaattg ccaacactta ctggcattac ttaacaggtg  33360
ggggcaggtg ctggaaatgc ttaggaagcc cctgttcatg ctgagatgaa atccatcccg  33420
gtttaaaagc ttcctgtgaa gattttcaag gggttctgc agagaaaggg ggacatttct  33480
gcaatcaccc aggcaggggt gacctggctt tgatggcacc tcttacacaa aaccaatgtg  33540
agtgtctcac ctgttcagaa gtgttaggat tgtttggaaa tcttacctcc ccacaaccca  33600
tcgaaaagtt tctccagaat caaaataaac ctgcccgtta tcatttaaaa ttgtggggat  33660
atccaggatg tttcatttct ggagtaggac tgtgggctgt tgttcctgcc acacatggtg  33720
ctggtcatct tctctaatgc cttaatactt ccctcactgc tggattgatg ccttgcagga  33780
gctgtaaccc ctgtgtgctt cttgcagtaa agcccagaaa tcaccaggca aacagtctcc  33840
ttacatcccc gtttaactcc ttatgttgtg tccactttcc tctctgctgt cagaggcagg  33900
gagaaccacc ctttccaaag ctgtcccaag ctcactcaca caggcaccct agccaggcca  33960
tagaggacct agcccttgca ggagaaacag aatgtgagaa tgtgagaatg tgagaaagga  34020
gtaaggcatg gggcagagcg actcgtccct aatgctgcct aggaggcagc cagacctaga  34080
```

-continued

```
gaaagaggct tccagatgtg aaatgagttt acttcatgac acctgatcct gcagagatag  34140
cagcttgggg catggggaga gagaacccag cagctctctt gggttttcat gctgggctct  34200
aaatagaaag actggagggt ttgtcaaata tttaccaaaa gattcaccta caaggtcctg  34260
ggataggtca atcaggaagg ggtcagctgg tcctcagtgt tgcagtccaa catgacagtg  34320
tgctgaagcc cagactgctg tgggtgggag agactttcct aaatccccat aacatgtcaa  34380
cttttacctg ccaactggaa cctcatttct tcacaaacac ctgcaaacat attttgattt  34440
gttaatttca ttttatgaaa ggaagggaaa agggatcttt ataaatttaa tataaaatat  34500
aaagacacct ggtgtaagtt gtcctgagag gaaataaata actttaagca gtatcattat  34560
taaatagaaa tgttttaagt gaacttctta tgcagttaaa tatttcctct gcttgaaaac  34620
ccttttatgt ccttctccaa cctgagtctt acctgaccaa ctcatgaaca ctatttcctg  34680
ggagaacaca ctccctaacc tctaagcaca gccatgttct aaatgcaccc aaaatacacc  34740
tgctgtttat aattatgtgc cttttatttc tctcctcctg gattgttaca tacttaaggg  34800
ttagaattgt ctttatcctg ttcattattt gcttgacact tgaggtaagg atggggcata  34860
agggctgcac ttgatacata tttgttatat aagttaagta actcaacata ttagaaaaga  34920
cctacccatc cacacaagaa aacaaaacca tatgtggctg acaaaaatta gccaatttaa  34980
agggcgcggt ggctcatgcc tgtaatccca gcactttggg aggccgaggc aggcagatca  35040
cgaggtcagg agatgagacc atcctggcta acatggtgaa accccgtctc tactgaaaat  35100
acaaaaaaat tagccggacg tggttgcggg tgcctgtagt cccagctact cgggaggctg  35160
aggcaggaaa atagtgtgaa cccgggaggc ggagcttgca gtgagctgag atcccgccac  35220
tgcactccag cctggggcga cagagccaga ctccatctca aaaaataaat aataataata  35280
ataataaaat agaggtaacg taggacgggc gcgatggctc atgtctgtaa tctcaccact  35340
ttgggaggcc gagatgggcg gatcacttga ggtcagaagt tcaaggcgag gctggacaac  35400
atggtgaaac cctgtctcta ctaaaaacac aaaaattagc tgggcgtggt ggcacgtgcc  35460
tgtagtaaca gctactcagg aggctaaggc aggagaatcc ctcgaacccg ggaggcggag  35520
gttgcagtga gacgagatca tgccactaaa ctctagcctg ggtgacagag caagacaccg  35580
tctccaaaaa aaaaaaaaag caaagtggag gtaatgtaga taagttgaaa ttagtgaaag  35640
aaaaaaaaac agaaggcaga aaaacaatgg aagcaaaaac ttgtttcaag aatcactgct  35700
acaaacactc taacaaaata acccaatatc tagtagtttt tttagaaagg aaaaatagta  35760
caaagaaaca acttatttcc tgacttttta atgatcgcca ttctaactgg cgtgagatgg  35820
tatctctttt ctttcttttt tttttatttt tcatttttga gacagagtct ctctctgtca  35880
cccaggctgg agtgcggtgg tgcgatctcg gctcactgca agctccgcct cccgggttca  35940
cgccattctc ctgcctcagc ctccccagta gctgggacca caggcgctgc caccgcgcct  36000
ggctaatttt ttgtattttt agtagagacg gggtttcacc gtgttagcca ggatggtctc  36060
gatctcctga cctagtgatc cacccgcctt ggcctcccaa agtgctggga ttacaggcgt  36120
gagccaccgc gcccggctgg tgtgagatag tatctcattg tggttttgat ttgcatttct  36180
ctgatgacca gtgatgatga gcatgggtga agctggaagc catcattctt tatatatata  36240
tatatacata tatatatatt ttttttcatt atactttaag ttctagggta catgtgcaca  36300
acgtgcaggt ttgttacata tgtatacatg tgccatgttg gtgtgctgca cccattaact  36360
catcatttac attaggtata tctcctaatg ctatccctcc cccctccccc caccccacaa  36420
caggccccag tgtgtgatgt tccccttcct gtgtccaagt gttctcattg ttcaattccc  36480
```

-continued

```
acctatgagt gagaacatgc gatgtttggt tttttgtcct tgaaatagtt tgctgagaat  36540
gatggtttcc agcttcatcc atgtccctac aaaggacagg acctcatcct tttttatggc  36600
tgcatagtat tccatggtgt atatgtgcca cattttctta atccagtcta tcattgatgg  36660
acatttgagt tggttccaag tctttgctat tgtgaatagt gctgcaataa acatacatgt  36720
gcatgtgtct ttacagcagc atgacttata attctttgag tatataccca gtagtgggat  36780
ggctgggtca aatggtattt ctagttctag atccctgagg aattaccaca ctgacttcca  36840
caatggttga actagtttac agtcccacca acagtgtaaa agtgttctta tttctccaca  36900
tcctctccag cacctgccgt ttcctgactt tttaatgatt gccattctaa ctggtgtgag  36960
atggtatctc attgttgttt tgatttgcat ttctctgatg gccagtgatg acgagcattt  37020
tttcatgtgt ctcttggctg cataaatgtc ttcttttgag aagtgtctga tcatatcctt  37080
tgcccacttg ttgatggggt tgtttgtttt tttcttgtaa atttgtttga gttctttgta  37140
gattctggat attagccctt tgtcaggtga gtagattgca aaaattttct cccattctgt  37200
aggttgcctg ttcactctga tggtagtttt tttgctgtgc agaagctctt tagtttaact  37260
acatcccatt tgctaatttt ggcttttgtt gccattgctt ttggtgtttt agacctgaag  37320
tctttgccca tgcctatatc ctgaatggta ttgcctaggt tttcttctag agtttttatg  37380
gtgttaggtc taacatttaa gtctttaatc catcttgaat taatttttgt ataaggtgta  37440
aggaagggat ccagtttcag ctttctacat atggctagcc tgttttccca gcaccactta  37500
ttaaataggg aatcctttcc ccatttcttg tttttgtcag gtttgtcaaa gatcagatgg  37560
ttgtagattg tggtattatt tctgagggct ctgttctgtt ccagtagtct atatctctgt  37620
tttggtacaa gtaccatgct gttttggtta ctgtagcctt gtagtatagt ttgaagtcag  37680
gtagcgtgat gcctccagct ttgttctctt ggcttaagat tgacttggca atgtgggctc  37740
tttttggtc ccatatgaac tttaaagtag ttttttccag ttctgtgaag aaagtcattg  37800
gtagcttgat ggggatggca ttgaatctgt aaattacctt gggcagtatg gccattttca  37860
cgatattgat tcttcctacc catgagcatg gaatgttctt ccatttgttt gtatcctctt  37920
ttatttcatt gagcagtggt ttgtagttct ccttgaagag gtccttcaca tccctataag  37980
ttggattcct agatatttta ttctctttga agcaattgtg aatgggagtt cactcatgat  38040
ttggctctct gtttgtctgt tattggtgta taagaatgct tgtgatttct gcacattgat  38100
tttgtatcct gagaatttgc tgaagttgct tatcagctta aggagatttt gggctgacaa  38160
aaaccacctg attatctcaa tagatgcaga aaaggccctt gacaaaattc aacagccctt  38220
catgctaaaa actctcaaaa gttaggtatt gatgggatgt atctcaaaat aataagagct  38280
atttatgaca aacccagagc caatatcata ctgaatgggc aaaaactgga agcattccct  38340
ttgaaaactg gcacaagaca gggatgccct ctctcaccac tcttattcaa tacagtgttg  38400
gaagttctgg ccagggcaat caggcaggag acagaaataa agggtattca attaggaaaa  38460
gaggaagtca aattgtccct gtttgcagat gacatgattg tatatctaga aaacccattg  38520
tcttttttt tttctttgag acggagtctc actctgtcgc ccagcctgga gtgcagtggc  38580
gcgatctagg ctcactgcaa gatctgtctc ccgggttcac gccattctcc tgcctcagcc  38640
tcctgagtag ctgggactac aggcgcccgc caccacgccc agctaatttt ttgtattttt  38700
agtagagacg gggtttcaca gtgttagcca ggatggtctc catctcctga cttcatgatc  38760
cgcccgcctt ggcctccaaa gtgctgggat tacaggtatg agccaccgcg cccggcctgg  38820
```

-continued

```
aaaccatcat tccaagcaaa ctatcacaaa gatagaaaac caaacaccgc atgttctcac  38880
tcataggtgg gagctgaaga atgagaacac atggacacag ggcagggaac atcacacacc  38940
gaggcctgtc gagaggtggg aggctggtgg agggatagca ttaggagaaa tacctaatgt  39000
aaatgatgag ttgatgggtg tagcaaacca acatggcaca tgtataccta tgtaacaaac  39060
ctgcacgttg tgcacatgtg cccctagaac ttaaagtata caaaagaaaa aaagaagcaa  39120
cttattacta gataaatggg ccaaggacac agagaggtca gtgccttaat aggaaacaca  39180
aacatcaaat gagaaaatga aaaacaaata caatctcact gattaagtaa agatactttg  39240
tgtatatgaa ttgatcaaag atacaataaa aatgaatatc ctgtactagc aagagtgaat  39300
tgaaattggc atccttggac cctgctatag ttgtataaat tactacatgc tattttatgc  39360
attcattcag agtgcttact gagtacctaa tatgcggcag atgcagggct aggagttagg  39420
gatgcaagag tgaacagaat agacattgtc ctgtgcttgc cgagcattca ctgaattgaa  39480
agaagcaggt gaataaaaat aattacattt cagcgcagtg agtgccatcc taagagaagt  39540
gtggggccta aagaggcaca aacaggtgca cacgactcag actgtcctag agaggtgagg  39600
cataaattgg ttctatagga tgagaagcaa ttagcaacgt gaaaacggtg tgtggaaggg  39660
tgaagttggg aggaggctct ctttgtgtcc cgggatctgc tgtgtgacca cacacacaag  39720
catacggggc tatataatga gtttctcaaa ataaatagag taaaaaggag aagggaaata  39780
aacaaatttc agaattggct agaggctagg aaaaaaaaac atgctggctg aagatacagt  39840
caatttcctc aaggatgtga caaagaagag ggctcatatg aatcacatga aaggctaaca  39900
gatttagaag aagccatgct gaaggatagc cttcttttga acagacacct ttgttttttt  39960
attgctgctg ttgttgtctg ctttctgatg aggggtctaa aacatccctc cttatctctt  40020
tatttgccca attattcttg ggttcagcta ctcagggttt ggagccctta actatattac  40080
atattttccc atatctaaac ggtttcatgt ctcttctatt agcccaccaa ctttatacta  40140
aaaaatcttt aagattcctg tttgctgtat aaattagttt gtttatgtat ttattcaata  40200
gagatttctt gaacttcaac tatatggctg acttgtgcta ggaactggta caatttggtg  40260
aattaaacaa gatggctctt ggcctcaagt agtttgttta taaacttttt tttttttttt  40320
tttgagatgg agtctggctc tgttgcccag gctggagtgc agtggcgcca tcttggctca  40380
ctgcaagctc cacctcctgg gttcatgcca ttctcctgcc tcagcctccc cagtagctgg  40440
gactacaggt gcctgccacc acgcccggct aattttttgt atttttagta gagacaaggt  40500
tttgccgtgt cagccaggat ggtctcaatc tcctgacctt gtgatccacc cgcctcggcc  40560
tcccaaagtg ctgggattaa aggagtgagc caccacacct ggcttattga taaattttgc  40620
attgatagag cacaacaaag aggtacaaat gaaacttcaa atacaaatta tatgattgga  40680
taagatatat gaaaaaaatg ggccaggcag agtggctcac atctataata ccaacacttt  40740
gggaggccaa tatgtaagaa ttgcttgagg ccaggagttc aagcccaacc tgggcaacat  40800
agcaagaccc catctctaca aaaaaagttt aatttaaata aatgacgtgg ttaaattgat  40860
agagaatggt tgagaagaca aactaaggca ggaagcccaa gaaataattt tctgaaaagg  40920
tgaaatttaa gctgataatt aattgaagga taacaagaga gttagcaaag atcaaaggga  40980
agatcaagat aaatccaggc atgtatgtat gtatatataa attacgcatg tatacatata  41040
tgtgtgtaat atatatacat atatatgcac atcatcccat ctgggccttc atatatatgt  41100
atatgtgtat aatatataca tatatatgcg cataggtgtg tatagtatat acatatatgt  41160
gcgcatagat gtgtatagta tatacatata tgtgcacata tatatgcaca tatatgtgta  41220
```

-continued

```
taataagtac acatatatat gcacatatgt gtgtataata tatacatata tatgcacata  41280
tgtgtgcata tatatacata tgtgcacata tgtgtgtaat atatacatat atgcacatat  41340
atgtgtgtaa tatatacata tatgcacaaa tgtgtatttt atatgcacgt atgtgtatta  41400
tatatacata tatgcacata tgtgtgtata atatatacat atatgcacat atgtgtgtat  41460
aatatataca tatatgcaca tatgtgtgta taatatatac acatatatgc acatatgtgt  41520
gtataatata tacacatata tgcacatatg tgtgtataat atatatacat atatatgcac  41580
atatatgtgt ataatatata tacatatata tgcacatata tgtgtatgat atatatacat  41640
atatatgaag ggccagagtg aatcacctag atttttctgg tggcctttac catgagaaat  41700
agcattataa atgggctgag cagcatgtga cacccagttg tcttttcttg tctgtctcca  41760
cagttgaggc tgcacaagtt aaatatttaa cttcttggtt tttcagctgt gttccagtca  41820
agagatgtac agagaggttt atctgtgctt ttccttccta catccttttt ctctttcagg  41880
gaatgtataa ggaaagtcag gagctattgt tgctcgtatg atggcagtat aaaaacagct  41940
aaagaaatca tagagaggtt gagcctgaca tctacaaact gctggacaaa taccaatagc  42000
cacctacttg tatctatagt ttttggcatg tagaataaaa tctcattctt taagctattg  42060
tcttgtgggt tttttgcttg ctttgtgcag ctcaaagcat ccctaactgg taaagtctcc  42120
aaaaaattct tttctcgtct cccattctgt gtctggtact cacatgaggg tattactgac  42180
cataggtgga ccccgattag gttatgacaa gcagagtaat tctatctcct tgctgcagtt  42240
cttagatcag atatgagaac ttaatcagtt ctgggcaatc aggtcatgta gattagaact  42300
tccattcatt tcatggcaat gttcatgaga atagaattag ggcttctggc tctgaagttt  42360
gtaccacttt ggcatttaga gttatctcag aaaaatgtat aattttttta aaaattcagc  42420
ttgttattta taagccagtt ttgttatttg ctcaagaaat catactaata atggtggtgc  42480
tttctggggt tgcgaagggg aaagaaaggc tcagaaccag gagagagagg aaggtatcag  42540
ggcagccctg taggcaatgg taagcaggca gattgtattt aaagagtaaa tggaaaccac  42600
taacgacttg cagactcatc taattgacat taggctttta aaatattgcc ctccttagta  42660
tactcagaat gaattgagaa gggaaagcat caaagttgag agtctgctaa gagatgaaga  42720
tgatgtagac atgatgaagg agggtatatt tgtggctcaa ttgaggaatg gaggatggat  42780
aggtaaggga catggaagat tagatctgga ttctcaggtt tcaggcttga gcactcggtg  42840
aatagtgtga tttttttttt ttttgagaca gagtctcggt ctgttgtcca ggctggagtg  42900
tagtggcaca atcatagctc attgcagcct tgacctccta ggctcaagtg atcatcccat  42960
ctcagcctcc caagtagttg agactataga agcacaccat cacacctggc taatttttgt  43020
attttttgta aaggcggagt ctcaccatgt tgcccaggct ggtctcgaac tcctgggctc  43080
aagcgatcct cagcctccca aagtgctggg attatagatg gtgagccacc gcacctggcc  43140
ataagtgtga tttgatgaaa tggagaaggg aggtgaaaaa caggttttgg atgaaaacag  43200
taaagagttc atacaaacac tcagtgacat gtcctaaaag aaatatgagg ttcacaatta  43260
ttaaagatgc ctagctcaag atagagaatc atagccctgc actggagcaa cccatttatc  43320
cagagtgaaa gcacagagta actagaagcg gatattctgg gaaactaaga cattaccacg  43380
tgtagtattg aaggaaaagc tgctacggag actaaaaaca gtacctggtt aagagataga  43440
aagtaagcca ggagagtgat agagatgaga atcaaaatag cagcatttca agccaaagga  43500
agtggccaat agtgtcaaac actgttgagt tattagaagt atttgagggg tttatttgca  43560
```

-continued

```
tttagtagga tctttgctga taagagaagg gaataaagga gattaagttc aaaggcatga  43620
cgcgtgttca cccttcactc aggtgagaga taatggtaac tttaactagg gaatgaataa  43680
tgaagatgga gattaattga aaaattgaga aataattggg ggttacattg ccaaaaatgg  43740
atgattgatg aaatgctaga aataaaaaca gggaggaatc aggtttatgg ccaggtttct  43800
gacatgcaca attttgtgtg tcgtatcagt tactgagttt gtgagaaaag agaaagcaga  43860
tttacgtggg aggaggatga gttcagtttt atatattttg agtttaacgt aaatgccagg  43920
catctaaaca gagatgtcca tttgattagg gataaatgca taagaaaaga tgcagattaa  43980
aatgtcatga acctatggat gggaagggat ggatttgcaa aggtattctc tgcttcacct  44040
gagcagttta ggcaggacag acactcttct gcttaatctc agacacttac accagctatc  44100
cacacttgat cttagccaaa aggccgagaa gcaatacacc agctatcctc aggtacttac  44160
attacttttt gttcctaaag gcatatgagt ttgggaatct cggagagtga gagggaagag  44220
gtgcaggatg gagcattgag gagaacaaat attacatgga aaagcagaaa gataactctc  44280
aaataatatc aagaaacagt gggaagagat taggaataag tgagatttag agaatgtagt  44340
tttagaaatg ccaaaggagg gattggtcag ttgttaaatt tagttgaggc atgaagcaat  44400
aaaataacta agaagtgttt actgaaatta ctcataaaga gattattttc attttatgaa  44460
gaacaatttc aatgggatag ttgtcaacag aaaccaaact tcagcgaatt aagtatggag  44520
caggatgtga atataaatga tgtatatatt caatggttga tggagagata ccagtattga  44580
agacatggcg agatctatat tataaaatgg agttactata caggattggg aatgcatcgt  44640
ccataggaat gagacagaag tatgaaatga ctgattgatg tatacctgtt gtatctgtgg  44700
cagaaagttg atggtgcttc tattttccca gaggagtgtc agggaaagtc aaaatttaag  44760
acagagaagg aaagtgatga gagagaaaga cagtcccaga tgtgtcccat agaatggaga  44820
aggcagggga tcttcccagg agaatctctc atgggagact ccagcagata ttagaaaatt  44880
taatttaccg atatgtacaa ggtaccacca ctgcatttct tatttgttcc acaaatgcaa  44940
gactgtctca gtatattcat catatctgta atcttaagaa aaaccacatg atcatgtcaa  45000
tgcatgcagg aaaggcatct gacaaaattc aactcccatt cataacaaaa gctctcagca  45060
atctaggcac agaaaagagc attaccaacc tggtaaagca cattataaaa gaaacaacaa  45120
ctactactat agttaacatt gcttagtgtg tttaatgacc aaaaactgga tgcttccctc  45180
taagattgga gggaagggta gagtatgctg tccactctta tcactccttt tccacttggt  45240
gatgaaagtc ctagccagtt caataagaca ggaaaaggaa gtaaaatgct tacaggctga  45300
aaatgaagaa ataaagctac ttctatttgc agatggcata attgtctatg tagagaatct  45360
caaataatgt ccaaaaaacc atacctgaat taagaagaga ctttagcaat gtcacaagat  45420
acggggtcaa cacacaaaac caattacatt tctatatacc agcaataact cttggaaaca  45480
gaaatttaaa catttaaaac tcagtaccat ttataataac tcaaaaatac ttatgaatac  45540
atacatcaaa acatatagga tctctatttt gaaaagctta taaagcactg attagaaaat  45600
caaaaaatac ctaaataaat ggagagaaat atcatgttca tagatcagaa gactcaacat  45660
ggtaaacaga tcaaacagac atgtaggatt catgcaattt ttatcaaaat cccagcagtt  45720
tatctggaat tgtcttgatt ttggcaccag aagtcccact ttctaggaat cccctctgtg  45780
ggatgtgaaa aaccccaaat ttttggccat gagtaaagaa gattggagaa aaaactagaa  45840
aacccatatg gcatcaccca aacaagggct gtatgcattt tactgccaaa tggagacagc  45900
acatattatc tgtttcttgt aattgctgtc actgtttttt tcctgaccac taatgcgtat  45960
```

```
aaccacgatt tgcagttcac agtgatcagt gaattactgt gagctgcaaa tcgtgaatca  46020
ttctaactct tgtgacttaa atatgtaaat gaagcatgtc gtaatcatga gtgtttgtct  46080
gtatttgact ttagctgtgg attaactgtt ctactttgaa tcaattttgt gctagttcag  46140
tttttaactt tacaaacctt gagaccatat tttctaataa ttcagatagt aaaaacacaa  46200
acaattacaa taccaatgca gcaaggccca gaaggctaaa tgattgtgtt attttaatgg  46260
tacatgaagg acacagacaa ctgtattaca aaggtaagta aacaaaacag agcatattgc  46320
acaataggca gaaaaataat gtggggctgg gtatggtaga ggaggttaca tgatctgtgt  46380
gactttgcta gggctgccgt aacaaagtac catagattgg gtggcttaag caacaaaaat  46440
ctatctcctc acagttatgg aggttggaag tcccagatca aggtgtcagt gggttggttc  46500
cttctggggg cagtgagaac atgatctgtt cctggtctct ttgcttggct tgtagatggt  46560
gcagatgact gtcttctttt tgtgtctttt cattatcatc cctctgtgtg aagactaaat  46620
tttaccattt aaggatgata taagcacgta attctaaaag gaacaaaagt ttcttttctc  46680
tttttctttt cttttctttt atttctgtta ttttttggat ttttggtctc ctaaacaaac  46740
actgatgttc agttgaaaat ggcagccact gaattacctt tggtatacca aacaaaccag  46800
cacacatcat tatatcattt tattgatttc tatttgaaaa tgagtaaagt tacattacct  46860
ttaaaattat tcgaacattc agtgacatat cctacaagag atatgaggtt cacagttaat  46920
aaagatgcct agctcaagac agagaatcat agccctgcac tggagcaacc catttatcca  46980
gaaagtgcag agtaactaga agtggatatt ctggaaaact aaaacattgt attagttttg  47040
gtatacaata caaaccagca cacatcatta tatcatttta ttgatttatg ttaacctaca  47100
agttgcattg aaaatgtctt tcaacaaaca aaatgggaaa ttttgataat agatacattg  47160
gttctttaca gtgtagagct gactctgaca agtcttactg tcaatcatgc tccctacaat  47220
acagcaagtg atgcgtcaaa taatgataac caaaaaaaaa atgcactcca cattttagac  47280
atgtttattt gaaaaatgga gctttaaatt atcttttggt ttctatgaaa cttttcatta  47340
aaccacagaa aacatgaaac aaaagattat taacatcttt tccaaatctg aactagaatt  47400
tgctcatcta tatgcatatc tggcagacag cacaaatgta aatttgccag actccattca  47460
gtctatgaac ttcttatcaa agaaaagata ttacctacta aatgcctcac acacatttaa  47520
tatagaactg ctaaaaaggg gcctggtgtg cttacttgtg attttaaggc tttcataatt  47580
aaaatttttc accacttttc agttttctta aaacatacag aaacaagaat cataacttcg  47640
gctttatgga aatggaagga gatagcatcc ttacacctat gcccacaaga cagcttgcat  47700
tgcggccagc cgtagaaaag ataccaaaat gttagcctgc cataaaatca tgttttcaga  47760
gtatgaaaga agaagaatgt tctctaatct gaaagcaaat taaggatgag aataaagaga  47820
aggggagaaa aatgcaacag aagtgaatat gctttttttcc caaaactgtt ggtgatcttt  47880
gaagaggtca tatggagcct agaaaatgat aagctggctg catttgagtt acgtgatgtt  47940
gtgttctggt tgcaacaaaa actaatacag caaaaacagg atgaacaaaa accctcatgt  48000
tttagggaaa tgatactatt tcagaacacg agaaaaggtc atcagaaaag atcagctaag  48060
ttaaatagaa ctttctctga gatggagtct ggctctgtca cccaggctgg agtgcagtgg  48120
tgcgatctca gctcactgca acctctgcct cccgggttca agccatcctc ctgcctcagc  48180
ctcctgagta gctaggactg caggcgtgca ccatcatgcc tggctaattt ttgtattttt  48240
agtagagatg gggtttcacc atgtgggtca ggctggtctt gaacacctga cctcaagcaa  48300
```

-continued

```
tctgcctacg tcagcctccc aaagtgctag gattacaggc gtgaaccacc acaccaggcc  48360
tgttttaaac agaattttct caatttcttt ttagaaattg taaattattt agaatacaaa  48420
tttgatttca caacttcaaa ttacctctgt gctttgaagc cattttcatg acaaagaggg  48480
ttaacttatg atagcatcca atacacttat gaatgttcat aaatcatgga ctttttttaca  48540
tgtcagcagc ctatatgatg gatctctaga tgcaaatgat ctcattaaca aacagatagt  48600
ctacgaaaat aaccctttaa atacaaagtg agtggtgttt ttttgaaagc tggacatgaa  48660
tttggtcaaa ttcaaaactc tgctgctgct ggtaagtaaa atcctaaata tcttatgtcc  48720
aaacactctt tttgtaaaca tatttagcta tgtttttaca tcagacttac cactggaatc  48780
aatgtaatgt ggacttgatg agaacagagc agcaagtcaa agtgaattat atgtttgact  48840
gtactcaatt ttatcaccac ataaaataaa agaaagatat catgaaggct gtaggcagta  48900
tagagaaata ttactaaaaa ggaaacagaa gaagaaaaaa tatatatatc ccactgtatc  48960
actggacaga aataaaaatg tcattcttac ttttaaattg aatattagaa tatcctatag  49020
tcatttttaa tttacattct cctcctaaaa gtcatatgat tacatatttt aagaataact  49080
gaatatagcc tacaatatat aagtatgcaa ttgggaatta aaataaattg ctgtaacaag  49140
aaatataaaa cattgttata tttttcatat atattacttg tttattaatc ctatcattaa  49200
ttactactaa ttagcactgt taattagtct ttgttttgtg taaaaaaatgt caggaggctg  49260
aggcaagagg atcactggag gccaggggtt caagcccagc ctaggcaaca tagtgagacc  49320
ccatctctac aaaaaatttt aaaattaact aagtgtggtg gcacatcttt gtagtcccag  49380
ctactccaga ggctgaggtg ggcagatcat gtgagcctgg gaggttgagg atgcagtgac  49440
ccatgatcga gctgctgtac tccagcctgg tgacagagtg agaacctgtc tctaaaataa  49500
atatataaat aaataaataa atgcagttcg tgtaacataa aaataagtga tatagaataa  49560
tagatatttt caaagaaacc tctattttat atgttatatt aaagtaataa tgtgtataat  49620
tattatatgt tacattatta tgatttattc tgtctgggtt aactctaaaa agttggccac  49680
cttagatata gacaagctga ttctaaaatt aatattgaaa agcaaaggaa ctagaacagc  49740
taaagaaaaa ataacttgta aaaagtgaat taagttaaaa aagtgtgctc taccaatttt  49800
aaggcttaag gcacaattca gcaatcaaga cagtggtatt tagcagaggg atagacacat  49860
agatcactgg agcagaatag ataactcaga attagaacca cacaagtaca gccaactgat  49920
ttttgacaaa ggtgcaaaag taattcaatg gaaggatagc cttttcaaca aatgatgttg  49980
gagcaattag acatcagcat gcaccaacaa acccccaaac cttcaacata aaccccacac  50040
ttcatacaaa aataaattca aaatggatta cagctctaaa tggaaaatgt gaatctataa  50100
aactttttaaa agaaaacaca ggggggaaat tgtcataaaa tggtgttaga tgcagagatc  50160
ttaggacacc aaaagcataa tccaccaaag aaagaacgga tcaatttgac ctcaacaaga  50220
ttaaaagcta ttattctctc aaagacactg gggttttttt tgttgttttt tttttttttgg  50280
tttgtttctt tttctttttg agacggcgtc tcgctctgtt gcccaggctg gagtgctgtg  50340
gcacaatctc ggctcactgc aagctccgcc tcccaggttc acaccattct cctgcctcag  50400
cctcccaagt agctgggact acaggcgccc gccaccacgc ccctctaatt ttttgcatct  50460
ttagtagaga cgggttttca ccgtgttagc caggatagtc tccatctcct gacctcgtga  50520
tctgcccgcc tcagcctccc aaagtgctgg gattacaggc atgagccacc acgccctgcc  50580
gaagtcactg ttaagagaat aaaaagacac agacttgggg aatgtatttg caaaccacaa  50640
gtccacagaa ggatttatat ccagaatata taaacaactc tctaaactca acattaagaa  50700
```

```
aacaaacaat cctattagaa aatagtcaaa gattgaacca gtagatggaa ggcaaacaca  50760
taaacaacaa aaaaaagatg gtcaacacca ttagccatta ggaaaatgca aactaatgtc  50820
acaataatgt atcactatac acagaaatgt aaaatataat aaaatatgct gtaaattatg  50880
acaaaagaaa atatactgtc ggctgggcac ggtggctcac ccctgtaatc ccaggacttt  50940
gggaggccga ggcgggcgga tcgcgaggtc aggagattga gatcatcctg gctaacacgg  51000
tgaaaccccg tctctactaa aaatacaaaa atttagctgg gcgtggtggc gggcgcctgt  51060
agtcccagct actcgggagg ctgaggcagg agaatggcgt gaacccggga ggcggacttg  51120
cagtgagccg agatggtgcc actgcactcc agcctgggtg acagaagcga gactccgtct  51180
caaaaaaaaa aaaaaatgaa taaataaaaa taaaaaagaa aggaaatata ctgtccatat  51240
ccaagagagg atatgaagta agtggaactc tcacatagtg ccaggggaat gtacaagcat  51300
acatacacca ttctgcaaaa tggtttagca gtttcttaca aagttatcac atccttaagc  51360
gtaacccaat tattctattc ttggttattt actgtacaga aataaaggca tatgttcata  51420
ccaaaactac gttgcaatga cctacaatta gaaacaagcc atatattttc caacatgcaa  51480
atggataaac tgtggtacat atattcaata caatattact cagcaacaga aaggaactaa  51540
atattgttac acatagcaac ttgaataaat ctgaaagacc ttatatgtat tcagagcaaa  51600
agaaatatca aagggttgca tactctacaa taccaattta ataacattct agaaaagaca  51660
aaattatagc attgaatgta acagataagt ggtttccaag attagtgggc agctgtgact  51720
gaaaaggggt aacagagaat ttctttgtga ggatggaaca gctctgtatc ctatgttgat  51780
ggttacacaa atctatccat gtaatatttc atagaactat aagctccctc agaaatgagt  51840
gcatttcaaa actggcaaaa tcggaacaag gtcagtagtt tacttagtag tattatacca  51900
atgttaattt catagttttg attattttta ctatgcttat gtaagttagc atcactggaa  51960
gaagctagac aaaacggaca taggaactct ccatactatt ttttcaactt ccatgtaagt  52020
ctaaaattat tgcaaaatga aaatttaaaa taaacgagtg ctaatagtag tgccagagat  52080
agaactatat attttttttt cttttttttt tttttgaga cggagtctcg ctctgtcgcc  52140
caggctggag taaagtggcg cgatctcagc tcactacaag ctccacctcc caggttcacg  52200
ccattctcct gcctcagcct actgattagc tgggactaca ggagcccgcc accacgcccg  52260
gctaattttt gcatttttag tggagacggg gtttcaccgt gttagccagg atggtctgca  52320
tctcctgacc tcgtgatccg cccgcctcag cctcccaaag tgctgggatt acaggtgtga  52380
gccaccacgc ccggctgaga tggagtcttg ctctgtcacc caggctggag tgcagtggcg  52440
cgatcccagc tcactgcaac ctccgcctcc cgggttcaag ggattctcct gcttcagcct  52500
cccgagtagc tgggactaca ggcgcacgcc accatgtcca gtttattttt gtatttttag  52560
tagagagggg gtttcaccat gttagccagc atggtcacaa cctcctgacc tgattcgccc  52620
gcctcggcct cccaaagtgc tgggattaca ggcatgagcc atcgtgcccg gccagaacta  52680
catttttttaa ataattattt ttaagggaaa agtatggcat tcatcctctt gaatacatga  52740
tgtgccagat aatgtgagaa aactaaaatc caacatttta caataagcag attataaatg  52800
ctatgtcata aaaagagaaa ggatgcactt ttataagtct gtaaaatcat aactgtcttc  52860
atgatatgat agcatagtaa ttatcatatg aaccacaatg gctcatgctt acaaaacact  52920
taatatgtga tcctttcaac aagcaagagt acgtgttatt attaccagca ttttatagag  52980
gaggaaactg aaaaacatag atgttaactc atatcctctt gatcactagc ttgttaatga  53040
```

-continued

```
cctcactggg atttttcatc caaggtggtc tggccctaga aactgtacag aatttagaaa  53100
attatgtaaa ataaaattct gaaaggtgta aagagaaccc acttgcagga ggagaaaata  53160
gccactctca gcatgttggt gtgttttctt tttgtgtgtg tgctttcatg catttattga  53220
ttaataaata aaatagtgac tgaaaatgta tgtgtgccaa tatttgttct agaaacatgc  53280
gctacagcac tgaatgaagg attcgaagtc cctgccagca tggaccatag agtctagtgg  53340
gagaagatag gtaatgcaaa ttttaaaagt acaagaaaac ttcaagccac aagtcttaga  53400
gtagaataag ggactaacat taacagggtt gtcagggaag gcctctctga ggagatgacc  53460
cttgggcaga gccctgaaag acacgaggga gtgagccaca cgaatttctt cgtgaaggag  53520
taaagcattt ggaacagagg acattgcctc tgcaattgtc caggtgctgg gactggatcc  53580
aaggtctgca aggagaccca tgtggatgga attgggtgag ggagatggaa tgtagcagag  53640
agctgcccag ggtcacgtcc ttctccccag ccgatatggc tcattcagaa actctcttta  53700
cacacccatc agcttccatt ccatgtttat tttattactt gtttgtttac tgaggaattc  53760
aatattccct tatccaggca gaaccgaatg tgcaggtgat actgctctgt ccactcccct  53820
tcacctttca ccaggcaaat ttccttgggt gtacttggaa gatgcattct catgggcacc  53880
cccgctggaa cctcatccca gcccagcctt gagggagctc agtagagctg ttgtcaatgc  53940
tcattctcca ttcttagtag acccagcaga acaagaggaa cctcaacccc aaaaccctcc  54000
acattggttc aagaagaaat tgaggtctct ccaggctgtt agtgaagggt gtggctgaac  54060
tctgccacct tgtgactgat tccatttctc ccttcccatc agatgcgtgg ttctccagaa  54120
actcttggga tgggaattta gttttcagga gatgctcatg acagaaccaa agaatgtggg  54180
gatgagaagc cacaaagaac ttttcaacat atagctaagc ccaaggatgt ccttaacaat  54240
gcaatggagg gcagatagtg agaagcaggc ctgagaatac tgtatatttc aagactgtct  54300
gagaagtagg gtggcaaaaa ataaataaat aaataaacaa gattgggtgt ggaaaggaag  54360
agctaagggg ttaaatcaca cttaagaact aaggggttaa gtggtatgct ctatgcaccc  54420
ttcctccatg tagctcctct caattgcctg tgacttgcat ataacaaatc ccaagctcca  54480
atgagtccaa tatctccttc cttcatctgt ccactgggga tcaaaacttc tgcacatttg  54540
tgtactccta actcattggg aaatgcatct gccagaccct agtcaaatct gcatcctctt  54600
cccaacagca cactacaatc taccctcact gtcctcaagc tcaccctgtc ctatttcatg  54660
aggaaatcta gacaacgtga gaagtcgctt caatgttttg tccttttact gttcataggt  54720
ggttcctaga cgcagtctct ctgcatttgt gcattttatt aagtaaaaat acaactcttc  54780
caccaccaca tcacatctcc ttgtagacag caactttctc tcagctcatc caaatatcct  54840
tccaattgct ccctctctcc tttgtagact catgccctga atatacttag tgattttctg  54900
tactggcagt aacaacagtg ctctttgtca cacatttcct attctgtgct gccctaagcg  54960
tttcacaact tggggcacag atatgtagtt cccagactga tagtagagtg tagcagagtt  55020
aatcaaagtg ttttttacac tgaaatgaag tgtaaatgaa gtttttttaca ctgaaatgaa  55080
gtttttttaca ctggcacctt tattctttga ccctgtcata ttttgaagta gaatgtccac  55140
tttgggtaaa cttttaatat aaatcatcag atgtcaagga aatttcaggg gtaagcaggg  55200
tcattacagt ggtatctcca gttctatttc acagtgatga atcctctatg ccttttgggg  55260
attctttgga taaaaggttt ggaaaggact tctgggttgg aagctaaaag ttccacacta  55320
atcataagat aaatatggat aaagcataaa attatcagac agcaaagagc cttgttgcta  55380
ctttaatccc ttctggatgt gatgcagaaa taggaatcta ctcaccatgg atggctccat  55440
```

-continued

```
tgaggaaatg gccgaactat taactaattt atattgactg cgtgttattt agcatgacag  55500
attagaatta caaggagtct gaaggaagtt gaaatccacc tgccaaatca ctccttcagg  55560
gctttcacta actgcataag aggagcacac caatggctga aagcagggct ggggaggtga  55620
agagtcatgg actctttact caacgcaagg tagtggctag gggaaggctg ccatgataca  55680
ggacgctgag aaagaccttg tagggtgcac agatgctacc taagtgcaag gtggcagccc  55740
gtagggattt tgtgcagaaa aagagaactg aagcaatcct cccagggtgc acaaaagctt  55800
ccttgagtgc acatcaatgg gccgacaaag actagaggca gagaattagg aagaagaata  55860
atctcctaag gctacaggac aagccaggaa aagagctgga gagtaaagaa aactctccat  55920
tgaacaataa caacaacaac aacaaaacta gcaagtgggt ttaaagaaaa aaaatacaag  55980
caggagaaag gagaggacag caaaacacag agacagagag attccctata ttcataaaac  56040
ataaaacaag ccgctggggc taatgcatac agagatatct gaagtctctc tggtcttaaa  56100
tttgaagctc cgcttaaagg aatgtcttcc tctcaccctc aaactatgtg aaattctcag  56160
tgtggagctg aatctaagta tacttgcaaa aaaatatctt atctaactca accgcgtatt  56220
agattgtttc agtcccacgt attattggtc tgatagaaga aagcttgcac tttttctggg  56280
agtaaatatc actttcttca gtctctattt gttcatacac attatctcct gataaaaaat  56340
attaagaaat ataggaagag gcagaaaaat gtgaagcatg aacaagcaag aaaacaacca  56400
gtagaagaag tcttagaggt aatctcaatg tgtgaattgg caaggaaaaa ctttaaaaga  56460
actatgataa atatgtttaa gtatctggtg caaaaggtag acaagataca tgagcaaatg  56520
aggattacgg caaaaagata actacaaaaa ggacaaacag aaatgttatt aaagaaaaat  56580
acaacatcaa aatgactaat tcattcaata ggcttcatag cagactggat acagcagcaa  56640
gagagacaat cagggaacat gaaggcagaa tgaaaagcat ccaaattgaa acacaaagga  56700
agagagagag aaagagtgaa agcactgaag agccatgagg caatttaaaa atatagtcat  56760
aacacatttg taatcggagg tacaggacaa taggagagaa aataagcgag aagaattctt  56820
tgcagtgata atggccatgg attttgtaaa aatggtgaaa tgtattatcc tacctaccca  56880
atacgctcag tgaatcccag tcaggataaa tacatagaaa ctcgcgcttt tgcttatttt  56940
tgtccaactg ctgaaaatca aagataaaat cttaaaagta gctgaatggg agagaacatt  57000
acaatacagt gaaacaaaga ataatgatgt cttattgcaa ggagacaatg acaaaacatc  57060
tttgttcatt ttcaaattta ttttactttt gaaattgaca gataaaattg tatatgttta  57120
tcctacacag catactgttt tgttttgcag tatatgtcta catacgtaga taacactgtg  57180
gaatagttaa atctagctaa taaagaaatg cattatctca catagttatc atttttgtga  57240
tgagaacagt taatatccac tccgttaacc atttttcaag aaaacaatat atcaccatta  57300
actgtagtca ccattttgta caatagatct cttgaactta ttcctcatat ctaactgtaa  57360
atatgtatcc tttgaccaac atatccctaa ccctcccttt cttctagcca ctctagcctc  57420
tgataatcac cattctactc tctacttcta tgtgatcttt ttaaaattcc acatgagtga  57480
aatcatacag tatttgtctt tctgtgtctg cctaatccca tttaacgcaa tctcctccag  57540
attcatccat gttgctgcaa atcacaggac ttccttcctt ttatggctga atagtattca  57600
gctgtgtata taaacacatt ttatttatcc atttatccat tgatggacac ttaggttgat  57660
tccatatctt ggctattgtg aataacactg cagtaaacat gggagtgcag ctgtctcctt  57720
gacatcttga ttatattttt aaacatacgc ttagtagtgg atttactaga tgatatgaca  57780
```

-continued

```
gttcaatttt ttaatttttg gagaaacctt catactattt tcattatggc tataataatt  57840
tacattctca ccaaaaaaat gtaatggttt tcttttctac acatccctgc caacatttgt  57900
tggtttttg tttgtttgtt tctgccgggg tgcatagtct tttgataat agccattcta  57960
actggagtga gatattattt cattgtaatt ttgatttgca tttccctgat ggttaatgat  58020
gtcaagcact ttttcatatg cttgttgacc atttgtatat cttcttttga gaaatatcta  58080
tgtatgtatg ttgcccgttt ttaaacctga ttattgggat ttttgctatt caattgtttg  58140
aggtttttt tttttttttt tttttttttt ttagatggag tcttgctctg tcacccaggc  58200
tggagtgcag tggtgcaatc tcaacttact gcaacctccg cctcccgggt tcaagcaatt  58260
ctgctgcctc agcctcacaa gtagctggga ttataggtgt gtgccaccat acccggatga  58320
tttttgtatt ttttagtaga gatggggttt caccatgttg gccaggctgt tctcgaactc  58380
ctggcctcaa gtgatctgcc caccttggcc tcccaaagtg ctgggattac aagcatgagc  58440
caccacacca gcctctttga ggttcttata agttctggat attaacctct tgtcagatat  58500
ataatttgca gatattttct cctgttctgt aggttgtctc ttcagtttgt ggattctttc  58560
ctttgctgtg cagaagcttg ttagtttgat ataatcccat ttatctattt ttgcttttgt  58620
tgcttgtgct tttgaggctt atccaaaaaa tcagtgccca aaccaatgtc atagagcttt  58680
tcccctatga tttcttctag tagttttata tttccaggtc ttacgtttaa gtatttcatc  58740
catattaagt caatttttgt atttggtgaa tgataagggt ctaatttcat ttatttgcac  58800
aaggatatcc agttcttccg acaaccttta ttgaagagac tgcccattcc tcattgtata  58860
ttttggtacc tttgttgaat atcagttggc tctaaatgag tgggttaatt tgtgtgttat  58920
tcattctgtt ccattggtct atgtgtctgg tttaaggaaa aataggattg tctgtttata  58980
attctatatc caacaaaatt tctttacaaa atgaaagtga aataaagtca tcatcagaca  59040
aagactgagg ggatttgttt catgcagatc tacactatga gaaatgctaa ggaaagtttt  59100
tcaggctgaa agaaactgag aggtgatgga aacctggata tgcagaaggt atgaagggag  59160
ccagaaagta catgatgtgt gcatgtgtgt gtgtgtgtgt ttctgtgtgt gtaataaaac  59220
gtgccactag taggcattta caattattta atatgcatta tacgagtatg aagacatgtt  59280
atgtgcttag tctaattatc ttcttaaaag cacagtatga aaaacagctg aatcttccct  59340
tcattacacc caactgaatt taaagaatga acaagaaact gccagaaaga acactgagta  59400
cccagatatg agtacagaaa ccccacatgc ctttctttct gattgtctat tatacaaagc  59460
ctccatagga ttactgggac acttcctcca gactagtgag taggatctag agataatcca  59520
ccactgccct gcatccactg tacaagatca tccaggtgaa tagagtgctg ggacccagtt  59580
tatcatttct taatccatta cctcaatgaa catggccact ttgcttactt cacttctgct  59640
ttggatgttg ccacttgagt ttccttttca tcaagtagcc aggtgctagt cattgcccag  59700
tgaatctcca ggtctctagg cttctcctag agatagctga aatgggttcc tagtcactaa  59760
tgcctttaat cagattttct catatggcaa cccacttttt gccatatgct aaaatatatc  59820
cctccatgaa tcttaatgtt gcatctagcc tgcctctcct tcaagacttt gcaaaatgtc  59880
atattctctg caatgacttc ctgtttcttt atctccatag ctttcattac cttatagcat  59940
gtactacaat gtgcttgtta tacttattgt ctctctccct atactagaat atgagctctc  60000
gaagggctga gatttttgcc tgtatgcttc aatgatgtat ttccagaacc tacaggactg  60060
cttgttatat agtaagtgct cagtaaattt tgcttaatga gaaggtatat acaatgtaca  60120
cacaattatg tttatattag tttaatatat ttgatataat atgctttaca tatattacat  60180
```

```
gcaaatattt atataattaa tattaaacac acacatatat ataatgcagg tagtcctcat  60240
tttgcgcaat agtgtgttga ctgcaactca tgcgtgtttt gctttgcaga agatctcagc  60300
taccacagaa ttgtgcaaag taagttacac ttttcctgtg tgtgtaaatg tcagttaaat  60360
attgttttgt ttaaagcaag gacttcatag acatagatag atagatgata gatagataca  60420
tagatggata cacagataga tacatagata tcttcatatg tatatataca tataattata  60480
taaaagctca ctggctattt aaagtaaaag gaatagctac ctattgtggg gttttaaagc  60540
aaatatagat gtaaaataaa tgacaatgag aacacaacag ttgtaagaag tttaactgga  60600
attatacatt gtaaagctct tattaatgaa gtagatagta tttttgaggt agacagcact  60660
aaattaaata tgtatattat ataatgtgta accattgaaa aaacaaataa gatataaacc  60720
aaaagccaat gcagaagata aaatggaata ctaaaatact taattagcca taaatgtgaa  60780
acaaatgata acacacagat aaaagaagta ccaatacagt caacttatac tctaccctat  60840
cagtaattac gttaaatgtt ccatgaaaaa tggaagacat ttctaaaata gatttaaaaa  60900
ttataacctc agtgcgatga ttaaatttat gtgtgaattt ggcccatgca gtgcccagat  60960
atttggttaa acattatttt gtgtgtttct gaaaggatat ttcagatgcc taatgtcctt  61020
ttaactgaga catcaggtgt tttcctgtct ttggattgga actgacatat tgactttttt  61080
atggttatga gcctgccagc ctttggactt aaactacacc ctcagccttc caagttctta  61140
gctcttgggc acatactgga actaaaccag tggctgtcct aagattccag cttgctgagt  61200
ctcacggtgt agattttggg acttgccagc ctccataatc acatgagcca attccttata  61260
atgtctttct ctccctttct ttcatatata tatatataga gagagagaga gagtttggca  61320
ggttgatagt taaaaggatg caaataaaca gaggacataa ttacaaagct taagaaagct  61380
ggggtggctc tgctagtatt agacaaagta gacttcaaaa gaaggagtat gagcagaact  61440
aagggagata ttttgtgaga atgaagaacc aattcactaa aaagacatag tcacacatgt  61500
aatgtgtatg acctaataaa agagataaca ctaagttaaa ttgccaaact aaggagggaa  61560
aatagataag tctacaactg tgtttggaaa tgttaacata cttctttgag tgattgatag  61620
aaggaccaga ttttaaaaat cagtaaacat actgaagatg tgaacagtat gttcaaccaa  61680
ctagacctag gcgacattta tagatatatc tcactacagc agaatgcatt ttcttttcaa  61740
gtgctcacag aatattttaa acagactcaa tgctgggcat taaaccaggt tctaatataa  61800
aaattattca agccgaatcg ggcatactct tatcataatg gtattatatt cataattaat  61860
attattaaaa tttgtataaa atatcctaat gtttggaaat taaaccaaaa aataaaaaca  61920
gcccatgagt caaagaagaa atcacagtaa aaattatatt ttgaaataac tggccgggcg  61980
cggtggctca catctgtaat ccagcacttt gggaggccga cgcagatgga tcacgaggtc  62040
aagagatcga gaccatcctg gccaacatgg tgaaaccctg tctctactaa aaatacaaaa  62100
attagctggg catggtggcg ggtgcctgta gtcccagcta ctcaggaggc tgaggcaaga  62160
gaatcacttg aaccctggag gtggaggtta cagtgagcca agattgcgcc actgcactcc  62220
agcctggcaa cagagtgaga ctctgtctca aaaataaata aataaataaa taaataaatt  62280
attaaaaaat aacaaaccat aatgtgtaag atgctgctat aatagggcta agagataact  62340
ttatagcttt aaatatctgt actacaaaag agaatatatt taaaatcaat gacataagct  62400
tatacattaa gaatgcaaaa aacaggatta aaataaaaag aaactagaaa aatgtacaga  62460
atagcgccag gcgcaaggta gctcatgcct gtaatccagc actttgggag gctgaggcag  62520
```

-continued

```
gcggatcacg aggtcaggag atcgagacca tcctggctaa cacggtgaaa ccccatctct  62580
aatataaata caaaaaaatt agccgggtat ggtggtggtt gtctgtagtc ctagctactc  62640
tggaggccga gggaagagaa tggtgtgaac ccgggaggca gagcttgcag tgagccaaga  62700
tcgtgccact gcactccggc ctgggtgaca gagcgagacc ccatctcaaa aaaaaaaaaa  62760
aaagtaacct gcacatggat gtttataaca ggtttgttcg taatggacaa atcttggcag  62820
caaccagggt gtccttcatc aggtgaatgg gtaaataaac ttcggtacat ccagacaatg  62880
gaatattatt gagcattgaa aagaaatgag ctattaagct ataaaaatat atggaagtta  62940
actaaaatgc atgttattaa gtgaaagaag ccagtctgaa aaggatacat actatatgtg  63000
tccaactagt ttacattcca gaaaagataa aactatggag acagcacaaa gatcagtggt  63060
tgccaggtat ctgcagggga ggggagggga tgaataggta gaacatggag gatttgggag  63120
ctaggaaact atcccgtgtt atactataat ggtggatgta ttacattaga catttgtcaa  63180
aacacagaat gtacaatacc aagaggaaac ttaatgtgaa ctccagactt tgggtgataa  63240
tgacatgtca attgatgttc atcagctgtg agaagcatac aattttgctg gaggacgttg  63300
acattggggc agatcgtgtg tgtgctgggg gaaccaaggg gtgtatggaa acttgctgta  63360
gttttggctt aattctgctg tgaaccaaaa actgctctac aaaataaggt ctatttgata  63420
agaagaaaaa catgagttac caggccacaa aattaggaat attaaatgtg tattgctaag  63480
tgaaagaagc caatctggaa ggctacacat tttatgattc ccactacata tgatattctg  63540
gaaaaggcac aactatggag aaggtaaaaa aaatcaaaat ttgccagggg tttggtagga  63600
gaaagcacag gtttttttagg gcagtaaaat tcttctatat aataatgcaa tggtggacac  63660
agaaatctgt tatcacacaa ttgtgataac ccatttatca cacaattgtg tgaaaaccca  63720
taaaatgtat acataaagag tgaatactaa tgtaaactag ggagttcaat taatgatatt  63780
ggctcgttga ctgtaacaaa tataccgctc taacgcaaga cattaaaaat aaggggcatt  63840
gccaggggta gggggacagg gatggtggga gaggagaggg gatacatgag aagtctctgt  63900
acttgcctct catttttttct gcaaacctac aactgcttta aaaaataatc cattaattaa  63960
aaagaaaaga cacaaacaaa actcacaata aatgacatac catttctcat ttactgaact  64020
gcctaaaata ctgaaatgcc taaaataaaa atggctgact gactgtatca attttgcaat  64080
gatgtggatc cattggaacc ctcatatttg ctaattgcag tgtaaaactg caatcaccat  64140
ttcacatcca gttgaataac aaaaatcaaa aaagactgac actacaaaat tttgcaaggt  64200
tgtcaagtac ctggaattcg tatgcattct taattcttaa cattattctt atgttagagt  64260
gtaaaatggt ctaacccaac tatggagaac tcttacagtt tcttataaac agccgtctat  64320
cctatgaccc agacattcaa ctcccaggca tttacccaag ataaatggaa gcatatattt  64380
acaaaaggct tgtaaaataa tttgtaatgc agccttttttc tcataatagc atcagatttt  64440
aaatgtctca catgccaaca ggtaacagat aaattatgga gttataaata caatggaata  64500
cttttcagca tagaaaatag caaacttcca atacttgcaa catatttaca ttaaaaaatg  64560
ttgaacaaag gaatattgac ctctatctgt gtgtctttct ctctccctcc ctccctccct  64620
cctatgctga ttccatttta tgaattttta gaacaggcaa aataatctag ggtgagagaa  64680
ataaggaagt gtatgttttt ggagatagaa taattgactg gaaaagggtg cacagtaatt  64740
ttctttgata ataaaactat tatttatatt gttttgagtg ttaattactc agtggcaaag  64800
ctcattaaat tgaatacttt agatctgtgc atgttgttgc atgttaatta tatctaacat  64860
attttaaaag gttttggcag ccctggtgta atggtaagag tgatgggctg ggcacagtgg  64920
```

-continued

```
ctgatgccta cggtcccagc actttgggag gccaaggttg ggggctcact taaccccagg  64980
agtttgaggc cagcctgagc aaaatagtga gaccccatcg ctacgaaaaa caaacgaaca  65040
aaaatcacct gcgtgtggta tggcctgtct gcagtctcgg ctactcagga ggctgatgca  65100
ggagaatggc ttgagcccag gagtttcaga ctgccgtgag ctatgatcat accactgcac  65160
tccagtctgg gtgagagagc aagaccctgc ctggtggtca gcggcaaaaa gaaaaaaaaa  65220
gaatgcaagc tctcacaacg aatagattgg gatttaaatc tgaattctga tatgtattgc  65280
tagatcttct gagcctcaaa ttcttgccat gtaaaatcaa gccaaatact tatggatttt  65340
gtgagaaatc aatgaataga gtctattata ctctgaggat ggtattttat caaataataa  65400
attgttgata actagtagtt acactatttt aatccttcca attctttgtt ttcaaacctc  65460
atacttatga tatctcctat gctttttaaa taatttttct acttagactg tctatctgga  65520
tcacatgaat ctttcacagc ctcaggtttg ttttctttct tttcactgct acaatcagca  65580
tcacagctcc cctcacccca tgttccaagc agaagtgagt atttgattat tttcatcctc  65640
tatgaccaat atgaggttta aacaatgcaa caacaacacc ttattgtact aaaaaaccat  65700
atgaatatcc ctatatgact aacaatagat tcgtgaaatg tccctatgtg actaacgata  65760
gattagatta atgtccctat gtgactaaca atagatgtaa ataggacttg catcagattt  65820
ttctctgtag tcttatctat agcacagtgc tgggcatata gtgaatgctt aataaaaggt  65880
atttcataaa taagtaattt tagagtttat gaaaatcata actgattttg ttactcactt  65940
atgaatattt acacaaagtc taacagctac agaagattgg aagacaggca gttctggtgc  66000
taatcttacc atttcatttt gtagctcctt agtgaccact caatgcgagc tggggatacc  66060
aaggtgagca aaacaggctc ccgtctgctc ctagttccgc aattttccta ctcccatcac  66120
aatacttcag ttctcccttc cctgttttta aaaatcattt tgtatactgc tgttatatac  66180
tgacgtaagc cattaaaagt cctttctaat tagggaacag aggccaacat ttcatggatg  66240
ttttgtatgt ttttcccttt tgttttctac tcaccttgaa ttttcaagct gtttcatata  66300
aaagtgagga aagggaattt tgacaacact tggttcaaag gtgttgagga ggaagaacat  66360
atgcacagaa agggaaagag ggcttcagga agcaggaagg tttcacagga gtgatttggg  66420
aagacccaac acttgtggtc taatgcctca ctagactcag ggcaatatta tgttttgctg  66480
tgattaaggc agtcagtttt caaaaacgac ccgtatgtcc ctgtttcctc aggtgaattt  66540
tgctcacaag taatttgtaa atagctaggg agagccccag gaacagcctg ggtctgagag  66600
cactgactat ctgaaataag cagatgtttc ttccagggag aataaactgg gtttaccctc  66660
tttacttgtt cctatagaat caatggatac ataatctctg atttttccct gccggttaaa  66720
gaatgtttcc aagcagtggc aatagtgctg gtgtagaagt tattcatctt ccatttctaa  66780
ctactcctac gcacctgttt tttcctttgt ataataccta atcttttctt tctggctttg  66840
gtgttgcctc ttaacataaa ccggacctct tttcatagaa cagattcggt gggagttgac  66900
actgtatgtc agtgctattc actgacctcc aacatcagtg agaatagcca gaccctagtg  66960
ggagccattc attgtgtggg atgaccaaca gcatggtgga cggcaggata aacctgtcat  67020
aattcccgaa aataaacggt tagtgggaga acttaatctc tgtgtagttt atacatttgc  67080
attagagtgg aaaaaaagta tgctttagaa atgccctagg ctaaaaaata aactgatttt  67140
tccaaagcca tccatagcca gtaacagcca tgtagcagag ttgataatag caggtcctga  67200
gggttaggca tttagagttt gtccttctac agtgtttcca aacccccatg aaactgagaa  67260
```

-continued

```
atcctgtgtg gatctgggcc attaacccaa gggagaaacg aaaaccatga aacacggtag  67320
tatccattct gcagaagctt tttgtgtgct gtggtagatg gccttctctg gggatacaca  67380
ggagtgatgt ccagtagtcc acccttatcc ttgggggata tattctgaga ccccccctgtg  67440
gaggcctgaa actggaaata gtactgaatc ctatatgtac tacgatgttt tcaactgata  67500
gccgagacag ctactaagtg aataacaggc gggtagcata tacagcatgg atacactaga  67560
caaagggata attcatgccc caggcaggac gaaacagaac aatttcataa tactactcag  67620
aatggcatgc aatctaaagc ttataaatta tttctggaaa tttccattta atttttcgga  67680
ctgcatttga ttgcaggtaa ctgaaaccac acaatgtgaa actgcaggca caggagtgct  67740
actgtattcg ctacctgctc attaaccact tagtagctgc ttcagatatc agatctacca  67800
tcggtttccc agtgtttgtg ttcaaggaac ccttgtttta cttagtaata gccccaaaat  67860
gtaagaatag tgatcctggc aatttaggta tgccaaacag aagctatgaa gtgcttcctt  67920
gaaggaaaaa ggtgaaagtt cttgacttaa taaggaaaga aaaaatcgca tgctgagatt  67980
gctaagatat atggcaaaaa caaaactatc tgtgaaattg tgaagaagga gaatgaaagg  68040
gatacatggt atatataagg tttggtgctg tctccaggtt cgggcatcga gagttttgga  68100
atgtatcccc tgcaggtaag gtgggggagg ctactgtatc atcaagcacc cttaaaaatc  68160
tgactgtttt gaaaagagtt tcctgggaat aacaacatcc cttaagtgtc cagaaaatca  68220
ctgaaacttt acccccaaat tcttctatta ttgtttaagg caataataac attgggagtg  68280
tgtacatacc ttctcttggg tccataaatt accaaatttg aggacccctg gctaagggta  68340
cctgggaagg agtggggtgt acccttcatc gtcctcatct gccccctggt ggcacgtttt  68400
gtcactctgg actcctgccg taggctgcca acagcctatt taaacgaaac atccttgata  68460
tttagtgctt tgtatatttc cagaaagctt ttcaattact gagattatca cttcctctca  68520
ccataaagtt gtatagcatt gcccaataat actattgtca tctgctttat ctgttaatac  68580
ttgatttgtc tcatatttaa actgattttt gtcacgagaa gtttccccag aaattttttt  68640
attctttgcc tgtttttcct atatatccaa atatatcaat ttttgatcta tttatatacc  68700
cattttgtta tcttcaggtg cgttatttgg ttttcatttt ttaaatttct ttcccattct  68760
gcagatgaaa aatactgaga aacctactct gttcctgcat ccgagccatt ccacaggcag  68820
ttttcccata ctaaaaatgc tgtcttccac tgatgtgtgg catgtctcag ttccgtgact  68880
tcttttcctc tctctctact cgctgctgtc cctttttctcc atgtgtctct aacatgcctg  68940
tgttcttcaa gacctagtgc aaccacattc cctcccacaa ctctattttc atgaggaata  69000
gccaagcagg actcccaaga catcatacag gagtgcctac agggtatctc tccttggcag  69060
tcccacagca ccgcaaatgc cctgtgtctg ccaatactca tcagcctctc ttcccgtgtg  69120
cctctcctgg gaccctaaga gagtaacagt ccctgcaact tcccactttc tccaggcagg  69180
gacttgtgtg ccttttccat gtctttgact cctttattca attataatac aggtatctgt  69240
ctgctataac tcctggaact ctcttatgta aatgcgcttt tttcattctc cgcctcacat  69300
cttagcccag accacaccat ctccccccgc cgccttggat accttccatg tttccagtgg  69360
tctgctccca ctccacactg cagtacagtg atttttctaa aacatggatg ggttcctgtc  69420
actcccctgt gaaaagtcat ccatgtggag tctgactggt ctgcatttgg ggactggaca  69480
gagtgagaag ggatcctgtg tcagccagga ctccggtaga cgcccctatg caatatccac  69540
ttgtggtggt cgggggcggg gaaggggcgg gattgagccc ccttcccccc tcctccttac  69600
tgcggaaagc tgcggagcga gcagcactca cttcctattc agcattcagc agggagggag  69660
```

-continued

```
cctctgaaca gccacgtagg cattctcttc tctctggagg aaaaggccca gcagctgtcc  69720
gaggaaaaga cccaccagct gtcagcaaag ggacatgtcg cagctaagta agaatctggg  69780
tgactcgagt cctccggcgg aggccccgaa gccgcctgtc tatagccgcc ctacggttct  69840
gatgcgggcc ccgcccgctt cctcccgggc tccgccagtc ccttgggatc cacctccaat  69900
tgacttgcag gcttcattgg ccgcttggca ggcacctcag cctgcctggg aggccccaca  69960
gggccagctg cccgccccgg tggttccgat gacccagcct cgctgcccct agggggcccg  70020
atagtcccgg gctcccccgc tggggggccc gatgggtaag cctccgactc ccggggtcct  70080
gatggtgcat cctccacctc cgggagcccc gatggcccag cctccgaccc cgggagtcct  70140
gatggtgcat ccttcagctc ccggagctcc catggcccat cctcctcctc cggggacccc  70200
aatgtcccac cctccccctc cggggacccc aatggcccat cctcctcctc cggggacccc  70260
gatggcccat cctcctcctc cggggacccc gatggtgcat cctcctcctc cggggacccc  70320
gatggctcat cctccccctc cggggacacc gatggctcat cctccccctc cggggacacc  70380
gatggctcat cctccacctc cggggacacc gatggctcat cctccccctc cgggtacacc  70440
gatggcccag cctccagctc cgggagtcct gatggcccag cctctgactc cgggagtcct  70500
gatggtccag cctgctgctc cgggagcacc gatggtccag ccgcctccag cagccatgat  70560
gacccagcct cagccttcag gagcaccgat ggccaagcct ccaggtccag gagtcctgat  70620
gattcatcct ccaggtgcga gagctccgat gacccagcct ccagcttcag gagcaccgat  70680
ggcacagccg gcggccccac ctgcacagcc gatggcccca cctgcacagc cgatggcttc  70740
ttgggccccg caggctcagc ctctgatcct gcaaatccag tctcaagtta taagggctcc  70800
tccgcaggtt ccccagggcc cgcaggcacc cccagcgcag ctagccacac ccccgggctg  70860
gcaggcgacc tcgccaggat ggcaggccac gcagcaaggc tggcaggcca ctcccctgac  70920
ttggcagacc acgcaggtca cctggcaggc accagccgtt acctggcagg tgccgccgcc  70980
catgcgccag gggcccccgc ccatccgccc tggcccacca cccatccgcc ctggcccacc  71040
accggtgcga caggccccac cgctgatccg ccaggcccca ccggtgatcc gccaggcccc  71100
acccgtgatc cgccaggccc cacccgtgat ccgccaggcc cccgctgtga tccgccaggc  71160
cccacctgtg atccgccagg ccccacctgt gatccgccag gctccacctg tgatccgcca  71220
ggccccgccg ctgatccgcc aggcgccgcc gcccatccga cctgccccac aggtcctggc  71280
cacccagcca ccgctctggc aggccctgcc acccccacct ccactgcggc aggccccgca  71340
ggctaggctg ccggccccgc aggtgcaggc ggcgccgcag gtgccatacg gccccacctg  71400
ctacgcaggt acccgcggcg ccgcccgctg gcccgcaggt gccccagcct gtgctgccgg  71460
ccccgctgtc tgccccactg tctgccccgc aggctgtgca ctgcccttcc atcatctggc  71520
aggcccccaa aggtcagccc ccggtgccac acgagattcc aacgtcaatg gaattccagg  71580
aggtgcagca gacacaggcg ctggcctggc aggcccagaa ggcccccact cacatctggc  71640
agcccctgcc tgcccaggag gcccagaggc aggctccccc cttggtccag ctggagcagc  71700
cctttcaggg agccccgccc tcccaaaaag ccgtgcaaat ccagctaccc ccccagcagg  71760
cccaggcatc gggtccgcaa gcggaggtgc ccacactgcc gctccagcct tcctggcagg  71820
caccgcctgc agtcttgcag gcccagcccg gacccccggt agcagcggca aattttcccc  71880
tgggctccgc taaatcattg atgactccat caggagaatg cagggcctct tctatagacc  71940
gcagggctcc tctaaagagc gcaggacctc ctcgaaggag cgcagggccc cttcaaaaga  72000
```

-continued

```
ccgcatgatc tttgctgcca ccttctgtgc tcccaaggca gtgtcagctg cgcgagcaca  72060
cctgccagct gcctggaaaa acctgcctgc cacaccggag acctttgctc cctcctcaag  72120
tgtcttccca gctacctccc agtttcagcc tgcctctctg aatgccttta aaggcccctc  72180
tgctgcctca gagaccccaa agtcactgcc atatgctctg caggatccct ttgcctgtgt  72240
agaggccctg cctgcagttc catgggtccc acagcccaat atgaatgcct caaaggcatc  72300
gcaggcagtg cccaccttcc tgatggctac agcagctgcc ccccaggcaa ctgccaccac  72360
tcaagaggcc tccaagacct ccgtcgagcc gccacgccgc tccggcaagg ccacccggaa  72420
gaagaagcat ctggaagccc aagaggacag ccgtggccac acgctagcct ttcatgactg  72480
gcagggccca aggccctggg agaatctaaa tctgagtgac tgggaggtcc aaagccctat  72540
ccaggtctcg ggtgactggg agcacccaaa cacccccgt ggcctgagtg gttgggaggg  72600
ccctagcacc tccaggatcc tgagtggctg ggaagggccc agcgcatcct gggccctgag  72660
tgcctgggag ggcccgagca cctccagggc cctgggtctc tctgaaagcc cagggagctc  72720
tctgcccgta gttgtgtctg aggtcgcaag tgtctctccg ggatccagtg ccacccagga  72780
taattccaag gtggaggcac agcccttgtc tcccttggat gagagggcaa atgcgttggt  72840
gcagttcctc ttagtcaagg accaagccaa ggtgcctgtc cagcgctcgg agatggtgaa  72900
agtcatcctc cgagagtata aagatgagtg cttagatatc atcaaccgtg ccaacaataa  72960
gctggagtgt gcctttggtt atcaattgaa agaaattgat accaaaaacc acgcctatat  73020
tatcatcaac aagctgggct accatacagg gaatttggtg gcatcctatt tagacaggcc  73080
caagtttggc cttctgatgg tggtcttgag cctcatcttt atgaaaggca actgtgtcag  73140
ggaggatctg atctttaatt ttctgttcaa gttagggttg gatgtccggg agacaaacgg  73200
tctctttgga aatactaaga agctcatcac cgaagtgttt gtcaggcaga agtacctaga  73260
gtacaggcga atcccttaca ctgagcccgc agagtatgag ttcctctggg gccctcgagc  73320
attcctggaa accagcaaga tgcttgtcct gaggtttttg gccaagctcc ataagaaaga  73380
tccacagagc tggccattcc attaccttga agcgctcgca gagtgtgagt gggaagacac  73440
agatgaggat gaacctgaca ccggtgacag tgcccacggc cccaccagca ggccccctcc  73500
ccgctaatag gtgtagcaga gatctcgctc ctgtgtttcc ctggccagag gccactgaca  73560
gggtgggggg acatttttgt tcctggtgtt tgtgttccag ttccacgagt gtaagtttgg  73620
attttcaact tggtttcgta tctgccaaag ctttgtacat tttttatgtg gtgttgattt  73680
caatcggcta ctgttctgtt ctgtattttg gcatctgtgt ttttaagtga gatctgtggt  73740
tctctgtttt gtgttataat tgttatgttt tggtatcagc tttgtgctgg ctttgtgaaa  73800
tgaattgaga agctatccat ctcatttctg gtatagttca tgtagcattg taatcggttg  73860
ttctttgaac gttcaaatga ctcatcagta aaaactgtct acagagaagt aaatatctat  73920
atctatatat ataaatatac tttcagcata acagaagtgt ttgtctttat tctaattttt  73980
acactagatg gtggaagcca agttttgccg tattctctga atagacatga atagcaagac  74040
tactctcagt tatagtaaaa accacggtga tggaattgtt ttccaaggag agtactccat  74100
tcatctttat aaggatgcag tgatttcagt gggtggttat acataagatt tctccaggag  74160
attaattaaa gcacacacgt tagtgcccag ctggtaacgt tgttattaga agcagaaatg  74220
tccttaaggg tatgtggaga agaagggcca tctgcctgca ggactacaaa taaccaggtg  74280
gtcccgcttc atggagaatt tggccaaaag ggtatttgtc aatcatgtgg cccgtggggg  74340
ggtgtccagc agttcaaatt tgggtttcat caacacactg ctaccgggat ggaaacgtgc  74400
```

tccctgcagg atatccaggc ttataacagg gaaaaggaaa aaacagtctt catttaatta 74460
gaaaccctgc agattgccag cagtagtggc tgggttaggg gagggcgtgg cagggtgcat 74520
tcctatcaac atagagttct aggggaaggt cctgggggga agggtcattc taacttgtag 74580
gggaaggcag ccggcaacgc ctgaagttgc tgaacaaccg cggtcagccc ttggctatga 74640
acctggtcta ggcaggaaag ggacaaggga atgaactggc ctgagtgttt tgaggaagga 74700
tattcaagca cacaccaggc tggtgtacac aaaaggacgt tcttgtggtc atactctctt 74760
cctgtggaca ggggaccatc agccctactt gccaccgcat actgtcttat cagaaggaag 74820
aaatccaatc ccatatcccg cttctagggt gaagccaaag tcccagatgc ggttagtggc 74880
gatggtggaa ttctcctgcc acctagcggc agattagagg tgccaccgca gctgccgcag 74940
caacagcccc tcccacagtg cttaacttca caaccatgta tatacttgga ttgcagctac 75000
tccttgcttc accacttttg ctcataattt tatctatatc tgtgcccaga gattccttct 75060
tttctcttat aggccaaggt agcatctgtt ttcaagtcca atccgctctt cactcaacaa 75120
tttctatcct tggtcctgca gcgctgccac ttaggaagct gactaggaga ggagcccaca 75180
agatgcagac tctactccta gcacccgcag aactgagctt tccaggacga tgatccccgc 75240
cccaggacct gccaggccgc aggagctctt tctcaagttg tctaagtggt caggtagtcc 75300
aaaaactggg aggcagtttc ctataaactc cttgggtcag agagtcctgc gcatttgtcc 75360
gcaagcaatg tttacttatt tttacaacaa cagcaaatgt ccattgaagg agacagcaat 75420
gccccagctg agaactgtcc ccaaaggagg tttagctggg ccagtaaagt ggcatattgg 75480
tctagtattt cttgtttgtg tttagtttat ttatgattgc ttataaagtt ttctccagac 75540
cattaactca tggcgtgcct gagcaagatg ctctttgtgg aacaaaattt gggactttgt 75600
tccaaatttg ggactttgtc ccatcatggg actttggtgc catacttaag gtgggggctg 75660
gctctgctcc atggtagaga ggcttacttc ccagctgcaa acctccctct cacacgtgac 75720
atatatctaa tggccttctt taagtaatgc caaggactta aagcctaaat ttgtttatat 75780
tgtaatgaga tataaattgc aacaatgaaa aatgtgttca ttaccaatga gtaaactagt 75840
tagatattca actgaaaagt ttaagaaagt gcagctaaca tgacagtgaa aagcagaaaa 75900
caaagaccag caatatagaa aaatacaggt taaaaaacag cgggaactgg ccgggggtgc 75960
ggtggctcac gcctgtaatc ccagcacttt gggaggccga ggagggtgga tcacaaggtc 76020
aagagatcaa gacaaccctg gctgacaagg tgaaacccca tctctactaa aaatacaaaa 76080
attagccggg tgtggtggcg agcgggcacc tgtagtccca gctactcggg aggctgaagc 76140
aggagaacgg catgaatcat ggaggtggag cttgcagtga gccgagatcg caccactgca 76200
ctctagcctg ggcaatagag tgagactctg tctcaaaaaa aacaaaaaca aaaacaaaaa 76260
caaacaaaca aacaaaacag tgggaacgaa ttcaaatccc acttatttga aagtgctaaa 76320
atgtagaaaa tgtagaaaat gtaacacaaa tctttttttac tataaaattg agcaaaaagc 76380
ccaaacctag taataggcaa aatgtatcac aggaaaaaaa tggcaaataa ctgttgaaac 76440
tgttacacct cactaataaa gatagaaata ttaaatctgt attccagttt tcatttatta 76500
aattgtcata gaataaacta aaaccccatg taatgtccaa tgtcaatgat attgttatga 76560
aactggaacc attatacaca accagtgaaa gtataagtta ttacaatttg cctggaaatc 76620
aatgcagcca actctgtctt caaaaggctt taacatggta atactatttt acctagaaat 76680
tcttcatttg ggaatatgtt gaatgagaac aatccacaga gaaggcaaag acttcttcat 76740

-continued

```
agagaaagct gttcatgaac atatgggaaa tttatcaggg tgtgagcagg ccccctccc  76800
caatataaac ctacagtgtc aagggagtac agtgagtttc tgctgaaaaa accacaggct  76860
tcctcagaaa acaacttgta gtttgtttca acacacagaa aatgaaagac tcagcatcca  76920
ccattatggg ctgtagagaa gtcattgcac tctgtgcctg aaaattttaa aactaggtgc  76980
tagcacactc tccaaagcca taaatgacct cagtaaaata tatgatttct agtgaagaaa  77040
aactatagtt ctcaaagtga tgaaattcaa tgtgctccta tgtcgagtgt tcaactataa  77100
gcaagttaat attttaggat atttgtctta agaagatgat ctgaattttg gaataatttt  77160
actcaaagac attactcctg agagcaacag agaaaaggac cggttgtttc tcaaagccac  77220
cagtgaatca accttgtcag caaacgagag ttaaggattg tggctgcaat tgacagagga  77280
ctttcaagat taaggggccg gggccctgtg gccgcagtaa tatccatttt actgggcatg  77340
tagcctatat tattgatttg ccctcagagt tataggcacc cccagaactc agcaattcac  77400
cccgatggtc atgatacttg aaaggataca tcattcttgc actcctgccc ctagctgccg  77460
gggctggaag cctgggtccc tttttctctc tgatttgatc ggttgtcagg tcttgcccgt  77520
tttgccaatt tgtatgtcag tgttttttct cctctccatc cctgtggaca cggcaccctg  77580
ccagaacttg gcagtttcct ttttcatggt ctctgccttc agtactgccc cttaatcaaa  77640
cctccacatt ggctgcacag gggcctctgt gccgccgcca cacagctgtg cacacctcat  77700
aatgcctctc cctgcctaaa gcatttcaag gccttcagtg ttccttagag taaggtgcag  77760
caaccctcag ctcaccttcc acacgtgagg gtccaggagc ggctggttag agtaggttta  77820
cctacagaga aatctacaga ccatgccagg ggtccctctg tgggacagct caaagaattc  77880
ctcggattct gaattgaaag cctaagcaga ccaccaggag ggtcctaaag ggaaaaaggc  77940
cttgatatac agggcccaag ctacattttc ctgtgtgcaa gcaaatttgt tctttcggat  78000
ctcccagagg gttccattgt gaattccacc aagggatata tacaacacta ctagcacagt  78060
aagtagtaca atcctctaat ctgtcgagat tctgaaagtt gtacctgcct ctttttaaga  78120
gatgacactt acgaggagcc ttcttcatta tcagcttcct cctactctta ttagtgacgc  78180
taaatagatc atcctggctg tgtcagcggc atgcgcttct ctgtgcaaat ggtctggttc  78240
tgcaagctgc ccattcacct cccaatgaga cttgctttct gtgctatccc ttgttctgag  78300
tgaattcagc ttgtgagctg ctgttaacag aagcaatcac cacagaacat tttctagacc  78360
caggagactt cctggagctt ctctccaatg gctcagaatc ttcccctgaa acagccagct  78420
ggatggggcc acaaagctgt ggaatcaaaa tattggcctt gtaacaagct tctgcgagaa  78480
agcctcaaaa acattctgtt ttgaaataat catagattca caggaaatag caaaaactgt  78540
gcagggtagt ctcatatacc cttaacctag tttcccccag tgtttatatc ctgtatagct  78600
gtagtacaac atcaaggacg tggacactgt accatctgca cgttcagctc aactcaatgc  78660
catcttatca cgtgtgtaga tagtgtaact agcactgcaa tcaagatgca gcactcttcc  78720
accaccacca agatttctcc cacgctactc ctttacagct gtgtccatct ctttccccca  78780
catccttaac ctctggcaat cactactctg atcttcatct ccataacttt gtaatttcaa  78840
gaatgtgctc taaaagcatt aatacctttg agactggcgt ctttcactga gtatcatgcc  78900
ctcgacatcc atccacactt ttgtatcagt cattcatttt ttgatgctaa taaaatattt  78960
actgttttgt gggattggct atttccattt tttagctact gcaaagttgc taggaacatt  79020
taagcgcagg tttttctaag gacacacatt ttcatttgtc tgtggcaaat gcccatggcc  79080
ataattgctg tatcatttga taggtctatg gttacttatt caaagagcct ttcaaactat  79140
```

-continued

```
tttccagagg gactgtaaca ttttacattt ccaccagcaa tgtatgagaa caaatttctt  79200
tctttttttt tcttttcttt tttttttttt tcttttttttg agatggagtc tcactctgtc  79260
gcccaggctg gagtgcagtg gcgccatctc agctcactgc aagctccacc tcccgggctc  79320
acgccattct cctgcctcag cctcccgagt agctgggacc acaggcgccc gccaccacgc  79380
ccagctaatt ttttgtattt ttagtagaga cggggtttca ccgtgttagc caggatggtc  79440
tcgatttcct gacctcgtga tccgcccgcc tcggcctccc aaagtgctgg gattacaggc  79500
gtgagccacc gcgtctggcc ccagaaatcc aatttctctg caacctcacc agcaattgat  79560
ataatctttt tgttgttgtt gttaattcgg ctgtcctaat aggtgtgtgg tgatatggca  79620
ttgtggtctt aatttacatt cctcttatgg ctggagttgt cgaacatctt tctgtcggct  79680
tctcatttct atatcctcat tgataaaatg gcttagtttt tctaagtgac tttttttttt  79740
ttttttttga tggagtcttg ctctgtcgcc caggatggag tgcggtggtg ccatcttggt  79800
tcactgcaag ctccacctcg tgggttcaag cgattctcat gcctcagcca ccagagtagc  79860
tgggaccacg ggcgcacacc actatgcctg gctaattttt tgtgttttta gtagagatgg  79920
ggtttcacca tgttggccag actggtctcg aattcctggc ctcaagtgat ctgcccgcct  79980
cagcctccca aagtgctgag attacaggca tgagccacgg tgcccaggct ctaagtgagt  80040
ttttttaaaa atgtattggg ctttgagaat gatttctata ttccggatat gagtccttta  80100
ttatatatgc attttgcaag tcttttcccc agtgttgagt gtggctttcg ttatcataac  80160
cgggcctttc acacagcaaa agttttaaat ttcgatgaag tctgattgat tttgtttttc  80220
ttttatgggt catgatcatg gtgtcatata tatgtaagta ctcttcatca gaccccaggt  80280
gccgaagatt ttctgttatg ttttcttcta aaaatgtaat cgttttatgt tctgtattta  80340
aatctatgat cgattttgag ctaattttga ataaggcgta aagtttaggc tgagattctt  80400
tctttgctgt gtgtgtgtgt ttgtgtttgt gttttgtttt gttttgtttt tgcctttgga  80460
tgtccagtgg tttcattaac attttaacat ttgttaaaaa tactatatac tatcctttca  80520
acattgaata ttttcttttg cacatttgta aaaattcagt tagccctatt tacgtgtgct  80580
atttctgagt tctgaattct atattctgtc ccatttgctt gataagatag gtatttaaaa  80640
gatagatata gatatgtgta ttatacagag atatatccct ccaccaatgc catactgtcg  80700
tgattattgc agtcatataa taagtcttaa aattgagtat agggattctt cccatattct  80760
tttttcaaaa ttatgtttag ctattctaga tcttttgatt tttcacataa attttaaaat  80820
aagcttgcat atatttacaa aatgtcttgg tggaattttg ataggaattg agttaaactt  80880
gtatattaag tgggggagaa ctgacattta ctgcattgaa tcttccaatc cataaccaca  80940
gtatatcgct ccatttattt ggatcttttt tggtttcttt catcagcact tgtatttttc  81000
agcatacatg tcctatacat gcttattaag tttataagta tttaaaaata aataaggttt  81060
atttttgagt gattgtatat tatattatat taggtgagct tatcttatta tattatatta  81120
tgtttttttga aatggagttc cagttttgtc acccaggctg gagtgcagtg gcacgatctc  81180
tgctcactgc aacctctgcc tcccaggttc aagcaattct tctacctcag cctcctgagt  81240
agctgggatt acagacgcct gccaccacgc ccggctaatt tttttgtatt tttagtagag  81300
atggggtttc accacattgg gcaggctggt ttcgaactcc tgacttcagg tgatccgcct  81360
gcctgggcct cccaaagtgc tgggattaca ggtgtgagcc accatgcctg gccctatatt  81420
atattataag ttttagtttc cacctgttca actcaaaact caaaatggtt gagttttgta  81480
```

-continued

```
tgttgatctt gtagcttgca ccttgctgaa ctcacatatt agttctagga gttttcatat  81540
atcctttggg attttctttg cagaccattg tgtcatctgc aaatagagac agttttattt  81600
cttcctttca tatttgtatc cttctttttt ttttgagacg aagtcttggt ctgtcaccca  81660
ggctggagtg cagtgatgcg atcttggctc actgcaagct ccgcctccca ggttcacccc  81720
attctcctgc ctcagcctcc caagtagctg ggactacggg cacctgccac cacgcccggt  81780
tcattttttt ttgtattttt agtggagatg gggtttcacc atgttagtcg ggatgatctc  81840
gatctcctga cctcgtgatc cacctgcctc agcctcccaa agcgctggga ttacaggcgt  81900
gagccaccgc gcccggcctc ccttgggatt ttctttgcag accattgtgt cgtctacaaa  81960
tagagacagt tttatttctt cctttcctat ttgtataatt ttaaagtaaa aagtccctta  82020
ttatgctgga tttccagtga tatgttgaat aggagtggtg agagcagata tgaattcctt  82080
gctcctgatg ttaggaagaa aacattcagt tttttgctat gaagtataat gttagctgta  82140
ggttttgtgt aggtacccta tatcaagttg aggaagttcc cttctatttc tatttttctt  82200
agagtttttt ttctttttgt catgaatggg tatgaagttt tgtcaaatgt attttctgca  82260
ttgattgcta tgatgatgtg atatttttct ttttagctag tcaatatggt ggattatttt  82320
catttatctt ttagcattga atcagccttc tatttctaga ataaacacaa tttgatcatt  82380
ttatatgtat gtaattgctg aattctcttt actaatattt tgttaggatt tttacatcca  82440
tattcatgaa gaatgtttgt tcatagtttg gctttttttgg attgtttttg tctgattttg  82500
gtatctgggc actatttatt ttataaaata aattgttccc ttcttttctg ttttctgaaa  82560
gagattgtgt aaagttggtg ctaattcctt tttaaacatt tggtagaatt cgccagtgaa  82620
accatctggg catggagatt tctgttcttc ggaaagcatg tgtataattt ctcaatgaag  82680
cacatttgca tcatttcagc atttgtttct gatgactttc gtttctcatt ccagttgaga  82740
tttttgtggt tcttggtgtg aagagtgact ttttattgta tcctaaatat tttgggtgtt  82800
gtgttatgag actttggatc taattaaatt cttctctttc aatagacttt cctttttaag  82860
agactgtatg agtgggaaat aaggacccca cctcagtacc gcctggtagg aacataagtc  82920
cgggaccccc aggtggtctc catggacacc cagtgagcgg gaggccgtgc tctccagcac  82980
agagctgggg taaaagttca gcttctgcac tctgcctttg ctgacaccac cctgttcaga  83040
ggggaagagg ccccttttca ttgctcgcct gtgaactcca aggacagaaa atggggaggg  83100
aggcctcatt agcatgggaa ggcttctcac ttgccacccc ttaacagcac cccagcaggg  83160
aaggtgcagg aaggtaaaag ttcaagctcc ccaggttgtc tccgtcggca ccacactgtg  83220
gcagcttgtt actgcctggt gaacgtcgaa gtcccagatt ctcaccctga caccacacca  83280
gcaggggagg gctacctcag tatcaccagg ccaggctgga agtctaggct ctcccctctg  83340
tcctgctgag tgggtcgagg gtggggccac aagttttcct acgggcgttt gtctccagta  83400
gggaaactag cctccgaaag ttttctgtct tgctagcttt ctcctttcat ggtcttttgg  83460
ctagtgattg caggttattc aggggccttt tgtgtgtggt ctcataggag gggatattca  83520
tggattggga agaagacaat tttaagtgtg cccggaacag agtgagtatc agagttgaat  83580
aggctaggat aaggcagcag gtgtaaaaat ccagaaagcc ggctgggtgc ggtgctcacg  83640
cctgtaatcc cagcactttg ggaggccgag gcgcgtggat cacaaagtca ggagatcaga  83700
ccatcctggc caacacagtg aaaccccgtc tctactaaaa atgcaaaaaa agtagccggg  83760
cgtggtggca ggcgcctgta gtcccagcta cccgggaggc tgaggcagga gaatggcgtg  83820
aacccgggag gcggagcttg cagtgagccg agatcacgcc actgcactcc agcctgggca  83880
```

-continued

```
acagagcgag actccgtctc aaaaaaaaaa aaaaaaaatc cagaaagcca aaatctgcct  83940
acaaaatgcc cattatcagt ccaatctacc tgacgccttt tctactgagc ttaatctgcc  84000
tccccatgca tttccgtaaa gtaggcaatg acagctatta tcattactta ggcttttctc  84060
ttttggatag ctgctttatc caacctccta ttctccaatt cacaattgaa ttggaaacag  84120
cgtgatcatc ggtagagagt gtattgggga aaaatattcc atgcagatat tggataaaca  84180
atttttaaat ttattttgct ggtactcaga cacccatgct tgtcaatttt atgttaggag  84240
accaaacttt tttatcattt aggcagaatc caactccatc cttccccata ccccattaat  84300
gagtaatgca ttggccaggc ttggtggctc acgcctgtaa tcccagcact ttgggaggcc  84360
gaggcaggtg gaccacttga ggtcaggagt tcgagaccag cctggtcaac atggcgaaac  84420
cttgtctcta ctaaaagtac aaaaattagc ccagtgtggt gacaagcgcc tgtacaccca  84480
gctacttgag aggctgaggc aggagaatca ctggaaccca gtaaacggag gttgcagtga  84540
gctgagatgg cgccacacgc cgctgtactc ccgtctgggc aatagagcaa gactctgtct  84600
caaaaaaaaa aaaaaaaaaa gcattaagtg tgtgtagcat tctctattgc ttcccatttc  84660
cactctttcc acttgatcca gtctccttct ttgctgatag agacttgatt tgtaaggatg  84720
tttactctcc aatttattca ttaatcataa atcccttcct tcatccaggg tcagcttaat  84780
cataataaat tcaagtatca ccctccattc atgcacatgt ggcaaaatct agtcggaagg  84840
gtttgtggat attttcctcc ataataaaag cattgtttta aaaagagacg gccaggcatg  84900
gtggctcacg cctgtaatcc cagcactttg ggaggccgag atgggcagat cacctgaagt  84960
caagtcagga gttcgagacc agtctggcca acatggtgaa atctcgtctc tactaaaaat  85020
acaaaaaatt tgccaagcgt ggtagcagat gcctataacc tcagctactg gggaggctga  85080
ggcaggaaaa tcgcttgaac ctgaaaggca gaggttgcag cgagccgaga ttgtgccagc  85140
cactacactc cagcctgggt gacagagcga gactccacta aaaaaaaaaa gagagagaga  85200
tttgaaaata gtttgtcttc agcactgatg ctctaatatc tgcatgggat tccgggaact  85260
gccctagtaa gcacacagtc gtgaaagaaa catcaccaaa aatctcagga acaaaggcag  85320
aaaccaccca tggcttcagt gatccggttg agccactgta tcaagaaatc ctggaatggc  85380
ctacctgtag ggcatttaaa aagtaatttt agttgggttg tattttactt atagctacaa  85440
gcatctgaat tgatcccaag cattccgcag tctgatttgg gcaacaagtt acgtgtttct  85500
cctccaagta gccatagatt cctggtttca tgcaccagca ccgcttcttt gacttttggt  85560
agagtcccca ggtcaggtgg gtgctgggga ggctccaagt aacctcaaga caaacatgag  85620
atggaatacc tcatctccct agtcaatttt actcaaatag aaattttttg aatgcaaaat  85680
accgtgcaga aacatattac aataaccaac gaccataaat tacaatgaaa cttgattcac  85740
ttctgaatca ctatttactt tcagcccttg ttttcttaca tggtatttgg gactcagagg  85800
cttcatggtt gcagcaggtg taagcatgca cacaggattt tttttaaacc catcagggaa  85860
ctaaggttac agggcaacct gccaccctga aatccagaga gaaggttact ccagggagat  85920
acagcatgta agacacagag aaaaagccac tgggcaccct aggctggagg aagccctaag  85980
agctcgcttt agacaggaat accgaaatct catcccatct tgggggaggg aagtgcaccc  86040
agtccagcgt cactccagcc ttcttgtgtc ataaacttga tgacctagat gaaatgaggc  86100
aattctttga aagacaccaa ctgccaaaac tcactcaagg agaaatagct acctaaaaca  86160
ccagcccccg atgctttcac tggtgaattc taccaaatat atatatatat ttttttgaga  86220
```

-continued

```
tggagtctct ctgtgtcgcc caggctggag tgcagtggcg cgatctcggc tcactgcaag  86280
ctccgcctcc cgggttcatg ccattcttct gcctcagcct cccgagtagc tgggattaca  86340
ggcgcctgcc accacgcccg gctaattttt tgtatttatt tttattagag acggggtttc  86400
accgtgttag ccaggatggt ctcgatctcc tgacctcgtg atccacccac ctcggcctcc  86460
caaagtgctg ggattacagg cgtgagccac cacaacccag cctctaccaa atttttaaaa  86520
agaaatagta caaattaaca cttttttttc tggaaagttt gaggttggaa tactgcttaa  86580
ctcattttat gaagctagca tattcatatg aacactacct gattcattta tgaagctagc  86640
attaaccaaa accagataaa gacattacca aaaaaggaga ctatggagaa atacctctga  86700
ttaattgaga cacaaatctc cctaacatat tttaacaaat catatccagc aatatataag  86760
aggaacaata taatgtgacc aaatggggtt cattccagga aggcaaggct gattcaacat  86820
ttataaatac tgatgtatat aatttatcct attaacagta taaataagaa aaaatatgat  86880
catgtcaata gatgtagaag atatattcaa caaaattcaa cacccattca tgatatacag  86940
tcttgaaaac tagaaatagc agggatcttc cttaacctaa taaagggttt atatgaaaag  87000
tttgcagcta attttattct aaatgactag agaaagaatg ctttccctct aaaatcaaga  87060
ccgcatgaca ttggtgaaag agtagccaca tagatcaatg gagtagaata gaaaactcat  87120
taatgaatga acacaaatat tgtcaatgga tttgtggcaa aggtgcaaag gcaattcagt  87180
ggtgaaagaa tacttttttta acaaatgatg gtggaaaaat tggatgtccg tattcaaaaa  87240
gtgaactttg acacagatct cacatcttac acaaaaagtg actcaaagtg gattatagaa  87300
ctaaatataa aatgcaaaag tacaaaactc ttagaggaaa atatgggata aattttcatg  87360
gctttgagtt tgttgacaaa tttttagata tgataaaaaa tacaacccac aaaaaaattg  87420
ataaattgga ctttattaaa attatgtttc cctctgtgaa attaactctt gagggaatga  87480
agaaacaagc ttcaaccttg gaggatatat ttgcacgtca catatctgat aaaggacctg  87540
tatccaaaat acacaaagaa ctcttacaat tcagcaaata aaaacaaata accaaactca  87600
taaataagca aaagaatacc ttatataaca tgttcaagac acctgtagat agtgtacagc  87660
aagtccttgt tttagacttt tttcttcatt atattattca ctatttatac aattcccaaa  87720
taggagtgtc taggagcttt tctcatgaaa aagagggaag tgatctaaaa ttacgaaact  87780
gaagcctgag actaagatta cacattttac acacatgcat atcactattt ttcattctaa  87840
aatgagtgtt tttctatatc agagaaatta tattcaattc cattttgtag gactctatag  87900
cagagcctct ccgatatgaa cctgtttaat ttgtataatg ttgataatta ttttccattc  87960
acaataacaa caacaaaggc tttttacact atatagtttt cagcaacaaa ctgcagtcac  88020
ttcagtgtct agctccgagg tctatgaagt agagtttatc gggccatcta gtggccacta  88080
gatcaaccaa cagttttttg tattttctgt tactgtgaac aactacaggc ttcactaaat  88140
ttacactaag tctaaaaaag ctaaaactag acctccctgc agactgtcta caactgtcct  88200
gaacataaca taattcatga cccatatgtt ttgctaatgt aacaattgta ttgtatcttt  88260
gtggtattgc accttacacg gggcaccagt tgaggtatgg cgtcttacca gagggcatta  88320
gctgcggggg tttgcccgca gaccctgacc caaaagacgg atgaataaaa cgtacattga  88380
catacagata ctttgtttcg ccagtccagc tgagcgtccg actgcctgca caccaggaga  88440
ggtttgtcac tgcggctggt cctgagcagc ttgcacttca ggcatttatt tagtatacaa  88500
tgaacaacag aagctttgag taaacacact tgaggataat taacatggtt aagaaagtag  88560
ttttacaaat gattaaaact taggtactac ggtttaaagt aaataccatt agggggcaat  88620
```

-continued

```
ttccctagtt gacctccccg cccctacccc cacccacaac cacccagagg gccatttggc  88680
ttaaagatta gttaatggag gtagggtaaa cagaagtaac tggggaatcc tctattgttc  88740
ctagtattta ccctatgacc tagtgctcta aggtaagaac cggctgcctt tagcctgttc  88800
aattattaca agctatttaa gcttttggcc tttcaaaaga tttgtgatta tttcctataa  88860
ctttccctaa tattcccttt aatatttttg ccattatcct aagtgactca caacagatct  88920
taatataatt attacataaa tgtataatcc atatttttta gacctgatta attgaatgat  88980
tcagtgggat atatcaattt ttcctctttc cattgtaata aatcttgttt aagtcactaa  89040
catgtcttgc ctggaagatt attatctcct aactggtccc ttgtcatcct ctctggattc  89100
ttaaaattca ttcaacaaag agtaactcaa tcttttaaag acctgtgtat catagtaaga  89160
tcatggattt tctctgctta aaattttcca atgaggtttc atcacaatta taatgaaatg  89220
tgaactcctt ttcactgttt acacagtcct gtgggatctg gtctccacac tcctcttaaa  89280
cttcatttcc taccactctc ctctccattc actagaaacc agctatatta ttttttgtcg  89340
tcgttgtgtg ttgtttctta aacacattct cccagacttt gggctttggg tgtgttgttt  89400
gtctaactgg aataattggt gcccacatac ctacatgggt tgcttcttct ctaaaaccat  89460
gggtggttgc agaccaaata ccatgtcctc aaaaatgtat tccttcttag ttactcagaa  89520
attaaacacc agctgcaatc aaagaaactc gcaaatctca gtggcttagt tatatattac  89580
attatattaa tcatgtaaac ttcagtatgg gtaaagggga gtgaagactg agaagttctg  89640
ttccatgaac cattcaagga ctcactcggg caccgatcct tttatgactt ggctctcttc  89700
ctggttctca gaatccatgc cgttcacctg tcagagaaag taaaagagtg tggaggatta  89760
tgtcagagat ttttataaac tgtatttggg agtggagtac tttatttcta cctatattag  89820
ttggaattca gtcacatgac ctcaactaac tgcagctagg gatggtatat gtggggcagc  89880
tgtgtgccca agagaaaaca ggatttgatg cgatcacagc gttctcctct gccatggtag  89940
cccttgtgtt tatcaaatat ccactttaca cttcctttta aatgttgaac acactctccc  90000
tagaggagac aatccaaaat tcacctacgt attgaatcca gctcaaagtt caggatttca  90060
gaattatact cagccttctc caccaagttc tgccgtggtt tgtcaaggtc agggacccag  90120
gaactaaaaa gataagttat gtttcaaaca gccaataggg ggaagcaaaa aataaccata  90180
atgagaattc tcgtttggaa acgaaaagga ggcacattac cgttatggac tcacaggaat  90240
tacggaatct tgctggtact tgatgatgtg tctgtgaagc aagtgggaat tagtattcca  90300
gaagagcaaa tacatgggat agaattttag ttgccacctt ttcaggtaag atgggataga  90360
aatggagtcc ctgaaataag aagtatgttt ctgtacattt caatactgaa ccaagaaagg  90420
acatgtggct tgatgatacg ttgaaatatt tatctgggtg tttcacattt ttcctctccc  90480
tcttcccatg tgtactctga gggtcagacc acttgcagac atgagtcacc tactttgaag  90540
gagcaaccag aactctgact ccaaagagta aaacttgata acggaaaaga cagtgaaaag  90600
aaatattctg tttcacactt acagagttag ttttaaaatg gtcctaagag gtgaagagaa  90660
catgctgatg gaagaaagaa cggaatggat aaaatttgat ctcgagaggt gaggttaaag  90720
ctgaggttga tggtaggata caaatggatg ttcttttaca gcacaaatca tttttatagc  90780
aggatcctga ctcagtgctc aggtctgttt ctcctggaac tttctcttgg gagaagtcaa  90840
cccatcagcc attgagcatc ttatgcttat ctgtccttcc ttgtttgtat ccaatgattc  90900
tggacacttg tagataattc taggaccaag ggtgagttat ttgaatacag tgggagatga  90960
```

-continued

```
tagcagaata agcacctagt cacagtcagt ttagaatgac tcttatagaa agtagactct  91020
gattcagcat gaagaaaaat ctataaagca aatggaaaac aaaaaagggg cagggttgct  91080
attcttcttt cagataaaac agtctttaaa acagcaatga tcatgaaaca caaagaaggg  91140
cattacataa taataaagag ttcaattcaa tgagaagatt taattgtcct aaatatatat  91200
gcaaccaaca ctggaacatc cagattaaaa aaacattttg ttagagacct gagaagacaa  91260
ttagatatcc atacaataat aatgggagat gtcaacgccc cactgacagt attagataga  91320
ttatagaagc agaaaactca caaagttatt caggacctaa aactcgacac ttggccaaat  91380
agacctaaca taacaacaac agaatataca tttttctcag ctgcccatgg catatacact  91440
ctataatcac tcacacactc agccacaaag caattcgcaa caaattcaaa ataaatgaaa  91500
tcatcccaac cacatggtca gacacagtac ggtaaaaata gaaatcaata ccaagaagat  91560
ctctcaaaat cacacgatta catggaaatt aaaaaatcta ctactgaatt tgggtaaaca  91620
ataaaattat ggcaaaaatc aagacatttt ttgaaactaa tgaaaacaca gatacaacat  91680
accagaatat ctgggacaca gctaaacagt gtgaagagga aagtttacag cattaaatga  91740
ctacatgtaa aagttagaaa tacctcaaat taacaaacta aaatcacacc taaaggaact  91800
agaaaagcaa gagcgaactg atgacaaggg taacagaaga aaataaataa cccaaatcag  91860
agctgacctg aatgaaatgt agatgagaaa aaccatgtaa aacatatcaa agaaaccaaa  91920
agcatgttcg ttaaaataat aaataagatt ggtagactgc tagctagaca aagaaagtaa  91980
aaagatccga ataaacacaa taagaaatga caaagaggac attactacta atcccaaaga  92040
aatacaaaaa gtcctcagag gctattatga acacctttat gtacacaaac tagaaaacct  92100
agaggaaatg gttaaattcc tggaattgaa tctggaagaa attgaaaacc tgaacatacc  92160
aataataagt ttcaaaattg aatcagtaat ttaaaaaata ccaaccccaa aaagtcctgg  92220
accagagaga ttcacagctg aattgtatca gacatataaa gagattcagt agtatcaata  92280
ctactgaaac tattccaaaa aatagaggag gagggactcc tccctaactc attctgtgat  92340
gccagcatta ttctgatatc aaaacctggt agagacacaa tgaaaaaaga aaacttcagg  92400
ccaatatccc tgataaacat agatgtaaaa atcctcaaca aaatataagc aaaatgaatc  92460
cagcagcaca tcaaaaggat aatccaccac aatcaagtag gctttattct tggggtgcca  92520
agttggttca acagatgcaa attttaaaaa atgtgattaa tcacataacc aactagaaac  92580
aaaaaacaca tgattatttc aacagatgta gaaaagactc tcactaaaat tcaacatccc  92640
tttatgttaa aagccctcaa tcaactaagc atcgaaggaa catacctcaa aataataaga  92700
accatctgtg acaaacccac agccaacatc atactgaatg ggcaaaagct ggaagcattc  92760
cccttgagaa ctggaacaaa acaaggatgc ccactctcac catttctatt caacatagta  92820
ctggaagtcc cagctagagc aatgaggaaa gagaaagcaa taaaaggctc caaataagaa  92880
gaaaagaagt caaactatct ctcttcacag attgtatgat tctataccta aggaaacgcc  92940
atgttatctg tccaaagctt cctaggtctc ataaacaact taaacaaagt tttaggatac  93000
aaaatcaatg tacaaaaatc agtagtattt ttatatacca ataacatcca atctgagagc  93060
caaatcaaca acacaatccc cttcacatta gacatacaaa aaatataata tatatagaaa  93120
tccagctaac cagggaggtg aaagaccttt acaacacgaa ttaaaaaaca ctgctgaaag  93180
aaatcagaga caacacaaat ggaaaaacat ttcatgctca tggataggaa gaatcaatat  93240
tgttaaaatg gccatactac ccaaaacaat ttatagattc aatgcttttc ctatccaact  93300
accgaggaca tttttcacag aattagaaaa aaactattcc aaaattcata tggaacagaa  93360
```

-continued

```
aagagcccaa atagccaagg caatcccaag caaaaagtac aaagctagag gcatcactct  93420
acccaacttc aaactatact gcaaggctac agtaaccaaa acatcatggt actgacacaa  93480
aaacagatac aaagatcaac agaacaggtt agggaatcca gaaataaagc catatactta  93540
tttttacaaa tgtgagaaaa tatttacaaa atatgcatcc aacaaaggcc caatatccag  93600
agtctataag gaacttaagc aaatcaacat gttaaaaaca atctcattta aaaatgctga  93660
aagaacatga acagacattt ctcaaaataa gacatacacg tggccagcaa ggatatgaaa  93720
aaatgctcaa catcactaat catcaaagaa atacaaatta aaacatcaat gacatactat  93780
ctcataccag tcagaatggc tattattaaa aagtaaaaaa aacaaacaaa caaaaaaaag  93840
cacatgttga tgatgttgca gagaaaaagg atggctattg aggatataaa ttagttcagc  93900
cattgtggaa agcagtttga agatttctca aaaagcttaa aacagaacta ccattggatc  93960
cagcaatccc attactgagt atatacccaa aagaatataa attttttttac cataaaggca  94020
tatgcatgtg tatgttcatc ataacactat tcacaataca aagacatgga atcaacctag  94080
atgtccatca actgtggact ggataaagaa aatgtggtac atatacacca tggaatacta  94140
tgcagccata aaaaagaaca agataatgcc ctttgcagca acatggatgg agctggaagt  94200
cattatccta agcaaactaa cacagcagca gaaaacctca tgttctcaat tataagtggt  94260
agctaaacat ttagtacata tggacacaaa aaaaggaaca atagacatca ggacccactt  94320
aaaagtggag ggtgagagga gggtgagaat tgaaaaacta cctatcagtt actatgctca  94380
ttaattggat gtcaaagtaa tctgtacacc aaacccctgt tacacataat ttacccattc  94440
aacaaacctg cacatgtacc ccttgaacct aaaataaaag ttggaaagaa aaaaaaaagg  94500
accctctgat tcaggaaagg ggtgcataca tggtccatgc tatataggac atgccataac  94560
tgttggagtt ctctgatatg tagttgtctt tcctactagg ctataagctc tatgatggca  94620
aaagtagtgt ctcctttcct cattatttat tcctcagctc ttagtgcagt gcctgactta  94680
tagtaagttc tcaataaaat gtgttgaata aatgaataac tttccagtag ccatttattg  94740
ctcaactcaa tgagagtcag gcatcaaagc ctgtacattt tctgtgtttg taccaggtcg  94800
gagacaaatg tttatgaaac atagatgaag tccctagaac cttcttcaga aataatgaat  94860
tgtgttaagg tttttgtgcc ccagatcttc aagttgacca taaagattcc accgtgtcta  94920
acaattaacc caacttcacc atctaggata gaccatttgg tggttagagg gtggtgggta  94980
tcgattcttg gcaaccaaag cctaaagttt atgcctcaac tgagctttga gggagcaaat  95040
tacatgatat agacttatgt actatgcctt catcctttgt attggcagca atccttagat  95100
aagcgagatg gcttttaagt gaaaagtcac ctaaggacat gaatagcata aggtacatgg  95160
tgagcaaaac gacttgatct acgtattttg gagttcccgg actagtaggg gtgggaagga  95220
agacagagta ataggtaggt agacaatata atgcaatcat aatatgatat aagtttaatg  95280
atactgaaag tacaatggat tatagaatca caaatcagca atagttaatc agtttaagaa  95340
ggttaggaaa tgctatccag cagaaatgtc actaaaattg aaacttggcc aaatgagtgt  95400
taaaatactg gggatcagat gttccaaaca ggagagcatg gatgaaggcc cagagaagag  95460
agagatcata gggcatgggt gggaagaaat gggggcgagg agaaggcagg gaaagatcaa  95520
gaatgatagg aatgatgtac ttcggtgaaa gtatggtgca tttaaagaac tgcgataaga  95580
tcattgttgc taaagcttca tgtgtgcttg cattcgtgtg tgtgcataca cgtgcgtatt  95640
catgagaagg ggttggatat agacaacagt acatctggaa acacgaagaa ataatacaat  95700
```

-continued

```
gaaagagaac atgcattata gtaataggtt tggcctttgt tcattctaat agcaacagga  95760
agcctctgaa ggttttaatc aaatttgctt tttgggagag ataaaataac aaccttctct  95820
tcattctcct taagtcgttc catcttttag tgctcctttt gtctggttaa aaactctagg  95880
gcttaagtgt aattgatttg gaaaaatcac caatgagtgt cagtgtcatt tgggggcttt  95940
gaaagtaacc aagagcttgc atgcatagct tcgttaagac cattcgcact aggctgggtt  96000
gcctttgatg cctttgtatg ggttcagatt cttagaaaga gaactatcta tggttcataa  96060
aggagaccct ttccttcact atgcttaggg tgaaagtgca tccctcccct tcccttccag  96120
agtcagcaga caattaggaa aacaaattaa ccattctctc caccaaccgc taaatcagct  96180
taaactgagc tgaagcaaaa gtgactaaga agcagtggtc ataagaggtg gtataaaagc  96240
cacttggtga ccagaatccc attatgcaac aaggcgaagt gggggcagac aaggagaggg  96300
caggcaccct ggatatacat tttgagggag gtgactgtgg caagggacag agaaaatgcg  96360
agttacaaga tgatgaaacc atcccatgag actgcctctc agatatggga cgtgggagtg  96420
tgctaatgag actgaaacgc acaacccata gtttctgtcc cagattccaa attttacatc  96480
tctttgtggt aactggcaga actctacaga aaatcgaagt agaaatattc tttgtggttt  96540
attagctatt tggtttgtag agggaaggtg agacattatc agtacctgta atgggaatgg  96600
tgagctccac tccatggctg ttgcatggca ggaggctaca tccaaaacat gtccttctgg  96660
gcagagagaa ggcaggcacc ctggatacag catttcaagg gagatgactg tggcaaggga  96720
cactggttac ttttccacct ggataactgt aagcctactc caaaacattc tattcctaca  96780
ttcccaggac agagggtcct tctccttagg ttacaaagat catcctgact tgggtaaagt  96840
gaatgaattg tggtggggat aattaagacg gcaggggagc cagacgcaag ctgttgcaac  96900
aatccagtag tgagcagaag ccggctaaac gaagacagtg gcagtggggt ggagaaaaaa  96960
ggcagaattg gagaattcaa gaagtcagaa cttgctaatt accttgcact ccaggtcaag  97020
gctgacatag ggaaatgatg atagagccaa ggtttctggc ttgaggaact ggatgaggaa  97080
tggatgtttt taagtggaaa agtgaagaaa gacagggaga tcttgagatg gcagagaagg  97140
gataaattcc atttgtgata ttgacatttg cattgcatat ccaggaaata atgtcacaca  97200
ggtagatgtg gttgtctttt gttgttgtta tttgtttgtt tattgcttca ttccggacag  97260
tattttaggt gttccagaaa gcattcatac atatggttgt ggatttagct ccaaatgtga  97320
gtggatagaa aaatatggga gtcagcacag acagtggatg aaaccctgca tgggactgag  97380
acgctgaagg ctgagtagat ggacaagaaa caagccaagg atgaggactc tagaaagcat  97440
cccagtccag gcaggcagtg gaagaaagac ctacaacaga gaaaattcga aaacaagatt  97500
caaaagaacc acagaggcac tgggaaaacg tgatggtaag gaatccaggc agagagacaa  97560
tcaagcactg cacacagatt tagatggtga tagaaagtca tgaatcgggt ttagcagaaa  97620
taaggtacta gaaggggaat ttgataagag tgatataaga aaaagaaaac atgaagaaat  97680
ggaagcgagg gtctagaaat taattctaaa taggggactg gtagagggta atcgagggaa  97740
atagatggaa gacaagcaga agtgagtgcg tgtgtgtgaa aaagaatgtg tgtgtttgta  97800
tgtgtttgtg tttgtgtgtg taaaattgtg ttcgcttgtg tgcaagtgtg ttcacacatg  97860
tttgtgtgta taggtttaaa tttgtgcgtt tgtgtgtatg catgtgtcaa tatgtgtgtt  97920
tgtgtttgtt ggtgtgtatt taagtgtgtg tgacttgtga ctgtgtatct gtgtacacgt  97980
gtgagtgtgt ataactgtgt atgtacacat gttaatgtgt ttgtatgtga aactgtgtgc  98040
acttgtatgt gttcttgtgt gtttcagtgt ttggtgtttg tgagttatgg cttatgtgtt  98100
```

-continued

```
tgtgtgactg tgtgacttct ggtgtgtctc tgaaagggtg ttttgtatat gtacagtgaa  98160
tgtgtatttt gtgtgtgttt gtgtgtacat gagtatgtat atgtgtgtga gtgtgtgaaa  98220
gtatgtaact atgtgtgtga ttatgctttt gtgtgtgtat gtattcatgt taatatgtgt  98280
tgtgtgtgaa agtgtgagca ctttgtggtc ctgtgtgtgt ctatgtttct gtgtgtgtgt  98340
tcgtgttttg tatgaatgtg tgtggctgtg aatttttgtc tgtgtgtgaa atagtgtttt  98400
gtgtgagtgt acacgtgtgc caaagtgtat ttatgtttat gtgattgtgt gtaactgtgt  98460
gtgactatgt gtgtgtaagt gcacatgtac taatgtgtgt gtttctgggt aaaagtgtgc  98520
acttgtttgt gtgttagttt gtgtttgtgt gtgaatgtgt gttagtgtgt tggtgtatgt  98580
gactgggtga cggtgtgaaa gggtgttatc tgcatgtaca ctgcatggat tggtgtgttt  98640
gcgtgtgaat gtttttgtgt gtggtgtgct tttgtgtttg tgtgtatgta tgtgagtgta  98700
tgtttgagtg ttcgtgtgtc tgtgtgtctg tgtgaaaggg tatctgtgtg tttgtatgtg  98760
aatgtgtttc tatgtggtgt gtttttgtat ttgtgtttgt gtatgcaagt gtttctgtgt  98820
cagtgtgtac acgtaagtga gtgtgtgttt ctgtgtacat gtgtttttgt gtgagggtgt  98880
gtctctgttc acataggcac ttggagtaaa tatagaggtc acctgcttga atcttgctct  98940
accactcatc agtgacattg tagcattgga gactttttt tcacttaatt ttttgtttta  99000
attttaggtc cagggttatt aatatatgtg caggtttgtt atatagataa gctcatgtca  99060
caagcgtttg ttgtacagat tatttcatag tccaggtact aagcctagtg tccaaaagtt  99120
atttatttat ttatttattt ttgtttattt atttttgag atggagtctc cctctgtcac  99180
ccaggctgga gtgcagcggc gcgatctcac ctcactgcaa actctgcctc ccgggttcag  99240
gccattctcc tgcctcagcc tcccgagtag ctgggactac aggcgtctac caccacacct  99300
ggttaatttt ttgtattttt agtagagacg gggtttcacc atgttagcca ggatggtctc  99360
gatttcctga cctcgtgatc cgcccaccta ggcctcccaa agtgctggga ttacaagcgt  99420
gagccaccgt gccctgccca aaagttattt tttctgatcc cctccctcct gtcaccttcc  99480
cccctcaagt aggccccagt ctctgctgtt cccctctttc tgtccatgtg tcctcataat  99540
ttagctctta cttataagtg agaacatgtg gtacttggct ttctgtttct gcattagttc  99600
gcaaaggatg gtggcctcca actccatcca tattcctgca atagtcatga tcttgttctt  99660
ttttatagct gtgtagtatt ccatggtgta tatgtaccac attttcttta ttggagactt  99720
aaacttattc acaattatgt cataaataaa attaatctga caatagctac ctcactatga  99780
tgattttaaa agttatagcc agccgggcgc agtggttcac acccgtaatc ccagcacttt  99840
gggaggtgat gcggagggat cacgaggtca ggagattgag accatcctgg ttaacatggt  99900
gaaaccccgt ctccactaaa aatacaaaaa tttaaccagg tgtggtggca ggcgcctgta  99960
gtcccagcta ctcgggaggt ggatgcagga gaggggcgtg aacccgggag gcggaggttg 100020
cagtgagcgg agatcgcgcc tctgcactcc agcctgagca acagagagag actccatctt 100080
aaaaaacaaa caaacaaaaa aaacagttat tgcctagagt ttctaaaatt ctactgcatt 100140
tttgtgttct ttcaagtctg ctaaaattaa gaacttccta caatttccag gcaagatctt 100200
tgttaagatt ctttgaaata actgagaact atttcaggaa agcaagggtt aggggccata 100260
gaagagggct ttattctcct tgattctctt caaaatgcag tgccacacaa ctcattcatt 100320
caagtactca tttattaagt aaatatttat atattttatg ctgtgttctg ggaacgactc 100380
cgggagattt gatatataaa atgatcaaaa cataaaaagt agtacctgca tggagcttac 100440
```

-continued attctattag aaaagccaaa aaattagcaa tatagataaa cctataaatt atataatact 100500
ttagaaagta ataatgcact atagaaaaag aaaaagctag atcaaggcaa agtagatcaa 100560
agtttccagg aagagctgca attttatgtg gaacggccag ggaaggcttg aatgagatca 100620
aatcatttca acaacgaccc caggatggtg aggtcattaa caatatgcac cgtgcagagg 100680
gaaagccagt gtacacgccc gaaggctgaa gaatgtccgg tgttcaaaga acaacagaag 100740
gccatcgtga ctgaagtgct tttaaagagg aagaggtggt aggagatgag gtcagtatgt 100800
ggtaataaag cattgcaagg attttagctt tgagattgag agctgttgga aggtttgacc 100860
agaggagtcg taagacttgg gttttgaaat aatcgctatg cttgccccac tgatgataga 100920
ctgtaacagc acgatagtgg aagcagggaa atttctttct ttctttcttt cttttttttt 100980
tttttttttt gagacagagt ctggctctgt cgcccaggct ggagtaaagt ggcgcgattt 101040
tggttcactg caagctccgc ctcccgggtt cacgccattc tcctgcttca gcctccggag 101100
tagctgggac tacaggatcc cgccaccaag cccggctaat ttttttgta tttttagtag 101160 agacggggtt tcaccgtgtt agccaggatg gtctcgatct catgacctcg tgatccgccc 101220
gtctcagcct tccaaagtgc tgggattaca ggtgtaagcc accgcgccca gccgggaaat 101280
ttctttaaaa ctactgcaat gatgtaggct agaaatgatg gtggcttttt accagagtga 101340
caggaatgaa ggttttgaga aagtggctat atatatatta tatatgtgtg tttagatata 101400
tatgtatatg tatatataat gtagagcctg caaaatttcc taccagcctc catagattat 101460
gcacacaaaa ataaatcacc ttatgacaaa tgcaagggtc tgagcaattg gaaagatgga 101520
gttgccacca attgagatgc ggaaagttat tgctgatgga acagtttttg agggactcat 101580
ggggcacaaa gtgttcttct tcggactttt aaaggtatca gacatccatt agacatgtta 101640
atagagatgc tgaatggaca gttgggcata taagtgaaac ttaggaactt aggaggaagg 101700
tttgtactag agatataaat gttggtatca tcaacatata gatgttattt aaagccatat 101760
aacttgatga ggtcatcgag ggagtgactg tcggtagagc agagcaacag ggatgaaacc 101820
ctggatgcac ttttcattag gaagttaact tacagaggag atatctacaa aaaaggagga 101880
aggaggaacc agaggtaaga gaagcaccga ggggatgagg ggtttctaga agccaaagga 101940
agaggtatgt cattgaagaa gacaccatca gatgtgtcac atactgtggg tagcaaagca 102000
agatgaagac tgagaatgga ccattggatt cagcaacatg gagatcatcc atgaacttag 102060
taagggaagc tccaatagag gtgagtggtg aaagccagag tggagtggct ttaagagagg 102120
acagagtctg ggtgcggtgg ctcacgcctg taatcccagc actttgggaa gctgaggtgg 102180
gtggatcaag tggtcaggag atcgagacca tcctggctaa cacagtgaaa ccccgtctct 102240
actaaaaata aaaaaaaaaa aaaattagct ggacgtgttg gtgggcgctt gtagtcccag 102300
ctactcggga ggctgaggca ggagaatggc atgaaccccg gaggcggagc ttgcagtgag 102360
ctgagatggt gccactgcac tccagcctga gtgacagagt gagactccat ctcaaaaaaa 102420
aaaaaaaaaa gagagagaga acagaaagct gaattggaga tagtgagtat acacaatgtt 102480
ttggagagtt tcactttaaa gagaatcaaa gatatggggc aatggctgat aatagaacta 102540
tggttaaaag gtttttactg ttgagataag aaataccagc acaagcacta tttacaatag 102600
caaagaattg gaaccaacct aaatgcccat gaatgataga ctggataaag aaaatgtggc 102660
acatatacca catatacact atggaatact atgcagccat aaaaaagaat ttcaccgagc 102720
acagtggctc acgcctgtaa tcccagcact ttgggaggct gaggtgggtg gatcacgagg 102780
tcaggagttc cagaccagcc tggtcaatat ggtgaaaccc cgtctttact aaaaatacaa 102840
aaattagctg ggtgtggtgg tctgtgcctg tagtcccagc tactcagtag gctgaggcaa 102900
aagaatcgcc tgaacccagg aggcggacgt cgcagtgagc cgagatcatg ccactatact 102960
ccagcctggg caacagagca agactctgtc tcaaaaaaaa aaaaaaaaaa aagaataagt 103020
ttatatcctt tgcagggacg cggaaaccat cattctcagc aaactaacac aggaacagaa 103080
aaccaaacac cgcatgttct cactcataag tgggagttga acagtaagaa cacatggaca 103140
cagggaaggg aacatcacac accagggcct gtcggggggt gggggacaag gggagggaga 103200
gcattaggac aaatacctaa tgcatgcagg gcttaaaacc tagataacgg gttgataggt 103260
gcaacaaacc accatggcac aggtatacct aggtaacaaa cctgcacgct atgtacatgt 103320
accccagaac ttaaagtaaa aattaaaaaa agaaattcca gcacagtttt atgttcatga 103380
gaatatttta attaagtgtg atacattaat aatatataga gagaggggag aattactgaa 103440
ggctaccact ggatatgcaa gaagggttgg gaactaatag accagtgcaa ggaatggcat 103500
taaatacaaa tttttacagt gtgtctgtgt cctcaacctg tggtgtgggt atcactgaag 103560
tctgtgaacc cttccctcta atcaatctgc tgatatttag gtataagtaa tgctttataa 103620
agttcctgaa agttatttat tttgctctat gggatctcct ttagctcttg tcttaatcca 103680
ttcaggctgc tataacagaa taccatagac tgggtggctt ataagcaaca gacatttagt 103740
tctcatagat ttgtaggctg ggaaatccag ggtcaaggtg ctggcagatt tggtgtctgc 103800
tgagggcctg cttcctggtt caccaatggc tgtttttacg ctgtgtcctc acatggagga 103860
aag 103863

<210> SEQ ID NO 3
<211> LENGTH: 110608
<212> TYPE: DNA
<213> ORGANISM: Homo sapiens

<400> SEQUENCE: 3
gatcatcaga gtgacagaat gagaagccac catctggcca ccatcacgat catcatcaca 60
atcacgacga gtcaccaaga gactaaaact actgagtaaa agcttagaaa cggctgggcg 120
cgctggctca cacctgccat cccagcactt tgggaggctg aggtgggcgg atcacaaggt 180
caggacatcg agatcgtcct ggccaacaca gtcaaacccc atttctacca caaaaaatta 240
gccaggcatg atggcgcgtg cctgtaatcc cagctactca ggaggctgag ccaggagaat 300
cgcttgaacc caggaggcgg aggctgcagt gagcggagat cgcgccattg cactcctgcc 360
tgggcggcag agtgaaactc tgtcccagaa aaaaataaag cttagaaaga ggctatgtag 420
tctcgagata aatccagccc tatgaggcac atgtcaatca cagagggaaa gctatgcacg 480
cacaaagcat gtgtgaatca gagagaaagc tatgcacgca cgatgagtag aagacaaaca 540
cgtcctgcaa ggagacggag gcgcagggaa ggggcggcag ccgtcctccc aagacatgag 600
gacttctagt tcagtctgag accttggtgc agggctgggc gagtaaacaa atgcaaaaga 660
ataaggacct cgaggtcggg cgcggtggct caagcctgta atcccagcac tttgggaggc 720
cgaggtgggc gcatcacgag gtcaggagat tgagaccatc ctggctaaca cagtgaaacc 780
ccgtctctac caaaaataca aaaaacttag ctggacgtgg tggtgggtgc cagtagtccc 840
aactacacag gaggctgagg cacgaggatc acttgaacct gggagacgga ggctttagtg 900
agctgagatt gcaccactac actccaacct ggctgacaga gcgagactgt ctcaaaaaaa 960
aacaaacaaa caggtctggt gtacccagaa tggaggcacc acgagttgct gaagaaggaa 1020

-continued

```
actttattca gtctatgata ccaggacagt tgtccatgct gccaggcaaa aagaaaaact   1080
ggattctgat ctcattatca gtacacaaac agcgacaatt agtaacactg acacagccct   1140
gactgtgctg ctggagggtc cgaagcactc tctgcacagc ggtgaatccc cacaatagcc   1200
ctctagggaa ggtgctgtta tcacccacgc gagacacacg aaggaaaggc acggctttgc   1260
agcagcaggg tcacgattcg aacccaggtg gcctgctctt atgataaact taaatgtgta   1320
aaactttatg ctcaggaaaa tataagagaa tgtcttcctg accctttttg gggtaggaca   1380
ataatttctc taaccaaacc ccaaaagcat gacccattaa aaaaagggtc aggtggacta   1440
acttggctaa atgaagaatt ctgtttcacc aaagtacacc acaaagtggg ccgggcgcag   1500
tggctcatgc ctgtaatcct agcactttgg gaggccaagg tgggcggatc acttgaggtc   1560
gggagctcga gaccagcctg accaacatgg tgaaaccctg tttctactaa aaatacaaaa   1620
attaaccagg tgtggtggta tgcacctgta atcccagcta ctcgggaggg tgaggcagga   1680
gaattgcttg aacccaggac ggggaggttg cagtgagccc agactgcgcc gctgcactcc   1740
agcctgggca acagggtgag accctgtctc aaaaaaaaaa aaaaaaggcc agacttggct   1800
cacgcctgta atcccagcac tttgggaggc tgaggtgggt ggatcacctg aggttgggag   1860
ttccagatca gtctgaccaa catggagaaa ccccatctct actaaaaata caaagttggc   1920
cggcatggtg gcacatgcct ttaaccccag ctgctcagga ggctgaggca ggagaatcac   1980
ttgaacacgg gaggcagagg ttgtgatgag ccaagatcgc gccattgcac aacagcctgg   2040
gcaataagaa caaaactctg tctcaaaaaa aaaaaaaaga aacaaaaaaa aatatatata   2100
tatatataca taccataaag tgaaatcaac agccacaacc tgggaaaaaa tacttgcaac   2160
atggcaaagg attaatatcc agaaagtata aagaattcct acaaaccaag tagaaaaaca   2220
ggcaaaaaaa aaaaaatgtt ggcggggcat ggtggctcat gcttgtaatc ccagcacttt   2280
gggaggccaa ggcgggcaga tcacctgagg tcaggagttc gagaccagcc tggccaacat   2340
gatgaaactc cgtctctacc aaaaatacaa aaattagcca ggcgtggtgg caggcgcctg   2400
taatcccagc cacgcaggag gctgaggcag cagaatcact tgaacctggg aggcggaggt   2460
tgcagtgagc tgagactgcg cctgctccag cctgggtgac acagcaagac tccgtctcaa   2520
aaagtaaaga aaaaaaaaaa acaaaacaac atatttcaca gagaagaatt tatgtttttg   2580
gagaaggagt ttcgctcctg tcgcccaggc tggagtgcag tggtgagata tcagctcact   2640
gcaacctcaa cctcccaggt tcaagcgatt cacagaggac aatttctaaa aggcaaataa   2700
gaagcaggaa gggtgcatgc tccttctcta ctgccctgta acagtcattc cacacttacc   2760
acctcaaaac aacaaatgct tttgatgttg gctcctgtgg ggcagcaatc tgcgggaagc   2820
ttagccaggc acctctggct taaggtccct cctgaagctg cagtcacacc atggaccagg   2880
gctgtgacct catccgaagg ctcaactggg gctgaggccc acctctgagc tcactcaggt   2940
ggacgctggc tgggttcagt tccttgctgg ctataggtgg aaagggcccc caccagtttc   3000
ttgccagctt ctccacagga cgccccacag cctgacagga gctttcatcc agcaagctca   3060
tcagggagtg ggagagagca gccaggacag gagcccagac ctttctgaac ctcatctcag   3120
aagtgacatc cttcccttct gctgtctggg cacagctccc cgggtggagc ccgaggacta   3180
gaaggaaaag aaaacttgga tttaaaatgg gataaagcca taggagctgc tcgtcccacc   3240
acaggaatct caacgccggg ttactgacaa agcgtcactt tgcacctcgt ccaactgtgc   3300
agacctctcc tagccaggcc cctgcaccag aggttaagaa tccgtgcccc tggtcaggaa   3360
gtccaggtgg gttcaaacgg ccagcaggga atttcaggca aaatgtgtcc caaatcttca   3420
```

-continued

```
aaccatgccc cagaactcag acctcccccct gggagttcgt cccaaggaaa ccacctgcaa   3480
gaggctcagg ctgcagggga cactccgctt ccaaaacccg gaagctggag accacacaag   3540
tgcccaacgc caaaggcacc ccgtggaggg acgccctgtg ccctcccccg accaggtgac   3600
ccgctgcgcc ctacacatct tcaccaggaa acatctgtta tcgatgtgga cgaagcgcag   3660
cctgcactcc cagatccgct cattttcgtt ctgccctccg ttttacgatt cgcctacact   3720
gaaaatgcgt gagtggagtg gaaagccttc ctactcctgc ctcagcgacc ccttctaaaa   3780
tactgcctcg tttggcctga aaatgtgatt tgcaggcttc ctgagcaaag tagatttcac   3840
tccattaaag aaaaaaaaaa agaaaaggca ccgaacgggg ctcggctgtc gggagttttg   3900
ctttagtttt ttgcgtgttt tgttttgtgt tttttgttg ttgttgttct ttttgcggcc   3960
acgcacaccg cgttcccagg cttcagggcg tgggggtcgc cgtggactcc cggacgtgaa   4020
aacgcttaaa gccagctggg aaaaccccac cagcgttttc cgcgcacagc gccagccata   4080
ggaaaggacc cccaggagcg aatccgggca gggaaacccc ggacgcccgc acactcagca   4140
tcagtaccgg cacccagcac ccagcaccga gcaccgagca cgcagcaccc agcaccgatc   4200
accgagcaga gcaccccgca cgcagaaccc accgagagcc tgatgcagtc tccgccgcag   4260
gcatagcgct aggccccggc gccttcacaa caaagggacg ctggcgggcg gggcctgaga   4320
ggcgcgcggt ggaggggccg ggcgcgaggc cgcggagaca gctcggagct cggcactggg   4380
gagtggcaca gcgctggcgg atccaggtgg gcttcacggg gcgcccgcgg gaccggaaat   4440
gacgcgcaga accctgcatc gggctcctcg ctgccccgcg ggcgccgctc ctcagtgccc   4500
cagagccacg gagccgggga aacgcgccgc ggcccacaac gcccccgcgg ctgcccgttg   4560
gttccgcccg ggccgttcta ctccaggcag acgggaggag aaacacggcg cgctcagcgt   4620
cccctccccc gttggttctg ctcgggccct tccactgcag gccgacgggg gtggaaacac   4680
gcagtttttt tttttttttt aaggtctagg gtaacacggg gcttttaagt gcctctccgc   4740
tgccgcctgg tggtccagcc cggccgttg cagtgcagcc acacggggag ggacacggcg   4800
cgccgagtgc tccgggcggc cgcacgttgg ttccgcccgg gccgttccac tgcaggcaga   4860
gggagaggac gacggtgcgc gtagtgcatc cccgtggccc gttggttccg ccggggccgt   4920
tccactgaag gcagaagggg ggggaccgtg gccccacccc ccgcggcagc ccgttggttc   4980
cgcccgggcg gttccgcccg ggctgttcca ccagcggcac ttcagggcgg gatcggccag   5040
tctgtggagg cagcggcctc taagccccgg agggtttact gcccaggttt gggttccagg   5100
aataagaaat ccactgaata ggcttaactt agaagacaca aaggcgcctc ctggcggaag   5160
tggccacgct ccgcccagcc tgagggaaag ctgctctgac agctgggccc ggagctgcgg   5220
ggggcggggc cgccgcgcgg ggtgaggact cgcctcaggg cgctgattgg ctggtggcgc   5280
gctccggggc ggggccttcg tatccaggct ggcgtcgggg ctgccgcggg acatccggag   5340
cagacacccg cgggcgcgcc tgcggccccg aggacccccg gctccggagc ttcgtcgagc   5400
gttttcctag cgttactttc ccaaataatt ttcaggaatg aagttacggc taaagggctc   5460
tttagagatt acttttgggc cgggcccggt ggctcacgcc tgtaatctca acactttggg   5520
aggccgaggc cggcgcatca cgaggtcagg agcttgagac cagcctggta tggccaacgt   5580
ggtaaaacgt cgtctctact aaaaatacaa aaattggccg ggcgtggtgg cgggcgcctg   5640
taatcccagc tactccggag gctgaggaag gaggatcacc tgaacccggg aggcggaggt   5700
tgcagtgagc cgagatggcg ccactgcact ccagcctggc gacagagcga gactccctgt   5760
```

-continued

```
caaaagaaaa aagaaaagat tacttttggc cgggcgaggt ggctcacgtc tgtaatccca   5820
gcattttgag aggctgaggc gggcggatcg cctgaggtca ggagttcgag accagcctgg   5880
ccaacatagt gaaccccccc ccatctctac taaaaataca aaaaaaaatt acccgggtct   5940
cgtggcgcgt gcctgtggtc cccgctactc gggaggttga ggcaggagaa tcgcttgaac   6000
cttggagttg aaggttgcag tgaggcgaga tagcgccgct gctctccgac ctgggcgaca   6060
gtgggagact tcatctcata aataaataaa taaataaata ttacttttac gttttgttaa   6120
acttccactt gtttttgttt ccgttgcatg aaccttcgta aagcttcagg aggctgatgg   6180
cagcctcctt ccccaggctt ccccgtggcg cccgcagccg ggttgggcca gaggctggga   6240
ctgtttcctc ccgtggggtc tttggtgggg atgtccccag aggagtgggg caggaggagg   6300
ggcacggagc gcccccggga gccggtcaga gcgcagcgat ggtgtctgtg gttccaacca   6360
ctcgggaggc tgaggtggga ggatggcttg agcctgggag cttgaggctg cagtgagcta   6420
gaatcacagc accacactcc agcctgggcg acagagtgag acccttgtct cacaaaaaaa   6480
aaaaaaaaaa aaaaaaaaaa aaaaaaaagg ctgggtgcgt tggctcgcgc ctgtaatccc   6540
agcactttgg gtggccgagg cgggcggatc acgaggtcag gagatcgaga ccatcctggc   6600
taacacgatg aaaccccgtc tctacaaaaa atacgaaaaa aaattagccg ggcatggtgg   6660
cacgtgcctg taatcccagc tacttgggag gctgaggcag gagaatcact tgaactcagg   6720
aggcagagct tgcagtgagc caagattggg ccactgcact ccagcctggc gacagagtga   6780
gactccgtca aaaaaaaaaa aaaaaaaaaa aggaagaaag aaaattataa aatgaagtga   6840
aattaacgca gtggagtgcc acctgcctgc tgcctgagtt cactatccac acggagttca   6900
taaatttgag agcagtttac aaagtagatt ctcctacttt ccaggaaacc cagaaatgtc   6960
tggtgatttg cccaacagtc tcagctgttg tggtcagcag ggccgctgtg gtatccaaat   7020
gatttcaaaa gcagatttat aaaaagtact cctttttttt ttgagatgga atttcgctct   7080
catcgcccag gttggagtgc agtggcacga tctcagctca ctgcaacctc cgcctcccgg   7140
gttcaagtga ttctcctgcc tcagcctcct gagtagctgg gattacagat gtgtgccctc   7200
acgcccagct aatttttata tttttagtag agacagggtt tcaccatgtt ggccaagatg   7260
ttctccatct cctgaccttg tgatctgccc gcttcagcct cccaaagtgc tgggattaca   7320
ggcgtgagct accccacgcc cggcctttat ttttttttga gacggagtct cactctgtcg   7380
cccaggctgg agtgcagtgg cgcgatctcg gctcactgca agctccacct cccaggttca   7440
agagattctt ctgcctcagc ctcccgagga gttgggatca caggcacccg ccaccatgcc   7500
cagctaattg ttttgtattt ttagtagaga cggggtttca ccgttgttag ccaggatgct   7560
cttgaactcc tgacctcatg atccacccac cttggcctcc caaagtgctg ggattacagg   7620
tgtgagccac cacgcctggc ctctcaaagt ttttatagca aagccttaca tttcatgagg   7680
aaccatgcat tttattttat ttttgagatg ggggatctcg ctactttgcc caggctgggc   7740
tcaaactcag ggctctctgg cctcagcctc ccgagtagct gggtctgcag gtggctgtca   7800
ccgtgctggg cctggggtgt gcgtattaat gattttggaa tagtgtctgg aagcctgtgt   7860
gctttcctct cttcctctcc ccagaaggac ctcccacctc gtcctcccaa agtgttggga   7920
ttacaggtgt gagccaccat gtcccctctc tttgctattt tgcctgggag gagtgtatta   7980
ataattttaa ttttaaagtt ctttgattat gttctagttt gattattgat catttacttc   8040
ttagctattt atattcttcc ttgagtcatc ggtttctgcc ctttgacaat ttttctgtga   8100
atgttttgtg tcgattatat gagctttgtc tgtattgaga acatccacga attgtattat   8160
```

```
tgcatctgtt ttgctagttg agaacatcga cctgctgtat tattgcaaat gttttcctgc   8220
ttgcatgtag tcatttgttg tgcatattaa tgaatttcta tccacatgac gccggaaggg   8280
gatagagtgg gtggggagga agagggaagg gtccccacct ggagacccag cctgcaggcc   8340
actcggccac ctgcgcagag gtaggggagc agcagccgct catgcccctg caatttgtcc   8400
tcatcagcag gtggggaaac tgaggccggg gagttctcca ggccaaggtc actcacgggc   8460
aagttcccgc agcctttgga ccctccatac atgtcagggc cgctcatgct ttcctgggcc   8520
cttcactggt ttggaggaac catcctgttt cccagagcgc actgcctgtc tctgagtgta   8580
tgtgtctcag tggcgtccat gtgtattttt ctgtgtgtgt atctgtgtga gtctgtgtgt   8640
gtggtgtgtt tgtgtctgag tgtgtggtgt tagcgtgtgt ctcagtggcg tccatgcata   8700
tttttctgtg tgatgtgtct gtgtgtgtgt ctctgagtgt gtggtgcctg cgtgtgtctc   8760
agtggtgtcc atgcatattt ttctgtgtgg tgtgtctgtt tgtgtgtgtg tgaatctacg   8820
tgggtgtttg tccatctttt tgtctggcct cctgtcccct ctgcacagag cagctgggtg   8880
gggatgctgg tcctgggggc ttgtcagcag gatgtgggcg tggggcagcc ctgggtgagg   8940
cctgagtaca ggccccaggt gcctcctgca caggggtggc tgagccggct cctctgtggc   9000
tcccgggtcc ccaccgccgg tcactgggca ccacctgtcc tggccaccca ctcctgccca   9060
ccctgctctc cgcaggggcc tccttcctct ttcagctgtg cgccctggtt gtggaggctc   9120
ctaaggaggt tgtggcctcg gtttaccacc tgccttggct ccttggtgtt gccagaccct   9180
gaaggcagcc catgccctgg ctgagatcct tctggggcag gatgtgctgg aagcagctga   9240
aacatgtggt gatgtaccag ctcctgctgt cccctacatc cccagcaccg ccagccttcc   9300
ctgggctcct ccagctggct tctctaccct gtacctgccc caccctgctt tcccccgacc   9360
ctactacccc ccaaccagac ttccagctcc aggcagggtc gcagcctcct gggctcccag   9420
caggacaggc ctcacccaga ccccgcagga gccgtgggac ttgggctggg tctttgggcc   9480
tggctgcagc ccctttggac ctgacctgag gagacaccct ggctgtggga ggcagggtgg   9540
gggtgccggg cccagcacag aggtgcccag ggtgcaggct ggcactggcc cggcagggac   9600
cgtggatgcc gccgtttcag gctcgaaaag gtttccatgc cccagagcct gagcccggca   9660
gcccccgagg atgtcttggg gcctctgtgc tccccaaagc caagaaggtt aggcttgacc   9720
cacagcctct tccaggccgg ggaggcagag gcgctccagg tcggtagggc ggggcccaca   9780
gcccagggtt tcacgtcccc aaaacggggc agggtgctgg aggggcaggt gtccacaggg   9840
tggtcgtttt ggtctctcct ggacttgcac gcgtgtagtg cagactggct gccggcaaag   9900
ccctgagcca cattcatctg ggccttgtta ggacaacagg gacggtgcgg ggtggggggg   9960
ttgcggggcg caggaccacg tcagtggagg gagggaggcc gatatcggtg cccaggctgg  10020
gcccaggggc cagcgggtcc tcacctggct tgtggctgcc cctgttaggc agcccggatg  10080
gaggggctct tccagccctg ctggccccgg gaatgcaggg actcaactcc ccctggtctc  10140
agtggctctt ccgggagcaa cacagcctgc ccgagtcgac accacccctc gggtttgagt  10200
cccttctgtc taccccctacc cccgccaggg cactgccccc ttgcccggaa gaggcagcgg  10260
cacccccagc cccttgggga ggatgccctg ccggccccac actcggtgga tgggcatttt  10320
ggggctagga tttaatgggg gtgaccctgc ccgacccctc tatgttggtt ccacggcgtc  10380
agaagaaagc tgttattaac ccagcttatt ttctacaagt cttgtttatt gaaaggatct  10440
gaaaagcgta ataaggcttt caatgacatt taatacattt tcaagaaatt aatatgaaac  10500
```

-continued

```
attaaaattt acttcaaaaa tccaaagttt tctagatcat tcccatctca cgctgcttta  10560
gaggtcagtt cacaccttct gtgttcagat gagcggctgg aattctgaac actgccgtct  10620
tccagcccta acgctgggcg ctggtccctc tctcctaagc ccacggctgg gcttcccctg  10680
tgcccagggt catggcggac ttcaagccag gccggctgcc cagaatcaca ctcagggttt  10740
ttggacgctc aagtccacag atgctgaggt gcccagacga gggtgagcag ggagacacat  10800
gcctcggaga acgtgcccag gctgggccag gcggctgcgg gaagctcctc acgggcagag  10860
gagaacgtct tgtgccttcc ttatcgatct ccagcagatg agggcaactt tgtgtgcaaa  10920
actcagagag cagttactca aaaaaaagac acccgggcag cagtaaccag gacaccaggg  10980
tccgaccacg gcctccacac acctgtgccc gtggaagacg cgggcgccgg ggtaggcagc  11040
atccacgtgc tccacagctg ctggtgctgg gcaggctgga gactcacggg agaggcagga  11100
ggagaatcag cgtgttgagt ccctcgctgt gttagtgtga aaaattctca ttacagttgc  11160
aaataaaagg gatcacgatc actagccccg gaaaccctca tctcccggac catcaggatc  11220
gcactgaaca gaatggtccc ctaatggtcc ctgaggacag cgtcttgcag aacataaatg  11280
taaacattga atggcagacg actcccttcc ccttgaaatc ttcacaaaag tgtgtacgag  11340
aaagtatgta catcagcact tcagaaaagg ggcccacagg acgtgtgcgg ggtgtgcagg  11400
gtgtgcgggg tgtgcggggt gtttgagggt ccggatgtgc gtcccgaggt cggagggttg  11460
gacgcccctg tgtccagttg ttgggagggg tgggaggcct cgccctgctg ttcagcccct  11520
tcccctccac tgggccgcgt tcccagggac gtgcaacagg gcgctcaggt taggagaccc  11580
gaaaccacag gcagacagga cccgccacgc ccgctcccag ccctgggcac ccccaccccc  11640
gtttccttcc agtccatttt ccgcggcagt ttttggtcct ggggaccgtc accgatgcct  11700
cccacgcacg ctttcttccc tgaagggaga cgtcgctgcg ctgggcctct cggcggtccc  11760
ccccacccgg gtcccgggcc cactggcccc ccgcagacgc cgctacacgc tgactccagc  11820
caggctgcgc tgggaccact tcaacctcac ctacaggtgc gccctggctg ggccccgggg  11880
gagggggcgc ggccggcgcc cgctgagctc actctccctg caggatcctc tccttcccgc  11940
ggaacctgct gagcccgcgg gagacgcggc gggccctagc tgccgccttc cgcatgtgga  12000
gcgacgtgtc ccccttcagc ttccgcgagg tggcccccga gcagcccagc gacctccgga  12060
taggtgggcg cccgcccccg ccccggcccg gccctgcgcg cccggcctct cagccccgtg  12120
ctccccccag gcttctaccc gatcaaccac acggactgcc tggtctccgc gctgcaccac  12180
tgcttcgacg gccccacggg ggagctggcc cacgccttct tcccccccgca cggcggcatc  12240
cacttcgacg acagcgagta ctgggtcctg ggccccacgc gctacagctg gaagaaaggt  12300
gaccgtccag gctggcctcc tggaggcctc tcctctgcag cacagtgggc tgccgcggtc  12360
gggctttggg gcagacggca ggagggacct tccggggtgg tggctgccac tggagtctag  12420
caggcaagga ggggagcccg tgggagcccc catcccggca gccctgaact ccctttccca  12480
tccccctgcg cctctggagc gggagctgga gctgcattcc tgggggccga gctcaccgcc  12540
tgggcccaga acattcttat ctttccgtgg ctgcggccga gggcggctcc gcggctgcgc  12600
tccagcagat acaccgggcc tcggggagct ggcccacggg cggcggggct gggcccgggg  12660
ctcccaggcg ctgacccccg gggcccgcag gcgtgtggct cacggacctg gtgcacgtgg  12720
cggcccacga gatcggccac gcgctgggcc tgatgcactc acaacacggc cgggcgctca  12780
tgcacctgaa cgccacgctg cgcggctgga aggcgttgtc ccaggacgag ctgtgggggc  12840
tgcaccggct ctacggtgag tccctttgtc gggcgggagg gcggggaccg ggcggtcctg  12900
```

-continued

```
agccaggccg tgctccccac gctcccgaca ggatgcctcg acaggctgtt cgtgtgcgcg  12960
tcctgggcgc ggaggggctt ctgcgacgct cgccggcggc tcatgaagag gctctgcccc  13020
agcagctgcg acttctgcta cggtgatgcc cacggggccg ggacagggct gcgtgggagc  13080
tgggccttgg ccatggtcgg ggctgagggg gcactgacgg ggctctttcc cccacccgga  13140
gcagaattcc ccttccccac ggtggccacc accccaccgc cccccaggac caaaaccagg  13200
ctggtgcccg agggcaggaa cgtgaccttc cgctgcggcc agaagatcct ccacaagaaa  13260
gggaaagtgt agtgagtgag cgccccgggc ggtcctcggg gtgggcagcc cgcgggcggc  13320
cttggggcag gggtgcgggg caggcagcgg gggggggctg tgcctgcagg agacgccccg  13380
ccccccctgca gctggtacaa ggaccaggag cccctggagt tctcctaccc cggctacctg  13440
gccctgggcg aggcgcacct gagcatcatc gccaacgccg tcaatgaggg cacctacacc  13500
tgcgtggtgc gccgccagca gcgcgtgctg accacctact cctggcgagt ccgtgtgcgg  13560
ggctgagccc ggctgataaa gcactttctc tctgatggct cctcgctcat tcttgggagg  13620
gcagcgggca gccagtctgg gcaggtggac accccagccc ctggtccacc gagagctggg  13680
cgtcctcggg gctgggcacc cctgcttccc cgcacagcgg accacaggta cagcacagga  13740
cgggacgggc tttgctaagg tggcccctgg gaaagtggga taagaggagg ccccagtgac  13800
aggggcagca cgtggagcag cacctggggt agccccagaa gcctgggttc tgtctaggac  13860
ttgctcagag ctgggggagg gaggcaaagg gggcttcctg aaagatgtgg ctgggatggg  13920
cctccaggat cttctgcaag gagatgtggg tgggggctgg gaggactggc acagggtggg  13980
ggaccacctt gccagagtgg aggcccccca ggaggtagga gctcccctcc tgcctgggga  14040
agacactggc ccacatgggg tcagaggcca cagccgccca ccccaccctc ttcccctaga  14100
gcccggtggt ctgcgactcc cctcccacac atggtcccgg gtcactcaaa ggacgacacg  14160
gggagctttc ctcgaagaat attttaatac attttaaaac tcaacaacct tgtataaaaa  14220
cctgtcgagt ctgctggcac agctggggct gggggttggg ggccgggggc ctgtgtggac  14280
agggctggtc tggacgagtg ggttggggca agagggcatc gctcatccca acacagaaac  14340
aggtctccag ctccgaagat taaacaatcc acccggctcc caccagttcc tttccaaatc  14400
acggcccagc cagccccgtg cgtgtcgaga gtgggagagg gtgtgtggag gtttgtgctg  14460
ccccacgtgg gcacccgaag atgccctggc aagtcacgga gaaaacacag ctctttcctc  14520
cacaacaagg aaaatgattt aattctacaa atttacaaac caaaatacaa aaacaaaaca  14580
tggagcacaa agtaagacga ggagttccga gtctcatcgc agctccagcc gcagtagcca  14640
cgcctgtggt cccggctgag ttctccccat gacggggtcc actctgacct tcagaacttg  14700
aggctgaagc cggggcccgc ggcagaggcc ccctggttcg tggtggtaag gtggaagccc  14760
gtctccttca ggtcgtcgtc accctgggac gagtcggcta ccgtgagaac cctgcccaag  14820
ccagccccac ctgtgggcac gccccacccg ccaggcccct caccagctgg ctgtagccca  14880
ggcctccctc agggggcctc gggctggtgc cccgcttcac acgctgctgc tcgctcttgg  14940
cgggccacgt ggggaacatg gaggggtcga tggggagggg ggtctcgcgg aaatactcat  15000
gcttgaggcc gtcctcagcg ctgatcctcc tcccggggaa gtaggtcagg aacctggggg  15060
gagagggcca gaggcccagg aggtgctcgt gtgctccact gggtccccca aagatgggct  15120
gtgttgggac ggggctcagg gcatgggacg ccaggcacca gagcagttct ggaacgtggt  15180
gagccagcag gtaggcctgg gactgggaag tcaccgctat ggctcgggac ctcccgccac  15240
```

-continued

```
ccggctgcac tgggctcact tgttcatgag gtcgaagccc tggtctgaga gcagagcccc  15300
gaagcgcttg cggaggttgt tgtaggggtg ctcgctgaag gtcatctttt tgactactgg  15360
gagctcactg tagccgggcc agattttctc actgggggtc cccagctcct gaaagacaga  15420
ggtgcttcaa cagccacacc aagtggccca cagtgttggc acctgtgtcc cgtcagagaa  15480
gacaagccac caggagggct ctcagtggcc ctggtcccca tctcaaccca gcacctgtgc  15540
gccccgcagc cccattcctg caactcctct gaaatccata gcgcacctgc ggcagggcca  15600
gacccacctt gaacactttg ttgatctgat cgatttccga attcccgggg aacagaggct  15660
tctgagtcag cagctccccg aagatgcagc ccactgacca catgtccacg gccgtggagt  15720
attcctaaga cgccaggaga ggtgttcagg aaggccagtg cccgcgaagc tgtgggaggc  15780
tgcatggggg acaggggagg cactcagacg cccaggactc accttggcac caagcagcag  15840
ctctggggcg cggtaccact gggtcaccac gaccggggtg taggccttca gaggggatcc  15900
gtactcccgc gccagcccaa aatcacccac ctgcaacgac agatgggcgg ctgtgggtgg  15960
gcctgggcgg gtcaccctgg gatgggccac tcggaggggg gctcaccttg aggatgccgg  16020
cgtggctcag cagcaggttg gacgtcttga ggtcacggtg caggatccag ttgtcgtgca  16080
ggtgtttcac cccccgcagc agctggatca tcagggtctt cacctcccct gggagggagg  16140
gaggctccca tgtggacccg gccgccccaa gcccagggca ctcagggtgg cccgctcgcc  16200
tcggcagcaa cagaggcttc tcagggcttt ccctgtggat gcagctggcc ctccctgcag  16260
cactgtcacc gcgggggtga ccaggacact gcccccactt gtacgcagac aggaccccgg  16320
ggcgcggctg tacctggcag gaagggctgt ttcatggtct ccatcaggct cttgaggtcg  16380
tgctccacgt agttcatcac gatgtagatc ttgtccatgt tgctgcccac cacaatctcc  16440
tgcagggcac ggctctgtgg gtgctgggca cctccaggcc cccacccacc cctgcacccg  16500
ggcgcagatg ctgagggaca gtaaggacct ccggtgccac ccgggaggca aatacttgct  16560
tctgtgtggt ctgtgaaggg ctccactaag tgcaggagag tgtaggaagc acccggcccc  16620
aggacagcac ggggccctgt cggaaaagcc ttccacccgg ggccaggcgt ggtggggcca  16680
tgctcactct aacggtgaca atgttgggat gctgggcctt gaggatggtg ttgatctccc  16740
tcagggacgt gatcgggaag ccctccttct ccttctccat cttcagccgc tttagagcca  16800
caatttcatc tgtgaagaaa atacagacgg cactgagagg cattctcaaa gtcacggtac  16860
caacagtgga ctcgttcagt gaggaccgca ggcagtgccc aaagcgccag catttcacgg  16920
aggggggtct cgttctaggt gggggcacgt gggcaccagg agaacgcccc agctgaggtc  16980
tcggcaacac ccacggcttc ccactcaaca caccacagac actcacagcc acctacagcc  17040
acctgggatc ccagcggcca cgccgactcc acatcgactt ccccaacaga gccggcctca  17100
cctgggatcc cagtggccga ctcccaacag agttcccggc tcacacacct gcttgggtgg  17160
gacgctggga acgcaaacct gcacaccagc cccggcacag accactccac gcgctgggcc  17220
tcggccctgt ggggcaggcc gcctgctact gcaagggagt ggcaaagccc cagggccagg  17280
ctgacctctg gcttctagag gtgctgaggg gtccaacctc cagtagctgc tcaggtgaag  17340
cgggcccagg tgcagtcgca gctctcgggc agccagcccc tgccccactt cccctgcctt  17400
tgtggggtga ggggacccca cccacctgtt ttcttgtctt ttgctctgta gaccactcca  17460
taggtgccct cctcgatcct gttcaggcac tggaactcct cgacgctccg gcagccctgg  17520
gaaggaagcg cctgtgtgag gtctcagtgg ccatgccagc tggagggagg gcggctgcgt  17580
ccacaggcac ggcacaccca gcacggggca ggtgcagggc agagccttgg gactgggccg  17640
```

-continued

```
ggggtggagc tgggagcagc tcagttcttt caaagtctct ttccttgcaa aaccatctga  17700
cactttatta tgaaacaaaa ccagtgtgaa caaaaggcca tcccagccag gtgcaagggc  17760
tcaggcctgt aattccagca ctttgggagg gcaaggcagg aggattgctt gagcccagga  17820
gttcaagacc agcctggcca acatagcaac actctgtttt cttttttct ttttgagatg  17880
gagtctcgct ctgtcaccca ggctggagtg caatggtgag atctcggctc actgcaacct  17940
ccacctcctg ggttcaggcg attctcctgc ctcagcctcc ctagtagctg ggagtatagg  18000
tacgcaccac cacgccaggc taattttgt atttttagta gagacaggat ttcaccatat  18060
tggccaggct ggtctcgaac tcctgacctc tgatccgccc accgcctcgg cctcccaaag  18120
tgctgggatt acaggcgtga gccactgtgc ctggccaaaa ctcttctcta caaaataaaa  18180
aaattagcca ggcatggtgg cttgcgcctg tagttccagc tactcaggag gctgagatgg  18240
gaggattgtt tgagcctggg aggtggaggc tccagtgagc tatgattaag ccactccact  18300
ccagcctgga tgacagagac agacccagtc tccaaaaaaa aggccatccg gagagtctct  18360
ctgtcaaagt ggatgtgtcc cctgcttgta ccaggatgac actgaggacg ggccctacct  18420
gccaggcgca gcatgatgcc ccatgccagg gcacctaccc ctcggtgtac cttggggccg  18480
gtgcccaggc cggatgtcac gtactctggg tggcctgtgg cccgacgcct acgctcagca  18540
gcactaaggg gcagaggcgc tcacaaggca tagggcagtc gacagaggcc tgctgcatgc  18600
gccagagaga acctctccgc ccacaggcac caaggagggg gccgagtccc tgccggtctc  18660
ccaggccccc gaggccactg gtaccttctc aggcttgtcc cttccaaatc actcccaaca  18720
atatcctgcc ttattgatag ctgcctgagc aaaaggcttc tggtcacaca tctacactga  18780
ctcccgtagc cgctccccca tccaagccct gcacagatgc cggtaacaag gccttggtgc  18840
ctacataacc cgcccacgca ggggtcaagt ggaaggcact gctctccagt gcggaggagg  18900
acgcaactcg ggcagcagtg acagcagcgc ggccgcacgc ccaggctgcc tttcaagccg  18960
cagagcagtc ctgcgggcag ctccctgtcc acccagttcc gtccagcatg agaaagaggc  19020
gggacctaga agcatgaggg gccagtggct gtgcccgccc gtcactgccc cagtgggccc  19080
agcagccctg tgaggcgaca gacgccaaca cgggggccag gcttcgctca gcccctgtgg  19140
taactccgac tgccaatgcg gacagcggcc cggggcgagg ggagggcctg acctgcaggg  19200
ccggcaggta cttgggcagc tcctgcttga gctcgatggg caacagggca ggggagtcgg  19260
gcacatagtc gccctctgtc agggcgctgc tctgcggcgt tccctcaccc acttcttcct  19320
ctgcttcttc actctccccg gaatctcggt cgaaccgtga ctctggaact ggaaaagttg  19380
aacctaatta cgaagctagg agtaagtaag gatcatgaac ctcctcctgc cccgggggca  19440
tcaagcgcgt ggcagggctg ccccgtgtcc cgctgggagg tgctggcgct gggctctcgt  19500
cccctggaca cagggcaccg aggcctaaga gtgctggcag gctcggctga gacagagccc  19560
ggatgctgag ctgggaggag gcgtcgggtg tcatgtgggg gacaagccca catccacgtc  19620
caccaggctg aggacataac ctcactgcct gtcggaggct gggccaggcc tctgttctgc  19680
agggacaggc ccggagccac catctgacgg gcctcccctg tggggaactg gtcctgggct  19740
tcccagctcc tcggccctgc tgggcactca ggacgccctt ggtcagcact gtgcctcgct  19800
gaggaatgcg ggccccaccg gcacagcctg gagcggccaa cgaatcaggc ggcctcccag  19860
accctggcgt gccccacgcc gcgcaggacc ggctgtctta ggagagggct gctgcactcg  19920
gagacagaca aggagggggc tctgtctcca gggaggttct taccaaccaa gaggtggttt  19980
```

-continued

```
tcattttctc gttcttcatc ttcactcatt tcttcctcac ttacttcttc tgcaagagaa  20040
aggaggcgtc tgctcagacc agcaccgggg cgagtgctgc cacaggcagg atgcgggctc  20100
cgcttcagct aagcaacaag tgttcccaag aatggatatg gaggctgggc gcggtggctc  20160
acgcctgtaa tcccagtgct ttgggaggcc gaggcgggtg gatcacctga ggtcaggagt  20220
tcgagaccat cctggccaac gtggtgaaac cccgtctcga ctaaaaatac aaaaattatc  20280
cgggcgtggt ggcgcacacc tgtactccca gctacttggg aggctgaggc gggaggatca  20340
cttgaacccg ggaggcagag gttgcagtga gccgagatca tgccactgca ctccagcctg  20400
ggcaacagat caagattcca tctcaaaaaa acaaacaaaa agaatcgatg tggaggtgtc  20460
ccgagagagt cctagataga agggagtttc aactccccg cccgccagct acttctctgc  20520
ggtttctaac actatagtga agtcacaaca cctcacacag tcgtcgcggt gcctcaccgg  20580
cagactgctc tgatgcctcc tcagagttgc tgccggtctc ctcctcctcc tcttcctctt  20640
cctcctcctc ctcctctgat tcttcactgg tgctcccttc ctcctcctcc tcttcctcct  20700
cctcctcttc ttcctcagaa cctgagcctg attccgctgt agaaagacag cagagcagag  20760
ggtgaacctg ggccttcctg ggcagcagtg gtcaaggcct tggccaggcg gttccaggta  20820
cctgacgagg actcggccga gctggtcttc ctctcgctgt cgctgatgtc ctgtaagtcg  20880
gacagcaggt ccctttcttc cattttctct tcttttactt atgagataaa ccataaaggt  20940
gaatttgggg aaatgttttt aaacaaacaa gctaccacca ccccaaaact agtgcctttc  21000
acgtaacgat taactttgct tggtcggaaa ccagctcatc cacagacgct ggaagccact  21060
tctctaacgg ggccagtggc gaatgtccca gcggataaac acacgtcctg tgtcctggcc  21120
gcacacagac actcacggtc cctctcacga cacgagagga cttcagccag cacatctctc  21180
actttcttct gaagcggtta cttagctggg ctttaaatga atcctacaca cttatgccaa  21240
acatccccca gaaaagactc acactgtgct ggcttctgcg caggcgccgg cctggcctca  21300
cctggcttcc ggccgtctcc caactcgaac cgctcccgcg gcggccgagg cgggctgcga  21360
ctccagtggc tggctttcac tttgtcgctg tagtcctctc tcatcgttcg gtgatgtgca  21420
gacactggcg cgcagggcag agagggagat ggcactagca gcactgcctt cctcaaaagg  21480
ccccacccgg cacagctgcc tcgtctccca cacccgcacc tggcagacac acccacagcg  21540
tgcacagggt gctgacagca tcggggtcag aggccagagg tctcccagga agcccaggga  21600
gaaaaagctc caacctggag gccgtgagcc cgaggaccca ggtggacctt ctagactgat  21660
cttcactggt caaaaaggaa ggggcgggag aagattctgg aaagatggag taggaagcac  21720
tgggaatcag tctccccacc gagacaacac ttgcatcaca ggatcaggcc tgtgcaacta  21780
ctgaggtgct ctggagtcta ctgaaggttt gcaacttcag gggaatctt ggagagtaaa  21840
ctgtgattca ttaatcaacg tcaccgcttc gcacattagt ggctcccacc tcactccccg  21900
ctggcaggca gcagcctgca tgcagctcgc cggacccagg tgggcagacg gacacacaca  21960
cccgaggtca gtgtgatgac tgcgtgtccc accccagagg catgaagagg cagcagccac  22020
ggccaccccc aagctgaagg tacttccagg gcatgagcac cacgtccccc gttgcccccct  22080
tcatttctct ctattccccc tttaggaggc agacacttca ggacaagaac attaaaaaca  22140
tctgtattga cgggaacgtt aaaaagtggc tgcacgtgac caggaaaagg ctcaggctca  22200
gaaaagaccc gtgaagaccc tgagtttcca caacaggccg accccacaga cacagcccag  22260
cacaaccaaa acaacaagtg cacacccttg agtggggacc aggaagaatc acatcatgag  22320
aatcaaatgt ccattttttt gactaagaaa aacacaagag aaacaaagaa acaggacagt  22380
```

-continued

```
atgtcccatt cagaggggaa aaaaagaagc caacagacac ggttcctgaa aatcacctga  22440
cggtagatgt cccagacaaa gattttaggg aactgtctta aaccttcagt tcctcagaga  22500
acgaaaggaa gatgtggaga aagtcaagaa aatgacgcgt gaacacgacg gaaatatcaa  22560
cagagacaga agatccaaca agaaaccaga gagaaattcc agagctaata agtacatgct  22620
cacaatagac actaaaaagt aaatattcac aacagaaact cacaggcaga tgtgagcagg  22680
cagaagaaat aatcggtgag cctgaagaca ataaaatcac atcgtctgag gaaaagaaag  22740
cagaagagac tgaagaaaag ggagcagtgc tgagcggcct cggggacccc aacagatctg  22800
tgggagccca ggagggagga gaggagcaga gagggtatct gaagaattcc tcaaaacccc  22860
cacattggat gaaaaccgta aatataaaca ttagagaggc tcagtgaact ccaggtagaa  22920
tgaagtcaag aggcccacag gaaaacccat tattaaacag ttgaaagcct aaggcaaaga  22980
gaatcttcaa agcatccaag ggatcctcaa ttaggtcatc agattaaagc atccaaggga  23040
tcctctataa gatcatcaga tttctcatca gaaactttgg aggccagaag acaatgggct  23100
gaaatagtcc aagtgaaaag gaaaaactgt cagctaggca tgagggttcc ttgagcccag  23160
gaattcaaga ccagcctggg caatacaggg acaccttgtt tctactgaaa aatgagccag  23220
gtgtggtggc acacgctacg cctgtaggtc ccagctacgc gggaggctga ggtgggaaga  23280
tcacttgtgc ccaggagttc gaggttgcag tgagctatga tcgctccact gcactccagc  23340
ctgggcaaca gaagaagact ctgtctcaaa acaacaacaa caaaattgtc aaccaagaac  23400
cacgtatcca gcaaactttc cttcaaagat gagggagaaa tgaggatatt ctcagataaa  23460
caaaagcaga gggagttcat tactactaga cctagacctg ccttgaagaa taagctccag  23520
ggagttgtgt ggggtgtaag gaaaggacgc gagacagaaa ccggaagctg ggtgaagaaa  23580
taaagatctc cattaaggtg aggacgtggg tgactataaa agctcgtact ggccggccgc  23640
ggtggctcac gcctgtaatc gcagcactgt gggaggccga ggtgggtgga tcacgaggcc  23700
aagagatcaa gagactattc tggctaacac ggtgaaaccc tgtctctact aaaaatataa  23760
aaaaatagct gaacatggtg gcgggtgcct gtaatccctg ctactccgga ggctgaggca  23820
ggaggatcac ttgaacccgg ggggcagagg gtgcagtgag ccgagatcgc gccaccgcac  23880
tccagcctgg gggacaagag caaaactctg cctccaaaaa aaaaaaaaaa ggcaggggcg  23940
aaaagcaagc accggaacca agcgcccgcc tgtgacagca agtgcccagc accaggggc   24000
agcagacacg cgtcccgccg agcacagctg cccaccgcgc cgcctacctt ccctgcgggc  24060
ctcccgctcc ttgcgccgct cctccgcccg ccgctcgcgc tccttctgct cccgctgctc  24120
cttctgctgc tcccgcatct tgcgctcccg ctcccgcttc ctttctaact gctccaagcg  24180
gtccctgaag aggcacacgc catcattccc cctaaacaga agcttgctta tcgcgttttt  24240
gtccacattt gtaagctggc tttctacgta attcaatccg tgaagttttt ttttcatttt  24300
tttattttat tttctttgag acggagtctt catctgtccc ccaggctgga gtgcggtggc  24360
gcgatctcgg ctcactgcaa cctccgcctc ccgggttcga gcgattctcc tgcctcagcc  24420
tcccgagtag ctgggattac aggcgtgcgc cctgtactcc cagctaattt ttgtattttt  24480
agtagagacg agggtttcac catgttagcc aggatggtct caatctcctg acctcgtgat  24540
ccgcctgcct ccgcttttca aagtgctggg tttacaggcc cgagccaccg tgcccagctg  24600
ccatttccaa ttctaattaa taaatgatcc atttctttcc attcgatcgg tgtttgcttc  24660
atggattttg ggctctgtgg ttagatgcat tcacatgtat cattgctgta tcttcctgct  24720
```

-continued

```
gtattggcct gtttctggct gtgaagtcct tgctccttct tgtttctagc tttttttttt  24780
tttttgagac agggtcttgg tttgtcaccc aggctggagt gcagtggcgc aatctcggct  24840
cactgcaacc tccatctcac gagttcaagt gattctcata cctgagcctc ccgagtagct  24900
gggattacag gtgtgcacca ccacacccag gtgatttttg tatttttact agagacaggg  24960
tttcaccatg ttggccaggc tggtttctaa tatttcttaa catctgtttt gtctggtatg  25020
agtacagcca ttcaagctct cctatgacag ctgatgtttg tacgctgcgt cttttcctgt  25080
tctctagcag acagcataca gttagatctt gtttttctat ctgataatct gccctgtctg  25140
tttggggcac agagaccttt cacatgtcat ataattacac gtacagttgg atttactttc  25200
cttgctttgt tgtgtctttt ttattcttcc ctttttgatt ttaaattaca tacgtttagc  25260
ataccatttt aatttatttg tactttttag aacactaaga aaacaacttt cttagtggtt  25320
gctctaggga tcaccatatg cctcatgata ctagctcaag tccagtacaa tataaaactg  25380
ttgtaacaca gcttcattcc ctgtcttctt tgtgcagtcc atttatgcca cataccacga  25440
caacagtgta attattttac acaatcgtag ttccagtaaa acctaagatg tgaggagaga  25500
tatttacagg atattgacgt caacctacac ttgctatctg cagtgcctgt ccttccttcc  25560
tgaggattca agttaccgtc tggtgtcatt tctattcaac ttgaaggtct tcctttagta  25620
tttcctttaa ggcaggtttc gccaacaatg aatcccacca gtctctgctt ctcagggaat  25680
gtcgttcgtt ccctttcact tgtgtagaac agttttgatt cctggctgat ggttcttctc  25740
tctaagcagc ttgagtatgc cactccactg ccttctggcc tccattgttt ctaagaagtc  25800
agtggctggc ggtattgaag ctcccctttc atgggatggg tcattcttct ctgagccctt  25860
tcaacatttt ctctttggcc tttgccagtt tgactatgat gtgactttgc atttattcta  25920
gttcaaactt cctgtgctct tgaatgtgca tattttttaa ttaaaatttg gaaagttttt  25980
aaccattatt gtaacaaata tctttcctct ctcctggaac ccccattcga cgtgctttgg  26040
tacagcagat gttgtaccac gggtttctga ggctctgtgc atttttcttg tttttttctc  26100
tctgttcttc agaatggata atttctactg ctccatccac aagttgtttc caagccttta  26160
ctaaattcaa catctggaca ctcaagacag tttctactga tgatgttctt cctcagtacg  26220
ggtcacactg tcatacttct ttgtatttta gataatacat ttgtagcaat tctggattct  26280
aagttttccc tttcgttgtt accaccaagg cctgtctggt tgtccgtgaa atccatctcc  26340
ctcatagctc atggccaccc cgttccttcc cacatgccta ttttaatttt caaccttggc  26400
ttcctagggg tcaccaccat ggctgcacag cttagcaatt agccagcact ggaaaaaggc  26460
tgggctcaaa tacctcgagc acagtaaggc ttccttggcc cacggctgtg tgtggacagg  26520
gagcacactg aacgttcagg cgtcattcgc atctgtggcg gcttctattt tctgctaggt  26580
cctttcacgc agctgcatcc tcagggctgg tcacaagtgg gtggcggctc gagctctctc  26640
cagtctctgc tgcacgtctt tggcgggatc acagctgctc ccaaccacac tgtacttcat  26700
tctagcagac ctcttggcct tttcctccct ccactgagga tgctggtggg caaggccact  26760
gcccactgct ctaaacggag taaccccttc caaggcagca aggaaactgc aggtcctgca  26820
gctgccctgt cccagtggaa cctccgtgct tccaagtgca gagtggaagc agtaaaggga  26880
gcagctctca ggccagaagg tcagattctt actgctttta cccacagctc agcagttttc  26940
caagcatcag tgcttctcag attatcctta tcagtttcct ttttgtcaga gacaaggtct  27000
ctctacgttg cccaggctgg cgtcatgcgg tcctctggcc ttagcctccc acgtagcata  27060
tgctaccaca cccagttctg gattggctga tctgaatcgg ccctacccag aagtctgccc  27120
```

-continued

```
ccaacaattt ttgttcattc actctcctgt ctttaccttc tgggaaatca atatgacagc  27180
ccaaatttca tctaccaacc tccacttcta tcccaagctc tactctcgtg ggacaagaca  27240
cactcaatgt ctggcacagg gcgtggcata catgaatgtt tcacacacta acaggaacta  27300
ggccaactga aaccttgctc acccagcagc ggtctcggac cttgacccct gggcctcagt  27360
gtctcccaca cccttcggca tcaacaagaa ccagcgccct ctcatcatct ttacatgctg  27420
tgtacccagc cctggctgct ggcaaacatc gctgcacacg cccttccgct tcagactcct  27480
ctcttcctgg agcagcttgc aagctttctg tggactcact ctgaaggcgg agatgggcct  27540
gctcgcacct ggcctacagc ctttttcctg gttcacagaa cagatctggg gctacaccga  27600
tgttctttct tgggaatctg gctcataaag gggaacgaat atacagacta atggccagga  27660
gtcctaggag tccagtgtcc cgatttccag actgtttcaa ggtttttggg atctcccttc  27720
tcctttttt gagacagtct cactctgtca accaggctgg agtgcagtag catggtcata  27780
gcttactgca gccttgacct cccaggctca agggatccaa ccacctcagc ctcgtaagtg  27840
ctggaattct agcgtgagcc actgcgcccg gcgggacgtg cagatttctg atcccttcat  27900
tgtcttccct caatcaaatc acacccgttc ttacttccag atgcagtgaa aactcactcc  27960
ctcaggacag ttctcttggt cagcctcgtc cagcgttcac tgtgctgttt ccatgtctac  28020
cacttctgca acaaatgtga cttctattgc caaattcttc ttcattgctg tgacaggaca  28080
cactaccacg gccctttcat aaagtcctca actgacccag cccactcacc tttctctcct  28140
ggaatgctcc cttgccattt cccttctctt ctgtctttcc cattcccggc gagctttatc  28200
ctgttcttct cgatgtcgtt tccgacgttc gtgctctctt tctttcactc tagcatgctt  28260
ccctaatgag aaataaagtg tcatgcaaag aaacctcact tcaaaaattt cacgaggccg  28320
ggcacggtgg cttacgcctg taatcccagc actttgggag gccgaggcgg gtggatcacc  28380
tgaggtcagg agttcaaaac cagcctggcc aacatggtga aaccccgtct ctactaaaaa  28440
tacaaaaatt agctgggcgt ggtggcaggc acctgtaatc ccaggtacta agggaggctg  28500
aggctgtaga atcacttgaa cctgggaggt ggaggttgcg gtgagccgag atcgtgccac  28560
tgcactccag cctgggcgaa aaagtgagac tccatctcaa aaaaaaaaaa aaaaaaaaaa  28620
aaaaaaaaaa aaaaaatcac atgaaaatga aattaaatca agaacattaa atatttaaat  28680
aatgatgtta agtaatccta atcttttttt tttttttttt gaagagacag ggtctcacta  28740
tattggccaa gctggtcttg aactcctggg ctcaagtgat cctccatcct tgtcctccca  28800
aagtgctggg attacaggcc tgggccactg cacccagtcg aataatcatg attttatgtt  28860
aaataaaaaa ctttgaaaat agaaaactat ctgcagtaag cgtctaatta tgaagaaaga  28920
agaaaaaaga aaaacaattc tgctatcaca gaagagaatt gtaatattca tcttttaaaa  28980
attttctata ctgaataaac tataattatc agttttataa tacaaaaacc actcttcaca  29040
aagactacag aacaaagctt tgctatcagt gggcttctcc actgtgcaat gaagccacat  29100
taattaatca agcgtattta taataatgag atttcaatcg ggctccaggt ccaattttcc  29160
taacacccgt aagaatctcc tgatgttggt acgagatcaa actgctcaag cctaacccat  29220
tctttggact tgagcaaata cccattttgg ggtgtgtttt tctcctatac ttgttgaatt  29280
caggtcattt taaatgtaaa caaactgctc ccaaacaata taatggggga gagaaaaccc  29340
cagaggaaaa atggactagc cattctgaat ggtctgtgac acacgcacgc tttcagctag  29400
agtttgctct ctctggtttt cggtctgtga cacacgcatg ctttcagcta gagtttgctc  29460
```

-continued

```
tctctggttt tcggtctgtg acacacgcac actttcagct ggagtatcct ctctatagcc  29520
cctctgaacg gtctgtgaca cacgcatgct ttcagctaga gtttgctctc tctggttttc  29580
ggtctgtgac acacgcacgc tttcagctag agtatcctct ctatagcccc tctgaacggt  29640
ctgtgacaca cgcatgcttt cagctagagt ttgctctctc tggttttcag tctgtgacac  29700
atgcatgctt tcagctagag tattctctct atagcccttc tgaatggtct gtgacacacg  29760
catgctttca gctggagttt gctctgtctg gttttcggtc tgtgacacac gcatgctttt  29820
agctagtttg ctctctatag cccttctgaa tggtctgtga cacacgcacg ctttcagcta  29880
gagtttgctc tttctggttt tcggtctgtg acacacgcat gctttcagct agagtttgct  29940
ctctctggtt ttcggtctgt gacacacgca tgctttcagc tagggtattc tctctatagc  30000
ccttctgaat ggtctgtgac acacgcatgc tttcaggtgg agtttgctct ctctggtttt  30060
cggtctgtga cacacgcatg ctttcagcta gagtattctc tctatagccc ctctgaacgg  30120
tctgtgacac acgcatgctt tcagctggag tttgctctct ctggttttcg gtctgtgaca  30180
cacgcaggct tttagctaga gtttgctctc catagccctt ctgaatggtc tgtgacacac  30240
gcacgctttc agctagagtt tgctctctct ggttttcggt ctgtgataca cgcacgcttt  30300
cagctagagt ttgctctctc tggttttcgg tctgtgacac acgcacgctt tcagctagag  30360
tattctctct atagccattc tgaacggtct gtgacgcacg tatgctttca gctagagtat  30420
tctttttttt ttttttgaga cggagtcttg ctctgtcgcc caggctagag tgtgcagtgg  30480
tgcgatagcg gctcactgca agctccgcct cccaggttca tgccattctc ctgcctcagc  30540
ctccagagca gctgggacta caggtgcccg ccaccacgcc cggctaattt tttgtatttt  30600
tagtagagac tgggtttcac cgtgttagcc aggatggtct tgatctcctg accttgtgat  30660
ccacccgcct cagcctccca aagtgctggg attacaggct tgagccacca cgcccggcct  30720
tcagctagag tattctctct atagcccttc tgaatggtct gtgacacacg catgctttca  30780
gctagagttt gctctctcta tagcccttct gaatggcctg tgacacacgc atgctttcag  30840
ctagtttgct ctctctggtt ttcggtctgt gacgcacaca tgctttcagc tagagtttgc  30900
tctctatagc cctctgaat ggtctgtgac acatgcatgc tttcagctat tctctctata  30960
gcccttctga acggtctgtg acaccattat gctttcagct acagtttgct ttctctggtt  31020
tttcagtggt gctctgggga aggcagaaga gtaggaacag gaaagaaacc acacttgaac  31080
atgatgtcaa agaaagtaaa tgcttctgta ccccccttctg ctgaatggct atgatgccta  31140
catttttctt ttctctttc atcttttctg tgatgaactt tttctttccg agacatttgc  31200
tggggtggtt tgatggccaa agaatcatct tcttctcctc tgaaataaaa cacaacagca  31260
ctgcgtcatg cttgagaaag tgcggaaaag catcaggcta ttatgaggtt ttttcaaccc  31320
agaaaaatgc atgattcaga taggaacgaa gctgaaacat catttaaaaa attacattaa  31380
ttctccaact tcaggcatct tttttttttt ttttttttag acggagtctc gctctgtcac  31440
ccaggctgga gtgtagacac gcgatctcgg atcactgcaa cctccacctt tccgggttca  31500
caccattctc ctgcctcagc ctccggagta gctgggacta caggcacccg ccaccacacc  31560
cagctaattt ttgtattttt agtagagacg gggtttcact gtgttagcca agatggtctc  31620
aatctcctaa cctggtgatc tgcctgcctc ggcttcccaa agtgctggga ttacaggcgt  31680
gagccaccgc gcccggccta ggagtcttaa gattcagatg aaaaatgtaa gaaatcaatg  31740
ttttgtgcag atggaacgaa atgcctctca gaggacctgc agggggtgag gggcaggttc  31800
attagcttga ctgtggtgac agtttcaggg gcatgtaaaa atacatcaca tcttatttat  31860
```

-continued

```
ttaatttaat tttatttatt tatttatttt atttgagatt ggagtcttgc tctgtcgccc  31920
aggctggagg gcagtggcga gactctcggc tcactacaag ctctacctcc tgggttcatg  31980
ccattctcct gcctcagcct tccaagtaac tgggactaca ggcgcccacc accacgcccg  32040
gctaattttt tttgtatttt ttagtagaga cggagtttca ctgtgttagc cagggtggtc  32100
tcgatctcct gaccttgtga tctgcccgcc tcagcctccc aaagtgctgg gattacaggt  32160
gtgagccgcc acgcccggcc tgtatttatt tttttgagat ggagtctcgc tctgttgccc  32220
aggctggagt ccagcggcgc aatcttggct cactgcaacc tctgcctcct gtcccaggtt  32280
cgagcaattc tcctgcctca gcctccggag tagctgggag tacaggcgtg cgctaccaca  32340
cccagctaat ttttatattt ttagtagaga cggggtttca ccatattggt caggctgatc  32400
tgaaactcat gacctcatga tccacccgcc tcagcctccc aaagtgctgg gattacaggc  32460
atgagccatc gcacccggac ttattatttt tttcagacag aatcttgcta tgtcccccag  32520
ggtagaatac agaggcacaa tcttggctca ctgcaacctt tgcctcccac attcaagcaa  32580
ttctcctgcc tcagcctcct gagtagctgg gactacaggt gtacaccacc atgccaggct  32640
aatttttgta tttgtagtag agacaggctt tcaccagtaa ccctaggaaa gagtaaacct  32700
caatagttgt aacagcatgc cctgtcacag taatcctagg tcgtggctcg cacctgtaat  32760
cccagcattt tgggaggccg aggtggacgg atcaccaggt cagaagatcg agaccatcct  32820
ggctaatttt ttgtattttt agtagagacg gggtttcacc gtgttagcca ggaggctgag  32880
gcaggagaat ggtgtgaacc agggaggcgg agcttgcagt gagccgagat ggcgccactg  32940
cactccagcc tgggtgagca agactcttga gacaccgtct caaaaaaaaa aagagtacac  33000
ttcagtattt acaacagcac actgagcaca ctgtcacagt aaccctagga aagagtaaac  33060
cttaatagtt acaatagcac accccgtcac gtaaccctag ggaagagtaa acctcaatag  33120
ttaaaacagc acaccccgtc acagtagccc taggaaagag taaacctcaa tagttacaac  33180
agcacaccct gtcacggtaa ccttaggaaa gagtaatctc agtagtacaa cagctacaac  33240
acgccctgtc acggtaactc taggaaagag taaaccttaa tagttacaat agcacacagt  33300
tgtcacagtg accctaggaa ggactggcca ggccagggct gtgtacagtt gggtcttgca  33360
catctgtaca tccgctcacc tgtcttccat tgagtcttct cttctatacg gggagttcct  33420
tattgtgatc tccatgcagt gatctctcag ctccccctcc tcaagggaat cccgcttgga  33480
atcccggtca tcagactaag aagcaaagag aaagttaatc attttcttta taagtttttt  33540
tttcttcata gataaaagta tttttaatga taatcaaacc tgggcaacat cccaaaacaa  33600
actttcacat gtactctgaa tgagccagtg ttataaaata taaagaattt ttggccaggt  33660
gcagtggctc acgcttgtta atcccagcac tttgggaggc cgaggcgggt ggatcacgag  33720
gtcaggacat taagaccatc ctggctaaca cggagagacc ccatctctac taaaaataca  33780
aaaaattagc ttggcatgtt ggtgagcccc tgtagtccca gctactcagg aagctgaggt  33840
aggagaatgg tgtgaacctg gccctgggcg acagtgcgag attccgtctc aaaaacaaaa  33900
aaaaagctaa caaagtgagc acatgctatt ggaaaaatac tcaaagcaga gttgctacaa  33960
acctttaatt tggaaaaatt tcaatatctg tgaagcataa taaagtgaag tgcaaggtat  34020
gcctgtactc actaacatcc caaatgatgc tacaaatctt agcaaaagag gtactttgcc  34080
aatgcctctt accaaattac taaaaaggtt tcctgagtac attaccatgc aaaccaagaa  34140
agacgtaaaa tatttatatt aatttcaagg caagttccca ctatattaaa aatacttaga  34200
```

-continued

```
gatagtatta tgaatatact aataatgaac cgagaaaaat tagtccagtt ttgctaatga  34260
cttaacattc aacgtatttt attctccatg tatgctcaat ctagacacag ctttagtgtg  34320
ttaaatctgc ctttaatgtc aactgaatat tagaatacat tttgggctca cctgcgacat  34380
ttggaagtac aaaagaactt caccgaagaa gcgttgttct aatggaaaaa tgagggcaaa  34440
gaaattaaat ctcctttaag aaaaccactt acttaaaaaa atatggctta catttttttaa  34500
gcgttttatc tctgctttct cctcttgttc cttccttcgt ttcttttcct gaagaatttc  34560
atctaaagtt ttcactttcc aagagtcctt ttcatcaccc atttgagtta aaacactgca  34620
aaaagaaaaa taattcagcc tacatcagga cacagcaagc tatggtgctg aacacttgaa  34680
cctagtcact tttgagggat tcagaataaa tcctcattaa gaataagaag ttgtgcccgg  34740
cgcagtggct caagacggta accctagcac tttgggaggc cgaggcgagc agatcgctgg  34800
agttccggag ttcaacacca gcccgggcaa catggcaaaa cctcgtctct acaaaaaata  34860
caaaagttag cccagtgtgg tggcgcgtgc ctgtattcct agctacagga aggaggctgc  34920
tagaggcagg aggatcactt gaatcagaga ggtcaaggct gcaatgagcc aagactgcgc  34980
cactgcactc cagcctagat aacaaagtaa gacttggtta aaaaaaaaaa aaaaaaaagg  35040
taagctctag gctgaggcgg gtggatcaca aggtcgggag gtcaagacca gcctggccaa  35100
cacggcgaaa accctgtctc cactaaaaat acaaaactta gctgggcgtg gtggcgggtg  35160
cctgtaatcc cagctactcg ggaggccgag gcagcagaat cgcttgaatc cgaaaggcgg  35220
aggttccggt gagccgaggt cgcgtcactg cactccagca agaccccgtc tcaaaaaaaa  35280
aaaaaaaaaa aaaaaaaaaa aaaaaaacaa gaatgataag ttgtaagcca ggcaaggtgg  35340
cgagcgcctg tagtcccata tactctgcaa gctgagatgg gagaccgatt gagcccagga  35400
gttccaggct gaagtgcgct tgtgaacagc cactgcgctg cagcatgggc gacaaaaaag  35460
agtgatgggt tctgaaaaat gaccgcttga aatcaagtct cgtttctgtc attcttgtat  35520
ggtcttgggt aacgtaattc acctcagttc agtcttccgt acaaccagaa taacaacacc  35580
tacgtgatag tatcgatcgc ggattaaaga tcatccgttt aaaggctctt aactcaggac  35640
ctgccactca tcaaacactg cttttactgt cagaatctgc tagaaagacc gcttggacta  35700
cgtgaagcca ctagcacact ggacagctgc accttgagac cggggagatg ctccgagatg  35760
tgctcgcgaa caaggccacc tgacccgggc actgggctat ttcctcgggt tcagtcccgc  35820
acacttgagg ttcagcctgg cagacgttgg ctccagacag cgtttggacc cgccgcctcc  35880
accacccaaa gttccgtgcg ggatgagact gtccgcggaa gcgagggtgt cgctcgcccc  35940
cgggcccggg tccgccccgc tccgaggcct gctcggaaga aagacctcgg tgcgcagttc  36000
tcgtcgcgct cccacacctg gtccgcccag tcggaactca cccctacggg gccgcggccg  36060
gtccctgagc ctgagaagaa acagcaaccg gcgctcgcca gaagtatcct cacttcctgt  36120
gttgacgcct aatgatgata taatagccga cctctggccc agaactcaag acgacagggg  36180
ctcgctctgt gcggcacttc ctgtgtctgc gcgggatgat gacgcataaa acagcgcttg  36240
ctcaggtcca ggactccaaa agaaactgcg ccgtgagctg cacttccgac ttcggcgcgg  36300
gccggggcgc cgagcagagc gacgccgact tttggagcag tttgcgcctg cgcggaacgc  36360
gtggccggct tccggaatcc taccgggact tttccggtag cgaagcccgc gcctgtgcca  36420
aggcttgcga gcagaatgcc ttcgcgatgg acgcccgcat tccacccccct tgaccgctgg  36480
gacccctagt ggcgggtggg tggagcgcgc tccatttacc tgctggttac ctcgtgaggc  36540
gcctcaggtc tgtgtgtctt gtaaaggccg atctcggaat ttaactctga accttactca  36600
```

-continued

```
gaaacaaagc agggagagct cttacgatgt gattttattt tatttattca tgtatttact  36660
tttgagtcgg agccttgctc tgccgcccag gttggagtgc agtggcgtgg tcttggctca  36720
ctgcagcctc ctcccgggtt caaggaattt tcctgcctca gcctcccgag tagctggaac  36780
cacaggcccg cgccaccacg cccggctaat tttatattt ttggtagaga cgaggtttcg  36840
ccatattggc caggctggtc tcgaactcct gacctcaagt gatccgcctg cttcgtcctc  36900
ctaaagtgct gggattacag gcgtgagcca ccgcgccggg ccttttacaa tgtgattttg  36960
aagctgacac tggcagtggg tcctcaaagt gcagactcac tgggtatggt gcttccccca  37020
actcccaggg ccccactcca aacccatgga ttcagagcat tgcaggagaa gaggataaaa  37080
cgagcaatta attccctttc catatgtcag gttttcctct tgccttgaaa agtcacagaa  37140
aaatgcttta gacatctgaa tctcaggaaa caaacaatgg aagataaaca tccgcattta  37200
ctgggcctga aatgggaaaa tgaaagatgt ggcaagaaac tgacaagggc ccaagaaggg  37260
cgatgggtat cggaattctt ttcatcccgg aatgaaatgc tgcttgcttt gtgtacccaa  37320
gctctttttt tatttttatt tttttgagac ggagtctcgc tctgttgccc aggctggagt  37380
gcagtggcgc gatctcgggt cactggaagc tccgccaccc ggattcacgc cattctcccg  37440
cctccactcc attcgcccgc attaggctcc tgagtacctg tgactacagg cgcctgccac  37500
catgcccggc taattttttt tttattttcg gtagagacgg ggttttaccg tgttagccag  37560
gatggtctca atctcctgac ctcgtgatca gcctgcctct gcctcccaaa gtgctgggat  37620
tacaggcgtg agccaccgcg cctggcctcc cccaagctct taatgttgct tcctgagttc  37680
ttggtaactg gggaaatctc cctatttttt tatttttatt tttttttgag acggagtctt  37740
gctctgtcgc ccaggctgga gtgcagtggc gcaatctcgg ctcactgcaa gccccacctc  37800
ccgggttcaa cgccattatc ctgcgagcct cagcctgccg agtagctggg actacaggca  37860
cccgccaccg cgcctggcta attttttgta ttttttttag tagagacggg gtttcactgt  37920
gttcgccagg atggtctcga tctccttacc ttgtgattcg cccgccttgg cctcccagag  37980
tgctgggatt acaggcgtga gccactgcgc ctagctattt ttattttttc tgatagggag  38040
actcgctctg gcccaggctg gagggcagtg gcgggatctc cgctcattgc aagctccgcc  38100
tcctgggttc acgccattct cccgcctcca ctccattctc ccatcttagg ctccagagta  38160
gctgggccac catgcccggc taatttttttg tatttttagt tgagaccggg tttcactgtg  38220
ttagccagga tggtcttgat ctcgtgacct cgtgatctgc ctgccttggc ctcccaaagt  38280
gctgggatta caggcgtgag ccacagcacc ctgccctttt ttttgagaaa taagtctcac  38340
tgtgtcaccc aggctggagt agagtgacac aattttgggt aactgcagct tccacctccc  38400
aggttcaagt gattctcctg cctcagcctc ccgagtagct gggactacag gcgcccacca  38460
ctacgcccgg ctaatttttt tgtgttttta gttgagacgg ggtttcactg tgttagccag  38520
gatggtcttg atctcatgac cttgtgatct gcctgccttg gcctcccaaa gggttgggat  38580
tacaggcgtg agccacagca ccttttttttt tctgttttga gagaaagtct cgctgtgtca  38640
cccagactgg agtgcagtgg cacaattttg ggtaactgca gcctccgtct cctgggtaca  38700
agtgattctc ctgcctcagc ctcccgagta gctgggatta taggcgtgcg ccaccacacc  38760
tggctaactt ttgtattttt agtagcgaca gggttttgcc atgttggcca ggctggtctt  38820
gaactcctga cctaaagtat ctgcccacca gcctcccaaa gtgctggaat tatagtcatg  38880
agccaccgtg cccggccaaa aatctccagt ttacccttcc tttgtgaaat ctgttgagta  38940
```

-continued

```
cccaaatgca gccactcatg tcaaacccta acaaaatcga ccccagagcc cacgaggagg  39000
gggtggcctc gcacttgcgc ttgataggag ctgccacaaa ggcctttccc aaccagaact  39060
ttgggtccag ccacttctgt gaagagcctc tttgctagca atagccagcc ccaccggtga  39120
acaaagtagc atgaacacca gaggtccaca aggaagaaaa caaagcagtc catatttaac  39180
atttatttta ctttgctgag caagaatcat agacagctac taccacggct gcttcgtttg  39240
gacaaaaata accaggaggc atccacggga ttagttacac ggtatcaact taccaccaca  39300
gcagaatcaa cagtgactcg ctaattaaca gaaccgtttg ctagaaagca ctaatctagt  39360
tatataaata ctgaaatagg tcacatgcaa aacactataa acgttttgtg tgatgtactt  39420
ttagttctcc atagttttgt ttggtataaa ggaaatataa tttggctgtg acgtagactg  39480
ttgatgtaat tttcaagttt tcctgtatgg ggaaagttgc cctgactgtg gccctttttca  39540
aggtggagcc tccaacacca cgttggcaga ttcagactcc gtgaacagtc taaatgagca  39600
agtcagctga atgccacttt cagatggaag ggaaatgaga tggaaaacaa caaaaaagga  39660
ctgccaggcg gaacagtttc caaccgagtt ttcgttgagt gaggatccag cagccatcaa  39720
actcaaacat aggggcccgc agggaaactg gaggaaatac ttcagagaca gcaaagctga  39780
aggtttctgt gctctgaggg atccgagagt ggatgtccca ctcctgtatc ctcagccaga  39840
cacagaacta gccagattca ttagggaagc tcagatgctc tcattctata aagtaaggcc  39900
cccagcaggg cacgtacata cattgggaaa gaagaaaccc cttagtacca tgttggtcaa  39960
aggcaagaga gagaattcta tttccatctg gaatgtcatt cttgtttact tcttccaaca  40020
gtgaaatact tccaggcctt cgaaaggcca tcctttggac acatgtaaaa agctgtcttg  40080
ttggcccgtt attcccactg acccgtctga gtgatcaccc aggagcgcgg cggcagcaag  40140
cagagctcac cggatttggg acaaggattt taaaggcagc tacaaagctg agctctattt  40200
gctgatgata gtctctgttc agctgtttaa aatgactgtc tgactcacca tggtaatttt  40260
tcacaaatta aaaacacatt ttgggttgtg caacagtgtt ctcatctttc caggcaggca  40320
gattatttta atgctgttat acagggaatt gggactctcg gattttcttt tttaaccttt  40380
ttatgccttt cagtagggga agtttccttg aaagttagag agctgcaaat ctctaagtat  40440
caatgtaaag aagccgatga cccaattcgg aaggtggttc aagtgttctg tttgtttaca  40500
aaggcacaga ccacgaccat ggacacaccc agtggaagta accacacccg gtgtgttcct  40560
agaagctcat ctgtgacagt tcaacaagaa cttactattc tagaaaagta ttacacaaag  40620
ttatttaaaa aaatgtctgt acaatcgtta acacggccaa gccaggcctt gggttttgcc  40680
tcttggtgtc cagctgtgct gggaatgcca tgaagaccag cggctggaaa ctgacttggg  40740
catggagaag agactgaggg agagggaggg gacagcacga ctgagcaagg gcacagtgct  40800
ggctgcctca tgggctccag gctccttctg ccaggatgag gaagaggccc cagagcagcg  40860
ttacacagga aatcaaccta tttgctaatc ctttggaaaa acgtttgttt ctggtccaca  40920
aacagaaaat ccaaacagga tggcagctcc ttgtgagggt ggaggggagg gcaccagatt  40980
ctgtgcggct ggaaattcca aggtgctcag aaccaggcgc ctgcacctct ccttatgcca  41040
gaccacaatc ttcaaagagg ccggcagcca tattctcgat ggggaggtgg acaaggccac  41100
cctgggagtt gctttcaatc tgtcctcaca aatcaacaac tccccgccac ctccagagca  41160
ttttctaata gtgtttgttt ttgagacgga atcttgccct gttgcccagg ctggagtgca  41220
atggcacgat cttggctcac tgcaacctcc gcctctgggg ttcaaacaat tctcctgcct  41280
cagcctcctg agtagctgag attacaggca cccaccatca cacccagcta atttttgtat  41340
```

-continued

```
ttttggtaga gacagggttt catcatgttg gccaggctgg tctcgaactc ctggccttgt  41400
gatccgccat ctgcagcctc ccaaagtgct gggattagag gcctgagcta ccgcagccgg  41460
tcttctatta gtttttgagg aaagcagaaa aaaagaaatg gaaacccagg gaaagtcacg  41520
tgacaaaaca tcttcgcagc gcagtgagca cacacctggc ctgtcctcca cacacaggtc  41580
agcggtttta tagaagcggc tgaagcaggt gtagtagccc acgcctatat tctcgacact  41640
acaggaggct gagtgggaag gattgcttga gccgaggagt tcaagaccag cctgggcaac  41700
aaagcgagag cccagctcaa caaaaaaata gccaggcatg gtggcacgtg cctgtggttc  41760
cagccacatg ggaggctgag gtggatcact tgagcccagg aagtcgaggc tgcagtgagc  41820
caagatcatg ccactgtact ccagcctggg tgacagacag agcaagactg tctcaaaaaa  41880
ataaaaaggt tacttgtggg ttaaaaagcc tcacttcggt ccatcatcat ggcagacttt  41940
tttgagtagg tagaagttaa tgagtcagaa ttattgctct gtttctgaac gattttatct  42000
tcaggagggg ctatttttgt atttcccagg tgagaagcca aatggaaaac cagtgaagtg  42060
accatgggtg ccaaaggcct aaagagcagg cagggaaatg agactcggga ccactggagc  42120
cccatgctgc ctctgacaag ccctggagct ctgggtctca aaggctggct ggcaacaggc  42180
tgcaccgggc atgggaatcc gccggctgcg agattggggg taaagagctc agacatggtc  42240
agaagcctct gcctaacaca cggctccagt agccactcct caggcctcct gcgccctcgg  42300
gggtgcgtga cacaggagga tgagttgagc tggctggtgg ccccagtgtg ccgtactact  42360
gtcccttggg gagagtggga cagggtgggc gcctgacaca caccacgcgc cccagaaaca  42420
ttcagtgtgg acgtttcctt tttcagcaag gacggcgccc aggtaaacgc cacgtaaccc  42480
aaaccatcaa cactgcagcg tcctgcccaa ggctcacgtg gggaaccgga caggtgctag  42540
atgatgatag gaacggtggg ctctgaggga ggacagacag gctcacccca cggggacctc  42600
agaacagcct gcctcatact cagagtccaa aaaagaaaag gaacgtacac atctcctccc  42660
aagttaaaca cgagaggttt gtcctcaacc tcagggctgg aaaccaccac aggtaggagg  42720
ctgggcacgg gggctcggcc tgtcatccca gcactgtggg aggtcgggtg ctagaatccc  42780
agcactgtgg gaggccaggc acgggggctc acgcctgtaa tcccagcact atgggaagct  42840
gggcgtgggg gctcagcctg taatcccagc actgtaggag gccgggcgcc gtggcgcatg  42900
cctgtaatcc cagcactgtg gatggccgag gcaggcggat cacgaggtta ggagttcgag  42960
accatcctgg ctaacacggt gaaatcccat ctctgttaaa aatacaaata actagctggg  43020
tgtggtggcg ggtgcctgta atcccagcta cttggaaggc tgaggcagga caatagcttg  43080
aacgcgggag gaggaggctg cagtgagctg agatctcacc actcactgca ctccagtttg  43140
ggtgacagag cgagactctg tctcaaaaaa aaaaaaaaaa acaagaacat ctcccacaca  43200
ctcacagtgc ctttgtagcc ccagggaaag caatccctta agatcatttg ttgggtgaaa  43260
agggtaccaa gtacacagtg ttaggaccgt gcaaaaaaag ggtgacagga agtacccttt  43320
gcaaactttc cataatgtgt acttaattca ctgctcttat aaaatgaaat taaataaaac  43380
aaaaaaatac tactgaaaaa taattgggca acatgcggtg gctcacgcct gtaatcccag  43440
cactttggga ggccaaggca gacggatcac ctgaggtcgg gagttcgaga ccagcctggc  43500
caagatgatg aaaccctgtc tccactaaaa atacaaaaat tagctgggca tggtggcagg  43560
cacctgtaat cccagcttct cgggagactg aggcaggaaa atgtcttgaa cctgggaggt  43620
ggggttgcag tgagccgaga tcgcgccact gcactccagc ctgggcaaca gcgtgagact  43680
```

-continued

```
ctggctccaa aaaaaaaaaa aaaaaaagga aaaataattg ggctgagtgt ggtggctcat  43740
aattgcagtc ctagcgcttt gggaggccaa ggtgggtgga tcacttgagg ccaggagttc  43800
aagatcagcc tggacaacac agcaaaatcc catctctcaa aaaaagtaaa ataaaataaa  43860
ataacaaaaa acaaaaatta gcccagcgtg gtggtggaca cctgtagtcc cagctactca  43920
ggaggctgag gcgagaggat cacttgagca gggaggcgga ggttgcagtg agctgagatg  43980
gcaccaccac actccagcct gggtcacaga gcaagactct gtctcaaaaa aaaaaaaaaa  44040
gttttttttt tttgaaccac tgctaacaat cactaatgtt cactaaaaca ctaggcttca  44100
ggagcatttg gaaataattc ctgaccgcac aaagaaacat gctggtgaga gacagtgacc  44160
aagcccagga gaccaccatg agttccagaa aaagtgagag agagcggcca cttttcctgt  44220
ctcggagata cctcctactc aggacgcagg aagcatgggg cagggcagcg ccatggacaa  44280
ggcgactcgg tgcagggcct gcgggacctg caggtgagag gaagcacaag ctccagctcc  44340
tcagctgtgg aacgctgcgt gcgtggtgca cagctaccag ctcggatggg tatttgagaa  44400
tttaccgcac tgacttggac cagacggaaa gcagagaaga gggagagcta cacctgactg  44460
tccaccattc ccgccagccc caacgtcggc ttttcacttc atgtttgggg acaattacac  44520
ctcctcatga cagatcagaa gtttcagaaa aaaggtccgc tgatttccgc aacagggtat  44580
gaggtggcca gctgctgatg ccagctgcat ggactcctat acttgctggt aacataacct  44640
cattcctttg tatttgccac caaaaagtct ccagtctttt tttttttttt tttttttttg  44700
agacggagtc tcactctgta gcccaagctg gagtgcagtg gcacaatctc ggctcactgc  44760
aacacccgcc tcccgggctg aagtgattct gatgcctcag cctcccacgc agctgggact  44820
acaggtgcat ttcaccaggc ctggctaatt ttttgtgttt tagtaaagac agggttgccc  44880
atgttgccca gggtggtctc gaacccctga gatcaggcaa tctgcctgcc ttgacctcca  44940
gtccacctgg ctagtctcca gtctttaaat tgcacctttg gccgggtgca gtggcttgca  45000
cctgtcatcc cagcactgtg ggaggccgag gcgggcggat cgcctgaggt caggagtttg  45060
agaccagcct ggccaacatg gtgaaacccc gtctccacta aaaatacaaa aattagccgg  45120
gcatggtggc acgcgcctgt aatcccagct acttgggagg ctgaggcagg agaatcactt  45180
caacccggga ggcggaggtt gcagtgagcc gagatcaaac caaagaaatc cagctctggg  45240
tgacagagca agactctgtt tcgggaaaaa taaaatacat aggcagggcg cggtggctca  45300
cgcctgtaat cccagcactt tgggaggctg aggcgggcag atcacaaggt caggagatcg  45360
agaccatcct ggctaacacg gtgaaaccca gtctctacta aaaatacaaa aaaaaattag  45420
ccgggcgtgg tggcggacgc ctgtagtccc agctactcgg gaggcagagg caggagaatg  45480
gcgtgaaccc aggagacgga gcttgcagtg agctgagatg gcgctactgc actccagcct  45540
gggcgacaga gcaagactcc atctcaaaaa ataaaataaa atacataaac aaataaattg  45600
cagcttcatt caatctgccc agttacagaa gtggaaagaa gctgaaggat cctccccgtt  45660
tctagagctg caccgcatgg cacaggaagc agtggccaca ggtgtctgtt caagttcaaa  45720
ctgacagcaa tcagcttgaa ttccgaatct ggttcttgtt atattctcca catttcaagg  45780
gctcagaagc cgtatgtggc cagtggctcc tgcactggac agcccagaag agaccattcc  45840
attcctgcag acaaaactag tcgcagcacc ctgctattct agacagaaag cactcaattt  45900
caaaaacctt caaactcaga gacttctagt ggagatttcc ctaaatacct atttcacaca  45960
gtttacggtt tattttacag tttctcattt gttttttgt tttatttatt ttttttgaga  46020
aggactctcg ctcccatccc ccaggctgga gtgcagtggt gagatctcga ctcactgtaa  46080
```

-continued

```
cctctggctc ctgggttcaa gtgattctcc tgcctcagcc tcccgagtag ctgggattac  46140
aggtgcccag catcacaccc ggctaatttt tgtattttta gtagagatgg ggtttcacca  46200
tgttggccaa gctggtcttg aactactgac ctcaagtgat ccacttgcct tgtcctctca  46260
agtgctggga ttacaggcat gagccactgg gcccggccta tcgtttgcat ttcaaacagc  46320
atgggtataa aatagcctag taattacact gcatagccac agtcatcccc gtggaagaga  46380
atcacatgtg tcccttataa aaatacctag atttctggtc tcctttgtaa acaacctgga  46440
cacactcaac tcttgggaag ttcctctgct cacctgaaag tcaccgggga gattttcccc  46500
atgagggcgt acgccgtgac gctctgaagg tggaacagga ctccgtctgt cagaagcagc  46560
agcaccacgt cctggttgta gctgaagctc ttcccgctcc tcccgatcac tgggacgtcc  46620
tatgtggcaa acaaaagggt actctattgg tttccatttt ccatttacta atcatccacc  46680
acgaacaccc agcgccactc ctgcccagaa actgggtaaa gctgctgcca ctgaggacag  46740
ccctgaaaat gcctcgaggg gacagctgaa ctgtgcactc atccattttc tgtttttttgt  46800
ttgtttttat tattttttgc actaattaat tttcaccatg cagatgcaaa tggacaacaa  46860
gcacatgaaa aaggctgaac atcaccatca tcaggaaaat gcaacagaaa ccccaatgcg  46920
gggccgggcg tggccagtct ggccaacacg gtaaaacctc gtctctacta aaaacataaa  46980
aactaaccag gcatggtggt gggcgcctgt aatcccagct actcaggagg ctgaggcagg  47040
acaatcactt gaacccggag gcggaggttg cagtcagctg agatggcacc actgtacccc  47100
agcctgggcg acaagacaga gacttctctg ggctgccaga ggctccggaa gccgggtgcc  47160
tcaggccgtg gcagttccgt cactctccaa cgcctccccc acagacttct ttttgctaaa  47220
tggtatcaag attttctcgt tgttgtcagc aagagagttg gttttctaac atctcatcga  47280
ccatggctgg aggtcaaatc gatgttttaa acttgctgga aataaacggt tcctttcttg  47340
catggctcga tgagcaataa ggttcctctg tgtcattttg tttacgattt ttaggattgc  47400
tttttaaagc cggacacggc ggctgatggc tgtaatccca gcactttagg aggccgaggc  47460
aggaggatca cttgagataa ggagttcagg accagcatgg gcaacacagc gagaccccat  47520
ctctatagaa aacacaaaaa tgaggctggg ggtgctcata cacgcactga gggttgaccc  47580
tggtgttctt gccttcttag attcttctgg agctggagat gaactcggac ctcaaggccc  47640
agctcaggga actgattatt acagcagcga gggaaactga agttggtggt ggtgagaaag  47700
ttatcatggg caggtacagc agctcacgcc tggaatccca gcactgtggg gagctgaggc  47760
gggaagatca cgaggtcagg agctcaagac cagcgtggcc aacatggtga aaccccgtct  47820
ctactaaaaa tacaaaaatt agctgggtgt ggtggcacgt gcctgtaatc ccagctactc  47880
agggggccga agcaggagaa tcgcttgaac ccgggaggca gaggctgcag tgagccaaga  47940
ttgcgccact gcactccagc ctgggcaaca aagcgagact ccatctcaaa aaaaaagagg  48000
gccggctgtg gtggctaaca cctgtaatcc cagcactttg ggaggctgag gcgggcggat  48060
caacgaggtc aggagatcga gaccatcctg gctaacacaa tgaaacccag tctctactaa  48120
aaatacaaaa aattagccgg atgtggtggt gggcgcctgt agtcccaact actcaggagg  48180
ctgaagcagg agaatggcga gaacccggga gatggagctt gcagtgagcc gagatcgcac  48240
cactgcactc cagcccgggc gagagagcaa gactccgtct caaaaaaaga aaaaaagaaa  48300
aaggccaggc gcaatggctc acgtctgtaa tcccagcact tagggaggcc aaggcgggca  48360
gatcacttga ggtcaggagt tcgagagcag cctggccaac agggtgaaac cctgtctcta  48420
```

-continued

```
ctaaaataca acagaattag ctgggtgtgg tggcagacag ctgtagtgcc agctacttgg  48480
gagtctgagg caggagaatc gtttgcacct gggaggcaga ggttgcagtg agccaatact  48540
gagccactga actccagcct gggcgacaag gcgacactct gtctcaaaaa aaaaaaaaaa  48600
aaagaaagaa agaaagaaaa aaaaaaaaaa ggaagttatc ataatctttg ttcttcttct  48660
gccactgaaa taattccaga acatccaagt ctggctagta cgtgaattgg agaaaaagtt  48720
cactggtaag tatgtcgtct attgcttaga ggaaaattct gcctaaacca actcaaaaaa  48780
ggtgtacaaa aaataagcaa aagcgtccca ggatccacgc tccgacagct gcgcacgtcg  48840
caatcctcga ggactcggtc ttcccaggtg aaattgtggg caggagaatc cgcgtgaaat  48900
ggacacagca gctcacaagg gttcattcgg acaaagccca gcagaacaac gtggaacgca  48960
aggtccaaac tttttctggt atcgataaga agctcacagc caaggctgtt aattctgaat  49020
ccccagagtt cccagtttca attgttaaga aaaatgacta acgtatactc acagtgaaaa  49080
aacaaaaaga cacacaaaat acaaaaatta gctgggcatg gtggcacatg cctgaggtcc  49140
cagctaccca acaggctgag gtgggaggat tgcctaagcc tgggaggccg aggttgcagt  49200
gagtcgtgac ctcgccactg cactgcagcc tgggcgacag agcaagaccc tgtctcaaaa  49260
acataaaaaa aacaaaagaa aaaaaacaaa aaaaaaccag agttgacttt taggctttga  49320
ttttgttata atcacctaaa cgtgtgtgcg ggtctcaagt gcatgtgggg caagcccaac  49380
cccatcctgg accctcggcc tcctcccgtc cccaaaggca gacagacact tccctcggcc  49440
ttaagatctt gtcgtttctt aaataagcga acacgtgtgc acccccacac tccgttcaag  49500
atgccgcgct ctgtgggcgc ctctgctcct cgctggtttt catgcagcca cactgggtac  49560
gcgacatggg gctgacatgt cactggaaat cgcctgtgag tcattaagag gtgggagagg  49620
caggagcctg ggttgcagct gaggtcaggg gctggggccc aggacaggcc tgtggtggcg  49680
ggtgctgggg aggctgtggg gtgctggcac aggagggccc acggaccagg ggccacggcc  49740
gcctgtatgg tgctggccga aggcggcccc cgcccgtcct cttcggatca gtgattggca  49800
cctgcagtaa tcttgcttgc caggaatctg cccagccccc acctgtctcc ccacccagtt  49860
agggccacga gacacaaccc tgccctgacc tccgcatgcc agtgtgagaa cacctggcag  49920
acgccaggct ccaagacacc cccgcacatg tgaccgtgag agaagtgaag gcactgccag  49980
tgtgggcacc actctgagtg gtcctcgcgg cagagcccca tggcaggcag cagagacggg  50040
caccacggat ggaggcctgg gatggtgggg cgcaggcgga ggggtggggc ccagggggcc  50100
tcacctgtgt actcccccag aatcatccga gacatgatca ccgtgaagat gggggcggag  50160
ctcttcaccg tctcagcaaa cgaaaccgcc acatttttca ggctgaccaa acccaaaacc  50220
acagttgcaa acctaaaaat gagccaaaag caccatcacc ttagaacgag tctgtctgcc  50280
tgcacccacc gggcaggctc tccaaggggc tcgctcgctc ggttggcacg tcggcccctc  50340
tccgcccacc tcctcatcac caacatggtg cctggacccg cttctgtgac gctttaggtc  50400
gagcccccag gaaacggcac tgcgtccaat gggaagtgac ttctgccacc ccttgaaaac  50460
gtcccagaga caaggaggca ccctgtcctg agaccaccag cccggaaaga agctgactga  50520
acacacgtgg cagtgagagc cacgaagcca cattcatttg gtgtcctgaa atctggacag  50580
ccctggtgct tttataaagt ctgcactgaa aactcaccag ccagcagagt ccccgctcta  50640
gtaacgagag ggactttaca tttaaagaaa aagagacact caaccaaaac caggagattc  50700
tttacctcat cagacccaca aacagcatcg tcataaggaa gttgggtggg taggaaagcc  50760
gggccttgtg ctgatataaa cagcaaggaa cgagggtttt cacacacccg ataaccgtgg  50820
```

-continued

```
tggacagcat ctgcaccgca cctgcgggag ggagggggcc gaagacaaga gggagaatca  50880
cccctcccgt gcctgcagtg ggctccaccc ccggtctccc atcctgacct gggctccccc  50940
ggccctcccg ggtggttgct ggctgctccc tgtggggtgg caggtggccg gcttccaccc  51000
tgcccgagcc gccgcctacc tagcatgctg ggctcgcctc ccagcaggga caggatgtac  51060
ttgttgagga agagcgtgca gaagctgaag aagaaccaca gcgtgaggta gagcagcgcc  51120
cgcgagctcc acacacccaa gtctgactcg atgaccgtgg tctccgtgat ggtgacggtc  51180
agtacgttct catctgtgcc gccgtcgctc ttggcaaaaa caatcttctc acttcggtga  51240
ccaaacagag agccccagct gagaggcgac ctgcctttcg gcttctcttc ggagccagga  51300
accagctctt ccagtgctgg ggttttcacc gaggacgaca tgctgaagcc acagccacga  51360
acgattttac ctccaggctg ggcagcatgg gtcaccgtga ccgcccgggg gtggggccgc  51420
agcagggact ccgggcgcca ggaacgaggc caccagggcc tctcccaggc aaagcgtaga  51480
agcagacgct aaaatattaa gaaaaggaaa cacatcaccc gttttgaaca tttaatgtcc  51540
tcaaaggttt caaccaccaa tttaaaatca ctttgaaaat gcaattgggc cgggcacggt  51600
ggctcacacc tgtaatccca gcactttggg aggccgaggc aggtggatca ccttaggtca  51660
ggagttcgag accaccctgg ccaacatgac gaaaccccgt ctctactaaa aatataaaaa  51720
ctagcagggc atggtggccg gcgcctgtaa tcccagctac tcgggaggct gaggcagaag  51780
aattgcttga acccaggaga cggaggttgc agtgagccga catgatacca ctgcactcca  51840
gcctcagtga cagagtgaga ctctgtctca agaaaagaaa aaaagaaaat gcaatcgttc  51900
actgtccaaa gatttttagc aattgaatcc cgtttttctc tgcgcgtgtt ggcggatcct  51960
tgctcttgag agacggtctc ctggcacact tgactgtcgt cctggcagac ctggggctgt  52020
gggtccttca cgccctgcct ggcagctgca ccttctcgat gggctttgtg gctgccgctg  52080
ccgggtgccc aggactaatt ccatgctact ttcttttttt ttgagacggg agtctcgctg  52140
tgtcgcctag cctgaagtac agtggcgcga tctcggctca ctgcaagctc cgcctcgcgg  52200
gttctcgcca atctcctgcc tcaggctcct gagtagctgg gactacaggt gcccgtcacc  52260
acgcccggct aatttttgt atttttagta gagacggggt ttcacagtgc tagccaggat  52320
gatctcgatc tcctgacctc atgatccgac ctccttggac tcccaaagtg ctgggattac  52380
aggcgtgagc ctccgtgcct ggtcttttat ttttttgaga cagagtctct gtcgcccagg  52440
ctggagtgca atggcgcaat ctcagctcac tgcaacctct acctcccggg ttcaagtgat  52500
tctcctgcct cagcctcctg agtagctggg attacaggca cccgccacca tgcccagtga  52560
atttttgtat ttttatttca ttttttagat ggagtttcac tcttgttgcc caggctgcag  52620
tgcaatggca cgatcttggc tcaccacaac ctccgcctcc caggttcaag cgattctcct  52680
gcctcagcct cccaggtagt ggggattaca tgcacgtgcc accaaaccct gctgattttg  52740
tatttttagt agagacgggt tttcgccatg ttggccaggc tggtctcgaa ctcctgacct  52800
cgtgatctgc ccacctcggc ttcccaaagt gctgggattt acaggcatca gccactgtgc  52860
ccagcctccc ttttcttttt ttttttggc tgactcatgg gttagaattc tggattgggc  52920
aaacacataa acattttgta catgacgaga gccagatttc atcatgtgag tgaagcgaga  52980
tgcaaacacg aaaggaagtc cttcaaggca gccttgtagt gaaaaaataa aaataaaaat  53040
gaaaaaaaga ggctgggcac ggtgactcac gcctgtgatc ccagcacttc gggaggctga  53100
ggtgggcgga tcacaaggtc aggacatcga gatcctcctg gccaacacag tcaaacccca  53160
```

-continued

```
tttctactac aaaaaattag ccgggcatga tggcgcgtgc ctgtaatccc agctactcag  53220
gaggctgagc caggagaatc gcttgaaccc aggaggcgga ggctgcagtg agcagagatc  53280
gcgccattgc actccagcct gggcggcaga gcgaaactct gtcccagaaa aaaataaagc  53340
ttagaaacaa gaggctatgt agtctcgaga tagatccagc cctatgaggc acatgtcaat  53400
cacagaggga aagctatgca cgcacaaagc atgtgtgaat cagagagaaa gctatgcacg  53460
cacgatgagt agaagacaaa cacgtcctgc aaggagacgg aggcgcaggg agggggtggc  53520
agccgtcctc ccaagacatg aggacttcta gttcagtctg agaccttggt gcagggctgg  53580
gcgagtaaac aaatgcaaaa gaataaggac ctcgaggtcg ggcgcggtgg ctcaagcctg  53640
taatcccagc actttgggag gccgaggtgg gcgcatcacg aggtcaggag attgagacca  53700
tcctggctaa cacagtgaaa ccccgtctct accaaaaata caaaaaaatt agctgggcgt  53760
ggtggcgggc acctgtagtc ccagctactc gggacgctga ggctgagaca ggagaatggc  53820
gtgaacccag gaggcggagc tttcagtgag ccaacatcgc gcctttgcac tccaccctgg  53880
gcgactgagc aagaccctct ctcaaaaaaa aaaaaaaaaa agcaaaacag aataaacata  53940
cgtaggccag gtgcagtagc tcacgcctgt aatcccagca ctttgggagg cagaggcggg  54000
cgtatcacct gaggtcagga gtttgagacc agccttgcca agatggcgaa atcctactaa  54060
atacaaaaat tagctggaca tggtggtggg tgccagtagt cctaagtaca caggaggctg  54120
aggcacgagg atcgcttgaa cctgggagac ggaggcttta gtaagctgag attgcaccac  54180
tgcactccaa cctgggtgac agagcgagac tgtcttaaaa aaaaaaaaaa aaacaaacag  54240
gtctggtgta cgcagaatgg aggcaccacg aattgctgaa gaaggaaact ttattcagtc  54300
tatgatacca ggacagttgt ccatgctgcc aggcaaaaag aaaaactgga ttctgatctc  54360
attatcagta gacaaacagc gacaattagt aacactgaca cagccctgac tgtgctgctg  54420
gagggtccga agcactctct gcacagcggt gaatccgcac aacagccctc tggggaaggt  54480
gctgttatca cccacgtgag acacacgaag gaaagacacg gcttcgcagc agcagcgtca  54540
tgattcgaac ccaggcggcc tgctcttatg ataaacttaa atgtgtaaaa ctttatgctc  54600
aggaaaatat aagagaatgt cttcctgacc ctttttgggg taggacaata atttctctaa  54660
ccaaacccca aaagcatgac ccattaaaaa aagggtcagg tggactaact tggctaaatg  54720
aagaattctg tttcaccaaa gtacactaca aagtgggcca ggcgcagtgg ctcatgcctg  54780
taatcctagc actttgggag gccaaggtgg gcggatcact tgaggtcggg agctcgagac  54840
cagcctgacc aacatggtga aaccctgttt ctactaaaaa tacaaaaatt aaccaggtgt  54900
ggtggtatgc acctataatc ctggctactt gggaggctga ggcaggagaa ttgcttgaac  54960
ccaggacggg gaggttgcag tgagcccaga ctgcgccgct gcactccagc ctgggcaaca  55020
gggcgagact ctgtcttaag aaaaaaaaag gccagacttg tctcacgcct gtaatcccag  55080
cactttggga ggctgaggtg ggcggatcac ccgaggttga gagttccaga tcagtctgac  55140
caacgtggag aaaccccatc tctactaaaa atacaaaatt agccaggcat ggtggcacat  55200
gcctttaacc ccagctgctc aggaggctga ggcaggagaa tcacttgaac aggggaggca  55260
gaggttgtgg taagccaaga ttgtgccatt gcactccagc ctgggcaaca agagcaaaac  55320
tctgtctcaa aaaaaaaaaa gaaaaaaaat atatatatat atatacatat acacacacac  55380
acacatacca caaagtgaaa tgaacagcca caacctggca aaagatactt gcaacatgac  55440
aaaggattaa taaccagaaa gtataaagaa ttcctacaaa ccaattagaa aaacaggcaa  55500
aaaaaaaaaa atattggcgg ggcatggtgg ctcatgcttg taatcccagc actttgggag  55560
```

-continued

```
gccaaggcgg gcagatcacc tgaggtcagg agttcgagac cagcctggcc aacatgatga  55620
aactccgtct ctaccaaaaa tacaaaaatt agccaggcgt ggtggcaggc gcctgtaatc  55680
ccagccacgc aggaggctga ggcagcagaa tcacttgaac ctgggaggcg gaggttgcag  55740
tgagctgaga ctgcgcctgc tccagcctgg gtgacacagc aagactccgt ctcaaaaaga  55800
aaagaaaaaa aaaaaacaaa acaacatatt tcacagagaa gaatttatgt ttttggagaa  55860
ggagtttcgc tcctgtcgcc caggctggag tgcagtggtg agatatcagc tcactgcaac  55920
ctcaacctcc caggttcaag cgattcacag aggacaattt ctaaaaggca aataagaagc  55980
aggaagggtg catgctcctt ctctactgcc ctgtaacagt cattccacac ttaccacctc  56040
aaaacaacaa atgcttttga tgttggctcc tgtggggcag caatctgcgg gaagcttagc  56100
caggcacctc tggcttaagg tccctcctga agctgcagtc acaccatgga ccagggctgt  56160
gacctcatcc gaaggctcaa ctggggctga ggcccacctc tgagctcact caggtggacg  56220
ctggctgggt tcagttcctt gctggctata ggtggaaagg gcccccacca gtttcttgcc  56280
agcttctcca caggacgccc cacagcctga caggagcttt catccagcaa gctcatcagg  56340
gagtgggaga gagcagccag gacaggagcc caggcctttc tgaacctcat ctcagaagtg  56400
acatccttcc cttctgctgt ctgggcacag ctccccgggt ggagcccgag gactagaagg  56460
aaaagaaaac ttggatttaa aatgggataa agccatagga gctgctcgtc ccaccacagg  56520
aatctcaacg ccgggttact gacaaagcgt cactttgcac ctcgtccaac tgtgcagacc  56580
tctcctagcc aggcccctgc accagaggtt aagaatccgt gcccctggtc aggaagtcca  56640
ggtgggttca aacggccagc agggaatttc aggcaaaatg tgtcccaaat cttcaaacca  56700
cgccccagaa ctcagacctc cccctgggag ttcgtcccaa ggaaaccacc tgcaagaggc  56760
tcaggctgca ggggacactc cgcttccaaa acccggaagc tggagaccac acaagtgccc  56820
aacgccaaag gcaccccgtg gagggacgcc ctgtgccctc ccccgaccag gtgacccgct  56880
gcgccctaca catcttcacc aggaaacatc tgttatcgat gtggacgaag cgcagcctgc  56940
actcccagat ccgctcattt tcgttctgcc ctccgtttta cgattcgcct acactgaaaa  57000
tgcgtgagtg gagtggaaag ccttcctact cctgcctcag cgaccccttc taaaatactg  57060
cctcgtttgg cctgaaaatg tgatttgcag gcttcctgag caaagtagat ttcactccat  57120
taaagaaaaa aaaaaagaaa aggcaccgaa cggggctcgg ctgtcgggag ttttgcttta  57180
gtttttgcg tgttttgttt tgtgtttttt tgttgttgtt gttctttttg cggccacgca  57240
caccgcgttc ccaggcttca gggcgtgggg gtcgccgtgg actcccggac gtgaaaacgc  57300
ttaaagccag ctgggaaaac ccccaccagcg ttttccgcgc acagcgccag ccataggaaa  57360
ggacccccag gagcgaatcc gggcagggaa accccggacg cccgcacact cagcatcagt  57420
accggcaccc agcacccagc accgagcacc gagcacgcag caccaagcac cgatcaccga  57480
gcagagcacc ccgcacgcag aacccaccga gagcctgatg cagtctccgc cgcaggcata  57540
gcgctaggcc ccggcgcctt cacaacaaag ggacgctggc gggcggggcc taagaggtgc  57600
gcggtggagg ggccgggcgc gaggccgcgg agacagctcg gagctcggca ctggggagtg  57660
gcacagcgct ggcggatcca ggtgggcttc acggggcgcc cgcgggaccg gaaatgacgc  57720
gcagaaccct gcatcgggct cctcgctgcc ccgcgggcgc cgctcctcag tgccccagag  57780
ccacggagcc ggggaaacgc gccgcggccc acaacgcccc cgcggctgcc cgttggttcc  57840
gcccgagccg ttctactcca ggcagacggg aggagaaaca cggcgcgctc agcgtcccct  57900
```

-continued

```
gccccgttgg ttctgctcgg gcccttccac tgcaggccga cgggggtgga aacacgcagt  57960
tttttttttt tttttttta aggtctaggg taacacgggg cttttaagtg cctctccgcg  58020
gccgcctggt ggtccagccc gggccgctgc agtgcagcca cacggggagg gacacggcgc  58080
gccgagtgct ccgggcggcc gcacgttggt tccgcccggg ccgttccact gcaggcagag  58140
ggagaggacg acggtgcgcg tagtgcatcc ccgtggcccg ttggttccgc cggggccgtt  58200
ccactgaagg cagaaggggg gggaaccgtg gccccacccc ccgcggcagc ccgttggttc  58260
cgcccgggct gttccaccag cggcacttca gggcgggatc ggccagtctg tggaggcagc  58320
ggcctctaag ccccggaggg tttactgccc aggtttgggt tccaggaata agaaatccac  58380
tgaataggct taacttagaa gacacaaagg cgcctcctgg cggaagtggc cacgctccgc  58440
ccagcctgag ggaaagctgc tctgacagct gggcccggag ctgcgggggg cggggccgcc  58500
gcgcggggtg aggactcgcc tcagggcgct gattggctgg tggcgcgctc cggggcgggg  58560
ccttcgtatc caggctggcg tcggggctgc cgcgggacat ccggagcaga cacccgcggg  58620
cgcgcctgcg gccccgagga cccccggctc cggagcttcg tcgagcgttt tcctagcgtt  58680
actttcccaa ataattttca ggaatgaagt tacggctaaa gggctcttta gagattactt  58740
ttgggccggg cccggtggct cacgcctgta atctcaacac tttgggaggc cgaggccggc  58800
gcatcacgag gtcaggagct tgagaccagc ctggtatggc caacgtggta aaacgtcgtc  58860
tctactaaaa atacaaaaat tggccgggcg tggtggcggg cgcctgtaat cccagctact  58920
ccggaggctg aggaaggagg atcacctgaa cccgggaggc ggaggttgca gtgagccgag  58980
atggcgccac tgcactccag cctggcgaca gagtgagact ccgtcaaaaa aaaaaaaaaa  59040
ggaagaaaga aaattataaa atgaagtgaa attaacgcag tggagtgcca cctgcctgct  59100
gcctgagttc actatccaca cggagttcat aaatttgaga gcagtttaca aagtagattc  59160
tcctactttc caggaaaccc agaaatgtct ggtgatttgc ccaacagtct cagctgttgt  59220
ggtcagcagg gccgctgtgg tatccaaatg atttcaaaag cagatttata aaaagtactc  59280
cttgtttttt tttgagatgg aatttcgctc tcatcgccca ggttggagtg cagtggcacg  59340
atctcagctc actgcaacct ccgcctcccg ggttcaagtg attctcctgc ctcagcctcc  59400
tgagtagctg ggattacaga tgtgtgccct cacgcccagc taatttttat atttttagta  59460
gagacagggt ttcaccatat tggccaagat gttctccatc tcctgacctt gtgatctgcc  59520
cgcttcagcc tcccaaagtg ctgggattac aggcgtgagc taccccacgc ccggccttta  59580
tttttttttg agacggagtc tcactctgtc gcccaggctg gagtgcagtg gcgcgatctc  59640
ggctcactgc aagctccacc tcccaggttc aagagattct tctgcctcag cctcccgagg  59700
agttgggatc acaggcaccc gccaccatgc ccagctaatt gttttgtatt tttagtagag  59760
acggggtttc accgttgtta gccaggatgc tcttgaactc ctgacctcat gatccaccca  59820
ccttggcctc ccaaagtgct gggattacag gtgtgagcca ccacgcctgg cctctcaaag  59880
tttttatagc aaagccttac atttcatgag gaaccatgca ttttatttta tttttgagat  59940
gggggatctc gctactttgc ccaggctggg ctcaaactca gggctctctg gcctcagcct  60000
cccgagtagc tgggtctgca ggtggctgtc accgtgctgg gcctggggtg tgcgtattaa  60060
tgattttgga atagtgtctg gaagcctgtg tgccttcctc tcttcctctc cccagaagga  60120
cctcccacct cgtcctccca aagtgttggg attacaggtg tgagccacca tgtcccctct  60180
ctttgctatt ttgcctggga ggagtgtatt aataatttta attttaaatt tctttgatta  60240
tgttctagtt tgattattga tcatttactt cttagctatt tatattcttc cttgagtcat  60300
```

-continued

```
cggtttctgc cctttgacaa tttttctgtg aatgttttgt gttgattata tgagctttga  60360
ctgtattgag aacatccacg cattgtatta ttgcaactgt tttcctagtt gagaacatcg  60420
acctgctgta ttattgcaaa tgttttcctg cttgcatgta gtcatttgtt atgcatatta  60480
atgaatttct atccacatga cgtggagtca gttaggaatc agttaggacg ccctcgctgt  60540
gtgggagact gatgggtcca ggcgctgtgc aaaccccgcc tccaaagtgc atccttggct  60600
cactgggacc ttccgggttg tgctgctctt gcttcacagc ctctctgggt ctccctgccg  60660
tctgctgacc tcggggcagg gtctacccag gctgagcggc ccatgggctg tgggattcct  60720
ttcctctgcc ttcaggtcct ggatgatgta gaaggcagga aggaaagcag tcatggctag  60780
ctctgtcctg ccccccttcgg ggtccccccc ggcccacagg ctcctccttg tcccccagcc  60840
agcctcagtc tgggtctggg ctcccgctgg ggaggagggt gagacctgcc ggcccaaagg  60900
agctgaagtt tcccaagggg cgttgaggac agcagggaag tgtggggtgt gaactgaggc  60960
cccagagaag ggtctgtgcc aaggccccat gggtggggag gaagaaggaa gcgtccccac  61020
ctggagaccc agcctgcagg ccactcggcc acctgcgcag aagtagggga gcagcagccg  61080
ctcatgcccc tgcagtttgt cctcatcagc aggtggggaa actgaggccg gggagttctc  61140
caggccaagg tcactcacgg gcaagttccc gcagcctttg gaccctccat acacgtcagg  61200
gccgctcatg ctttcctggg cccttcactg gtttggagga agcttcctgt tgcccagagc  61260
gcactgcctg tctctgagtg tatgtgtctc agtggcgtcc atgtgtattt ttctctgtgt  61320
gtatctgtgt gagtctgtgt gtgtggtgtg tttgtgtctg agtgtgtggt gttagcgtgt  61380
ctcagtggcg tccatgcata tttttctgtg tggtgtgtct gtttgtgtgt gtgtgaatct  61440
acgtgggtgt ttgtccatct ttttgtctgg cctcctgtcc cctctgcaca gagcagctgg  61500
gtggggatgc tggtcctggg ggcttgtcag caggatgtgg gcgtggggca gccctgggtg  61560
aggcctgagt acaggcccca ggtgcctcct gcacaggggt ggctgagcca gctcctctgt  61620
ggctcccggg tccccaccgc cggtcactgg gcaccacctg tcctggccac ccactcctgc  61680
ccaccctgct ctccgcaggg gcctccttcc tctttcagct gtgcgccctg gttgtggagg  61740
ctcctaagga ggttgtggcc tcggtttacc acctgccttg gctccttggt gttgccagac  61800
cctgaaggca gcccatgccc tggctgagat ccttctgggg cgggatgtgc tggaagcagc  61860
tgaaccacgt ggtgatgtac cagctcctgc tgtcccctac atccccagca ccgccagcct  61920
tccctgggct cctccggccg gctcctctac cctgtacccg ccccaccctg ctaccacccc  61980
ccaaccagac ttccagctcc aggcagggtc gcagcctcct gggctcccag caggacaggc  62040
ctcacccaga ccccgcagga gccatgggac ttgggctggg tctttgggcc tggctgcagc  62100
ccctttggac ctgacctgag gagacaccct ggctgtggga ggcagggtgg gggtgccggg  62160
cccagcacag aggtgcccag ggtgcaggct ggcactggcc cggcagggac cgtggatgcc  62220
gccgtttcag gctcgaaaag gtttccatgc cccagagcct gagcccggca gcccccgagg  62280
atgtcttggg gactctgtgc tccccaaagc cgagaaggtt aggcttgacc cacagcctct  62340
tccaggccgg ggaggcagag gcgctccagg tcggtagggc ggggcccaca gcccagggtt  62400
tcacgtcccc aaaacggggc agggtgctgg aggcgcaggt gtccacaggg tggtcgtttt  62460
ggtctctcct ggacttgcac gcgtgtagtg cagactggct gccggcaaag ccctgagcca  62520
cattcatctg ggccttgtta ggacaacagg gacggtgcgg ggtggggggg ttgcggggcg  62580
caggaccacg tcagtggagg gagggaggcc gatatcggtg cccaggctgg gcccaggggc  62640
```

-continued

```
cagcgggtcc tcacctggct tgtggctgcc cctgttaggc agcccggatg gaggggctct  62700
tccagccctg ctggccccgg gaatgcaggg actcaattcc ccctggtctc agtggctctt  62760
ccgggagcaa cacagcctgc ccgagtcgac accacccctc gggtttgagt cccttctgtc  62820
taccccctacc cccgccaggg cactgccccc ttgcccggaa gaggcagcgg cacccccagc  62880
cccttgggga ggatgccctg ccggccccac actcggtgga tgggcatttt ggggctagga  62940
tttaatgggg gtgaccctgc ccgacccctc tatgttggtt ccacggcgtc agaagaaagc  63000
tgttattaac ccagcttatt ttctacaagt cttgtttatt gaaaggatct gaaaagcgta  63060
ataaggcttt caatgacatt taatacattt tcaagaaatt aatatgaaac attaaaattt  63120
acttcaaaaa tccaaagttt tctagatcat tcccatctca cgctgcttta gaggtcagtt  63180
cacaccttct gtgttcagat gagcggctgg aattctgaac actgccgtct tccagcccta  63240
acgctgggcg ctggtccctc tctcctaagc ccacggctgg gcttcccctg tgcccagggt  63300
catggcggac ttcaagccag gccggctgcc cagaatcaca ctcagggttt ttggacgctc  63360
aagtccacag atgctgaggt gcccagacga gggtgagcag ggagacacat gcctcggaga  63420
acgtgcccag gctgggccag gcggctgcgg gaagctcctc acgggcagag gagaacgtct  63480
tgtgccttcc ttatcgatct ccagcagatg agggcaactt cgtgtgcaaa actcagagag  63540
cagttactca aaaaaaagac acccgggcag cagtaaccag gacaccaggg tccgaccacg  63600
gcctccacac acctgtgccc gtggaagacg cgggcgccgg ggtaggcagc atccacgtgc  63660
tccacagctg ccggtgctgg gcaggctgga gactcacggg agaggcagga ggagaatcag  63720
cgtgttgagt ccctcgctgt gttagtgtga aaaattctca ttacagttgc aaataaaagg  63780
gatcacgatc actagccccg gaaaccctca tctcccggac catcaggatc gcactgaaca  63840
gaatggtccc ctaatggtcc ctgaggacag cgtcttgcag aacataaatg taaacattga  63900
atggcagacg actcccttcc ccttgaaatc ttcacaaaag tgtgtacgag aaagtatgta  63960
catcagcact tcagaaagtt taaaagagtc tctaaaaagt atatacagga tttaaactac  64020
cttcctggga gcagaagcta cgtgaggaat gtgtgggtcg ctggcgatgc cagccccctt  64080
cccgctgagt gtcccagact cagtgctggc ctcaagcggg gagggctgga tggcagggga  64140
cgcatccaac cctctccaga aactgagcag aacaaaaccg ccttgccagc cactggcaag  64200
accatgcttt caatggcgcc tccgccaggg gcttccctgc agaagtttta ggggaagagg  64260
tgcaggtcaa ggggaaaagc atggcagctc aaggaaggtt tttggctgag acatttatta  64320
tcaacattga aggacaggtc gagtcattct gactcctctg aatttcaacc gactgatttg  64380
cggaaaaata tcctggcatg gaaattgcgg cagctggagg ccgcgctcca gggacccacc  64440
gcggggtgtc agcaggacag aagcactccc agcccatttc tcacgcttct ttagaaatgc  64500
aaaaaaagtc agacatttta aaaaaacagc tgatctggac aaaaggcaga cccaggctct  64560
aacccagcta cagaaaggaa gtggccgtgc cactgagaca ggcggtcaca gacacacgca  64620
gattggtctg tccccagagg gcgcttggag ggcagcggaa ggattcgggc ctggataggg  64680
gcttgaccta gccctcctcc tcctcctcct cctcctcctc gaagtgggct tgcttcttcc  64740
ggacgttcca atgcaggcac tgggcgaggc tctcaaacca gtcgctcacg gggtcccgca  64800
cacagatgga ggggagcggg tagcatgagg tagtgatgct gatgctggga cgggagagca  64860
gcagcctgag ccagggcttc cagaaaggcc caccccccggc caagaaccct tcctccctcc  64920
ctccctggga atggccggga ctcttttcct gtggggccgg gcagcccctc cccgaggcag  64980
gcttgagcag tgccccatgg gtgctgggac agagccatcc caggtcctgg aggggacggt  65040
```

-continued

```
gcagggaact gacaaactct gccccagggc cctcaggggt gaggtcccag gaggtgggtg  65100
ggggtgggca gcagtgccag gggggacacc ctcaggcctc tgctggggcc aggcctgcat  65160
gtgccaccgt atgcgacccg ctgcccccag gacgggtgcc ccgactgtga tgctgcaaga  65220
cccagggact caggccctgt ggtgccctag gggacaagct gtgtctacag gccaaccgca  65280
agagggcagg cgctgcctgg cccggggagg aggttggcag gcagcgccca gcccggcatg  65340
cagcccacac ctgtctccat ggcggatctc ttgtctcttc cgtccatcaa aggacaccca  65400
tgctgtgttc cttgcttcag gtgacagcat gatctgaggg tcaagcaggg agaggtgtgg  65460
gcccccagct gtggggagga cgcttctagg cacccacccc tgagtgctcg ccagaggtcg  65520
aaggttgggc agctctgacc ctgccttgcg gacggtgcag tgcacgtcct acaggcaccg  65580
gcccagctca gcaccgccag agaccaacaa tggcagaaag cccctcagac ccgggccctg  65640
ggcaccttga tggacagaac tcgggcacca gcaagggaag gcttgcatct gagggggcac  65700
aggatggccc taggatgacg aggccgcgtc tgaggctgga gccagcatgg cagagcgggg  65760
tgctaggtcc cggctttgtg ttgcacgggg tcaaatgact cacaaaccgg aaaaggagtg  65820
tcgttggctc tgaccttcag ctcgacccct gcggggacca cgatgggccg gaaggacagc  65880
gagtgggggc agatgggcgt gatcatgatg gccggcacgt tggggtggat catggaggcc  65940
ccggccgcgg ccgcatacgc cgtgctgccc gtcggggtgg acacgatcac tcctgacagg  66000
gacaggcgca ggcgtcactc ccgcccgagg gacgctcagg gccccaggac agtgctgcgg  66060
gccttaccgt cgccctgcac cgtggtgatg aggtgtccgt ccaggtagac atccacattg  66120
gacaggtagg aggaggggcc tctgtcaatc accacctcat tcaggacctg gaggggcgac  66180
agcattgcac actcagggcg ggggatgccg cacggctcgc agacaccctc cgtctcaccc  66240
agccgggctc tccggaaggt cctcatccct gggaccgaag tcgcccccacc ctgggcccct  66300
caccgaggcc gaggcgcctc cactcacctg gtactgcatg gcctgcttcc cgacatccat  66360
gtccaggcct gcagcctgcg agccgttctc acccagccca ttgtgcacgg ccgtcttctt  66420
cccccggagc tccttcacca ccctgacctt cagccgactc cggagaacaa cagctgcgtt  66480
ccctgaggtc cagcaggagt cagagggcat gcatcaggga agtcagtggg gtcaggggcc  66540
ccaccccagg gaggccagtg ggagtcagag ggctctttct tctcccaagt tgacacactt  66600
ctgtgccttt ttctttttat tttgagatgg agtctcactc tgtcacccag gctggaatgc  66660
agtggtgtga tcttggctca ctgcaacctc tgcctcccag gttcaagtga ttctcctgcc  66720
tcagcctccc aagtagctgg aactacgggt gcgcaccacc acgcccagct aatttttgta  66780
tttttagtag agacggggtt tcaccgtgtt ggccaggatg gtctcatctc ttgacctcgt  66840
gatccgcccg cctcgacctc ccacagtgct gggatgacag gcgtgagcca ccgcgcccgg  66900
ccgacacttc tgtgccttct gagagtgaga atcagctcac ttctgcccaa cacacatggc  66960
agcttcaacc tgtgatctgc tgaaacttct cagtgtcagt aaaaggtttg aaccactcaa  67020
gatttagaaa tccctgaatc ttgaaacctt taaatgttgc tccatgcatc attaaatgaa  67080
aataaacccc ccgcaagcaa gcgagacagc agcgccatga tcagagctcc tgtgggctcc  67140
agaacattcc aactcaccct ctatcacctg agtaacttgg gactgaaagt tctcaaagct  67200
gaatggggtc aggaagccca gggagcccag gtggaaggcc atgaccggag ggacgctgcc  67260
ctgtgagccg acggagaggt cactcagtgc ccacgccgtg cacccccgca ccacccagct  67320
ttccagcagc acctcaggag ggacccagct ctgtggggac agcaccccga ccctctgcag  67380
```

-continued

```
gagggactgg ccatgtggac aagcggaggg ggacgtcgca ggccagggtg ggccgggcca  67440
ccagggccaa ggttggtgtg gggagctggt gaggaacaaa ggtggcaggg ctgagcggcc  67500
ccctgggcac ggagggctgg gggagctggc gagggcgggt gggaggcagc cttggggtcg  67560
gagcctcgcg ccccacaggt gctaatgggg agatggggag aaaagcaggg cgggctgcgg  67620
gcatttccgg tgtcaccaac atgcagtggg ccaagggcag agccagggtc ccccacacag  67680
cgtggcccta cagccccagg ggagagctgt gctgctgaga aaccaggaag aggagctcaa  67740
gggaggccca gaggggatgg gccagtaggc gaggtcgttt cccaggaccc accaccctgc  67800
gccactccct gctgtcccag gcgggcgctg gccaccccca gccgtagcac tgtgtccaca  67860
ctgcccctgg ccccaccgtc gcaccccacc gggctgccac catgggcctc agtgctggcc  67920
gctctaggtg actgctctcg tataaagggg tgaaaagcaa tggaagccat gcttgtgagc  67980
ccctcgttac gcagcaccta gactagaacc tggtgtgggt ctggaaatgt cagcgcttca  68040
cctggaaaag cgaggaagcg tacagcagcg tcccgtctcc ccccaggcag atgatgaagt  68100
ctatctgatt ggaaatgtca tcataatcta ggaaacacaa agcaaaacca agaagaggct  68160
gtcacacagt ggcccctctg tggcgcagtg cgcagacacc aatgacaagg gcaacagtgc  68220
cagaagcttc caatggggcg gggaactgtg ctggagaaac caaggacaga gctgctgaca  68280
gcccaccttc tcgaaaggta cagaatttct tcttcactgc cccaaagctt tcatcgctgg  68340
cgatggcagg gtcttctagc actttctttt ccacatacac gatcatgttc tcctggaagc  68400
aaagtgccaa cctgctcatt ccacctgcag accccaccct cctgcaggga ggttcccgac  68460
tcacgggcgc tgtggtcaga gacctggcat cgtggcctgc atgcccgccc ccccacgctc  68520
acgctgaaac ttcatcacca acgcgccagg aggaagcagg acctttaaga gatgactggg  68580
cggagggggc tccctctcag gaattgacta aggctgttat ttcaggagtg gctttcctgg  68640
gcgccgcaac ccccacgcct gctcttctga agagaagaca cagcaggaag gcccacgtca  68700
gatgtggccc cttgatctcg gacttcccgg cctccagggc cacgagccca ccagctcatt  68760
gttggtcacc cagtctggtg cttgccatgg cggcacacac aaacccagac acccggcaga  68820
tccccactca gtccccagtt ccagacaagc agccgttgcc cagcacttga ggtggttccc  68880
atggtctcac ggggcggtga tgtggatgga ggccccccca actccatgtg caccccaggc  68940
ccccttcccc cctgccccgc gtgcctccat gaggtgcgtg cagagctcct tgaacggctg  69000
cagtaggctg gcatctctca tcttcttgat gacaaggacg ctctttgggg acttgttcca  69060
cgtcagccgc tggctcgcgg ggtcctgaat gtgcctttag gggaggagaa aagagttcac  69120
accagctgcg atctccctct tgcggaaaag gtgtatgact tagaaaataa aaaaaaaaat  69180
ctttaaaaag gtgttttcac ctcccaggga aacgtgctcg gtggccacgg gctcacaggg  69240
cctagggtcg cgccacagag acagggtcag gggtcagtag ggtccggagt gaccacctct  69300
cacctgcttg gcccatcaca cgcaggctca ggcccacaac ccccacccgg gcaccacgct  69360
gacccaagtg cacgcaccac agcccttccc agcccccggc cacttgcctg cctggctcct  69420
cagtgacgct ggtggggcag aaatgaccac gaaagcccat ggctgggcca ctctttgctt  69480
gatgccctcc tcaggccccc acgaaaaccc aaaccagttg acatggtgac tctgtcccta  69540
ggatcctctg cacacagttt ctggccccac gggagcccag gacccctcaa ggacccgctt  69600
ccccccctgc acacagctca ctacctccct gcatgaacgg actttaacct cactcactct  69660
cacagtaaaa atcacaggtt taaaagtccg tggcagccct gacacagcca cccgcgcttt  69720
gctggctctg accccgacca ctgtgcccgg tgtttctcca caggcaggc ccaccccggt  69780
```

```
gggattccca ttaccacgtt agtcacagaa aacatcccag cccagaaccg ggaacacaca  69840
ccacggagcc tgctcctgtt cccagaagcc aagggagggc gcagcggggc tggccaccgt  69900
cgtcagcgct caccgcctat cctcagcccc aaaggacaag ttcttatacc accgcgccag  69960
ccagctagtt ccaagttgcc caatcgagaa agctgctgcc tgccatgcct cttcccagca  70020
gtgacttccc caggagtgtg accgtcccac taacaccccc agaaccacaa cacagacgcc  70080
gatggcagcc acagggccac agaccttagc ccatcgcttg tgaccttcgg aagctggtca  70140
gcactcaccc tgtgcaggca ttactgggag gcgtggggtc actcatgcca tcccctatga  70200
gctcagcacc tgccgggtca cacatgtggc tcgcgaggta gcccctgcct gctgggagcc  70260
ggccagtgtg tccacagcat ccaggccacg cttggcgaac acgcggccgc cccatcggta  70320
tggtcctgac tgtgcgccca cactagaagc ctaagctctt catactcaaa actcaaagca  70380
aaacacaatt gtgatgagac ttggtaaagt tgttgtaaaa gcaactaagt caaaagagct  70440
tcctacactt ataaaaatca aacaaaacaa aacagtttcc tcattggtca catggtcctc  70500
ctgcctaatc ccttctgaaa aaaagtcctc agttcagcag caaagaggcc acacttcagc  70560
tccctgctcc taactgagcc gggtgggacc aagccctctg ttcccgtggc ctcagacctg  70620
gccaagtacc cagcctccag cctcgcccca gcactgcgcc agccaccgct ctggcccgcg  70680
gaaccggctg ggccccaggg aaggcaccct caggccacag tcaggtggaa gggcgttccc  70740
tgcctcctag cccgctgcgt cactctgctt ggctccggcc caagggcgtg caggtggctc  70800
acggtcctcc ggcctggtca gccagcaaag cccccgccct gcacacggct cccccctgctc  70860
tccccgccaa cagtcaccac tgacccagtg gcctggccta cacccattcc agccctgagg  70920
ctcagctgag cccagccaga gccaccagca gcggcgtcgt acaccggccc aggcacccac  70980
cgctgtgtgt gaccacaaac cagcgcctcg acctcttcct gggtcacctg caaagcagga  71040
caccagccct tgcaggcacg cacggctgtg ggtactgcac ggagagggca gggggtggcg  71100
tgaagcttgc aggcacacac ggctgtgggt actgcacgga gagggcaggg ggtggcgtga  71160
agccagcatg gccacagcct ggcccgcctg gccagctcct actgagactg tctcacacat  71220
gggtggccac gcacactgtg acacacgggc actcacgcac ctccacaaca caggcccacc  71280
aattccctgg acaacaaaac aggaagcggg tgccctcctc accaggcgcc cccacagggt  71340
cttgctctgg actatcaggg aagacggaag ttcagatgca tgggaagccc tgcccctcca  71400
cagcggggat gggaagcggg aggttatgat cccagagaca cagagcccag agggggcgtg  71460
ctcccatggg ggtgccgaga aagctgcatg cccctcaagg ctgccccaca aacccaccgc  71520
ttcctcctgc ggggctgtct ggcctcgggc agctcgggga ccactgagta cgccctggtc  71580
tgagggctga ggcagaacat gcacctgtcc ggtgaccccg ccctggcccg agtgactgac  71640
ggctggtgaa ggcagcagct gagatgcgag tgacaaagga gtggctctgc caggaccagg  71700
aagtgcaggg agggcaccag gcagcggggg agaggcccgg tggggtgcca gggacacagc  71760
aagcacagga tggcgggaca gagccacggc ggggccggga gggcagtgga gcactctggg  71820
tcacccacgt ggctgctgtg cagggaaggg atggtgaggc cgcggcgagt ggtcaggagt  71880
ccacacagcg gagggcagcc gggcaatagt gcaggggagc tgcttggata ttttgggatc  71940
aaagtgacag aatctgcaga tggactggat gagggaaagc aaacaggggt cgggcccccc  72000
gcctcaggca tttggcagca gtgacaggtc acagacactc cgggaaccag tggcactgaa  72060
agggctgggc ctcaaaagca caagtgcgag tcacttccat cctaaggggc tccgtcagcg  72120
```

-continued

```
tctggagcag caaggccaac ccccgtcctg cctgggacgc acgctgccgc ggggcccaca  72180
ctttgcagag cagctcctcg gatgactccc ccgtggctcc tgggacctga acttcggtga  72240
cagcccaggg ctggggcctc cgtccctgct gtgcgccccc agcctccatg gcaccggtgc  72300
ctgtcagcaa agggccatgc agtggccgcc cccgtatcac acggccgcat tgcgctttct  72360
ggtcaacagt ccccagcagc ctgcgcgctg gaacactcgg cccttccgca tggtcctccc  72420
ttgcagaaag tgaagcatcc atgactccgt gaaggaggag gccctgaaga gagcccgttc  72480
tgcacagagg aagagagccc gttctgcaca gaggcctgag agctgaggca ccagtcccag  72540
aagcaaaggc ttctctgggg aagaggcaat gaggatgtct accaggtgca gaatacgact  72600
ctcagggctg gctgggagct cacttttttc tctggagaca gtcttgctct gtcgcccagg  72660
cggaatgcac tttgataatc acagctccct gcaatctcaa cctcccaggt tcaggtgatc  72720
ctcccgcccc agcctccttg gcaactggga ctacaggtgt gtgcaacgat gcctgctaat  72780
ttttgtattt ttctgagtct gagtcttgct ctgtcgccca ggctggagtg caatggtgcg  72840
atcttcggct tactgcaaca tctgcctccc gggttcaagc agttctctgt ctcagcctcc  72900
caagtagctg ggattatagg cacgcgccac catgcttggc taatttttgt acttttagta  72960
gagatggggt ttcaccatat tggccaggct ggtcttgaac tcctgacctc gtgatccgcc  73020
ccccttggcc tcccaaagtg ctgggattac aggtgtgagc caccgcagct gaccaatttt  73080
tgtgtttttt gtagggatgg gctttcacca tgttgcccgg gctggtctca aactcctggg  73140
cccaagtgat ctgcctgctt cggactccca cagtgctggg actgcaggtg tgagccactg  73200
cgcccagcct ggattataat tctttacaca taaaacacag atatcagatc gatcactgtt  73260
gcgtttttcc catgacacta tgacgggcct ccaggcagaa tgtgttgaca aactgaacca  73320
tcaaatagca aacgcaaccc accccagaat tctcactcac tcttaaagaa acaaaaaggc  73380
agccctgagg atctcatgtg gaagccgcca cacccacggg ctgtgacccg gtctccaggc  73440
cccggctcgc ctgccgtcca ctttctcaaa gccactggaa aagccacagc tggggagccc  73500
ccgctcggat gcctgcactc agggggttca gggaggacgc ccatgtggct ttttgtttaa  73560
atgacctaaa catgtacttc tcacatgaag tgctagaatc ttcctcaaca cagcgatccc  73620
acaactccac acacatcccg aggactcccc catcccatgg cccccggcac tcacatgatg  73680
gtctaggggt tctctccctt ccaagaaccc cccgtcctgg ggccccagca ctcacatgat  73740
ggtctggggg ttctgcagca cacaggcctt tggtccaaaa gtggtcaccg ggcatggccc  73800
atgaagagag cgtgtcctcc tgtggggaga gggcagtgtc agagccacca gggcctgaaa  73860
ccagacatgc agtgacagac acagatacag aggaggttac acggtaaggc atacatgcaa  73920
tttgaaagat gccaactcca tctgcccagc agccacacaa tagcccttgg aaggttctgc  73980
ccaggtccat ggctgcactg gagcggcacc tgtgaggagc acgcatgccc acgcgccgct  74040
cagatcatga cccaagccgg ggagagcttc agcccaaaca aggaaaatgc cagggccagg  74100
gccagcctgg gatcagaatt cctcagtgtc tccaggaccc ctctctagat ctgcatttgg  74160
gactcaaaac ctgagacaac atctcatctc taaatcgtct agattaaaat tctagcacaa  74220
atgttcactc tgaactcatg tcaataaaaa agacgtaggc cgggcgcagt ggctcacact  74280
tgtaatctca gcacttcagg aggctgaggt gggtggatca cgtgaggtca ggagtttgag  74340
accagcctgg ccaacatggt gaaacccccca tccttactaa aaaaagaaaa attagccagg  74400
cctggtggcg tgtgcctgca gtccgagcta ctcaggaggc tgaggcaaga gaactgcttg  74460
aacccaggag gtggtggttg cagtgagccg agatcgagcc actgtactcc agcctggctg  74520
```

```
aaaaaagtga aactctgtct caaaatgaat gaatgaatga atgaatgaat gaatgaataa  74580
aagacgccag atgaacggct caacaacttt cctagtgatt taaacatggc caggtcacag  74640
ttaaatcacc cagccagggg ctgtggcagc cgcacgcgtc ctggggagaa tgctgtcagg  74700
accgctgtgc tcctcagggt ccagcactga ggctgccctc gtcctaggtg cccgggagcc  74760
tcccagtccc ttcacaaact cagaaaactt gcacacagct ggccaggcaa cggcccaaca  74820
aaatcctcaa gtcccaatgc agaagaacgg ccttccgctg cctcgcaggg ccagacaacc  74880
ccaggagagc cgtggtgccc tgagggctgc tccacaggtg acacaggcgt ggccatcagt  74940
ggtcacggac ttgtttacct cagcctttta aaaattggta agtacaggcc gggtgcagtg  75000
actcacgcct gtaatcccag cactttggga ggccaaggca ggcggatcac gaggcaggag  75060
attgagacca tcctggctaa cacggtgaaa ccctgtctct acacaaaaat acaaaaaatt  75120
agccgggcgt tgtggctcac gcctgtaatc ccagcacttt gggaggctga ggtgggcgga  75180
tcacctcaag tcaggtgttc gagaccagcc tggccaacat ggtgaaatcc catctctact  75240
aaaaatacaa aaattagaca ggcgtggtgg catatgcctg taatcccagc tactcaggag  75300
gctgaggcag gagaatcact tgaactcggg aggcagagct tgcagtgagc ctagatcaca  75360
ccactgcact ccagcctggg cgacagagca agactccatc tcaaaaaaaa aaaaaaaaag  75420
aagaagaaaa cgaagtacat tacaaaagaa ttttacttac ttacgaactg aaaagattat  75480
tgcggaaaac aatgtttctc gaagtgggtg ttgggattta atgtttcctt cccaaggaca  75540
ggctatgctt gggcgtattt ggctacctcc tcccccacct caccctgaag gcgcctgtca  75600
ctcactatgg aggcgacctc tgacccaggg ctgctgtcat caggttcaga atgcaacaga  75660
aatggtgcat tatgccaaag aacccacagg aaaaaaaaat aaaaccccaa agcaattctg  75720
ttcacgcagt cactgcgctg gggtggcctg gaggtacagg acaacgaccc ccactgacaa  75780
cgaggcaacg aggcatctga gaaaggctga gtggtgacgt ggtgcctgcg ggatgaaggc  75840
agccaccagc gctcgtagcc tcctggctca ggcagcgact ctgtagacag aaaacgtggg  75900
agtagcctgt ttctccacgg ctgccaccac gtcagaggcg ctacaggctc tcccatctca  75960
ctgggtaaga caacatgctt tctaagacta cttttcacca aaaagccccc cttgcatttg  76020
atagtcgtga tccttgttag gcagcgccgg ctctggcaag cttccaccta aaactcacca  76080
catttaccat caccagaacc gagagcacca tccccaggca ccatcacagc tgtgcttgtg  76140
cggccaccgt catgcaaagc ccggggcgct gttgcccaag cagcattgtg caagggtgag  76200
cgctgtgggc actcttggca caggagggag ccacttgccc aacatgtgag agggctgggc  76260
ccgcccaagg ccacgctcat aactctgcct ccaccagccc tgctcacagt gcagaacccc  76320
ccagccttcg cctctcaaaa caagcagagc caagagggat gtcccctcac accccagtga  76380
cttctgtaga gcaaatgttt ccaggccagg cacagtggct tgcaccggta atcccagcac  76440
tttgggaggc tgagacgggc agatcacctg acgtcagggg ttcaagacca gcctggccaa  76500
catggtgaaa ccccgtctct acaaaaatac aaaaattagc cgggcatggt ggtgcacgcc  76560
tgtaatccca gcttcttggg aggatgaggc aggagaatca cttgaacctg ggaggcggag  76620
gttgcagtga gccaagattg cgccactgca ctccagcttg gggacagag cgagactcag  76680
tctcaaaaaa aagtttcctc tccaagtgcg cttcagtcta acatcaaggg tcagcgtagg  76740
cgccagttag atggttctgt gctgatacag acagatagag aaacacggtg gcaccctgtg  76800
cctgtgctgg cacctgggaa cgtgcgccag gcaggtgtcc atgggccagg atccccttc  76860
```

-continued

```
aagggcacag cttcacctgg gcaaggaccc agcctcacct tccggatgca tcgacgcaga  76920
ctactcagga gaattcttca taatcgtttt aagaaagaat attatgaaat cagacgagaa  76980
aaaaaagagg aaccatccct cccagttgta cctgaactcc ttggtgctcc ccagggcggg  77040
cgaggcagac aggctgcgag acttggcccg gccccggatg gggtggttgt aactccaggt  77100
ctcatcgccg tggcaggccg agcagcagta agcagccgcg tctggactca attccttatt  77160
catggtcatt ttttcttgtt ccatttccat tgtcaggaaa tgagaacttc ggtcagaaaa  77220
acactgatgc cttaatttaa taaaataaat aatgtaaata aagtaaataa atatgtatga  77280
aacaataata atttacacat acatatgttc catttcatca aggggaaaaa atggctgaag  77340
tccaatttac caaagtactt tgaaaacaga ctgtttccat tgcaaagata tttaagaact  77400
actctaggtt tttggctggg tgccgtggct cacgcctgtc atcccagcac tttgggaggt  77460
agaggcgggc agatcacttg aggccaggag ttcgaaacca gcctcgcctg accaatatgg  77520
tgaaatcccg tctctactaa aaatacaaaa attagctgtg gtgggcgcct gtagtcctag  77580
ctactcggta gactgaggca ggagaatcgc ttgaacccag gaggtggagg ctgcagtaag  77640
tcgagatcat gccattgcac tccagcctgg gtgactagag tgaaacttca tctcaaaatt  77700
ttttctgtaa aataatatta acaaaaaaaa ttgtttcaaa aaagaacaaa atagaaagtc  77760
acactgtgtg gccaggtgtg gtggctcatg cctgtaatcc cagcactttg ggaggctgga  77820
gagaaaggat cagttgaggc caggggttca agaccactct gggcaacaaa gaactcttct  77880
ctagcaaaaa aaaaattagc cgggcatggt agcccatgag cgagaccctg tcttaagaaa  77940
agaaagactc tggccaggtg cggtggctca cctgaggtcg ggagtttgag accagcctga  78000
ccaacatgga gaaacccccca tctctattaa aattacaaaa ttagctgggc gtggttgcgc  78060
atgtctgtaa tcccagctac ttgggaggtt gaggcaggag aatcgcttga acccgggaag  78120
cggaggttgt ggtgagctga gattgtgcca ctgcactcca gcctgggcaa caagaacgaa  78180
agaaactccg tctcaaaaaa aaaaaaaaaa aaaaaaaaaa aaaaaaaaaa aaaagacagg  78240
ctcttttctc gtaaacaata caacacatta atgagagaga aagtgtgcaa tttcaaatac  78300
cctagtccag aaaagctgtc aaataaaatt gaaccagcag atatgttgtg aactccatgc  78360
cttgcatcgt gaattcagcg ccaatgaaat atttaccaaa ctgaccaata ttaagcctca  78420
aagaaaactg gtgaggatag aaaacctcac ccttttttcc ccttttttctt tttcttttt  78480
ttttttgag acaggatccc acctcagcct tccaagtagc tgggactaca ggagtacagc  78540
accacgtcca gctaattttt tttcctttgg tagagacagg gtgtcttgct ctgttgccca  78600
ggctggtctt caattcctgg cctcaagtga tcctcccaac tcagcctccc aacacagtgc  78660
taggattata ggcatgagcc accatgcctg gcctagaacc tcatcttttt tttttgaga  78720
cagagtctca ctctgtcgcc cacgctggag tgcagtggtg tgatcgcagc tcactgcaac  78780
gtctgcttcc cgggttcaag tgattttcct gcttcagcct ccctagcagc tgggactaca  78840
ggcgtgcgcc accacgctca gctaattttt ttgaattttt agtagagatg gggtttcacc  78900
atgttggcca ggctggtctc caactcttga cctcaaatga tctgcccgcc tcagcatccc  78960
gaagtgctgg gattacaggc gtaagccacc acgcccagcc tagaacctca tcttctgacc  79020
acaatacaat aaaaccagga agagatagaa acaaagaaaa gccctcagcc acttggaagt  79080
ttctgaactt tctcttaagc aacccaggga tcaaagtgaa gatcagaccc aacatctgga  79140
acacccagaa gctggaggtg acataaacag gctgccaggg tcggttcaat cccatcaaag  79200
ctgggtcaca gcccatggga aaccatgaac tgagcattca agccaataaa gccagaaata  79260
```

-continued

```
gaataaaaca agcttcagaa gaacagaaga ggggccgtgc acagaaacaa taaaaatcac  79320
tcaacagagg ctaaacacac aaaataaagc caaacatacc ttctcattaa agaagataaa  79380
tcttaatgag gacaaggtag attctggcat taaaaaggat aaatgtgaca ttatggactg  79440
aatgtgtcct ccccaaattt attttttatt tttattttgt agagacaagg tctctctgtg  79500
ttgcctaggc tggtctcaaa ctcctgggct caggtgatcc tcctgccttg gcttcccaaa  79560
gtgcttggac tataggtgtg agccactcca cccagcaatc cccccaaatt cctacattga  79620
agccctaact tccagtgtgg ctgaatatgg aggtgggcct ctaagaaagg agttaaatgg  79680
gcgcggtggc acacatctgt aatcctaaca ctgtgggagg ctgaggcggg cagatcatct  79740
gaggtcagga gctcaagacc agcctgacca acatagtgaa actctgtccc taaaaaatac  79800
aaaaattagc cgggcgtggt ggcgggcgcc tgtaatccta gctacttggg acgctgaggc  79860
aggagaaatg cttgaaccca ggaggcagag gttgcagtga gccgagattg tgccactgca  79920
ctccagcctg ggccacaaga gcaaaactcc gtctcaaaaa aaaaaaaaaa agaaaaaatg  79980
aggtcataag tgtggggtct gatcagacag aatgagcatc cttgtaagaa gagacaccag  80040
gctaggcacg gtggctcact catgtaatcc cagggctttg ggaggctgag gtaagaggat  80100
cacttgaggc caggagttca ggaacagcct gggcaacata gcaggattct gtctctacaa  80160
aacaaaaaca aaaacaaaac caaaacaaaa acagttggac acagtggtgc atgcctgcag  80220
tcccaggtac ttggaggctc cggcaagagg atcaatgagc ccaggagttt gaggttttgc  80280
agtgaactgt gattgtgctg ttgcactcca gcctaggcaa tagagaccct gtctcaaaaa  80340
caaaacagaa caccagagag ctctctcctc acctctgttc ccaccctcac tgggcacaaa  80400
agtaaagcca tgtggggaca cagagaagat ggccattaca gtgagaaaga gagtctttac  80460
gatgaaccaa attagctggg accctgacct tggactcttg gcctccagag ctctgagaac  80520
aaacattttt gttgtttacc cgccccctgc cccatgcctg tggcactttg ttacagcagc  80580
ctaaataaaa caactaaaat atgtgagatg atggcaaggt gggcagaagg aaagttcagg  80640
aactatggac acaagactgt gggccctatg ctacggtcaa agccaacggg ttctctgaat  80700
acccaaaagc tggttctctc tctggctgca ttctacaatc accttaggag cttcaaacaa  80760
caccaattcc tacgtgccct ccagactgaa tgatcagaac ctgaaggtac agcccaggca  80820
ccggcacttt aaaagagctc cccagaagat tctaatgttt agcgagaatt gacagtactg  80880
tcccagtggg tcaatatctc cctagcttaa gacataccag gcgggatgtg gtggctcacg  80940
cctgtaatcc cagtgctttg ggagaccaag gtgggcggat cacttcaggc caggagttca  81000
agaccagcct ggccaacatg atgaaaccct gtctcgacta aaagtacagg ctgggtgcgg  81060
tggttcacgc cagtaatccc agcactttgg aaggccgaag cgggcagatc acctgaggtc  81120
agatgtttgt gaccagcctg gccaacatgg cgaaaccccg tctctactaa aaatacaaaa  81180
aacaattagc cgggcgtggt ggtgggcgcc tacactccca gctactcagg aggctgaggc  81240
aggagaatgg cgtgaaccca ggaggcggtg cttgcagcga gccgatatcg cgccatggca  81300
ctccagcttg ggcaacagag cgagactccg tctcaaaaaa aaaacaaaaa acaaaaaaca  81360
aactagccgc gtgtggtggc gcgtgcctgt aattccagct gctggagagg gtgaggcatg  81420
agaattcctt gaacctggga ggcagaggct gcagtgagct gagatcgtgc cactgcactc  81480
taacctgggc gacagagcaa gactccatct caaatgaaaa gaaaaaaaaa aaaagaaaaa  81540
agacatacca gtgttttatt caaatacatg aaaaattcgg ccagacacgg tggctcacac  81600
```

-continued

```
ctgtaatccc agcattttgg gaagccgagg tgggtggatc atttgaggtc aggagtttga  81660
gaccagcctg accaacacag tgaaaccctg tctctactaa aaatacaaaa aaagggctgg  81720
gagcagtggc tcttgcctgt aatcccagca ctcaaaacaa aaacaaaaac aaaaacaaaa  81780
acaaaaacaa aaacaaaaaa attagcctgg agtggtggtg ggcacctgta actccagcta  81840
tgcaggaggc tgaggaagga gaacaggaga attgctggaa cctatgaggt ggagggtgca  81900
gtgagccgag atcgcaccac tcactccagc ctgggtgaca gagtgagact ctgcctcaat  81960
aaaaagaaaa aagaaaaaaa gaaaaaaaaa ccatgaaaaa ttcaatgaaa accagaacct  82020
acaaaaacat gtctggtata actactccta ttgaggacta tactagaggc cacagccagt  82080
gcaataacat aagaaaaaaa taaaaggtac agtgacagaa aaggtttggc atgaaatgta  82140
ggtctgttaa acaaaataag aaaaggaaca agtgaagttg tacttgcaga tgacatgaca  82200
tttctatgta gaaaaacaaa taagtgagtt tattagcaag gtttcagaag gcaaattcaa  82260
tacacaaaaa tcgcctgtat ttctatatac tagcaataga caacaggaaa ttgagaccat  82320
cctggctaac atggtgaaac tctgtctcta ctaaaaatac aaaaaattag ccgggcatgg  82380
tggcgggtgc ctgtagtccc agctactcaa gaggctgagg caggagaatg gtgtgaaccc  82440
aggaggcaga gcttgcagtg agcggagatc gcaccactgc accccagcct gggtgacaga  82500
gagagactct gtctcaaaat aataataata ataacaacaa tataatttac agctgggtgt  82560
ggtggctcac gcctgtaatc ccaacactgg gaggccgagg tgggtgggga tcacctgagg  82620
tcaggagttt gtgactagcc tgaccaacat ggtgaaaccc tgtctctact aaatataaaa  82680
aattaggcag gcatggtagc acatgcctgt aatcccagct atttgggagg ctgaggcagg  82740
agaatcactt gaacctgaga ggtggaggtt gcagtaagcc gagattgcac tgcagccttg  82800
gtaacaagag tgagatttca tcttataaaa aaaaaaaaaa tatatatata tatatatata  82860
cacacacaca cacatatatt attaaaaata tatatcttat taaaatatat atacatatat  82920
atgatctata atagcattaa aaatataaaa tatgtgggga tatatttggc aaaagacatg  82980
tcagaactgc acactgaaaa ctacaaaata ttgctgacag agatgaaagg aaacctaaat  83040
aaatggagag acataccatg ttcatggatt ggaggactca atattgagat cttagttctc  83100
atcaaattga tctgcaaatg ttacccaaac acaaccatca aaagccaagc aggcttctct  83160
aaaggaaagg acaagctgat aaaattcaca tgaaaatgta aagtatctag accagctgaa  83220
aaaactttga acaagaacaa acgcgaaggg ctaagttcat gacttgttga aaaactacgg  83280
gaaccagaca gcgtggcagc atcaagacgg acatacacat caaggaaaca ggacggccag  83340
cccaaaggta gacgccacag accctcacac acatgcagtc catgaatttt tgacaggtgc  83400
tgaggtgatt caacatgagg aggatcatct tttcacctaa tagttctgaa caactggaca  83460
gccacgtcta aaagaacgaa gcccaaccac ttcctcatac tacatacaaa tattaactca  83520
gaatggatta tagacctaaa tgtgaggact aaaactatga aactttttag aagaaagcac  83580
tggaaatttt tttttttttg tctttttgtg agacaggatc tcccactgtt gcccaggctg  83640
gagtacagtg gtgtgatctc agctcactgc agcctcaacc ttccaggctc aagcaatcct  83700
cccacttcag cctcccaagt agctgggatt acaggcatgc accaccacac ctggaaattt  83760
tttttttttt ttggtggaga tggggtctcc ctatgttgca caggctggtt tcaaactcct  83820
ggtctcaagt gatcctccca ccttggcctt ccaaagtgtt gggattacag gcgtgagcca  83880
cctcacccag ctggaaaaag tcttagtggt gtttaaaatc ttttatactt aatggaaccc  83940
tgaatttttt tttttttcc tgttttaggc agggtcttac tctgtcccca ggctggagta  84000
```

-continued

```
cagtgatgta atcatggttc actgtagcct ctacctactg tgctcagaca atcttcccac  84060
ctcagcctcc tgagtaccag ggactacaag catgcaccac catgcctgac taatttttgt  84120
atttttttgt agagatgagg ttttgccatg ttgcccaggc tgacctcgaa ctcctgggct  84180
caagcaatct ctctgcctca gcatcataat gtgcttggat tacaggcatg agccactgtg  84240
cctagccaaa acactgttaa gaaaattaaa atacagttgg gtgtggtggc ttgtgcctgt  84300
aatcccagca ctttgggagg ccgaggcggg aggatcgctt gagtccagga gttcaagacc  84360
agttctgtgt cttgctagtg gttatataat taatttaaga ggtaacactg catagagcca  84420
tacacacatg taaaactggt gaaacctgaa taaggtctat agtttagtta gcagtatttc  84480
aattccctgg ttttgatatt gtactatgga ggtgtatgga ggtgtaagat gttaacacaa  84540
gggccgggca tggtggctca tgcctgtaat cccagcactt tcggaggcca aggcgggcgg  84600
atcacctgag gtcaggagtt tgagaccagc ctgaccaaca tgcagaaacc gcgtttctac  84660
taaaaataca aaaaatcagc ccggcgtggt ggcgcatgcc tgtaatccca gccactcggg  84720
aggctgaggc aggagaatca cttgaacctg ggagggggag gttgcggtga gctgagatca  84780
cgccattgca ctccagcctg ggcaacaaga gccaaactcc atctcaaaaa aaaaaaaaaa  84840
aagatgttaa cacagaggga gctggtgaag ggcacagggg tctctctgta ctatttttac  84900
aacttcctat gaattagtct atgattattt tttttttccc cagacgaagt ctcgctcttg  84960
tcccccatgt tggagtgcaa tggcgcaatc ttggctcact gcaacatctg cctccagggt  85020
tcaagcaatt ctcctgcctc agcctcctga gtagctggga ttacaggtgc ccgccgccac  85080
acccggctaa tttttgtatt ttaagtagag atggggtttc accatgttga ccaggttggt  85140
cctcaaactc ctgacctcag gtgatccgcc cgcctcggcc tcccaaagtg ctgggattac  85200
aggtgtgagc caccgcaccc agccaattat ttcaaaataa acagttaata aaggtcagac  85260
acagtggctc acacttgtaa tcccagcact ttgggaggcc gaagcagggg aatcacctga  85320
agccaggaat tggagaccag cctgggcaac acagcaagac cccgtctcta caaaaacatt  85380
aataaaaaat aaacaaatca aaatcacaaa atgttaaaaa aaatgtatta ttactgctac  85440
attacctaga agctctattt tgtgtgtgtg tgtgtgtgtg tgtgtgtgtg tgtgtgtgtg  85500
tgtgtgtgtg tgtgagagag agagagaaat agagatattg agagactgag aggtagggtc  85560
ttgctctgtc acctaagctg gagtgcagtg gtgcaattac agcttactgc agcctcaatc  85620
tcccaggctt aagggatcct cccatgtagc tgagactaca ggcatgagcc actatgtcca  85680
gctaattttt aaattttttg tagagacagg gtctcgctac cttgaacggg ctgaccttga  85740
actcctgggc tctggtggcc ctcctgtgtt gacctcccaa agcattggga ttacaggcat  85800
gagccactgc acccagccta gaagctctgt tcatatttat ttgcgaagat caatttgatg  85860
actaagcagt aaactaattt ataaaataat attaaatatt aaaaccaact ttaaacaatt  85920
atcttcacct atgtatgtgt gtgtgtgtat atatatacac acacacacac acatatatat  85980
atatttaaca agtatctcca ataccacaac cagtgtattt tttgtttttt tgagatggag  86040
cttcgctgat gttgtccagg ctggagtgca gtggcgcgat ctcggctcac cgcaaactct  86100
gcctcccagg ttcaagcaat tctcctgcct cagcttccca agtagctggg actacaggtg  86160
tgcgccacca cgcccagcta attttgtatt tttagtggag acctgcctct taattctcca  86220
acatggaggg gtttctccat gttggtcagg ctggtctcaa actctcaacc tcagatgatc  86280
cgcccgcctt ggcctcccaa agtgctggga ttgcaggcgt cgccaccgcg cacggccacc  86340
```

-continued

```
attatgcctc ggcctcccac agtgctggga ttacgggcgt ggccactgcg cgcggccacc  86400
attgtgcctc ggcctcccac agtgctggga ttgcaggcgt ggccaccgtg cgcggtcacc  86460
actgtatttt ttgacaaggg tgagtcagga ctgacactta attcatttgt ttgatatatt  86520
aactgcttta aaaggacaca caatgctagc tgcaccaaag tgcattcaaa ttcctcatag  86580
catgaatcta attttaaaaa acctttgtag ggcgggcatg gtggctcacg actgtaatcc  86640
cagcattttg ggaggccgag gcgggcagat cacgacatca ggagttcaac accagcctgg  86700
ccaagatggt gaaactccgt ctctactaaa aatacaaaaa aaattagctg ggcgcggtgg  86760
caggcgcctg tcatcccagc tactcaggag gccgaggcag gagaatcgct tgaacccagg  86820
cggcagaggt tgcagtgagc tgagatcacg ccactgccct ccagcctggg ggacagagtg  86880
agactccgcc tcaaagaaaa aaaaaaaatc ctctgtatta ggaagtttta ttagaaaaaa  86940
atactagagc acaataagaa aatattcata acgaacttat acaaagtagc aaggaaaaca  87000
ttaagatgcc aataaataaa tgtgcaaaga acatgaacaa aagtcacaca cacacaaata  87060
caaacataat acacgagttc gttcccatgt aagaactcaa tcaatatttg ttgcaagact  87120
aaatgaaaaa ggaaaattta tttagtgaca gaaatgggga aacattcaac ctcaaccctg  87180
agtgggaaaa aacttactgc ccactaaatt acccatctca tctcaccccg gtaaataatg  87240
cccagtgctg gcatgcacac tggcagtata caaactgaga aagactttct ggaaagtgct  87300
acagccatgt gaccacaggg cttcaccctg tgacctcatt aaacctaagc agattacagg  87360
tctgaagggg gctttcttta gatgtggctc cacctactta ggggcagatg aagaaaacag  87420
gggtctgggc agttctgaat gggaaggcca ggcatcacct ccctcttcag ttgcacaaag  87480
tgtgcgtggc atcctcacat cccatctgcc tcaatttcgc tttttctctg aacacttttc  87540
accatctgtc tgaagcacac acacacattt tattcacttc cccattccca tgcatgaatg  87600
ctaggacctt tgcaattgtg ggccaggaaa gattgcaaat gataagccac cagcacagag  87660
agtagaaatg aaatcctggg gttacaagct aaagcattac tgacacccac ttgtccagaa  87720
cggctgaagc tgggcggtga ctgtcaacag gtatatacgg actagaaagt ggagctgctg  87780
gaggaggccc tgtaccttcc tgccatgaca cagcctcccc ccaagtgctg ggcttgtgtg  87840
ctcaacactc cctcttgctg tcatcctacc acacctgcag actggaggta atccagatgc  87900
aaggccgtcg agtcccgcaa acacccacct gcctcttaat tttccaagtg agacctacat  87960
ttcctcaagc gtgaagctca ataaaatcaa ctattgtttt ccgttttcat cacgagcgcc  88020
actttccccc tatttgttca ccgcctccac tccacaagaa ctgctcttga cttggccaac  88080
tttctgggac accctcacta caaggattta tgagtcaaac aggtttttgt gctagcctgg  88140
aaatctaact gctgacagca gttgtttcaa gaagaaaatg ctgttttgga accaaacagc  88200
aggctgccaa ctgaaacaac ataaacccac ctccaagttc aaatgaaaca aacaaacaaa  88260
aagactggtc caagtgaggc aagctgtggt ggctcacacc tgtaatccca gcactttggg  88320
aggccaaggt gggctgatca cgaggtcagg agttcgagac aagcctggcc aacacagtga  88380
aacccgtctc tactaaaaat acaaaaatta gctgagcgtg gtggtgggcg cctgtaatcc  88440
cagctactca ggaggctgag gcaggaaaat cacttgaacc cgggaggtgg aggttgcagt  88500
gagccgagat tgtgccactg cactccagcc tgggcaacag agctagactc tgtcttaaaa  88560
aaaaaaaaaa aaaaaaaaga ctggtcaaag tggcttacgt ctgtaagatc agcactttgg  88620
gaagtggagg caggaggatc tcttgaggcc aggaggttga gactagcctg gacaacacag  88680
tgagactcta tctctacaaa aaattttata aatcagctag gtgtggtggt gcaggcctgt  88740
```

```
aatcccagct actcaggagg ctgaggtggg aggatcaatt gagcccagga atttgaggtt  88800
acagtgagct ataatcatgc caccataaac acgcctggag gacagagtga ggccctgttt  88860
ctaacataca cacacatata cacacagaaa catctcgaga ggacacctcc aaatgatgaa  88920
gctattttgt tgggtactgc ggtggcacct gtgattcctc aagtagcttg gaatcagcgt  88980
gctaacacca taaagtggct gcaaaagtcc cagtgaagtc actgctgaga gcaaacaggc  89040
cttacagaga agttccaagg ggacaggaaa tttccagagg cttgagagga caatgttcag  89100
gggaataagt acttgaaggg aattatctaa caaggtgtta aagtaactag cttcttagac  89160
aagatgacat caggaggaaa aaaaaactta ttaaggcaaa catgtcagtt tcaggccaac  89220
taaggctgtc agagagacat ggaacacaag aagagaagag ttttgaaatg tattcccatc  89280
aagagccaag aataatgaac ttttgaatgt aaaacttagt gtgttccaaa acaagaaagg  89340
aaaaataact tgttactcgg aatcgaagcc aaaaggaatc tcattgcttg gggaggaggg  89400
atgggagggt gggggtggtc cttggcctgg gaaggaaaac tccaccaggc cttcggagct  89460
gggcacgccc tgttcccaca attaagaaaa aaaacgacga cctagagctc aaggccggtg  89520
ctgacatctg acctactgga tggcagccgc ctgtaggaac atcaccatag actattggaa  89580
ttttctggca agtactgggc actaaatcag agatgtgttt ttagagaatt ccatgccaat  89640
actgctgtat agaatctttt attcatactt tcccactagg tttgggcccc tctaagcttt  89700
cacgagtcaa agacccctcc tgcttgctga aaccacccac ggaaggccgg acaccgagga  89760
cctggccgcc caagcagagg cgactgacaa gcgcggtccg ggctggacgg ccccaccttc  89820
cccgcccggg agagccaggc cggacagcgg cctccctcag acccgtcccc aaggccgagc  89880
ctcgccctgg gccgtgctgg tgccccattc gggacggagc ggtggcccgt cagcacttcc  89940
acggcctcct cagcaggcca gatgggcagg gccggcctgg tgtctccccg cctggccgcg  90000
cgctcgcggg cagcgatgac cccaggcagc gggcgacccc aggcggacgg caggccgggt  90060
ctgctcactc accgttcgct gccgcgggcg cctgcggggg cgtctacatg ccggaccgag  90120
cccgcaggcc ccgccgccgc gccgccgcca gccgtcgcta cctggccctt ggcgccctgg  90180
ccgcctgttg ccccatggcc gcccggaccc cggcgccggc gccgccgagc agcaatgcgc  90240
cgcgcccgcc cactgcgcag gcgcacccgc cacgcatgcg cgctgccgcg cacgtggggc  90300
gtcccgcgcg tctgccgggt cccaccggcg ccgggacacc ccgcgcgggc gggaggcggc  90360
gggcgtggcg ggaaagaggc gggcggtggg gaagaggggc gaatcgcggt ggagagcagt  90420
gaccagggag tggaggcggg cagcggggac aggggcgggc gtccgcgact cgggtaggcg  90480
ggggtcggcg ccccgaggag ggcggccccc ggctcccgtc cccactcacc tgccgcgtcc  90540
ggagggcgcc cccgggtccg cccgccacgt ctacgcctag gcgcccccga cattgtgatc  90600
ccagcccggc gtcccgcccc caactcaccg ccaccgcggg cgggacctcc cggaccacgt  90660
gggccggctc aggggagtgc aggtgccccg cgagagctgg ccccgcccgc cgccgcttcc  90720
ctaattaccg ggctgtgaca cggtgtgggc cgagccggat ttgggaaccg aaacttagag  90780
cagctgcggc agcgctgcgc tccctcgggg ctgtccgtcg ggctgggag ggcggccctg  90840
cgcctggggg aaccgcgatc ggcctcacgc ccacctctag cggccaggtg cgccttgcac  90900
gcccacgaac gtcctcagag gtctacgctt gggatcccaa ggctggcagt ggagggagga  90960
cccggtggcc tggggcacct ctagggggac cagggagccg tgttttgcgc accccacagg  91020
ctggaggact cggggagttg ggggaggagg ccaaagccac aggagcggac tttgtagtgt  91080
```

-continued

```
ttgttggaac tgcgggtccc acccagcccg cacttgctga actggtggct gctcatcagc  91140
gccttcaggc ctcaaatatc ccaataatgt gccctatacc cagttctcag ctctcgagtc  91200
actgtcaggt aaactggcaa tgcacgacca gctgctctaa cctgctggtc ccccaggtgc  91260
cagacattgt tttgtttttc tgagatagtg tctcattcgt cccccaggcc ggagtccagt  91320
ggcgggctca cggctcactg cagccttgac ctctcaggtg caagcgatcc ttccacttca  91380
gcttccctag tagttgggac tacaagtagg tcccgccaca ctcgactact tcattcatat  91440
atatatatat ttgtgtgtgt gtgtgtgtgt gtgtgtagag atgaggtttt accattttgc  91500
ccaggctggg tctcaaactt cacccgcctc ggcctcccaa agtactagga ttataggcgt  91560
aagccactgc acctggccca gccattgttt tctgaggttc agtccctgtc tatactttct  91620
gtgtgatcac ctggcccagg gtcggtgtgg acctgagtcc tctgcagccc ttccccacac  91680
ccgcatacct gctctctggt caggactcct gggacttgaa tccagagaca cggaacacgg  91740
cctggccaag tcttcctgaa aaacacagct cttcagttca ggaccacagt gaagtacagg  91800
gcaccaaggg tgactggaaa gggaagcaag gatcatgaga acttggggga tttcttaagc  91860
tctgtaactt ctcccggggt tattttgcaa acccaactgt ttcaaagtga ccaccagcca  91920
cacccacaga agcggccttg agctgcccag ttctttttct ttggcggggg gagaggggc  91980
ggataagatc attaacataa taatgcgtga gctgagtttt tgcatatgat cattagcata  92040
ataatgcttg atctagatgg cgcacccaca agccaggcac tgagccaggc ctcagtagaa  92100
tcttctagag tggaggcagt caactgcttc tgcagaggca accagtgact gtcgtgggcc  92160
ccaggtcaca cagcaggtgc ccttcgcgtg tcccgctgtg tagggagctc cagcagctgc  92220
cccgtctgtg gcatgaaaac cctttgtcta ccctgggcct gggcactgcc tgcaggagag  92280
cttccctgtt tcagagatga gaaaacaaaa ccagggctgt ggtttccttc agctgacagg  92340
ttgtgcaatt tctcagggca ggccccggat atgaccttga agattcaggg gccaagatct  92400
cacacccaca cctcacccca ggcctggcca gcaataacta agaccaaagc tgggaaggct  92460
ccttagggca cccagaatgg tccaagaggc agctttgctt gggctgagac caaagggaag  92520
agatgttccc gcagcaggaa cagaagggtc cagggctatc atgggggctt ctgccagatg  92580
gtgcacagga agaggctctg ccttcaaggg attgggggtc aggaaaggcc ccctcctgcc  92640
tgaccaggcc ccagggatgg ggcagcagtg ggtggcatcc cctgccctga ccttcctcag  92700
ccccagggct gccattgctc aaggtggcag tggactcttc acataatttc gcattgtttt  92760
ttgtattctt taaggatggc tcccatgttg tttacttcag aacccccaaa acctggaccc  92820
atcctcttct gggggtcagc agggatgggg agggtggagg gagaaggggg aacggaggcc  92880
atgagggatg gagcaggatg gggtgcactg gggtacaggt tgctcctggg gaggctgagg  92940
agagagggaa gttggcttca ggtggcctgg ctccagtaaa ctgggtgaac gaagtctgcc  93000
cagaacccac aagggtaagt ggcctggagc ctggggaaag gatgactggg aaggactgag  93060
gctcccagtg aaggacatca gtatggcagg ctatctggtc atctcatcca gcctccagcc  93120
agcacccggc acaggccctg cccaggctga aagccaggat aggggcgtct gcaggggcca  93180
gtgtctggat ctgctcacat gacagtcttc tgtttggcct ggtttggggc gaggggcaac  93240
ctctttccca ggatgccagc catgtgcagg gcatactgag gattcaacag tggaaaccaa  93300
agtccatcag gtgttcacct tctagtgggg cagacgggca agaagcagaa ttggtggggg  93360
caggcagggg ttggggtaca gttttgacca aggtacccag ggacaagtgt ttctctctca  93420
ggcagaggca gcagcaagga ccaggaccct gaagtggtga gagcctagag tgggcgggga  93480
```

```
tcatcaacag taaccacctg gcaggactgg gactccctgt gtcctcacaa gatccttacc  93540
aagcagccta gtataagacg aagtctcgct ctgtagctca ggctggagtg tagtggcatg  93600
atctcagctc actgcaagct ccgcctcccg ggttcaagcc attctcctgc ctcagcctcc  93660
agagctggag ttacaggcgc acaccactga acccggctca ttttttgtat ttttagcaga  93720
gacggggttt catcatgttg gccaggctgg tcttgaactc ctgatctcag gtaatccatc  93780
cacctcggcc tcccaaagtg ctgggattac aggcgtgagc cacagcgccc ggccacagcc  93840
tggtacgttt attgtccaca tttttcacgc gggggccaga ggcacagaga ggccaagtaa  93900
cttgctcaag gtcacccagc gaggaaaggg agctgggggg tgggggtagg ggacagggcg  93960
aggccagaga gtagtgggag gggccgaggc ggcctttccc gggagcgctc ggttcccggc  94020
cggcccttct attggcccca gtcactcagg ctcccaggtc cggctcgggg gggagcgggg  94080
ggccgcgcca ggccgctgaa gtgtccccgt ttcgcgtggg cagagcgcgc ctccccacgc  94140
atcctgctga gggccagcct ctgctaggtg cgtgacacgg aggggacaga acggaaacct  94200
tgtcctgctc aagtgtggac gtgcgtgcca cgtgctagag taaaattgag gtggggaacc  94260
tccatccctg ggacatggag cacaggggcg accccgcgcc gcttggtcaa aggaggtccg  94320
aggccctgca ggaacagccc acagccggag cgagctgcag gtcactccac tgcctgtgtc  94380
cacctgcgac aggtgcgccc gcgcaagcgg ggcggagcca ggtgacccgg acacaggaag  94440
cgcgccaggg gcccccacac cgcggagctg ctggcgacaa agggcgctgc tcctgcatag  94500
gccaggctaa tgcaatctac aaactagatt tctgtgccta cagtttgaaa atgattgcag  94560
ttcactcagc cagtgtggaa ttatcctcct ctttccacac tgccttagtc agtgccgctg  94620
tccaagtgca cgttgttggc gcccgttttc atttcctgtt ttgctaagaa agtggggcag  94680
tggcctccat gcccgccaag ggacaggcag gccgccccag ggaggggtcc ccctcagctc  94740
tggctcttcc aggccaaagc caaggggaag gggcaccaga gggtcccagg tcccacatgc  94800
cagctccctc agtctgcggg gtgccaggct aggacacaga agccaacagg aatccccaaa  94860
gggaggaagt ggagtcgggg gtgtggcagc cgtgctgaga tgctcggcct ttatttactc  94920
tgggcaggga ccaagatagg ccactgcagg ccggcaccct gcctcccggc tgctggagcc  94980
cctccctccc aggaactgcc agccaggaaa gagcctcagg tactctctgc atttaatttt  95040
taattttttt tttcttttga cgcctccaag acaagttcaa ctctctagtg attttaagtg  95100
gggtttttgt aagacagctg gcagggttag ggcttgtgaa gaacttgcat gtctatgaag  95160
aactgattta tttcagggaa aagtggggga tgacgaagcc aggcgagccc accccgttca  95220
gcctgccaat cacacccact tcagcagcct aaaacagcac caggtcaccc caccagggag  95280
acaacgccat agtgtcactt gcagtgctgg cagatgggca cccttggtgg cgtcagaaac  95340
acacccagca ccttgcctgg agcagggcgg ctgggccctg ctccgtgaat cccaagtgcc  95400
ctatgggagc ctctccggcc agggactgcc agcctagagg aggggctgct gggttctctg  95460
gtgcccaggg gaggaggggg cctacaggta ctttctgctg agagccttct tcacttacta  95520
ggaaaaagtt tggctgggtg cggtggctcg gcctgtaatc ccagcacttt gggaggctga  95580
ggagggcgga tgacaaggtc aggagatgga gaccatcctg gctaagatgg tgaaaccccg  95640
tctctactaa aaatacaaaa attagccggg tgtggtggtg ggcacctgta gacccagcta  95700
ctcggaaggt tgagccagga gaatggcgtg aacccaggag gcagagcttg cagtgagccg  95760
agatcgcgcc actgcactcc agcctgggca agagcgagac tccatctcaa aaaacaacaa  95820
```

-continued

```
caaattagcc gggcatctgg gccaggcgcg gtggctcaca cctgtaaccc cagcactttg  95880
ggaggctgat gtgggtggat cacaaggtca ggagatcgag accatcctgg caaacatggt  95940
gaaaccctgt ctctactaaa aatacaaaaa attagctggg catggtagca ggcgcctgta  96000
atcccagcta cttaggaggc tgaggcagga gaatcgcttg aacctgggag gtggaggttg  96060
cagtgagctg agatcgcacc attgcactcc agcctgggca aaaaagagcg aaactccgtc  96120
tcaaaaaaaa aaaaaaaaaa aaattagcgg ggcgtcgtgg tacgtgcctg taatcccagc  96180
tacttgggag gctgaggcag gagaatcact tgaacccaga aggcagaagt tgcagtgagc  96240
tgagatagcg ccactgcact ccagcctggg ccacagagcg agactccaca tcaagggaga  96300
aaaaaaaaaa aagttccagc tgctggagcc atgggaatta aaaaattact tttttttttt  96360
ttttgagagg cagtcttgct ctctcaccca ggctggagtg cagtggtgcg atcttggctc  96420
actgcaaact ccgccttccc gggttcatgc cattctcctg cctcagcctc cagagtagct  96480
gtgattacag gcgtgtgcca ccatgcccag ctaattttgt attgcctatt taagatttta  96540
aaaaatcacc agtttggaaa gcagggaagt ggatggttct ggagcctagg agcggctatt  96600
tgggacacac acagccatgg ttttccacac taccatggcc agtgctcatt tttttcttac  96660
tagatgcagt tctttatatt cagaccaaga ggaacactca gttcagtccc aaggaaagct  96720
agtctctgga gtaacatcct cagacattct aagggaggga aatggcagag gagaaaggca  96780
aggcagccgc ctgtggagac tcccacggtg ctgtgggcaa ggcctatgcc tggggagggg  96840
tctgggcgat ggcaggtgga cctccctgct ctgctggcct gtgaggtgga gcttcccagg  96900
aacccctccg aggagccaat gcgccactca tggattctgt gacgtggtgg cggccatggc  96960
accgcctggc atgagcaggc ccgtcagacc tcacagcaac agggacagct tagggaagcg  97020
ggcgcgttgc aaactggaag tggacccgta aataatcacc acaccaaagt ccctcatgtc  97080
aaactgcttt attacatctt aaataacagt acagtttaat atagtatcta tcttgcatcc  97140
agcttccttg cagtacactg actttaaaat taaatacaaa aggtggaaag gggtaagggt  97200
gcagagagct ctacagagtt gttggacgga aagagaaaga aggggtttca tttgtattct  97260
ctttgccaga tccaggccta ccgcaaggtc acagcacagt tttgtataga atgttgcaga  97320
aaacaggatg gagaagccac tactgctgct atgaaggagt gcggggggcg gggcgggggg  97380
tcccacagaa cctgctttcc aaacgctgct gctgaacact ggccttgaaa tgaacaccag  97440
gacaatctgt gtgtgatggg aatgagccac ctcagatgtg gagggccctg aagaatccat  97500
ataggagggc aggctcttca ctccctctcc ctccctctct ctccctcccc accctcagaa  97560
tccaacagca gtcgtttgca acagaacttt ttttttttta aagaaataaa gaaaacagtg  97620
acttatcccg ctacccaagc gtgtagagcc gcgcgctgta ctgcttccga tatgtgccac  97680
agagcagcaa cgagaagtgg acagagccgc aatggttaca actgtaagag gttatttctt  97740
aaaagaaaaa gaacacctaa ggactgagtc ccatatgcac ttttgagcat ttctacagca  97800
tgcgattcta agagtaaacc cacccaatat ggcaaacaat caaaattttt aaaatttaac  97860
ttagaaagtc tgagatcatt attttcaaaa cattgatttg tacattgttt catacacaaa  97920
taattgactg actatccaag cacaggacag gcatctctct tgaaaacaga ggttcctcct  97980
agttgggggt ggggtagtgt taggctatta taaacttccc tccaacttca caaggaaacc  98040
caaagtgaga ttaaaaactc aactgagaag atagacagga tgggtcagga ggaacatggt  98100
gctggatctg agctcacttt tcagcaaagg tgaaggattc tctgatcacg catttgagac  98160
cgtccccgca tgtgcttggc cccatggctt ctgaacatgt tcttttctat gccacgtttg  98220
```

```
tgtgcaacaa tgatctgtga catcagacag aaaattaaaa accagggact gaatttacat  98280
cattgacaac atcagagagg ctgccctaga ctctctggtt ttgattaact gttgaacaca  98340
aaggaataca ttttaaaaag gaaatatgaa tgcttccaaa atcttgctac aaacatgact  98400
gaaatttgga cacgatgacc agatgaacaa agccctcagc atgttttgca tgaatgccac  98460
aaaacagggt cactggtcta aaattcaaat acactggtgg aaaagtgtgt ctgtctgaca  98520
attacactca agtttacctt ctggttaaca tttttattat atatttcctt ttaaaattca  98580
ttcaagacaa aaaagaaaac aaagacgatg gccccggaag gaatgcacaa tttgttttag  98640
tttacagcac agagatcttt ctctcaatgg gaattgtgct cttggtttca gcaataagtg  98700
aaggaaaaaa gatcttgccc ttttgaagtt ctgaggggag gtgtagggtg tccacgttag  98760
tacggttgga taggatatgc tctcatggta acgcgtccaa gttggaatgg tcttccagtc  98820
tccatggcat ccacatgctg ttttaaacag agtttaaaga aatgtgaaaa gaggcagaga  98880
atctaagtgc agacgcacag ccaggtcact gctcttccca tcactgcatg agtgtctgca  98940
gctgagggca cgtgacttca gctttctgta aacgtttccc acaacacaat tccaaatcaa  99000
tgctacatca acatttatct agaaaccgtt aatgacaact tcaaatgttc tatgagaaac  99060
acgcacagtt ctcctcagag aagggcattt gggctgctgc attacctact ggcgttagtt  99120
ccagatcttg aggaagctat cccaggaccc tgtcgccaca gccatgccat cgtcagtcac  99180
gcccaggcag ctgacgcggt tgtcatgccc agccaagaca cctgggagca aacaacagca  99240
gaatcacacc aaagcccaga ggcatcgatc tcacctgtgt gccatgttgt gacgaggacg  99300
gatggtgcat ctctcatggg acaagaccca gagtctccca cggccaggaa gggagggaaa  99360
gttgcatcca cgtggggaat taacctgcag catatggcca gccttgttaa aattcaaaga  99420
cacgcacaca cacgcaatcg ataaatccag agcccctggc attgacttct cagcactcac  99480
ttataaaact taaaaaaaga agcaaaggcc actatcaaaa aaatcaaaac tatcatcaga  99540
cgcagtggct taggcctgta atcccagcac gttggaaggc cgaggcaggc agatcatgag  99600
gtcaggactt tgagaccagc ctggccaata tggtgaaacc ccatttctac taaaaataca  99660
aaaaccagca gggcgtggtg gtgcgggccg tagtcccagc tactcaggag gctagggtag  99720
gagaatcatt ggaacccagg aggtggagct tgcagtgagc caagatcgtg ccagtgctct  99780
ccagcctggg cgacagagcg agactccatc tcaaaaaaaa aaaaaaaaaa tcaaaaccgc  99840
cccaatctca aagcaatctg taacacagga gcttagaggc atgagccgtt tttcctttgt  99900
ctgtgatccc tagagcccag cacaaggcac agaacacagg agtagcgatg gtggctgaga  99960
ccactggcac tgcactgtca ctgtcatgtg atgagggggc cttctgtcaa cactcccaat 100020
aaccttggct tggatcatca ccagccagaa gctccacttc ctcccagggg gatccgaagg 100080
cccatttcag ccaccctcct ccacctcctg cagccaccac acagctgagt acaggggccg 100140
gcgtgtgctc tgccaaggcc tgggctggct tccaccgccc ttcaacagca ctgtgactgt 100200
gagacttggc tggaaatggc tccactctgg tccccccagg ctggggagaa aaagaaatgt 100260
gtttaaccag gaggtgggag tggcacccat ccggaagcag gaagccccgg taagggccaa 100320
gacctggagc catgctccct tctgtcctcc caggtactga gacaaatgaa tctaagtctg 100380
taagtgtcaa cagttctcaa attcaaatgc ccaaatgacc atttttagta aggaagtctc 100440
atcttttgta cacctggcaa taacacgctt gcctttgata tgttaactgt aacggcaccc 100500
agaggtgtcc ctgcatggaa ctcctccccc tgaagcagag ttcagagggg aaagcacggg 100560
```

-continued

```
gctgggccct ggagcctgca cagctgaccc tctcctgccc actgactctc cccagagccc 100620
tccccgacgc atgtgggaag atctgctggt actcctcgga gtccacttgc ctggagggtc 100680
agagctgggc catcagtttg cgactgtcac tcctgctacg ccatgccaca gtcccaccga 100740
tactaaaaca ctgcagctta tgcaaccact ctgtgtttgc tctaaagata ccacgtaaat 100800
gtccacaaga cacagaaagg ccccatggcc acgtacctgc ccggtcggct ttgagtgcat 100860
cccagacgtt gcagttgaag tcgtcgtacc cagcaaggag gaggcgcccg ctcttggaga 100920
aggagacaga ggtgatcccg cagatgatgt tgtcatggga gtaagtcatg agctcctggt 100980
cagcacgaag gtcaaacagc ctgcaggtgg cgtcgtctga gccagtggca aatgcattgc 101040
catttggaaa gaactggaaa gagaaagcaa atcaagacat catgtaaacg ctcagaaaga 101100
aacattggga atatggattg ctcaatggta gggctgcaga gaacacagca ggcaaagacc 101160
agcaagactg tgctctggta agaacagagg gctgggccgg gtgcggtggc tcatgcctgt 101220
aatcccagca ctttgggagg ctgacgcggg tggatcacct gagatgggga gtttgagacc 101280
agcctgacca acatagagaa accccatcta tactaaaaat acaaaattag ctgggcgtgg 101340
cggcgtgcgc ctgtaatccc agctactcaa gaggctgaag caggagaact gcttgaaacc 101400
gggaggcggc ggaggctgcg gtgagccaag attgcaccat tgcaccccag cctgggcaac 101460
aagagcaaaa ctccgtctca aaaaaaaaaa aaaaagggtg gggggatggg ggaggaacta 101520
caggggactg ggatgggagg ggatttgcac tggggaggca cacaaacact gtgatcttgg 101580
acactgtgat tactgtcccc aaagagtaga atttattcca aaggatagtg agaaagtagt 101640
catcactgac aggtgtgcat gttgctgtag ctgccagcca tcagggctaa tctcatggag 101700
gaaggaggga agcgggctga ccaaggctgt ggtcaggact gcagcagagc tctgtccaac 101760
caacagatac atccttctaa gtctcctcac aaggccaggg gctggaaaca ctgcctagcc 101820
atccgcgtgc taaagaggag ggcaggttcc ctggttagct gtgcccctga ccagtaaggc 101880
tctgtaacca ctggtggcct gagttatctt actgtctttc ccctccagga tcccaaccac 101940
tgctcagctg tagaggtggg aacggggact ggcatacaac accctgtgag tatctgtgag 102000
acaagtggtc aacacagaga agtttcccat cgggagtttt ctgtatcccc atctgtacat 102060
gaggttgtat aaggatcaga aaggagaaca tctaatccag aaaagtttaa aatttagcaa 102120
tctgaacggc tagcagagac ggcagaggac ccgaccccac acctccaccc agactcacgc 102180
aaatggcatt gatgtcagac tcgtggccag tgaaggtctg ccggcacatg ccttctcgca 102240
catcccagag tttggctgaa gcatcacaag caccagagac gaacagtctg gtgtcaggag 102300
caagagaaag gctcatgaca tctccagtgt gtccggtaaa cgtggtcgtc tgctggccgg 102360
tctcgatgtc ccacagggca ctggagcagg agcgaatgac aaggggacat cagccttaac 102420
ttcttgggtg gctagtcatg tgacagacaa tctgtccttc aaaccaccca gggccacagt 102480
gagcctctgc actgttactt taaaaacgta aattgtttaa agacaaattt aaatgtaata 102540
caactttgga agggaaacaa agcaaagcaa gcaaaattat acagagatga gcacagggcc 102600
tgggcttcag aatgacggga tcgctacctc aactcaaatg ccagcaaaca gggagctggg 102660
ggcacttttc aagcagcacc actgaggctg tgccccctct ttggtcatgg atgggcatgg 102720
aaggggtggc aggaagctac gtggaggccc tggatggcgg aggggacgcg actctatctg 102780
tggctgctcc ctctgtgccc tcccttggcc tcccctccac agggtctcag aaaaggcagg 102840
caggagaagg ccaatgccag gtaaacaaat ggctcacagc aattctgagg tcctcctgcc 102900
ctttcctgga atcacaaaca ggagagcagc tgagttctca gtgatcacac ctggtatttt 102960
```

```
ttttttttt ttgagaccga atttcactct tgttgcccag gctggagtgc aatggcgcga 103020
tcttggctca ccacaacctc cgcctcccga gttcaagcga ttctcctgcc tcagcctctc 103080
cagtagctgg gattacaggc atgcgccacc atgcccggct aattttgttt gtatttttag 103140
tagagacggg gtttctccat attggtcaga ctggtctcga actcctgacc tcaggtgatc 103200
cgcccgcctc ggcctcccaa agtgctggga ttacaggcat gagccaccgc gcccggccat 103260
acctggtatt ctatcacatt tctgcttaac aagctgtcaa aaggtgagac gctgacagag 103320
ccctgcacag agcagaagcc tggctcaggt gtaaggacag ctgtgagggc cacacgccca 103380
ccaacatact attctcctgt gcctcgaccc atggaaggca acaccagaga gcactgtccg 103440
ttcatgtcag cctcagagga aagcctggct gggcctggca atgcaaatcc aatcagccaa 103500
tctcaacaga cactgcacag ggagcctcct ctctagggcc tgagggactg actgcagaag 103560
ggaagcaaga tacgtaaaag agtctgaaaa aaatgattaa tgaacagaag cactttaaaa 103620
atatcttcta ataaataaag tcttctcaag attgacaatc taggtgacaa atcttttgta 103680
aatctatgaa atttatacaa cgaggacacc ttataatacc acagatgctt tgctgacaag 103740
ttggttaagg gcccatgtct cggtgaaccc caccaactgc gtgactaggg gtctgtgccc 103800
tgggctgggc acagctcctg ccaccaaatc atgcctcaga agaccagaaa aacccacatg 103860
gccagctgaa gtctaaaatg actctcataa aataactatc tggacattta atttagtact 103920
ttgatgccac aaatgaaaaa attctagcat ttaagtgggc ttccgtttac ctgtaaggtg 103980
aaaacactaa aaatgaagtc tgatggaatc acttgaattg tgacgtctgt tatttttagt 104040
ctgtgctcat tgttcacaat gacatgatgc tatcagaaag ggacaatcaa aacccaccct 104100
actcccacct atcatcacct aaggaggtac aaatatatag aggggaaaaa aaagaagagc 104160
aggtactttg agcctgattg tagttaaaat atctatgttg gccaggcatg gggcgtcaca 104220
cctgtaatcc cagcactttc agaggctgac gcaggcagat cacgaggtca acggataaga 104280
gaccatcctg gccaacgtgg tgaaatcccg tctctactga aaatacaaaa attagctggg 104340
tgtggtggcg cacacctgta gttcccagct actcgggagg ctgagagggg agaattgctt 104400
gaatctggga ggcagaggtt gcaatgagcc gagatcacgc cactccactc tagcctggag 104460
acagagagag actctatctc aaaaaaaaaa aaaaaaagaa aaaaatgtgt attttagttc 104520
tcagctgctg aaaattaaac tttgtaaatt tattagaagt ataatgaggc taggcacgga 104580
ggctcacgcc tgtaatccca gcactttggg aggccgaggt gggcaggtca cctgaggtca 104640
ggagttcagg accagcctgg ccaatgtggt gaaacctggt ctctactaaa aatacaaaaa 104700
ttagtcaggc gtggtggcgg gcacctgtaa tcccagctat tcaggaggat gaggcaggag 104760
aatcatttaa acccggcagg cagatgtcgc agagccaaga ttgagccatt gtactccagc 104820
ctgggtgaca agaacaaaac tccatctcaa aaaaaaaaaa agtataatga attcacacat 104880
tgctactatg tgttttaaat cttaaggcca cttaaattac agatggccta atattatgtc 104940
aagaacctta tttcctccat gttcacagag gaatgtgcca ggggctgtgg gttctcaagg 105000
cactgcctgc cccgggtcag gtacttacca cgtggtgtct ccagagctgg tgacgatctg 105060
attgtcatcc aggaatcggc agcaggacag gtaacctggc aaagaacagg cctaagtgat 105120
gagctgaatc cagcaggcct tgcacccagc ctcatacata gagaaacaca ttggcccggt 105180
ggaagctcta cgtctaaggt aagaccagca ccatgctagt gaccttttat tcccatctgt 105240
gcacacagca gaaggtccac acgcactgct ggtgagggtg agagcctggc caggcaggac 105300
```

-continued

```
agcacgtccc acagagaccc acagctccgt gatgggggca gaagcagaaa ccacacccat 105360
gaaacataca catctttcat ctgctttact gtttgaccca tcaaaggctg gggatccctc 105420
gtctatttac tcattcaggg cacgctgact ccagtgccca ggaagcagcc ttaaccagac 105480
agacacctcc tgctctccta cagcccacgc tcagcaggga cagagaatga gaatcactga 105540
aagaggacat cagaaaggga gtgctagggg aaggaagagg acaaagtagg ggcctcacaa 105600
gatggaagcc aggagaggag ggaggacgag agtagactca gagaaggagg atccaaacag 105660
agggcccagc cagggcagga ggcggcgagg ccacagggtc agggtggcaa gggcctgcag 105720
gtcatggaag ggataacgaa ggcaacagga acgcggcatg gcagcaacac tgcagacacg 105780
ggggtgctcg tgaatatgtg tgggtgggtt tgttttcttg ggacagtggg ctgtgacacc 105840
cacatcagcg tgggcacaat tctgtgtctc tgagtattcc cacccactcc cactgggaag 105900
gaagcatcag aggcgagagc aggacacacc aagatgcccc gtcctaaaca acttccaaaa 105960
tgaggaaaag caacaacaaa aaatcagtcc gcaatatcca cacatgatga ctggtctcta 106020
ctaaaaatac aaaaattaag cgtggtggcg ggcacctgta atcccagcta ctcaggaggg 106080
tgaggcagga gaatcatttg aacccggcag ttcaagttgt taatgacttc tgttgaccat 106140
tatttctttt gtacattgat cacagttctg gtatttactg tggaactaaa agcatagggt 106200
caacaaacca gttagtgtgt gcccaggatt ggtgacagac tggccctaat ctgaagattc 106260
aggggttcca gtggcactgg tgattcttgg gatacctgtt tagatttgag tgtttactga 106320
aaagccttcc ccccaactac accccaggga gtcatgcgac actgcgtgaa tcagcaaaca 106380
acaaaaataa aatgcaccaa aagaagaaac ccactggggt tttaatgtag aaagtgtaag 106440
attacagaga aaacaaagca tttatttaac aaacattatt atcactattt tttgagacag 106500
agtctcgtgc tgtcgccagg ctggagtgca gtgatgtgat ctcggctcac cgcaacctcc 106560
acctcccagg tcaagcgatt ctcctgcctc agcctcccaa gtagctggga ctacaggtgc 106620
acgccaccac acacagctaa tttttgtatt tttagtagag atggggtttc accatgttgg 106680
tcaggatggt cttgatctct tgaccttgtg atccacccac ctcggcttcc caaagtgcta 106740
ggattacagg cgtgagccac catgcctggc caacaaacat tattaaactg gctctgacag 106800
aagaaaaata tgcatagatg acagagctca aaatattaac tacgtgccta cgaaagtatg 106860
cgtggtcaaa tacttcctgg aggccacacc acagggacac tagggaccac aaaggtgaac 106920
ccaagtccag ctcagaggag gatagccctg catacctggc gccccctgta gtgccctgca 106980
gcttgctgtc gtgccccgca gctcactgtc atgctcccgg gtctccaccc gagccctcct 107040
ccactggctt cctggttcac actcaccctt gcttcaggga agcaccccca ccccgtcaga 107100
tgcccatcca gaccaggcca ccgagccttg tagcacttag cctgtttgaa tgtgagcaca 107160
gaagggcagg aaagaagagt catggagacc tcagcacagc ctgcatctca cacaggggac 107220
caggcggagg cactcccaag tttactgcat gaaagaatca tgaccttggc tggacgcggt 107280
ggctcatgac tgtaatccca gcacttgggg aggctgaggt caggagtttg agaccagcct 107340
ggccaacatg gtgaaacccc gtctctacta aaaatataaa aattagccag ctgtggtggt 107400
gggtgctggg tctgtaatcc cagctactcg agaggctgag gcaggagaat cgcttgaacc 107460
caggaggcag aggttgcagt gagccgagtt cacagcggtg cactccagcc tgggcaacag 107520
agtgagactc tgcctcaaaa aaacaaaaaa catgacctca taggtctcaa agatgacctc 107580
tctgtcccac cctgtgcagg ctgtagtgaa gctacacaga atccatcagc ttcttactcc 107640
aagaaccaga gactgaaccc taaaatcaca gctctcaagc gctgataaaa tgatgtggac 107700
```

-continued

```
aagcatcagc tgacaggaac tatgaaggac aaggggaatg accgaatgta taagccacac 107760
atggcccctg acttacaatt ttgtgacttt atgatggttt gaaagacaca cgcatttaat 107820
aggaaaacca tgctccaagt acccatacaa ctattctgtg ttttcatttt caggagtgtc 107880
caataattta catgagatgt tcaacttttt cttataagat atgtattatg ttagatggtt 107940
ctgcccaacc agaggccact ctaagtgtct gtgcatgttc aggttggggg gtgaggtgtg 108000
tccagtgcgg ctggagagca ggatgggtgg tgcaatgccc agggtgcaag catactccat 108060
gaggcccagt ctgtgaacag agaccaggtc taaccccttc ttccaggaaa gcctcgtagg 108120
gccttctggc caagaggcca cgagtggtga agactgcaga ctctgaaatc agaaatacct 108180
gggctccact gtcagcatgg cagctgagga agagtgaaaa ttcctctaag ttcttttaga 108240
agtcccagcc tccccatgta actggggaac tgatgggagg agcagagctg tctgtgcaca 108300
taagaagttc tcagtaaatg gagacagtta ctatttctgt tattattgaa tttgaacaaa 108360
ttccctgggt atgtgtgggg ggacacttca ggtgaaaaca cgcccctcct cccctggtgc 108420
gggggcctgt gctgccaccc tctggaagcc tgcagagggg cagggaaaac agaccctgaa 108480
caaaagtgtg cacccagtga ggaggtgcaa gggcacaaag gtggcaccaa gtgcctcaag 108540
gagaggctga aacgcggcct ggggacctcg cagtggtctg gtcatatagg cagtgggtgt 108600
gaagggctgt cctgtgtctc atagggacca ctggctatag ggacaaggct gttaaagtcc 108660
aggagagagg gggtggcttg aagagaggca cggcagagag tggaagcgta ggagaaagat 108720
gggctcctgg gcatgtggtg tcagcagagg tgcctcaagg atagagtgag tccagagtct 108780
agaaaggagc agatcaccag gctctgggaa gagcacagca tgggtgcaca cactgctcta 108840
cccagcatgg ctgccgaccc aaagacagca aagccaagaa ggacacacaa gcgtggccag 108900
atgcagccct gtgaggaaac ttacccaaga acgggacgat gggcttgaga aaccatccat 108960
ctacaaggat ggcgtttgct gcagcaatgt ttataataaa ttgtgggaaa ctgtgaactg 109020
cctaaatgtc tcacaatagg aacaaattag tgcaccacac catgaaactc tctacagctc 109080
ctgagttaca gaacgacagt ataatactat agttatataa tactgtataa tactactgca 109140
taactattgt ataatactgt atttctggat ggaattatag ggtctcccaa cataaaagat 109200
gatgattcaa agttcctttc caaaattcct tttttttttt gagatggagt ctcgctctgc 109260
cacccaggct ggagtgcagt ggtgcggcct ctgctcactg caacctccgc caccccggtt 109320
cagcacttct cctgcttcag cctcccaagt agctgggact acaggcacct gccaccacat 109380
ccagctaatt tttgtatttt tagtagagat ggggttttgc catgttggca ggctggtctt 109440
gcactcctaa catcaggtga tccacctgcc tcagcctccc aaagtgctgg gattataggc 109500
atgagccacc gcgcccagcc ccctttccaa aatttctaca atgaacacac tttgaaaggt 109560
ttagttctcc tacctgcacc ctggagaaca tccctgttgg gagcaggggc aaggagaccc 109620
cacccaaggg aggcgcacag gacacactga aaggcaggcg ggcaaatgcc aagaagtcag 109680
ccatgaccac gcccagtccc tcactagtcc tcctccgaca ggtggtttca ggagcacctg 109740
tgccgcccca ggatcggctc caaggagcaa aaacaagacc gtgctggcga gggacaggct 109800
cagcctagac ctggagggaa aggtgcccag ccctgcaccg aggcatgcac ttggagagca 109860
gaggtgtttt cttcaagttc agtaagaagg aaaatgaaag agatgaggaa gtaacttgaa 109920
gatgtgaaag tgaggctcag agggttgcac agaggagtgc ccgggcacca tgagtgcctc 109980
catgatggtg tgaggctgtg aggcccacca gtgcagccaa gatactgggg ctggtaacag 110040
```

-continued

```
tgagcctcaa gcagacatcc cagtcaccag ctgccctgtt gtggctcctg aagcagggtt 110100

tacggggaga caacatatat ccccttctgt gtccaagctt gtgaggcctg tcagaaaaaa 110160

atccgctatt ttcatgaata tagaaaatgt tctgcttctc actatatgaa gacaccgtgc 110220

ctaaaaatgc caagttttgg ccaccacagt gggctctgtc actgacagct gtgcacgctg 110280

tatcatgaag gccttaggct ggacttctga tcaatgctta tgtatctgta gccatcttga 110340

tcagaatgat ccaggcaagg gccgccgtgt ctccactgcc cgagaggtat gcaaagaaca 110400

aagctctaag agcaagcgtt gagtctccct gcattggccc ttagggatct gctttgataa 110460

aaatctgaga ctggatcaga gggctggaaa taagcttttt ttggagacgg agtttcgctc 110520

ttgttgccca ggctggagtg tagtggagcg atctcagctc actgcaacct tgcctgctgg 110580

gttcaagtga ttctcctgcc tcaggatc                                    110608
```

<210> SEQ ID NO 4
<211> LENGTH: 59
<212> TYPE: DNA
<213> ORGANISM: Homo sapiens

<400> SEQUENCE: 4

```
ctaactaaaa taattgagta aaactcatag gtcaaagggg aattctaatt aagtgaaat      59
```

<210> SEQ ID NO 5
<211> LENGTH: 56
<212> TYPE: DNA
<213> ORGANISM: Homo sapiens

<400> SEQUENCE: 5

```
ctaaataaca tacttttaga taacccatag gtcaaagaag aagtcaaaag tgaaat         56
```

<210> SEQ ID NO 6
<211> LENGTH: 27
<212> TYPE: DNA
<213> ORGANISM: Homo sapiens

<400> SEQUENCE: 6

```
taaaaatgac ttgcaagaga atggtaa                                         27
```

<210> SEQ ID NO 7
<211> LENGTH: 27
<212> TYPE: DNA
<213> ORGANISM: Homo sapiens

<400> SEQUENCE: 7

```
taaaaagtat ttagaaccaa atgaaaa                                         27
```

<210> SEQ ID NO 8
<211> LENGTH: 60
<212> TYPE: DNA
<213> ORGANISM: Homo sapiens

<400> SEQUENCE: 8

```
taactaaaat aattgagtaa aactcatagg tcaaagggga attctaatta agtgaaatta     60
```

<210> SEQ ID NO 9
<211> LENGTH: 55
<212> TYPE: DNA
<213> ORGANISM: Homo sapiens

<400> SEQUENCE: 9

```
taagtaatat aagtaaataa tccataggtc aaagaggaaa ttttatggga aatta          55
```

-continued

```
<210> SEQ ID NO 10
<211> LENGTH: 25
<212> TYPE: DNA
<213> ORGANISM: Homo sapiens

<400> SEQUENCE: 10

aaaatgactt gcaagagaat ggtaa                                    25


<210> SEQ ID NO 11
<211> LENGTH: 26
<212> TYPE: DNA
<213> ORGANISM: Homo sapiens

<400> SEQUENCE: 11

aaaacatgtt ttgaactgaa tgaaaa                                   26
```